(12) United States Patent
Basu et al.

(10) Patent No.: US 8,409,641 B2
(45) Date of Patent: Apr. 2, 2013

(54) ENGINEERING ENZYMATICALLY SUSCEPTIBLE PHYTASES

(75) Inventors: Shib Sankar Basu, Apex, NC (US); Shengsheng Zhang, Cary, NC (US)

(73) Assignee: Syngenta Participations AG, Basel (CH)

( * ) Notice: Subject to any disclaimer, the term of this patent is extended or adjusted under 35 U.S.C. 154(b) by 185 days.

(21) Appl. No.: 12/744,483

(22) PCT Filed: Nov. 21, 2008

(86) PCT No.: PCT/US2008/084294
§ 371 (c)(1),
(2), (4) Date: May 25, 2010

(87) PCT Pub. No.: WO2009/110933
PCT Pub. Date: Sep. 11, 2009

(65) Prior Publication Data
US 2011/0041221 A1    Feb. 17, 2011

Related U.S. Application Data

(60) Provisional application No. 60/991,968, filed on Dec. 3, 2007.

(51) Int. Cl.
  *A23K 1/165* (2006.01)
  *C12N 9/16* (2006.01)
  *A61K 38/46* (2006.01)
(52) U.S. Cl. .......................... 426/53; 435/196; 424/94.6
(58) Field of Classification Search .................. None
  See application file for complete search history.

(56) References Cited

U.S. PATENT DOCUMENTS

| 2004/0096934 A1 | 5/2004 | Freyssinet |
| 2005/0246780 A1* | 11/2005 | Short et al. ........................ 800/8 |
| 2007/0196449 A1 | 8/2007 | Lei |

OTHER PUBLICATIONS

Wicker-Planquart, C., et al., "Site directed Removal of N-glycosylation Sites in Human Gastric Lipase," *European Journal of Biochemistry*, Jun. 1, 1999, pp. 644-651, vol. 262, No. 3.
International Search Report for related PCT/US2008/084294, Sep. 21, 2010.
Chen, R.,"Enzyme Engineering: Rational Redesign versus Directed Evolution," *Trends Biotechnol. 2001*, vol. 19, No. 1.
Fersht, A.R., et al., "Analysis of Enzyme Structure and Activity by Protein Engineering," *Angew. Chem. Int. Ed. Engl.*, Jul. 1984, pp. 467-473, vol. 23, No. 7.
Gormond, V., et al., "Production and Glycosylation of Plant-made Pharmaceuticals: The Antibodies as a Challenge," *Plant Biotechnology Journal*, 2004, pp. 83-100, vol. 2.
Gormond, V., and L. Faye, "Posttranslational Modification of Therapeutic Proteins in Plants," *Current Opinion in Plant Biology*, 2004, pp. 171-181, vol. 7.
Gormond, V., et al., "Biopharmaceutical Production in Plants: Problems, Solutions and Opportunities," *Trends in Biotechnology*, Nov. 2008, pp. 559-565, vol. 23, No. 11.
Greene, T.W., and L.C. Hannah, "Enhanced Stability of Maize Endosperm ADP-glucose Pyrophosphorylase is Gained Through Mutants That Alter Subunit Interactions," *Proc. Natl. Acad. Sci. USA*, Oct. 1998, pp. 13342-13347, vol. 95.
Kim, T., et al., "Shifting the pH Profile of *Aspergillus niger* PhyA Phytase to Match the Stomach pH Enhances Its Effectiveness as an Animal Feed Additive," *Applied and Environmental Microbiology*, Jun. 2006, yp. 4397-4403, vol. 72, No. 6.
Lei, X.G. and C.H. Stahl, "Biotechnological Development of Effective Phytases for Mineral Nuturtion and Environmental Protection," *Appl Microbiol Biotechnol*, 2001, pp. 474-481, vol. 57 [XP-002356775].
Lim, D., et al., "Crystal Structures of *Escherichia coli* Phytase and Its Complex with Phytate," *Nature Structural Biology*, Feb. 2000, pp. 108-113, vol. 7, No. 2.
Roesler, K.R., and A.G. Rao, "A Single Disulfide Bond Retores Thermodynamic and Proteolytic Stability to an Extensively Mutated Protein," *Protein Science*, 2000, pp. 1642-1650, vol. 9.
Ruoppolo, M., and R.B. Freedman, "Protein-S-S-Glutathione Mixed Disulfides as Models of Unfolded Proteins," *Biochemistry*, 1994, pp. 7654-7662, vol. 33.
Singh, P.K., "Significance of Phytic Acid and Supplemental Phytase in Chicken Nutrition: A Review," *World's Poultry Science Journal*, Dec. 2008, pp. 553-580, vol. 64 [XP009121761].
Smith, M., "In Vitro Mutagenesis," *Annu. Rev. Genet.* 1985, pp. 423-462, vol. 19.
Takagi, H., et al., "Enhanced Thermostability of the Single-Cys Mutant Subtilisin E Under Oxidizing Conditions," *J. Biochem.*, 2000, pp. 585-589, vol. 128.
Vohra, A., and T. Satyanarayana, "Phytases: Microbial Sources, Production, Purification, and Potential Biotechnological Applications," *Critical Reviews in Biotechnology*, 2003, pp. 29-60, vol. 23, No. 1 [XP0080602351].
Volkin, D.B., and A.M. Klibanov, "Thermal Destruction Processes in Porteins Involving Cystine Residues," *The Journal of Biological Chemistry*, Mar. 5, 1987, pp. 2945-2950, vol. 262, No. 7.
Wyss, M., et al., "Biophysical Characterization of Fungal Phytases (myo-Inositol Hexakisphosphate Phosphohydrolases): Molecular Size, Glycosylation Pattern, and Engineering of Proteolytic Resistance," *Applied and Environmental Microbiology*, Feb. 1999, pp. 359-366, vol. 65, No. 2.
International Search Report for related PCT/US2008/084303, Sep. 16, 2009.

\* cited by examiner

*Primary Examiner* — David J Steadman
*Assistant Examiner* — Paul Holland
(74) *Attorney, Agent, or Firm* — Joshua L. Price

(57) ABSTRACT

The invention provides a synthetic phytase polypeptide which encodes an en/ymatically susceptible phytase. Also provided are feed or food products comprising an enzymatically susceptible phytase, and transgenic plants which express the enzymatically susceptible phytase. Further provided are methods for making and using enzymatically susceptible phytases, e.g., a method of using an enzymatically susceptible phytase in feed and food processing.

6 Claims, No Drawings

```
                         SEQUENCE LISTING

<160> NUMBER OF SEQ ID NOS: 165

<210> SEQ ID NO 1
<211> LENGTH: 411
<212> TYPE: PRT
<213> ORGANISM: artificial sequence
<220> FEATURE:
<223> OTHER INFORMATION: engineered protein sequence

<400> SEQUENCE: 1

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270
```

```
Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 2
<211> LENGTH: 411
<212> TYPE: PRT
<213> ORGANISM: artificial sequence
<220> FEATURE:
<223> OTHER INFORMATION: engineered protein sequence

<400> SEQUENCE: 2

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65              70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Arg Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220
```

```
Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
            245                 250                 255

Leu Leu Gln Arg Thr Pro Glu Val Ala Arg Ser Arg Ala Thr Pro Leu
        260                 265                 270

Leu Asp Leu Ile Lys Thr Ala Leu Thr Pro His Pro Gln Lys Gln
    275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
        340                 345                 350

Leu Val Phe Gln Thr Leu Gln Gln Met Arg Asp Lys Thr Pro Leu Ser
    355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
            405                 410

<210> SEQ ID NO 3
<211> LENGTH: 411
<212> TYPE: PRT
<213> ORGANISM: artificial sequence
<220> FEATURE:
<223> OTHER INFORMATION: engineered protein sequence

<400> SEQUENCE: 3

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Arg Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
```

-continued

```
                    180                 185                 190
Gln Ala Leu Pro Ser Glu Leu Lys Val Ser Ala Asp Cys Val Ser Leu
            195                 200                 205

Thr Gly Ala Val Ser Leu Ala Ser Met Leu Thr Glu Ile Phe Leu Leu
        210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Val
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 4
<211> LENGTH: 411
<212> TYPE: PRT
<213> ORGANISM: artificial sequence
<220> FEATURE:
<223> OTHER INFORMATION: engineered protein sequence

<400> SEQUENCE: 4

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140
```

```
Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Ser Leu His Asn Ala Gln Phe Asp
                245                 250                 255

Leu Leu Gln Arg Thr Pro Glu Val Ala Arg Ser Arg Ala Thr Pro Leu
                260                 265                 270

Leu Asp Leu Ile Lys Thr Ala Leu Thr Pro His Pro Pro Gln Lys Gln
            275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410
```

<210> SEQ ID NO 5
<211> LENGTH: 411
<212> TYPE: PRT
<213> ORGANISM: artificial sequence
<220> FEATURE:
<223> OTHER INFORMATION: engineered protein sequence

<400> SEQUENCE: 5

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95
```

```
Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Ala Leu Lys Arg Glu Lys Gln Asp Glu Ser Ala Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 6
<211> LENGTH: 411
<212> TYPE: PRT
<213> ORGANISM: artificial sequence
<220> FEATURE:
<223> OTHER INFORMATION: engineered protein sequence

<400> SEQUENCE: 6

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
```

```
                  50                  55                  60
Gln Arg Leu Val Ala Asp Gly Leu Leu Pro Lys Lys Gly Cys Pro Gln
 65                  70                  75                  80

Ser Gly Gln Val Ala Ile Ile Ala Asp Val Asp Glu Arg Thr Arg Lys
                     85                  90                  95

Thr Gly Glu Ala Phe Ala Ala Gly Leu Ala Pro Asp Cys Ala Ile Thr
                100                 105                 110

Val His Thr Gln Ala Asp Thr Ser Ser Pro Asp Pro Leu Phe Asn Pro
                115                 120                 125

Leu Lys Thr Gly Val Cys Gln Leu Asp Asn Ala Asn Val Thr Asp Ala
                130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
                180                 185                 190

Gln Ala Leu Pro Ser Glu Leu Lys Val Ser Ala Asp Asn Val Ser Leu
                195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
                260                 265                 270

Leu Asp Leu Ile Lys Thr Ala Leu Thr Pro His Pro Pro Gln Lys Gln
                275                 280                 285

Ala Tyr Gly Val Thr Leu Pro Thr Ser Val Leu Phe Ile Ala Gly His
                290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
                355                 360                 365

Leu Asn Thr Pro Pro Gly Glu Val Lys Leu Thr Leu Ala Gly Ala Glu
                370                 375                 380

Glu Arg Asn Ala Gln Gly Met Ala Ser Leu Ala Gly Phe Thr Gln Ile
385                 390                 395                 400

Val Asn Glu Ala Arg Ile Pro Ala Cys Ser Leu
                405                 410

<210> SEQ ID NO 7
<211> LENGTH: 411
<212> TYPE: PRT
<213> ORGANISM: artificial sequence
<220> FEATURE:
<223> OTHER INFORMATION: engineered protein sequence

<400> SEQUENCE: 7

Met Gln Ser Glu Pro Glu Leu Lys Leu Glu Ser Val Val Ile Val Ser
 1               5                  10                  15
```

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
                35                  40                  45

Thr Pro Arg Gly Gly Glu Leu Ile Ala Tyr Leu Gly His Tyr Trp Arg
 50                  55                  60

Gln Arg Leu Val Ala Asp Gly Leu Leu Pro Lys Lys Gly Cys Pro Gln
 65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
                100                 105                 110

Val His Thr Gln Ala Asp Thr Ser Ser Pro Asp Pro Leu Phe Asn Pro
         115                 120                 125

Leu Lys Thr Gly Val Cys Gln Leu Asp Asn Ala Asn Val Thr Asp Ala
130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Ala Leu Lys Arg Glu Lys Gln Asp Glu Ser Ala Ser Leu Thr
            180                 185                 190

Gln Ala Leu Pro Ser Glu Leu Lys Val Ser Ala Asp Asn Val Ser Leu
            195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Ala Glu
        370                 375                 380

Glu Arg Asn Ala Gln Gly Met Ala Ser Leu Ala Gly Phe Thr Gln Ile
385                 390                 395                 400

Val Asn Glu Ala Arg Ile Pro Ala Cys Ser Leu
                405                 410

<210> SEQ ID NO 8
<211> LENGTH: 411
<212> TYPE: PRT

<213> ORGANISM: artificial sequence
<220> FEATURE:
<223> OTHER INFORMATION: engineered protein sequence

<400> SEQUENCE: 8

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Ala Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Ala Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400
```

```
Val Asn Glu Ala Arg Ile Pro Ala Cys Ser Leu
            405                 410

<210> SEQ ID NO 9
<211> LENGTH: 411
<212> TYPE: PRT
<213> ORGANISM: artificial sequence
<220> FEATURE:
<223> OTHER INFORMATION: engineered protein sequence

<400> SEQUENCE: 9

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Ala Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350
```

-continued

```
Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Ala Ser Leu
                405                 410

<210> SEQ ID NO 10
<211> LENGTH: 411
<212> TYPE: PRT
<213> ORGANISM: artificial sequence
<220> FEATURE:
<223> OTHER INFORMATION: engineered protein sequence

<400> SEQUENCE: 10

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Val Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Glu Ala Asn Val Arg Asp Ala
    130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Ala Leu Lys Arg Glu Lys Gln Asp Glu Ser Ala Ser Leu Thr
            180                 185                 190

Gln Ala Leu Pro Ser Glu Leu Lys Val Ser Ala Asp Val Ser Leu
        195                 200                 205

Thr Gly Ala Trp Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Ala Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
```

```
                305                 310                 315                 320
Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 11
<211> LENGTH: 411
<212> TYPE: PRT
<213> ORGANISM: artificial sequence
<220> FEATURE:
<223> OTHER INFORMATION: engineered protein sequence

<400> SEQUENCE: 11

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Val Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
                100                 105                 110

Val His His Gln Ala Asp Thr Ser Ser Pro Asp Pro Leu Phe Asn Pro
            115                 120                 125

Leu Lys Thr Gly Val Cys Gln Leu Asp Glu Ala Asn Val Arg Asp Ala
        130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
                180                 185                 190

Gln Ala Leu Pro Ser Glu Leu Lys Val Ser Ala Asp Val Ser Leu
            195                 200                 205

Thr Gly Ala Trp Ser Leu Ala Ser Met Leu Thr Glu Ile Phe Leu Leu
        210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Ala Ala Thr Pro Leu
                260                 265                 270
```

```
Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Ala Glu
        370                 375                 380

Glu Arg Asn Ala Gln Gly Met Ala Ser Leu Ala Gly Phe Thr Gln Ile
385                 390                 395                 400

Val Asn Glu Ala Arg Ile Pro Ala Cys Ser Leu
                405                 410

<210> SEQ ID NO 12
<211> LENGTH: 411
<212> TYPE: PRT
<213> ORGANISM: artificial sequence
<220> FEATURE:
<223> OTHER INFORMATION: engineered protein sequence

<400> SEQUENCE: 12

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Val Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Glu Ala Asn Val Arg Asp Ala
    130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Ala Leu Lys Arg Glu Lys Gln Asp Glu Ser Ala Ser Leu Thr
            180                 185                 190

Gln Ala Leu Pro Ser Glu Leu Lys Val Ser Ala Asp Asp Val Ser Leu
        195                 200                 205

Thr Gly Ala Trp Ser Leu Ala Ser Met Leu Thr Glu Ile Phe Leu Leu
    210                 215                 220
```

```
Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
            245                 250                 255

Leu Leu Gln Arg Thr Pro Glu Val Ala Arg Ser Ala Ala Thr Pro Leu
        260                 265                 270

Leu Asp Leu Ile Lys Thr Ala Leu Thr Pro His Pro Pro Gln Lys Gln
    275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
            325                 330                 335

Glu Arg Trp Arg Arg Leu Ser Asp Asn Ser Gln Trp Ile Gln Val Ser
        340                 345                 350

Leu Val Phe Gln Thr Leu Gln Gln Met Arg Asp Lys Thr Pro Leu Ser
    355                 360                 365

Leu Asn Thr Pro Pro Gly Glu Val Lys Leu Thr Leu Ala Gly Ala Glu
    370                 375                 380

Glu Arg Asn Ala Gln Gly Met Ala Ser Leu Ala Gly Phe Thr Gln Ile
385                 390                 395                 400

Val Asn Glu Ala Arg Ile Pro Ala Cys Ser Leu
                405                 410

<210> SEQ ID NO 13
<211> LENGTH: 411
<212> TYPE: PRT
<213> ORGANISM: artificial sequence
<220> FEATURE:
<223> OTHER INFORMATION: engineered protein sequence

<400> SEQUENCE: 13

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Val Gly Ala Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Ala Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Glu Ala Asn Val Arg Asp Ala
    130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
```

```
                    180                 185                 190
Gln Ala Leu Pro Ser Glu Leu Lys Val Ser Ala Asp Asp Val Ser Leu
                195                 200                 205

Thr Gly Ala Trp Ser Leu Ala Ser Met Leu Thr Glu Ile Phe Leu Leu
            210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Ala Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 14
<211> LENGTH: 412
<212> TYPE: PRT
<213> ORGANISM: artificial sequence
<220> FEATURE:
<223> OTHER INFORMATION: engineered protein sequence

<400> SEQUENCE: 14

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Val Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Ala Gln Leu Asp Glu Ala Asn Val Arg Asp Ala
    130                 135                 140
```

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
            165                 170                 175

Asn Leu Cys Leu Lys Arg Glu Lys Gln Asp Glu Ser Cys Ala Ser Leu
        180                 185                 190

Thr Gln Ala Leu Pro Ser Glu Leu Lys Val Ser Ala Asp Asp Val Ser
    195                 200                 205

Leu Thr Gly Ala Trp Ser Leu Ala Ser Met Leu Thr Glu Ile Phe Leu
210                 215                 220

Leu Gln Gln Ala Gln Gly Met Pro Glu Pro Gly Trp Gly Arg Ile Thr
225                 230                 235                 240

Asp Ser His Gln Trp Asn Thr Leu Leu Ser Leu His Asn Ala Val Phe
            245                 250                 255

Asp Leu Leu Gln Arg Thr Pro Glu Val Ala Arg Ser Ala Ala Thr Pro
        260                 265                 270

Leu Leu Asp Leu Ile Lys Thr Ala Leu Thr Pro His Pro Pro Gln Lys
    275                 280                 285

Gln Ala Tyr Gly Val Thr Leu Pro Thr Ser Val Leu Phe Ile Ala Gly
290                 295                 300

His Asp Thr Asn Leu Ala Asn Leu Gly Gly Ala Leu Glu Leu Asn Trp
305                 310                 315                 320

Thr Leu Pro Gly Gln Pro Asp Asn Tyr Pro Pro Gly Gly Glu Leu Val
            325                 330                 335

Phe Glu Arg Trp Arg Arg Leu Ser Asp Asn Ser Gln Trp Ile Gln Val
        340                 345                 350

Ser Leu Val Phe Gln Thr Leu Gln Gln Met Arg Asp Lys Thr Pro Leu
    355                 360                 365

Ser Leu Asn Thr Pro Pro Gly Glu Val Lys Leu Thr Leu Ala Gly Cys
370                 375                 380

Glu Glu Arg Asn Ala Gln Gly Met Cys Ser Leu Ala Gly Phe Thr Gln
385                 390                 395                 400

Ile Val Asn Glu Ala Arg Ile Pro Ala Ala Ser Leu
            405                 410

<210> SEQ ID NO 15
<211> LENGTH: 411
<212> TYPE: PRT
<213> ORGANISM: artificial sequence
<220> FEATURE:
<223> OTHER INFORMATION: engineered protein sequence

<400> SEQUENCE: 15

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
            85                  90                  95

```
Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
            115                 120                 125

Leu Lys Thr Gly Val Cys Gln Leu Asp Asn Ala Asn Val Thr Asp Ala
        130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 16
<211> LENGTH: 411
<212> TYPE: PRT
<213> ORGANISM: artificial sequence
<220> FEATURE:
<223> OTHER INFORMATION: engineered protein sequence

<400> SEQUENCE: 16

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
```

```
                 50                  55                  60
Gln Arg Leu Val Ala Asp Gly Leu Leu Pro Lys Cys Gly Cys Pro Gln
 65                  70                  75                  80

Ser Gly Gln Val Ala Ile Ile Ala Asp Val Asp Glu Arg Thr Arg Lys
                 85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Glu Leu Phe Asn Leu
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 17
<211> LENGTH: 411
<212> TYPE: PRT
<213> ORGANISM: artificial sequence
<220> FEATURE:
<223> OTHER INFORMATION: engineered protein sequence

<400> SEQUENCE: 17

Met Gln Ser Glu Pro Glu Leu Lys Leu Glu Ser Val Val Ile Val Ser
 1               5                  10                  15
```

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Tyr Val
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 18
<211> LENGTH: 411
<212> TYPE: PRT

<213> ORGANISM: artificial sequence
<220> FEATURE:
<223> OTHER INFORMATION: engineered protein sequence

<400> SEQUENCE: 18

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Tyr Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400
```

Val Asn Glu Ala Arg Ile Pro Ala Cys Ser Leu
            405                 410

<210> SEQ ID NO 19
<211> LENGTH: 411
<212> TYPE: PRT
<213> ORGANISM: artificial sequence
<220> FEATURE:
<223> OTHER INFORMATION: engineered protein sequence

<400> SEQUENCE: 19

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Tyr Trp Tyr Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Gly Gly Glu Leu Val Phe
                325                 330                 335

Glu Arg Trp Arg Arg Leu Ser Asp Asn Ser Gln Trp Ile Gln Val Ser
            340                 345                 350

```
Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 20
<211> LENGTH: 411
<212> TYPE: PRT
<213> ORGANISM: artificial sequence
<220> FEATURE:
<223> OTHER INFORMATION: engineered protein sequence

<400> SEQUENCE: 20

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Phe Tyr
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
```

```
            305                 310                 315                 320
Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 21
<211> LENGTH: 411
<212> TYPE: PRT
<213> ORGANISM: artificial sequence
<220> FEATURE:
<223> OTHER INFORMATION: engineered protein sequence

<400> SEQUENCE: 21

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
                100                 105                 110

Val His Thr Gln Ala Asp Thr Ser Ser Pro Asp Pro Leu Phe Asn Pro
            115                 120                 125

Leu Lys Thr Gly Val Cys Gln Leu Asp Asn Ala Asn Val Thr Asp Ala
        130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
                180                 185                 190

Gln Ala Leu Pro Ser Glu Leu Lys Val Ser Ala Asp Cys Val Ser Leu
            195                 200                 205

Thr Gly Ala Val Ser Leu Ala Ser Met Leu Thr Glu Ile Phe Leu Leu
        210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
                260                 265                 270
```

```
Leu Asp Leu Ile Lys Thr Ala Leu Thr Pro His Pro Gln Lys Gln
            275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Leu Tyr Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 22
<211> LENGTH: 411
<212> TYPE: PRT
<213> ORGANISM: artificial sequence
<220> FEATURE:
<223> OTHER INFORMATION: engineered protein sequence

<400> SEQUENCE: 22

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Cys Gly Cys Pro Gln
65              70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220
```

```
Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
            245                 250                 255

Leu Leu Gln Arg Thr Pro Glu Val Ala Arg Ser Arg Ala Thr Pro Leu
        260                 265                 270

Leu Asp Leu Ile Lys Thr Ala Leu Thr Pro His Pro Gln Lys Gln
    275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
        340                 345                 350

Leu Val Phe Gln Thr Leu Gln Gln Met Arg Asp Lys Thr Pro Leu Phe
    355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
            405                 410

<210> SEQ ID NO 23
<211> LENGTH: 411
<212> TYPE: PRT
<213> ORGANISM: artificial sequence
<220> FEATURE:
<223> OTHER INFORMATION: engineered protein sequence

<400> SEQUENCE: 23

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Glu Leu Phe Asn Leu
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
```

```
                    180                 185                 190
Gln Ala Leu Pro Ser Glu Leu Lys Val Ser Ala Asp Cys Val Ser Leu
            195                 200                 205

Thr Gly Ala Val Ser Leu Ala Ser Met Leu Thr Glu Ile Phe Leu Leu
        210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Met Arg Asp Lys Thr Pro Leu Ser
        355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 24
<211> LENGTH: 411
<212> TYPE: PRT
<213> ORGANISM: artificial sequence
<220> FEATURE:
<223> OTHER INFORMATION: engineered protein sequence

<400> SEQUENCE: 24

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Tyr Val
        115                 120                 125

Leu Lys Thr Gly Val Cys Gln Leu Asp Asn Ala Asn Val Thr Asp Ala
    130                 135                 140
```

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
            165                 170                 175

Asn Leu Cys Leu Lys Arg Glu Lys Gln Asp Glu Ser Cys Ser Leu Thr
        180                 185                 190

Gln Ala Leu Pro Ser Glu Leu Lys Val Ser Ala Asp Cys Val Ser Leu
    195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 25
<211> LENGTH: 411
<212> TYPE: PRT
<213> ORGANISM: artificial sequence
<220> FEATURE:
<223> OTHER INFORMATION: engineered protein sequence

<400> SEQUENCE: 25

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

```
Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Tyr Gln Ser
                165                 170                 175

Asn Leu Cys Leu Lys Arg Glu Lys Gln Asp Gly Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Tyr Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 26
<211> LENGTH: 411
<212> TYPE: PRT
<213> ORGANISM: artificial sequence
<220> FEATURE:
<223> OTHER INFORMATION: engineered protein sequence

<400> SEQUENCE: 26

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Ile Glu Phe Phe Arg Leu Pro Val Lys Leu Gly Glu Leu
        35                  40                  45

Thr Pro Arg Gly Gly Glu Leu Ile Ala Tyr Leu Gly His Tyr Trp Arg
```

```
                    50                  55                  60
Gln Arg Leu Val Ala Asp Gly Leu Leu Pro Lys Cys Gly Cys Pro Gln
 65                  70                  75                  80

Ser Gly Gln Val Ala Ile Ile Ala Asp Val Asp Glu Arg Thr Arg Lys
                     85                  90                  95

Thr Gly Glu Ala Phe Ala Ala Gly Leu Ala Pro Asp Cys Ala Ile Thr
                100                 105                 110

Val His Thr Gln Ala Asp Thr Ser Ser Pro Asp Pro Leu Phe Asn Pro
                115                 120                 125

Leu Lys Thr Gly Val Cys Gln Leu Asp Asn Ala Asn Val Thr Asp Ala
130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
                180                 185                 190

Gln Ala Leu Pro Ser Glu Leu Lys Val Ser Ala Asp Cys Val Ser Leu
                195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
                260                 265                 270

Leu Asp Leu Ile Lys Thr Ala Leu Thr Pro His Pro Pro Gln Lys Gln
                275                 280                 285

Ala Tyr Gly Val Thr Leu Pro Thr Ser Val Leu Phe Ile Ala Gly His
                290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
                355                 360                 365

Leu Asn Thr Pro Pro Gly Glu Val Lys Leu Thr Leu Ala Gly Cys Glu
                370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 27
<211> LENGTH: 411
<212> TYPE: PRT
<213> ORGANISM: artificial sequence
<220> FEATURE:
<223> OTHER INFORMATION: engineered protein sequence

<400> SEQUENCE: 27

Met Gln Ser Glu Pro Glu Leu Lys Leu Glu Ser Val Val Ile Val Ser
 1                   5                  10                  15
```

Arg His Gly Val Arg Ala Pro Thr Lys Ala Thr Gln Leu Met Gln Asp
            20                  25                  30
Val Thr Pro Asp Ala Trp Pro Thr Trp Pro Val Lys Leu Gly Glu Leu
                35                  40                  45
Thr Pro Arg Gly Gly Glu Leu Ile Ala Tyr Leu Gly His Tyr Trp Arg
 50                  55                  60
Gln Arg Leu Val Ala Asp Gly Leu Leu Pro Lys Cys Gly Cys Pro Gln
 65                  70                  75                  80
Ser Gly Gln Val Ala Ile Ile Ala Asp Val Asp Glu Arg Thr Arg Lys
                85                  90                  95
Thr Gly Glu Ala Phe Ala Ala Gly Leu Ala Pro Asp Cys Ala Ile Thr
                100                 105                 110
Val His Thr Pro Thr Glu Phe Phe Arg Leu Asp Pro Leu Phe Asn Pro
                115                 120                 125
Leu Lys Thr Gly Val Cys Gln Leu Asp Asn Ala Asn Val Thr Asp Ala
130                 135                 140
Ile Leu Glu Arg Ala Gly Gly Ser Ile Ala Asp Phe Thr Gly His Tyr
145                 150                 155                 160
Gln Thr Ala Phe Arg Glu Leu Glu Arg Val Leu Asn Phe Pro Gln Ser
                165                 170                 175
Asn Leu Cys Leu Lys Arg Glu Lys Gln Asp Glu Ser Cys Ser Leu Thr
                180                 185                 190
Gln Ala Leu Pro Ser Glu Leu Lys Val Ser Ala Asp Cys Val Ser Leu
                195                 200                 205
Thr Gly Ala Val Ser Leu Ala Ser Met Leu Thr Glu Ile Phe Leu Leu
210                 215                 220
Gln Gln Ala Gln Gly Met Pro Glu Pro Gly Trp Gly Arg Ile Thr Asp
225                 230                 235                 240
Ser His Gln Trp Asn Thr Leu Leu Ser Leu His Asn Ala Gln Phe Asp
                245                 250                 255
Leu Leu Gln Arg Thr Pro Glu Val Ala Arg Ser Arg Ala Thr Pro Leu
                260                 265                 270
Leu Asp Leu Ile Lys Thr Ala Leu Thr Pro His Pro Pro Gln Lys Gln
                275                 280                 285
Ala Tyr Gly Val Thr Leu Pro Thr Ser Val Leu Phe Ile Ala Gly His
                290                 295                 300
Asp Thr Asn Leu Ala Asn Leu Gly Gly Ala Leu Glu Leu Asn Trp Thr
305                 310                 315                 320
Leu Pro Gly Gln Pro Asp Asn Thr Pro Pro Gly Gly Glu Leu Val Phe
                325                 330                 335
Glu Arg Trp Arg Arg Leu Ser Asp Asn Ser Gln Trp Ile Gln Val Ser
                340                 345                 350
Leu Val Phe Gln Thr Leu Gln Gln Met Arg Asp Lys Thr Pro Leu Ser
                355                 360                 365
Leu Asn Thr Pro Pro Gly Glu Val Lys Leu Thr Leu Ala Gly Cys Glu
370                 375                 380
Glu Arg Asn Ala Gln Gly Met Cys Ser Leu Ala Gly Phe Thr Gln Ile
385                 390                 395                 400
Val Asn Glu Ala Arg Ile Pro Ala Cys Ser Leu
                405                 410

<210> SEQ ID NO 28
<211> LENGTH: 411
<212> TYPE: PRT

-continued

<213> ORGANISM: artificial sequence
<220> FEATURE:
<223> OTHER INFORMATION: engineered protein sequence

<400> SEQUENCE: 28

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Ile Glu Phe Phe Arg Leu
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Leu Ala Gly Cys Glu
    370                 375                 380

Glu Arg Asn Ala Gln Gly Met Cys Ser Leu Ala Gly Phe Thr Gln Ile
385                 390                 395                 400
```

```
Val Asn Glu Ala Arg Ile Pro Ala Cys Ser Leu
                405                 410

<210> SEQ ID NO 29
<211> LENGTH: 417
<212> TYPE: PRT
<213> ORGANISM: artificial sequence
<220> FEATURE:
<223> OTHER INFORMATION: engineered protein sequence

<400> SEQUENCE: 29

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Leu Ile Ala Tyr Leu Gly His Tyr Trp Arg
        50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Ile Glu
                165                 170                 175

Phe Phe Arg Leu Gln Ser Asn Leu Cys Leu Lys Arg Glu Lys Gln Asp
            180                 185                 190

Glu Ser Cys Ser Leu Thr Gln Ala Leu Pro Ser Glu Leu Lys Val Ser
        195                 200                 205

Ala Asp Cys Val Ser Leu Thr Gly Ala Val Ser Leu Ala Ser Met Leu
210                 215                 220

Thr Glu Ile Phe Leu Leu Gln Gln Ala Gln Gly Met Pro Glu Pro Gly
225                 230                 235                 240

Trp Gly Arg Ile Thr Asp Ser His Gln Trp Asn Thr Leu Leu Ser Leu
                245                 250                 255

His Asn Ala Gln Phe Asp Leu Leu Gln Arg Thr Pro Glu Val Ala Arg
            260                 265                 270

Ser Arg Ala Thr Pro Leu Leu Asp Leu Ile Lys Thr Ala Leu Thr Pro
        275                 280                 285

His Pro Pro Gln Lys Gln Ala Tyr Gly Val Thr Leu Pro Thr Ser Val
    290                 295                 300

Leu Phe Ile Ala Gly His Asp Thr Asn Leu Ala Asn Leu Gly Gly Ala
305                 310                 315                 320

Leu Glu Leu Asn Trp Thr Leu Pro Gly Gln Pro Asp Asn Thr Pro Pro
                325                 330                 335

Gly Gly Glu Leu Val Phe Glu Arg Trp Arg Arg Leu Ser Asp Asn Ser
            340                 345                 350
```

```
Gln Trp Ile Gln Val Ser Leu Val Phe Gln Thr Leu Gln Gln Met Arg
            355                 360                 365

Asp Lys Thr Pro Leu Ser Leu Asn Thr Pro Pro Gly Glu Val Lys Leu
    370                 375                 380

Thr Leu Ala Gly Cys Glu Glu Arg Asn Ala Gln Gly Met Cys Ser Leu
385                 390                 395                 400

Ala Gly Phe Thr Gln Ile Val Asn Glu Ala Arg Ile Pro Ala Cys Ser
                405                 410                 415

Leu

<210> SEQ ID NO 30
<211> LENGTH: 411
<212> TYPE: PRT
<213> ORGANISM: artificial sequence
<220> FEATURE:
<223> OTHER INFORMATION: engineered protein sequence

<400> SEQUENCE: 30

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Pro Ile Glu Phe Arg Leu Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300
```

```
Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 31
<211> LENGTH: 411
<212> TYPE: PRT
<213> ORGANISM: artificial sequence
<220> FEATURE:
<223> OTHER INFORMATION: engineered protein sequence

<400> SEQUENCE: 31

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255
```

```
Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Glu Phe Phe
        275                 280                 285

Arg Leu Gly Val Thr Leu Pro Thr Ser Val Leu Phe Ile Ala Gly His
        290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 32
<211> LENGTH: 411
<212> TYPE: PRT
<213> ORGANISM: artificial sequence
<220> FEATURE:
<223> OTHER INFORMATION: engineered protein sequence

<400> SEQUENCE: 32

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
```

```
                    210                 215                 220
Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                    245                 250                 255

Leu Leu Gln Arg Thr Pro Glu Val Ala Arg Ser Arg Ala Thr Pro Leu
                260                 265                 270

Leu Asp Leu Ile Lys Thr Ala Leu Thr Pro His Pro Pro Gln Lys Gln
                275                 280                 285

Ala Tyr Gly Val Thr Leu Pro Thr Ser Val Leu Phe Ile Ala Gly His
                290                 295                 300

Asp Thr Asn Leu Ala Asn Leu Gly Gly Ala Leu Glu Leu Asn Pro Ile
305                 310                 315                 320

Glu Phe Phe Arg Leu Asp Asn Thr Pro Gly Gly Glu Leu Val Phe
                    325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
                355                 360                 365

Leu Asn Thr Pro Pro Gly Glu Val Lys Leu Thr Leu Ala Gly Cys Glu
                370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                    405                 410

<210> SEQ ID NO 33
<211> LENGTH: 411
<212> TYPE: PRT
<213> ORGANISM: artificial sequence
<220> FEATURE:
<223> OTHER INFORMATION: engineered protein sequence

<400> SEQUENCE: 33

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175
```

```
Asn Leu Cys Leu Lys Arg Glu Lys Gln Asp Glu Ser Cys Ser Leu Thr
            180                 185                 190
Gln Ala Leu Pro Ser Glu Leu Lys Val Ser Ala Asp Cys Val Ser Leu
            195                 200                 205
Thr Gly Ala Val Ser Leu Ala Ser Met Leu Thr Glu Ile Phe Leu Leu
210                 215                 220
Gln Gln Ala Gln Gly Met Pro Glu Pro Gly Trp Gly Arg Ile Thr Asp
225                 230                 235                 240
Ser His Gln Trp Asn Thr Leu Leu Ser Leu His Asn Ala Gln Phe Asp
            245                 250                 255
Leu Leu Gln Arg Thr Pro Glu Val Ala Arg Ser Arg Ala Thr Pro Leu
            260                 265                 270
Leu Asp Leu Ile Lys Thr Ala Leu Thr Pro His Pro Pro Gln Lys Gln
            275                 280                 285
Ala Tyr Gly Val Thr Leu Pro Thr Ser Val Leu Phe Ile Ala Gly His
            290                 295                 300
Asp Thr Asn Leu Ala Asn Leu Gly Gly Ala Leu Glu Leu Asn Trp Thr
305                 310                 315                 320
Leu Pro Gly Gln Pro Asp Asn Thr Pro Pro Gly Gly Glu Leu Val Phe
            325                 330                 335
Glu Arg Trp Arg Arg Leu Ser Asp Asn Ser Gln Trp Ile Gln Val Ser
            340                 345                 350
Leu Val Phe Gln Thr Leu Gln Gln Met Arg Asp Lys Pro Pro Glu Phe
            355                 360                 365
Phe Arg Leu Pro Pro Gly Glu Val Lys Leu Thr Leu Ala Gly Cys Glu
            370                 375                 380
Glu Arg Asn Ala Gln Gly Met Cys Ser Leu Ala Gly Phe Thr Gln Ile
385                 390                 395                 400
Val Asn Glu Ala Arg Ile Pro Ala Cys Ser Leu
            405                 410

<210> SEQ ID NO 34
<211> LENGTH: 411
<212> TYPE: PRT
<213> ORGANISM: artificial sequence
<220> FEATURE:
<223> OTHER INFORMATION: evolved protein sequence

<400> SEQUENCE: 34

Ala Gln Ser Glu Pro Glu Leu Lys Leu Glu Ser Val Val Ile Val Ser
1               5                   10                  15
Arg His Gly Val Arg Ala Pro Thr Lys Ala Thr Gln Leu Met Gln Asp
            20                  25                  30
Val Thr Pro Asp Ala Trp Pro Thr Trp Pro Val Lys Leu Gly Glu Leu
        35                  40                  45
Thr Pro Arg Gly Gly Glu Leu Ile Ala Tyr Leu Gly His Tyr Trp Arg
    50                  55                  60
Gln Arg Leu Val Ala Asp Gly Leu Leu Pro Lys Cys Gly Cys Pro Gln
65                  70                  75                  80
Ser Gly Gln Val Ala Ile Ile Ala Asp Val Asp Glu Arg Thr Arg Lys
                85                  90                  95
Thr Gly Glu Ala Phe Ala Ala Gly Leu Ala Pro Asp Cys Ala Ile Thr
            100                 105                 110
Val His Thr Gln Ala Asp Thr Ser Ser Pro Asp Pro Leu Phe Asn Pro
        115                 120                 125
```

| | | | | | | | | | | | |
|---|---|---|---|---|---|---|---|---|---|---|---|
|Leu|Lys|Thr|Gly|Val|Cys|Gln|Leu|Asp|Asn|Ala|Asn|Val|Thr|Asp|Ala|
| |130| | | |135| | | |140| | | | | | |

Leu Lys Thr Gly Val Cys Gln Leu Asp Asn Ala Asn Val Thr Asp Ala
        130             135             140

Ile Leu Glu Arg Ala Gly Gly Ser Ile Ala Asp Phe Thr Gly His Tyr
145             150             155             160

Gln Thr Ala Phe Arg Glu Leu Glu Arg Val Leu Asn Phe Pro Gln Ser
                165             170             175

Asn Leu Cys Leu Lys Arg Glu Lys Gln Asp Glu Ser Cys Ser Leu Thr
            180             185             190

Gln Ala Leu Pro Ser Glu Leu Lys Val Ser Ala Asp Cys Val Ser Leu
        195             200             205

Thr Gly Ala Val Ser Leu Ala Ser Met Leu Thr Glu Ile Phe Leu Leu
210             215             220

Gln Gln Ala Gln Gly Met Pro Glu Pro Gly Trp Gly Arg Ile Thr Asp
225             230             235             240

Ser His Gln Trp Asn Thr Leu Leu Ser Leu His Asn Ala Gln Phe Asp
                245             250             255

Leu Leu Gln Arg Thr Pro Glu Val Ala Arg Ser Arg Ala Thr Pro Leu
            260             265             270

Leu Asp Leu Ile Lys Thr Ala Leu Thr Pro His Pro Pro Gln Lys Gln
        275             280             285

Ala Tyr Gly Val Thr Leu Pro Thr Ser Val Leu Phe Ile Ala Gly His
290             295             300

Asp Thr Asn Leu Ala Asn Leu Gly Gly Ala Leu Glu Leu Asn Trp Thr
305             310             315             320

Leu Pro Gly Gln Pro Asp Asn Thr Pro Pro Gly Gly Glu Leu Val Phe
                325             330             335

Glu Arg Trp Arg Arg Leu Ser Asp Asn Ser Gln Trp Ile Gln Val Ser
            340             345             350

Leu Val Phe Gln Thr Leu Gln Gln Met Arg Asp Lys Thr Pro Leu Ser
        355             360             365

Leu Asn Thr Pro Pro Gly Glu Val Lys Leu Thr Leu Ala Gly Cys Glu
370             375             380

Glu Arg Asn Ala Gln Gly Met Cys Ser Leu Ala Gly Phe Thr Gln Ile
385             390             395             400

Val Asn Glu Ala Arg Ile Pro Ala Cys Ser Leu
                405             410

<210> SEQ ID NO 35
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 35

```
cagagcgaac cggaactgaa actggaaagc gtggtgattg tgagccgtca tggcgttcgt      60
gcgccgacca aagcgaccca gctgatgcag gatgtgaccc cggatgcgtg gccgacctgg     120
ccggtgaaac tggccgaact gaccccgcgt ggcggcgaac tgattgcgta tctgggccat     180
tattggcgtc agcgtctggt ggcggatggc ctgctgccga atgcggttg cccgcagagc      240
ggtcaggtgg cgattattgc ggatgtggat gaacgtaccc gtaaaaccgg cgaagcgttt     300
gcggccggtc tggccccgga ttgcgcgatt accgtgcata cccaggcgga taccagcagc     360
ccggaccccg ctgtttaatcc gctgaaaacc ggcgtgtgcc agctggataa cgcgcaggtg     420
accgatgcga ttctggaacg tgcgggcggt agcattgcgg attttaccgg ccattatcag     480
```

```
accgcgtttc gtgaactgga acgtgtgctg aactttccgc agagcaacct gtgcctgaaa    540
cgtgaaaaac aggatgaaag ctgctctctg acgcaggccc tgccgagcga actgaaagtg    600
agcgcggatt gcgtgagcct gaccggtgcg gttagcctgg ccagcatgct gaccgaaatt    660
tttctgctgc aacaagcgca gggtatgccg gaacccggct ggggccgtat taccgatagc    720
catcagtgga acaccctgct gtctctgcat aacgcgcagt ttgatctgct gcaacgtacc    780
ccggaagttg cgcgtagccg tgcgaccccg ctgctggatc tgattaaaac cgcgctgacc    840
ccgcatccgc cgcagaaaca ggcgtatggc gtgaccctgc cgaccagcgt gctgtttatt    900
gcgggccatg ataccaacct ggccaatctg ggcggtgcgc tggaactgca gtggaccctg    960
ccgggccagc cggataatac tccgccgggt ggtgaactgg tgtttgaacg ttggcgtcgt   1020
ctgagcgata acagccagtg gattcaggtg agcctggtgt ttcagaccct gcagcagatg   1080
cgtgataaaa ccccgctgtc tctgaacacc ccaccgggtg aagtgaaact gaccctggcc   1140
ggctgcgaag aacgtaacgc gcagggcatg tgtagcctgg ccggctttac ccagattgtg   1200
aacgaagcgc gtattccggc gtgtagcctg taa                                1233
```

```
<210> SEQ ID NO 36
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 36
```

```
cagagcgaac cggaactgaa actggaaagc gtggtgattg tgagccgtca tggcgttcgt     60
gcgccgacca aagcgaccca gctgatgcag gatgtgaccc cggatgcgtg gccgacctgg    120
ccggtgaaac tgggcgaact gaccccgcgt ggcggcgaac tgattgcgta tctgggccat    180
tattggcgtc agcgtctggt ggcggatggc ctgctgccga atgcggttg cccgcagagc    240
ggtcaggtgg cgattattgc ggatgtggat gaacgtaccc gtaaaaccgg cgaagcgttt    300
gcggccggtc tggcccccga ttgcgcgatt accgtgcata cccaggcgga taccagcagc    360
ccggacccgc tgtttaatcc gctgaaaacc ggcgtgtgcc agctggataa cgcgaacgtg    420
cgtgatgcga ttctggaacg tgcgggcggt agcattgcgg attttaccgg ccattatcag    480
accgcgtttc gtgaactgga acgtgtgctg aactttccgc agagcaacct gtgcctgaaa    540
cgtgaaaaac aggatgaaag ctgctctctg acgcaggccc tgccgagcga actgaaagtg    600
agcgcggatt gcgtgagcct gaccggtgcg gttagcctgg ccagcatgct gaccgaaatt    660
tttctgctgc aacaagcgca gggtatgccg gaacccggct ggggccgtat taccgatagc    720
catcagtgga acaccctgct gtctctgcat aacgcgcagt ttgatctgct gcaacgtacc    780
ccggaagttg cgcgtagccg tgcgaccccg ctgctggatc tgattaaaac cgcgctgacc    840
ccgcatccgc cgcagaaaca ggcgtatggc gtgaccctgc cgaccagcgt gctgtttatt    900
gcgggccatg ataccaacct ggccaatctg ggcggtgcgc tggaactgca gtggaccctg    960
ccgggccagc cggataatac tccgccgggt ggtgaactgg tgtttgaacg ttggcgtcgt   1020
ctgagcgata acagccagtg gattcaggtg agcctggtgt ttcagaccct gcagcagatg   1080
cgtgataaaa ccccgctgtc tctgaacacc ccaccgggtg aagtgaaact gaccctggcc   1140
ggctgcgaag aacgtaacgc gcagggcatg tgtagcctgg ccggctttac ccagattgtg   1200
aacgaagcgc gtattccggc gtgtagcctg taa                                1233
```

```
<210> SEQ ID NO 37
```

```
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 37
cagagcgaac cggaactgaa actggaaagc gtggtgattg tgagccgtca tggcgttcgt      60
gcgccgacca aagcgaccca gctgatgcag gatgtgaccc cggatgcgtg gccgacctgg     120
ccggtgaaac tgggcgaact gaccccgcgt ggcggcgaac tgattgcgta tctgggccat     180
tattggcgtc agcgtctggt ggcggatggc ctgctgccga aatgcggttg cccgcagagc     240
ggtcaggtgg cgattattgc ggatgtggat gaacgtaccc gtaaaaccgg cgaagcgttt     300
gcggccggtc tggccccgga ttgcgcgatt accgtgcata cccaggcgga taccagcagc     360
ccggacccgc tgtttaatcc gctgaaaacc ggcgtgtgcc agctggataa cgcgaacgtg     420
cgtgatgcga ttctggaacg tgcgggcggt agcattgcgg attttaccgg ccattatcag     480
accgcgtttc gtgaactgga acgtgtgctg aactttccgc agagcaacct gtgcctgaaa     540
cgtgaaaaac aggatgaaag ctgctctctg acgcaggccc tgccgagcga actgaaagtg     600
agcgcggatt gcgtgagcct gaccggtgcg gttagcctgg ccagcatgct gaccgaaatt     660
tttctgctgc aacaagcgca gggtatgccg gaacccgggct ggggccgtat taccgatagc     720
catcagtgga cacccctgct gtctctgcat aacgcgcagt ttgatctgct gcaacgtacc     780
ccggaagttg cgcgtagccg tgcgaccccg ctgctggatc tgattaaaac cgcgctgacc     840
ccgcatccgc cgcagaaaca ggcgtatggc gtgaccctgc cgaccagcgt gctgtttatt     900
gcgggccatg ataccaacct ggccaatctg ggcggtgcgc tggaactgaa ctgggtgctg     960
ccgggccagc cggataatac tccgccgggt ggtgaactgg tgtttgaacg ttggcgtcgt    1020
ctgagcgata acagccagtg gattcaggtg agcctggtgt tcagaccct gcagcagatg    1080
cgtgataaaa ccccgctgtc tctgaacacc ccaccgggtg aagtgaaact gaccctggcc    1140
ggctgcgaag aacgtaacgc gcagggcatg tgtagcctgg ccggctttac ccagattgtg    1200
aacgaagcgc gtattccggc gtgtagcctg taa                                 1233

<210> SEQ ID NO 38
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 38
cagagcgaac cggaactgaa actggaaagc gtggtgattg tgagccgtca tggcgttcgt      60
gcgccgacca aagcgaccca gctgatgcag gatgtgaccc cggatgcgtg gccgacctgg     120
ccggtgaaac tgggcgaact gaccccgcgt ggcggcgaac tgattgcgta tctgggccat     180
tattggcgtc agcgtctggt ggcggatggc ctgctgccga aaaaaggttg cccgcagagc     240
ggtcaggtgg cgattattgc ggatgtggat gaacgtaccc gtaaaaccgg cgaagcgttt     300
gcggccggtc tggccccgga ttgcgcgatt accgtgcata cccaggcgga taccagcagc     360
ccggacccgc tgtttaatcc gctgaaaacc ggcgtgtgcc agctggataa cgcgaacgtg     420
accgatgcga ttctggaacg tgcgggcggt agcattgcgg attttaccgg ccattatcag     480
accgcgtttc gtgaactgga acgtgtgctg aactttccgc agagcaacct gtgcctgaaa     540
cgtgaaaaac aggatgaaag ctgctctctg acgcaggccc tgccgagcga actgaaagtg     600
```

```
agcgcggata acgtgagcct gaccggtgcg gttagcctgg ccagcatgct gaccgaaatt      660
tttctgctgc aacaagcgca gggtatgccg gaaccgggct ggggccgtat taccgatagc      720
catcagtgga acaccctgct gtctctgcat aacgcgcagt ttgatctgct gcaacgtacc      780
ccggaagttg cgcgtagccg tgcgaccccg ctgctggatc tgattaaaac cgcgctgacc      840
ccgcatccgc cgcagaaaca ggcgtatggc gtgaccctgc cgaccagcgt gctgtttatt      900
gcgggccatg ataccaacct ggccaatctg ggcggtgcgc tggaactgaa ctggaccctg      960
ccgggccagc cggataatac tccgccgggt ggtgaactgg tgtttgaacg ttggcgtcgt     1020
ctgagcgata acagccagtg gattcaggtg agcctggtgt ttcagaccct gcagcagatg     1080
cgtgataaaa ccccgctgtc tctgaacacc ccaccgggtg aagtgaaact gaccctggcc     1140
ggctgcgaag aacgtaacgc gcagggcatg tgtagcctgg ccggctttac ccagattgtg     1200
aacgaagcgc gtattccggc gtgtagcctg taa                                   1233
```

<210> SEQ ID NO 39
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 39

```
cagagcgaac cggaactgaa actggaaagc gtggtgattg tgagccgtca tggcgttcgt       60
gcgccgacca aagcgaccca gctgatgcag gatgtgaccc cggatgcgtg gccgacctgg      120
ccggtgaaac tgggcgaact gaccccgcgt ggcggcgaac tgattgcgta tctgggccat      180
tattggcgtc agcgtctggt ggcggatggc ctgctgccga aaaaaggttg cccgcagagc      240
ggtcaggtgg cgattattgc ggatgtggat gaacgtaccc gtaaaaccgg cgaagcgttt      300
gcggccggtc tggccccgga ttgcgcgatt accgtgcata cccaggcgga taccagcagc      360
ccggacccgc tgtttaatcc gctgaaaacc ggcgtgtgcc agctggataa cgcgaacgtg      420
accgatgcga ttctggaacg tgcgggcggt agcattgcgg attttaccgg ccattatcag      480
accgcgtttc gtgaactgga acgtgtgctg aactttccgc agagcaacct ggcgctgaaa      540
cgtgaaaaac aggatgaaag cgcgtctctg acgcaggccc tgccgagcga actgaaagtg      600
agcgcggata acgtgagcct gaccggtgcg gttagcctgg ccagcatgct gaccgaaatt      660
tttctgctgc aacaagcgca gggtatgccg gaaccgggct ggggccgtat taccgatagc      720
catcagtgga acaccctgct gtctctgcat aacgcgcagt ttgatctgct gcaacgtacc      780
ccggaagttg cgcgtagccg tgcgaccccg ctgctggatc tgattaaaac cgcgctgacc      840
ccgcatccgc cgcagaaaca ggcgtatggc gtgaccctgc cgaccagcgt gctgtttatt      900
gcgggccatg ataccaacct ggccaatctg ggcggtgcgc tggaactgaa ctggaccctg      960
ccgggccagc cggataatac tccgccgggt ggtgaactgg tgtttgaacg ttggcgtcgt     1020
ctgagcgata acagccagtg gattcaggtg agcctggtgt ttcagaccct gcagcagatg     1080
cgtgataaaa ccccgctgtc tctgaacacc ccaccgggtg aagtgaaact gaccctggcc     1140
ggctgcgaag aacgtaacgc gcagggcatg tgtagcctgg ccggctttac ccagattgtg     1200
aacgaagcgc gtattccggc gtgtagcctg taa                                   1233
```

<210> SEQ ID NO 40
<211> LENGTH: 1233
<212> TYPE: DNA
<213> ORGANISM: artificial sequence
<220> FEATURE:

<223> OTHER INFORMATION: bacterial codon optimized DNA sequence

<400> SEQUENCE: 40

| | |
|---|---|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aaaaaggttg cccgcagagc | 240 |
| ggtcaggtgg cgattattgc ggatgtggat aacgtacccc gtaaaaccgg cgaagcgttt | 300 |
| gcggccggtc tggccccgga ttgcgcgatt accgtgcata cccaggcgga taccagcagc | 360 |
| ccggacccgc tgtttaatcc gctgaaaacc ggcgtgtgcc agctggataa cgcgaacgtg | 420 |
| accgatgcga ttctggaacg tgcggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggata acgtgagcct gaccggtgcg gttagcctgg ccagcatgct gaccgaaatt | 660 |
| tttctgctgc aacaagcgca gggtatgccg gaacccgggct ggggccgtat taccgatagc | 720 |
| catcagtgga cacccctgct gtctctgcat aacgcgcagt ttgatctgct gcaacgtacc | 780 |
| ccggaagttg cgcgtagccg tgcgacccccg ctgctggatc tgattaaaac cgcgctgacc | 840 |
| ccgcatccgc cgcagaaaca ggcgtatggc gtgaccctgc cgaccagcgt gctgtttatt | 900 |
| gcgggccatg ataccaacct ggccaatctg ggcggtgcgc tggaactgaa ctggacccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagacccct gcagcagatg | 1080 |
| cgtgataaaa ccccgctgtc tctgaacacc ccaccggggtg aagtgaaact gacccctggcc | 1140 |
| ggcgcggaag aacgtaacgc gcagggcatg gcgagcctgg ccggctttac ccagattgtg | 1200 |
| aacgaagcgc gtattccggc gtgtagcctg taa | 1233 |

<210> SEQ ID NO 41
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 41

| | |
|---|---|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aaaaaggttg cccgcagagc | 240 |
| ggtcaggtgg cgattattgc ggatgtggat aacgtacccc gtaaaaccgg cgaagcgttt | 300 |
| gcggccggtc tggccccgga ttgcgcgatt accgtgcata cccaggcgga taccagcagc | 360 |
| ccggacccgc tgtttaatcc gctgaaaacc ggcgtgtgcc agctggataa cgcgaacgtg | 420 |
| accgatgcga ttctggaacg tgcggcggt agcattgcgg attttaccgg ccattatcag | 480 |
| accgcgtttc gtgaactgga acgtgtgctg aactttccgc agagcaacct ggcgctgaaa | 540 |
| cgtgaaaaac aggatgaaag cgcgtctctg acgcaggccc tgccgagcga actgaaagtg | 600 |
| agcgcggata acgtgagcct gaccggtgcg gttagcctgg ccagcatgct gaccgaaatt | 660 |
| tttctgctgc aacaagcgca gggtatgccg gaaccgggct ggggccgtat taccgatagc | 720 |

| | |
|---|---|
| catcagtgga acaccctgct gtctctgcat aacgcgcagt ttgatctgct gcaacgtacc | 780 |
| ccggaagttg cgcgtagccg tgcgaccccg ctgctggatc tgattaaaac cgcgctgacc | 840 |
| ccgcatccgc cgcagaaaca ggcgtatggc gtgaccctgc cgaccagcgt gctgtttatt | 900 |
| gcgggccatg ataccaacct ggccaatctg ggcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggcgcggaag aacgtaacgc gcagggcatg gcgagcctgg ccggctttac ccagattgtg | 1200 |
| aacgaagcgc gtattccggc gtgtagcctg taa | 1233 |

<210> SEQ ID NO 42
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 42

| | |
|---|---|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aaaaaggtgc gccgcagagc | 240 |
| ggtcaggtgg cgattattgc ggatgtggat gaacgtaccc gtaaaaccgg cgaagcgttt | 300 |
| gcggccggtc tggcccccga tgcggcgatt accgtgcata cccaggcgga taccagcagc | 360 |
| ccggacccgc tgtttaatcc gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggata acgtgagcct gaccggtgcg gttagcctgg ccagcatgct gaccgaaatt | 660 |
| tttctgctgc aacaagcgca gggtatgccg gaaccgggct ggggccgtat taccgatagc | 720 |
| catcagtgga acaccctgct gtctctgcat aacgcgcagt ttgatctgct gcaacgtacc | 780 |
| ccggaagttg cgcgtagccg tgcgaccccg ctgctggatc tgattaaaac cgcgctgacc | 840 |
| ccgcatccgc cgcagaaaca ggcgtatggc gtgaccctgc cgaccagcgt gctgtttatt | 900 |
| gcgggccatg ataccaacct ggccaatctg ggcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |
| aacgaagcgc gtattccggc gtgtagcctg taa | 1233 |

<210> SEQ ID NO 43
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 43

```
cagagcgaac cggaactgaa actggaaagc gtggtgattg tgagccgtca tggcgttcgt      60
gcgccgacca aagcgaccca gctgatgcag gatgtgaccc cggatgcgtg gccgacctgg     120
ccggtgaaac tgggcgaact gaccccgcgt ggcggcgaac tgattgcgta tctgggccat     180
tattggcgtc agcgtctggt ggcggatggc ctgctgccga aaaaaggttg cccgcagagc     240
ggtcaggtgg cgattattgc ggatgtggat aacgtaccc gtaaaaccgg cgaagcgttt     300
gcggccggtc tggccccgga ttgcgcgatt accgtgcata cccaggcgga taccagcagc     360
ccggacccgc tgtttaatcc gctgaaaacc ggcgtggcgc agctggataa cgcgaacgtg     420
accgatgcga ttctggaacg tgcgggcggt agcattgcgg attttaccgg ccattatcag     480
accgcgtttc gtgaactgga acgtgtgctg aactttccgc agagcaacct gtgcctgaaa     540
cgtgaaaaac aggatgaaag ctgctctctg acgcaggccc tgccgagcga actgaaagtg     600
agcgcggata acgtgagcct gaccggtgcg gttagcctgg ccagcatgct gaccgaaatt     660
tttctgctgc aacaagcgca gggtatgccg gaacccgggct ggggccgtat taccgatagc     720
catcagtgga acaccctgct gtctctgcat aacgcgcagt ttgatctgct gcaacgtacc     780
ccggaagttg cgcgtagccg tgcgaccccg ctgctggatc tgattaaaac cgcgctgacc     840
ccgcatccgc cgcagaaaca ggcgtatggc gtgaccctgc cgaccagcgt gctgtttatt     900
gcgggccatg ataccaacct ggccaatctg ggcggtgcgc tggaactgaa ctggaccctg     960
ccgggccagc cggataatac tccgccgggt ggtgaactgg tgtttgaacg ttggcgtcgt    1020
ctgagcgata acagccagtg gattcaggtg agcctggtgt ttcagaccct gcagcagatg    1080
cgtgataaaa ccccgctgtc tctgaacacc ccaccgggtg aagtgaaact gacccctggcc    1140 ggctgcgaag aacgtaacgc gcagggcatg tgtagcctgg ccggctttac ccagattgtg    1200
aacgaagcgc gtattccggc ggcgagcctg taa                                 1233

<210> SEQ ID NO 44
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 44
cagagcgaac cggaactgaa actggaaagc gtggtgattg tgagccgtca tggcgttcgt      60
gcgccgacca aagcgaccca gctgatgcag gatgtgaccc cggatgcgtt ctatacctgg     120
ccggtgaaac tgggcgaact gaccccgcgt ggcggcgaac tgattgcgta tctgggccat     180
tattggcgtc agcgtctggt ggcggatggc ctgctgccga aatgcggttg cccgcagagc     240
ggtcaggtgg cgattattgc ggatgtggat aacgtaccc gtaaaaccgg cgaagcgttt     300
gcggccggtc tggccccgga ttgcgcgatt accgtgcata cccaggcgga taccagcagc     360
ccggacccgc tgtttaatcc gctgaaaacc ggcgtgtgcc agctggataa cgcgaacgtg     420
accgatgcga ttctggaacg tgcgggcggt agcattgcgg attttaccgg ccattatcag     480
accgcgtttc gtgaactgga acgtgtgctg aactttccgc agagcaacct gtgcctgaaa     540
cgtgaaaaac aggatgaaag ctgctctctg acgcaggccc tgccgagcga actgaaagtg     600
agcgcggatt gcgtgagcct gaccggtgcg gttagcctgg ccagcatgct gaccgaaatt     660
tttctgctgc aacaagcgca gggtatgccg gaacccgggct ggggccgtat taccgatagc     720
catcagtgga acaccctgct gtctctgcat aacgcgcagt ttgatctgct gcaacgtacc     780
ccggaagttg cgcgtagccg tgcgaccccg ctgctggatc tgattaaaac cgcgctgacc     840
```

| | |
|---|---:|
| ccgcatccgc cgcagaaaca ggcgtatggc gtgaccctgc cgaccagcgt gctgtttatt | 900 |
| gcgggccatg ataccaacct ggccaatctg ggcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |
| aacgaagcgc gtattccggc gtgtagcctg taa | 1233 |

<210> SEQ ID NO 45
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 45

| | |
|---|---:|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aatgcggttg cccgcagagc | 240 |
| ggtcaggtgg cgattattgc ggatgtggat gaacgtaccc gtaaaaccgg cgaagcgttt | 300 |
| gcggccggtc tggcccccga ttgcgcgatt accgtgcata cccaggcgga taccagcagc | 360 |
| ccggacgaac tgtttaatct gctgaaaacc ggcgtgtgcc agctggataa cgcgaacgtg | 420 |
| accgatgcga ttctggaacg tgcggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggatt gcgtgagcct gaccggtgcg gttagcctgg ccagcatgct gaccgaaatt | 660 |
| tttctgctgc aacaagcgca gggtatgccg gaaccgggct ggggccgtat taccgatagc | 720 |
| catcagtgga cacccctgct gtctctgcat aacgcgcagt ttgatctgct gcaacgtacc | 780 |
| ccggaagttg cgcgtagccg tgcgaccccg ctgctggatc tgattaaaac cgcgctgacc | 840 |
| ccgcatccgc cgcagaaaca ggcgtatggc gtgaccctgc cgaccagcgt gctgtttatt | 900 |
| gcgggccatg ataccaacct ggccaatctg ggcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |
| aacgaagcgc gtattccggc gtgtagcctg taa | 1233 |

<210> SEQ ID NO 46
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 46

| | |
|---|---:|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |

```
ccggtgaaac tgggcgaact gaccccgcgt ggcggcgaac tgattgcgta tctgggccat    180
tattggcgtc agcgtctggt ggcggatggc ctgctgccga aatgcggttg cccgcagagc    240
ggtcaggtgg cgattattgc ggatgtggat gaacgtaccc gtaaaaccgg cgaagcgttt    300
gcggccggtc tggcccggga ttgcgcgatt accgtgcata cccaggcgga taccagcagc    360
ccggacccgc tgttttatgt gctgaaaacc ggcgtgtgcc agctggataa cgcgaacgtg    420
accgatgcga ttctggaacg tgcgggcggt agcattgcgg attttaccgg ccattatcag    480
accgcgtttc gtgaactgga acgtgtgctg aactttccgc agagcaacct gtgcctgaaa    540
cgtgaaaaac aggatgaaag ctgctctctg acgcaggccc tgccgagcga actgaaagtg    600
agcgcggatt gcgtgagcct gaccggtgcg gttagcctgg ccagcatgct gaccgaaatt    660
tttctgctgc aacaagcgca gggtatgccg gaacccgggct ggggccgtat taccgatagc    720
catcagtgga cacccctgct gtctctgcat aacgcgcagt ttgatctgct gcaacgtacc    780
ccggaagttg cgcgtagccg tgcgaccccg ctgctggatc tgattaaaac cgcgctgacc    840
ccgcatccgc cgcagaaaca ggcgtatggc gtgaccctgc cgaccagcgt gctgtttatt    900
gcgggccatg ataccaacct ggccaatctg ggcggtgcgc tggaactgaa ctggaccctg    960
ccgggccagc cggataatac tccgccgggt ggtgaactgg tgtttgaacg ttggcgtcgt   1020
ctgagcgata cagccagtg gattcaggtg agcctggtgt tcagaccct gcagcagatg   1080 cgtgataaaa ccccgctgtc tctgaacacc ccaccgggtg aagtgaaact gaccctggcc   1140
ggctgcgaag aacgtaacgc gcagggcatg tgtagcctgg ccggctttac ccagattgtg   1200
aacgaagcgc gtattccggc gtgtagcctg taa                                1233

<210> SEQ ID NO 47
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 47
cagagcgaac cggaactgaa actggaaagc gtggtgattg tgagccgtca tggcgttcgt     60
gcgccgacca aagcgaccca gctgatgcag gatgtgaccc cggatgcgtg gccgacctgg    120
ccggtgaaac tgggcgaact gaccccgcgt ggcggcgaac tgattgcgta tctgggccat    180
tattggcgtc agcgtctggt ggcggatggc ctgctgccga aatgcggttg cccgcagagc    240
ggtcaggtgg cgattattgc ggatgtggat gaacgtaccc gtaaaaccgg cgaagcgttt    300
gcggccggtc tggcccggga ttgcgcgatt accgtgcata cccaggcgga taccagcagc    360
ccggacccgc tgtttaatcc gctgaaaacc ggcgtgtgcc agctggataa cgcgaacgtg    420
accgatgcga ttctggaacg tgcgggcggt agcattgcgg attttaccgg ccattatcag    480
accgcgtttc gtgaactgga acgtgtgctg aactttatc agagcaacct gtgcctgaaa    540
cgtgaaaaac aggatgaaag ctgctctctg acgcaggccc tgccgagcga actgaaagtg    600
agcgcggatt gcgtgagcct gaccggtgcg gttagcctgg ccagcatgct gaccgaaatt    660
tttctgctgc aacaagcgca gggtatgccg gaacccgggct ggggccgtat taccgatagc    720
catcagtgga cacccctgct gtctctgcat aacgcgcagt ttgatctgct gcaacgtacc    780
ccggaagttg cgcgtagccg tgcgaccccg ctgctggatc tgattaaaac cgcgctgacc    840
ccgcatccgc cgcagaaaca ggcgtatggc gtgaccctgc cgaccagcgt gctgtttatt    900
gcgggccatg ataccaacct ggccaatctg ggcggtgcgc tggaactgaa ctggaccctg    960
```

```
ccgggccagc cggataatac tccgccgggt ggtgaactgg tgtttgaacg ttggcgtcgt      1020
ctgagcgata acagccagtg gattcaggtg agcctggtgt ttcagaccct gcagcagatg      1080
cgtgataaaa ccccgctgtc tctgaacacc ccaccgggtg aagtgaaact gaccctggcc      1140
ggctgcgaag aacgtaacgc gcagggcatg tgtagcctgg ccggctttac ccagattgtg      1200
aacgaagcgc gtattccggc gtgtagcctg taa                                    1233
```

<210> SEQ ID NO 48
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 48

```
cagagcgaac cggaactgaa actggaaagc gtggtgattg tgagccgtca tggcgttcgt        60
gcgccgacca aagcgaccca gctgatgcag gatgtgaccc cggatgcgtg gccgacctgg       120
ccggtgaaac tgggcgaact gaccccgcgt ggcggcgaac tgattgcgta tctgggccat       180
tattggcgtc agcgtctggt ggcggatggc ctgctgccga aatgcggttg cccgcagagc       240
ggtcaggtgg cgattattgc ggatgtggat gaacgtaccc gtaaaaccgg cgaagcgttt       300
gcggccggtc tggccccgga ttgcgcgatt accgtgcata cccaggcgga taccagcagc       360
ccggacccgc tgtttaatcc gctgaaaacc ggcgtgtgcc agctggataa cgcgaacgtg       420
accgatgcga ttctggaacg tgcggcggt agcattgcgg attttaccgg ccattatcag       480
accgcgtttc gtgaactgga acgtgtgctg aactttccgc agagcaacct gtgcctgaaa       540
cgtgaaaaac aggatgaaag ctgctctctg acgcaggccc tgccgagcga actgaaagtg       600
agcgcggatt gcgtgagcct gaccggtgcg gttagcctgg ccagcatgct gaccgaaatt       660
tttctgctgc aacaagcgca gggtatgccg gaaccggaat ggtatcgtat taccgatagc       720
catcagtgga cacccctgct gtctctgcat aacgcgcagt ttgatctgct gcaacgtacc       780
ccggaagttg cgcgtagccg tgcgaccccg ctgctggatc tgattaaaac cgcgctgacc       840
ccgcatccgc cgcagaaaca ggcgtatggc gtgaccctgc cgaccagcgt gctgtttatt       900
gcgggccatg ataccaacct ggccaatctg ggcggtgcgc tggaactgaa ctggaccctg       960
ccgggccagc cggataatac tccgccgggt ggtgaactgg tgtttgaacg ttggcgtcgt      1020
ctgagcgata acagccagtg gattcaggtg agcctggtgt ttcagaccct gcagcagatg      1080
cgtgataaaa ccccgctgtc tctgaacacc ccaccgggtg aagtgaaact gaccctggcc      1140
ggctgcgaag aacgtaacgc gcagggcatg tgtagcctgg ccggctttac ccagattgtg      1200
aacgaagcgc gtattccggc gtgtagcctg taa                                    1233
```

<210> SEQ ID NO 49
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 49

```
cagagcgaac cggaactgaa actggaaagc gtggtgattg tgagccgtca tggcgttcgt        60
gcgccgacca aagcgaccca gctgatgcag gatgtgaccc cggatgcgtg gccgacctgg       120
ccggtgaaac tgggcgaact gaccccgcgt ggcggcgaac tgattgcgta tctgggccat       180
tattggcgtc agcgtctggt ggcggatggc ctgctgccga aatgcggttg cccgcagagc       240
```

```
ggtcaggtgg cgattattgc ggatgtggat gaacgtaccc gtaaaaccgg cgaagcgttt      300
gcggccggtc tggccccgga ttgcgcgatt accgtgcata cccaggcgga taccagcagc      360
ccggacccgc tgtttaatcc gctgaaaacc ggcgtgtgcc agctggataa cgcgaacgtg      420
accgatgcga ttctggaacg tgcgggcggt agcattgcgg attttaccgg ccattatcag      480
accgcgtttc gtgaactgga acgtgtgctg aactttccgc agagcaacct gtgcctgaaa      540
cgtgaaaaac aggatgaaag ctgctctctg acgcaggccc tgccgagcga actgaaagtg      600
agcgcggatt gcgtgagcct gaccggtgcg gttagcctgg ccagcatgct gaccgaaatt      660
tttctgctgc aacaagcgca gggtatgccg gaacccgggct ggggccgtat taccgatagc      720
catcagtgga acaccctgct gtctctgcat aacgcgcagt ttgatctgct gcaacgtacc      780
ccggaagttg cgcgtagccg tgcgaccccg ctgctggatc tgattaaaac cgcgctgacc      840
ccgcatccgc cgcagttcta tgcgtatggc gtgaccctgc cgaccagcgt gctgtttatt      900
gcgggccatg ataccaacct ggccaatctg ggcggtgcgc tggaactgaa ctggaccctg      960
ccgggccagc cggataatac tccgccgggt ggtgaactgg tgtttgaacg ttggcgtcgt     1020
ctgagcgata acagccagtg gattcaggtg agcctggtgt ttcagacccct gcagcagatg     1080 cgtgataaaa ccccgctgtc tctgaacacc ccaccgggtg aagtgaaact gaccctggcc     1140
ggctgcgaag aacgtaacgc gcagggcatg tgtagcctgg ccggctttac ccagattgtg     1200
aacgaagcgc gtattccggc gtgtagcctg taa                                   1233
```

<210> SEQ ID NO 50
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 50

```
cagagcgaac cggaactgaa actggaaagc gtggtgattg tgagccgtca tggcgttcgt       60
gcgccgacca aagcgaccca gctgatgcag gatgtgaccc cggatgcgtg gccgacctgg      120
ccggtgaaac tgggcgaact gacccccgcgt ggcggcgaac tgattgcgta tctgggccat      180
tattggcgtc agcgtctggt ggcggatggc ctgctgccga aatgcggttg cccgcagagc      240
ggtcaggtgg cgattattgc ggatgtggat gaacgtaccc gtaaaaccgg cgaagcgttt      300
gcggccggtc tggccccgga ttgcgcgatt accgtgcata cccaggcgga taccagcagc      360
ccggacccgc tgtttaatcc gctgaaaacc ggcgtgtgcc agctggataa cgcgaacgtg      420
accgatgcga ttctggaacg tgcgggcggt agcattgcgg attttaccgg ccattatcag      480
accgcgtttc gtgaactgga acgtgtgctg aactttccgc agagcaacct gtgcctgaaa      540
cgtgaaaaac aggatgaaag ctgctctctg acgcaggccc tgccgagcga actgaaagtg      600
agcgcggatt gcgtgagcct gaccggtgcg gttagcctgg ccagcatgct gaccgaaatt      660
tttctgctgc aacaagcgca gggtatgccg gaacccgggct ggggccgtat taccgatagc      720
catcagtgga acaccctgct gtctctgcat aacgcgcagt ttgatctgct gcaacgtacc      780
ccggaagttg cgcgtagccg tgcgaccccg ctgctggatc tgattaaaac cgcgctgacc      840
ccgcatccgc cgcagaaaca ggcgtatggc gtgaccctgc cgaccagcgt gctgtttatt      900
gcgggccatg ataccaacct ggccaatctg ggcggtgcgc tggaactgct gtataccctg      960
ccgggccagc cggataatac tccgccgggt ggtgaactgg tgtttgaacg ttggcgtcgt     1020
ctgagcgata acagccagtg gattcaggtg agcctggtgt ttcagacccct gcagcagatg     1080
```

-continued

```
cgtgataaaa ccccgctgtc tctgaacacc ccaccgggtg aagtgaaact gaccctggcc      1140
ggctgcgaag aacgtaacgc gcagggcatg tgtagcctgg ccggctttac ccagattgtg      1200
aacgaagcgc gtattccggc gtgtagcctg taa                                   1233
```

<210> SEQ ID NO 51
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 51

```
cagagcgaac cggaactgaa actggaaagc gtggtgattg tgagccgtca tggcgttcgt        60
gcgccgacca aagcgaccca gctgatgcag gatgtgaccc cggatgcgtg gccgacctgg       120
ccggtgaaac tgggcgaact gaccccgcgt ggcggcgaac tgattgcgta tctgggccat       180
tattggcgtc agcgtctggt ggcggatggc ctgctgccga aatgcggttg cccgcagagc       240
ggtcaggtgg cgattattgc ggatgtggat gaacgtaccc gtaaaaccgg cgaagcgttt       300
gcggccggtc tggccccgga ttgcgcgatt accgtgcata cccaggcgga taccagcagc       360
ccggacccgc tgtttaatcc gctgaaaacc ggcgtgtgcc agctggataa cgcgaacgtg       420
accgatgcga ttctggaacg tgcgggcggt agcattgcgg attttaccgg ccattatcag       480
accgcgtttc gtgaactgga acgtgtgctg aactttccgc agagcaacct gtgcctgaaa       540
cgtgaaaaac aggatgaaag ctgctctctg acgcaggccc tgccgagcga actgaaagtg       600
agcgcggatt gcgtgagcct gaccggtgcg gttagcctgg ccagcatgct gaccgaaatt       660
tttctgctgc aacaagcgca gggtatgccg gaacccgggct ggggccgtat taccgatagc       720
catcagtgga acaccctgct gtctctgcat aacgcgcagt tgatctgct gcaacgtacc       780 ccggaagttg cgcgtagccg tgcgaccccg ctgctggatc tgattaaaac cgcgctgacc       840
ccgcatccgc cgcagaaaca ggcgtatggc gtgaccctgc cgaccagcgt gctgtttatt       900
gcgggccatg ataccaacct ggccaatctg ggcggtgcgc tggaactgaa ctggaccctg       960
ccgggccagc cggataatac tccgccgggt ggtgaactgg tgtttgaacg ttggcgtcgt      1020
ctgagcgata acagccagtg gattcaggtg agcctggtgt ttcagaccct gcagcagatg      1080
cgtgataaaa ccccgctgtt tctgaacacc ccaccgggtg aagtgaaact gaccctggcc      1140
ggctgcgaag aacgtaacgc gcagggcatg tgtagcctgg ccggctttac ccagattgtg      1200
aacgaagcgc gtattccggc gtgtagcctg taa                                   1233
```

<210> SEQ ID NO 52
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 52

```
cagagcgaac cggaactgaa actggaaagc gtggtgattg tgagccgtca tggcgttcgt        60
gcgccgacca aagcgaccca gctgatgcag gatgtgaccc cggatgcgtt ctatacctgg       120
ccggtgaaac tgggcgaact gaccccgcgt ggcggcgaac tgattgcgta tctgggccat       180
tattggcgtc agcgtctggt ggcggatggc ctgctgccga aatgcggttg cccgcagagc       240
ggtcaggtgg cgattattgc ggatgtggat gaacgtaccc gtaaaaccgg cgaagcgttt       300
gcggccggtc tggccccgga ttgcgcgatt accgtgcata cccaggcgga taccagcagc       360
```

-continued

| | |
|---|---|
| ccggacgaac tgtttaatct gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggatt gcgtgagcct gaccggtgcg gttagcctgg ccagcatgct gaccgaaatt | 660 |
| tttctgctgc aacaagcgca gggtatgccg gaacccgggct ggggccgtat taccgatagc | 720 |
| catcagtgga cacccctgct gtctctgcat aacgcgcagt ttgatctgct gcaacgtacc | 780 |
| ccggaagttg cgcgtagccg tgcgaccccg ctgctggatc tgattaaaaac cgcgctgacc | 840 |
| ccgcatccgc cgcagaaaca ggcgtatggc gtgaccctgc cgaccagcgt gctgtttatt | 900 |
| gcgggccatg ataccaacct ggccaatctg gcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |
| aacgaagcgc gtattccggc gtgtagcctg taa | 1233 |

<210> SEQ ID NO 53
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 53

| | |
|---|---|
| cagagcgaac cggaactgaa actggaaagc gtggtgattg tgagccgtca tggcgttcgt | 60 |
| gcgccgacca aagcgaccca gctgatgcag gatgtgaccc cggatgcgtt ctatacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aatgcggttg cccgcagagc | 240 |
| ggtcaggtgg cgattattgc ggatgtggat aacgtaccc gtaaaaccgg cgaagcgttt | 300 |
| gcggccggtc tggccccgga ttgcgcgatt accgtgcata cccaggcgga taccagcagc | 360 |
| ccggacccgc tgttttatgt gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggatt gcgtgagcct gaccggtgcg gttagcctgg ccagcatgct gaccgaaatt | 660 |
| tttctgctgc aacaagcgca gggtatgccg gaacccgggct ggggccgtat taccgatagc | 720 |
| catcagtgga cacccctgct gtctctgcat aacgcgcagt ttgatctgct gcaacgtacc | 780 |
| ccggaagttg cgcgtagccg tgcgaccccg ctgctggatc tgattaaaaac cgcgctgacc | 840 |
| ccgcatccgc cgcagaaaca ggcgtatggc gtgaccctgc cgaccagcgt gctgtttatt | 900 |
| gcgggccatg ataccaacct ggccaatctg gcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |

-continued

| aacgaagcgc gtattccggc gtgtagcctg taa | 1233 |

<210> SEQ ID NO 54
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 54

| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aatgcggttg cccgcagagc | 240 |
| ggtcaggtgg cgattattgc ggatgtggat gaacgtaccc gtaaaaccgg cgaagcgttt | 300 |
| gcggccggtc tggccccgga ttgcgcgatt accgtgcata cccaggcgga taccagcagc | 360 |
| ccggacccgc tgtttaatcc gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttatc agagcaacct gtgcctgaaa | 540 |
| cgtgaaaaac aggatgaaag ctgctctctg acgcaggccc tgccgagcga actgaaagtg | 600 |
| agcgcggatt gcgtgagcct gaccggtgcg gttagcctgg ccagcatgct gaccgaaatt | 660 |
| tttctgctgc aacaagcgca gggtatgccg gaacccgggct ggggccgtat taccgatagc | 720 |
| catcagtgga cacccctgct gtctctgcat aacgcgcagt ttgatctgct gcaacgtacc | 780 |
| ccggaagttg cgcgtagccg tgcgaccccg ctgctggatc tgattaaaac cgcgctgacc | 840 |
| ccgcatccgc cgcagaaaca ggcgtatggc gtgaccctgc cgaccagcgt gctgtttatt | 900 |
| gcgggccatg ataccaacct ggccaatctg gcggtgcgc tggaactgct gtataccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |
| aacgaagcgc gtattccggc gtgtagcctg taa | 1233 |

<210> SEQ ID NO 55
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 55

| cagagcgaac cggaactgaa actggaaagc gtggtgattg tgagccgtca tggcgttcgt | 60 |
| gcgccgacca aatttacccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aagtgggttg cccgcagagc | 240 |
| ggtcaggtgg cgattattgc ggatgtggat gaacgtaccc gtaaaaccgg cgaagcgttt | 300 |
| gcggccggtc tggccccgga ttgcgcgatt accgtgcatc atcaggcgga taccagcagc | 360 |
| ccggacccgc tgtttaatcc gctgaaaacc ggcgtgtgcc agctggatga agcgaacgtg | 420 |
| cgtgatgcga ttctgcgtcg tgcgggcggt agcattgcgg attttacccg tcattatcag | 480 |

-continued

```
accgcgtttc gtgaactgga acgtgtgctg aactttccgc agagcaacct ggcgctgaaa      540
cgtgaaaaac aggatgaaag cgcgtctctg acgcaggccc tgccgagcga actgaaagtg      600
agcgcggatg atgtgagcct gaccggtgcg tggagcctgg ccagcatgct gaccgaaatt      660
tttctgctgc aacaagcgca gggtatgccg gaacccgggct ggggccgtat taccgatagc     720
catcagtgga cacccctgct gtctctgcat aacgcggtgt tgatctgct gcaacgtacc       780
ccggaagttg cgcgtagcgc ggcgaccccg ctgctggatc tgattaaaac cgcgctgacc      840
ccgcatccgc cgcagaaaca ggcgtatggc gtgaccctgc cgaccagcgt gctgtttatt      900
gcgggccatg ataccaacct ggccaatctg ggcggtgcgc tggaactgaa ctggaccctg      960
ccgggccagc cggacaacta cccgccgggt ggtgaactgg tgtttgaacg ttggcgtcgt     1020
ctgagcgata acagccagtg gattcaggtg agcctggtgt ttcagacccct gcagcagatg    1080
cgtgataaaa ccccgctgtc tctgaacacc ccaccgggtg aagtgaaact gaccctggcc     1140
ggctgcgaag aacgtaacgc gcagggcatg tgtagcctgg ccggctttac ccagattgtg     1200
aacgaagcgc gtattccggc gtgtagcctg taa                                  1233
```

<210> SEQ ID NO 56
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 56

```
cagagcgaac cggaactgaa actggaaagc gtggtgattg tgagccgtca tggcgttcgt       60
gcgccgacca aatttaccca gctgatgcag gatgtgaccc cggatgcgtg gccgacctgg      120
ccggtgaaac tgggcgaact gaccccgcgt ggcggcgaac tgattgcgta tctgggccat      180
tattggcgtc agcgtctggt ggcggatggc ctgctgccga agtgggttg cccgcagagc      240
ggtcaggtgg cgattattgc ggatgtggat gaacgtaccc gtaaaaccgg cgaagcgttt      300
gcggccggtc tggccccgga ttgcgcgatt accgtgcatc atcaggcgga taccagcagc      360
ccggaccccg tgtttaatcc gctgaaaacc ggcgtgtgcc agctggatga agcgaacgtg      420
cgtgatgcga ttctgcgtcg tgcgggcggt agcattgcgg attttacccg tcattatcag      480
accgcgtttc gtgaactgga acgtgtgctg aactttccgc agagcaacct gtgcctgaaa      540
cgtgaaaaac aggatgaaag ctgctctctg acgcaggccc tgccgagcga actgaaagtg      600
agcgcggatg atgtgagcct gaccggtgcg tggagcctgg ccagcatgct gaccgaaatt      660
tttctgctgc aacaagcgca gggtatgccg gaacccggct ggggccgtat taccgatagc      720
catcagtgga cacccctgct gtctctgcat aacgcggtgt tgatctgct gcaacgtacc       780
ccggaagttg cgcgtagcgc ggcgaccccg ctgctggatc tgattaaaac cgcgctgacc      840
ccgcatccgc cgcagaaaca ggcgtatggc gtgaccctgc cgaccagcgt gctgtttatt      900
gcgggccatg ataccaacct ggccaatctg ggcggtgcgc tggaactgaa ctggaccctg      960
ccgggccagc cggacaacta cccgccgggt ggtgaactgg tgtttgaacg ttggcgtcgt     1020
ctgagcgata acagccagtg gattcaggtg agcctggtgt ttcagacccct gcagcagatg    1080
cgtgataaaa ccccgctgtc tctgaacacc ccaccgggtg aagtgaaact gaccctggcc     1140
ggcgcggaag aacgtaacgc gcagggcatg gcgagcctgg ccggctttac ccagattgtg     1200
aacgaagcgc gtattccggc gtgtagcctg taa                                  1233
```

<210> SEQ ID NO 57

```
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 57
cagagcgaac cggaactgaa actggaaagc gtggtgattg tgagccgtca tggcgttcgt      60
gcgccgacca aatttaccca gctgatgcag gatgtgaccc cggatgcgtg gccgacctgg     120
ccggtgaaac tgggcgaact gaccccgcgt ggcggcgaac tgattgcgta tctgggccat     180
tattggcgtc agcgtctggt ggcggatggc ctgctgccga aagtgggttg cccgcagagc     240
ggtcaggtgg cgattattgc ggatgtggat gaacgtaccc gtaaaaccgg cgaagcgttt     300
gcggccggtc tggccccgga ttgcgcgatt accgtgcatc atcaggcgga taccagcagc     360
ccggacccgc tgtttaatcc gctgaaaacc ggcgtgtgcc agctggatga agcgaacgtg     420
cgtgatgcga ttctgcgtcg tgcgggcggt agcattgcgg attttacccg tcattatcag     480
accgcgtttc gtgaactgga acgtgtgctg aactttccgc agagcaacct ggcgctgaaa     540
cgtgaaaaac aggatgaaag cgcgtctctg acgcaggccc tgccgagcga actgaaagtg     600
agcgcggatg atgtgagcct gaccggtgcg tggagcctgg ccagcatgct gaccgaaatt     660
tttctgctgc aacaagcgca gggtatgccg gaacccgggct ggggccgtat taccgatagc     720
catcagtgga acaccctgct gtctctgcat aacgcggtgt ttgatctgct gcaacgtacc     780
ccggaagttg cgcgtagcgc ggcgaccccg ctgctggatc tgattaaaac cgcgctgacc     840
ccgcatccgc cgcagaaaca ggcgtatggc gtgaccctgc cgaccagcgt gctgtttatt     900
gcgggccatg ataccaacct ggccaatctg gcggtgcgc tggaactgaa ctggaccctg      960
ccgggccagc cggacaacta cccgccgggt ggtgaactgg tgtttgaacg ttggcgtcgt    1020
ctgagcgata acagccagtg gattcaggtg agcctggtgt ttcagaccct gcagcagatg    1080
cgtgataaaa ccccgctgtc tctgaacacc ccaccgggtg aagtgaaact gaccctggcc    1140
ggcgcggaag aacgtaacgc gcagggcatg gcgagcctgg ccggctttac ccagattgtg    1200
aacgaagcgc gtattccggc gtgtagcctg taa                                 1233

<210> SEQ ID NO 58
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 58
cagagcgaac cggaactgaa actggaaagc gtggtgattg tgagccgtca tggcgttcgt      60
gcgccgacca aatttaccca gctgatgcag gatgtgaccc cggatgcgtg gccgacctgg     120
ccggtgaaac tgggcgaact gaccccgcgt ggcggcgaac tgattgcgta tctgggccat     180
tattggcgtc agcgtctggt ggcggatggc ctgctgccga aagtgggtgc cgcgcagagc     240
ggtcaggtgg cgattattgc ggatgtggat gaacgtaccc gtaaaaccgg cgaagcgttt     300
gcggccggtc tggccccgga ttgcggcgatt accgtgcatc atcaggcgga taccagcagc    360
ccggacccgc tgtttaatcc gctgaaaacc ggcgtgtgcc agctggatga agcgaacgtg     420
cgtgatgcga ttctgcgtcg tgcgggcggt agcattgcgg attttacccg tcattatcag     480
accgcgtttc gtgaactgga acgtgtgctg aactttccgc agagcaacct gccgctgaaa     540
cgtgaaaaac aggatgaaag cgctctctg acgcaggccc tgccgagcga actgaaagtg      600
```

```
agcgcggatg atgtgagcct gaccggtgcg tggagcctgg ccagcatgct gaccgaaatt    660
tttctgctgc aacaagcgca gggtatgccg aaccgggct ggggccgtat taccgatagc    720
catcagtgga acaccctgct gtctctgcat aacgcggtgt tgatctgct gcaacgtacc    780 ccggaagttg cgcgtagcgc ggcgaccccg ctgctggatc tgattaaaac cgcgctgacc    840
ccgcatccgc cgcagaaaca ggcgtatggc gtgaccctgc cgaccagcgt gctgtttatt    900
gcgggccatg ataccaacct ggccaatctg ggcggtgcgc tggaactgaa ctggaccctg    960
ccgggccagc cggacaacta cccgccgggt ggtgaactgg tgtttgaacg ttggcgtcgt   1020
ctgagcgata acagccagtg gattcaggtg agcctggtgt ttcagaccct gcagcagatg   1080
cgtgataaaa ccccgctgtc tctgaacacc ccaccgggtg aagtgaaact gaccctggcc   1140
ggctgcgaag aacgtaacgc gcagggcatg tgtagcctgg ccggctttac ccagattgtg   1200
aacgaagcgc gtattccggc gtgtagcctg taa                                 1233

<210> SEQ ID NO 59
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 59
cagagcgaac cggaactgaa actggaaagc gtggtgattg tgagccgtca tggcgttcgt     60
gcgccgacca aatttaccca gctgatgcag gatgtgaccc cggatgcgtg gccgacctgg    120
ccggtgaaac tgggcgaact gaccccgcgt ggcggcgaac tgattgcgta tctgggccat    180
tattggcgtc agcgtctggt ggcggatggc ctgctgccga agtgggttg cccgcagagc    240 ggtcaggtgg cgattattgc ggatgtggat gaacgtaccc gtaaaaccgg cgaagcgttt    300
gcggccggtc tggcccccga ttgcgcgatt accgtgcatc atcaggcgga taccagcagc    360
ccggacccgc tgtttaatcc gctgaaaacc ggcgtggcgc agctggatga agcgaacgtg    420
cgtgatgcga ttctgcgtcg tgcgggcggt agcattgcgg attttacccg tcattatcag    480
accgcgtttc gtgaactgga acgtgtgctg aactttccgc agagcaacct gtgcctgaaa    540
cgtgaaaaac aggatgaaag ctgctctctg acgcaggccc tgccgagcga actgaaagtg    600
agcgcggatg atgtgagcct gaccggtgcg tggagcctgg ccagcatgct gaccgaaatt    660
tttctgctgc aacaagcgca gggtatgccg aaccgggct ggggccgtat taccgatagc    720
catcagtgga acaccctgct gtctctgcat aacgcggtgt tgatctgct gcaacgtacc    780 ccggaagttg cgcgtagcgc ggcgaccccg ctgctggatc tgattaaaac cgcgctgacc    840
ccgcatccgc cgcagaaaca ggcgtatggc gtgaccctgc cgaccagcgt gctgtttatt    900
gcgggccatg ataccaacct ggccaatctg ggcggtgcgc tggaactgaa ctggaccctg    960
ccgggccagc cggacaacta cccgccgggt ggtgaactgg tgtttgaacg ttggcgtcgt   1020
ctgagcgata acagccagtg gattcaggtg agcctggtgt ttcagaccct gcagcagatg   1080
cgtgataaaa ccccgctgtc tctgaacacc ccaccgggtg aagtgaaact gaccctggcc   1140
ggctgcgaag aacgtaacgc gcagggcatg tgtagcctgg ccggctttac ccagattgtg   1200
aacgaagcgc gtattccggc ggcgagcctg taa                                 1233

<210> SEQ ID NO 60
<211> LENGTH: 1233
<212> TYPE: DNA
<213> ORGANISM: artificial sequence
<220> FEATURE:
```

<223> OTHER INFORMATION: bacterial codon optimized DNA sequence

<400> SEQUENCE: 60

| | |
|---|---|
| cagagcgaac cggaactgaa actggaaagc gtggtgattg tgagccgtca tggcgttcgt | 60 |
| gcgccgacca aagcgaccca gctgatgcag gatgtgaccc cgattgaatt ctttcgtctg | 120 |
| ccggtgaaac tgggcgaact gaccccgcgt ggcggcgaac tgattgcgta tctgggccat | 180 |
| tattggcgtc agcgtctggt ggcggatggc ctgctgccga aatgcggttg cccgcagagc | 240 |
| ggtcaggtgg cgattattgc ggatgtggat gaacgtaccc gtaaaaccgg cgaagcgttt | 300 |
| gcggccggtc tggccccgga ttgcgcgatt accgtgcata cccaggcgga taccagcagc | 360 |
| ccggacccgc tgtttaatcc gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggatt gcgtgagcct gaccggtgcg gttagcctgg ccagcatgct gaccgaaatt | 660 |
| tttctgctgc aacaagcgca gggtatgccg gaacccgggct ggggccgtat taccgatagc | 720 |
| catcagtgga cacccctgct gtctctgcat aacgcgcagt ttgatctgct gcaacgtacc | 780 |
| ccggaagttg cgcgtagccg tgcgaccccg ctgctggatc tgattaaaac cgcgctgacc | 840 |
| ccgcatccgc cgcagaaaca ggcgtatggc gtgaccctgc cgaccagcgt gctgtttatt | 900 |
| gcgggccatg ataccaacct ggccaatctg ggcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |
| aacgaagcgc gtattccggc gtgtagcctg taa | 1233 |

<210> SEQ ID NO 61
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 61

| | |
|---|---|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aatgcggttg cccgcagagc | 240 |
| ggtcaggtgg cgattattgc ggatgtggat gaacgtaccc gtaaaaccgg cgaagcgttt | 300 |
| gcggccggtc tggccccgga ttgcgcgatt accgtgcata ccccgaccga attctttcgt | 360 |
| ctggacccgc tgtttaatcc gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggatt gcgtgagcct gaccggtgcg gttagcctgg ccagcatgct gaccgaaatt | 660 |
| tttctgctgc aacaagcgca gggtatgccg gaaccgggct ggggccgtat taccgatagc | 720 |

```
catcagtgga acaccctgct gtctctgcat aacgcgcagt ttgatctgct gcaacgtacc    780
ccggaagttg cgcgtagccg tgcgaccccg ctgctggatc tgattaaaac cgcgctgacc    840
ccgcatccgc cgcagaaaca ggcgtatggc gtgaccctgc cgaccagcgt gctgtttatt    900
gcgggccatg ataccaacct ggccaatctg ggcggtgcgc tggaactgaa ctggaccctg    960
ccgggccagc cggataatac tccgccgggt ggtgaactgg tgtttgaacg ttggcgtcgt   1020
ctgagcgata acagccagtg gattcaggtg agcctggtgt ttcagaccct gcagcagatg   1080
cgtgataaaa ccccgctgtc tctgaacacc ccaccgggtg aagtgaaact gaccctggcc   1140
ggctgcgaag aacgtaacgc gcagggcatg tgtagcctgg ccggctttac ccagattgtg   1200
aacgaagcgc gtattccggc gtgtagcctg taa                                1233
```

<210> SEQ ID NO 62
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 62

```
cagagcgaac cggaactgaa actggaaagc gtggtgattg tgagccgtca tggcgttcgt     60
gcgccgacca aagcgaccca gctgatgcag gatgtgaccc cggatgcgtg gccgacctgg    120
ccggtgaaac tgggcgaact gaccccgcgt ggcggcgaac tgattgcgta tctgggccat    180
tattggcgtc agcgtctggt ggcggatggc ctgctgccga atgcggttg cccgcagagc    240 ggtcaggtgg cgattattgc ggatgtggat gaacgtaccc gtaaaaccgg cgaagcgttt    300
gcggccggtc tggcccccga ttgcgcgatt accgtgcata cccaggcgga taccagcagc    360
ccgattgaat tctttcgtct gctgaaaacc ggcgtgtgcc agctggataa cgcgaacgtg    420
accgatgcga ttctggaacg tgcgggcggt agcattgcgg attttaccgg ccattatcag    480
accgcgtttc gtgaactgga acgtgtgctg aactttccgc agagcaacct gtgcctgaaa    540
cgtgaaaaac aggatgaaag ctgctctctg acgcaggccc tgccgagcga actgaaagtg    600
agcgcggatt gcgtgagcct gaccggtgcg gttagcctgg ccagcatgct gaccgaaatt    660
tttctgctgc aacaagcgca gggtatgccg gaaccgggct ggggccgtat taccgatagc    720
catcagtgga acaccctgct gtctctgcat aacgcgcagt ttgatctgct gcaacgtacc    780
ccggaagttg cgcgtagccg tgcgaccccg ctgctggatc tgattaaaac cgcgctgacc    840
ccgcatccgc cgcagaaaca ggcgtatggc gtgaccctgc cgaccagcgt gctgtttatt    900
gcgggccatg ataccaacct ggccaatctg ggcggtgcgc tggaactgaa ctggaccctg    960
ccgggccagc cggataatac tccgccgggt ggtgaactgg tgtttgaacg ttggcgtcgt   1020
ctgagcgata acagccagtg gattcaggtg agcctggtgt ttcagaccct gcagcagatg   1080
cgtgataaaa ccccgctgtc tctgaacacc ccaccgggtg aagtgaaact gaccctggcc   1140
ggctgcgaag aacgtaacgc gcagggcatg tgtagcctgg ccggctttac ccagattgtg   1200
aacgaagcgc gtattccggc gtgtagcctg taa                                1233
```

<210> SEQ ID NO 63
<211> LENGTH: 1251
<212> TYPE: DNA
<213> ORGANISM: artificial sequence
<220> FEATURE:
<223> OTHER INFORMATION: bacterial codon optimized DNA sequence

<400> SEQUENCE: 63

-continued

| | |
|---|---|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aatgcggttg cccgcagagc | 240 |
| ggtcaggtgg cgattattgc ggatgtggat aacgtacccg gtaaaaccgg cgaagcgttt | 300 |
| gcggccggtc tggccccgga ttgcgcgatt accgtgcata cccaggcgga taccagcagc | 360 |
| ccggacccgc tgtttaatcc gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttccga ttgaattctt tcgtctgcag | 540 |
| agcaacctgt gcctgaaacg tgaaaaacag gatgaaagct gctctctgac gcaggccctg | 600 |
| ccgagcgaac tgaaagtgag cgcggattgc gtgagcctga ccggtgcggt tagcctggcc | 660 |
| agcatgctga ccgaaatttt tctgctgcaa caagcgcagg gtatgccgga accgggctgg | 720 |
| ggccgtatta ccgatagcca tcagtggaac accctgctgt ctctgcataa cgcgcagttt | 780 |
| gatctgctgc aacgtacccc ggaagttgcg cgtagccgtg cgaccccgct gctggatctg | 840 |
| attaaaaccg cgctgacccc gcatccgccg cagaaacagg cgtatggcgt gaccctgccg | 900 |
| accagcgtgc tgtttattgc gggccatgat accaacctgg ccaatctggg cggtgcgctg | 960 |
| gaactgaact ggaccctgcc gggccagccg gataatactc cgccgggtgg tgaactggtg | 1020 |
| tttgaacgtt ggcgtcgtct gagcgataac agccagtgga ttcaggtgag cctggtgttt | 1080 |
| cagaccctgc agcagatgcg tgataaaacc ccgctgtctc tgaacacccc accgggtgaa | 1140 |
| gtgaaactga ccctggccgg ctgcgaagaa cgtaacgcgc agggcatgtg tagcctggcc | 1200 |
| ggctttaccc agattgtgaa cgaagcgcgt attccggcgt gtagcctgta a | 1251 |

<210> SEQ ID NO 64
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 64

| | |
|---|---|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aatgcggttg cccgcagagc | 240 |
| ggtcaggtgg cgattattgc ggatgtggat aacgtacccg gtaaaaccgg cgaagcgttt | 300 |
| gcggccggtc tggccccgga ttgcgcgatt accgtgcata cccaggcgga taccagcagc | 360 |
| ccggacccgc tgtttaatcc gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggatt gcgtgagcct gaccggtgcg gttagcctgg ccagcatgct gaccgaaatt | 660 |
| tttctgctgc aacaagcgca gggtatgccg ccgattgaat ctttcgtct gaccgatagc | 720 |
| catcagtgga caccctgct gtctctgcat aacgcgcagt tgatctgct gcaacgtacc | 780 |
| ccggaagttg cgcgtagccg tgcgaccccg ctgctggatc tgattaaaac cgcgctgacc | 840 |

| | |
|---|---:|
| ccgcatccgc cgcagaaaca ggcgtatggc gtgaccctgc cgaccagcgt gctgtttatt | 900 |
| gcgggccatg ataccaacct ggccaatctg ggcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |
| aacgaagcgc gtattccggc gtgtagcctg taa | 1233 |

<210> SEQ ID NO 65
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 65

| | |
|---|---:|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |
| ccggtgaaac tgggcgaact gaccccgcgt ggcggcgaac tgattgcgta tctgggccat | 180 |
| tattggcgtc agcgtctggt ggcggatggc ctgctgccga aatgcggttg cccgcagagc | 240 |
| ggtcaggtgg cgattattgc ggatgtggat gaacgtaccc gtaaaaccgg cgaagcgttt | 300 |
| gcggccggtc tggccccgga ttgcgcgatt accgtgcata cccaggcgga taccagcagc | 360 |
| ccggacccgc tgtttaatcc gctgaaaacc ggcgtgtgcc agctggataa cgcgaacgtg | 420 |
| accgatgcga ttctggaacg tgcgggcggt agcattgcgg attttaccgg ccattatcag | 480 |
| accgcgtttc gtgaactgga acgtgtgctg aactttccgc agagcaacct gtgcctgaaa | 540 |
| cgtgaaaaac aggatgaaag ctgctctctg acgcaggccc tgccgagcga actgaaagtg | 600 |
| agcgcggatt gcgtgagcct gaccggtgcg gttagcctgg ccagcatgct gaccgaaatt | 660 |
| tttctgctgc aacaagcgca gggtatgccg aaccgggct ggggccgtat taccgatagc | 720 |
| catcagtgga cacccctgct gtctctgcat aacgcgcagt tgatctgct gcaacgtacc | 780 |
| ccggaagttg cgcgtagccg tgcgaccccg ctgctggatc tgattaaaac cgcgctgacc | 840 |
| ccgcatccgc cggaattctt tcgtctgggc gtgaccctgc cgaccagcgt gctgtttatt | 900 |
| gcgggccatg ataccaacct ggccaatctg ggcggtgcgc tggaactgaa ctggaccctg | 960 |
| ccgggccagc cggataatac tccgccgggt ggtgaactgg tgtttgaacg ttggcgtcgt | 1020 |
| ctgagcgata acagccagtg gattcaggtg agcctggtgt ttcagaccct gcagcagatg | 1080 |
| cgtgataaaa ccccgctgtc tctgaacacc ccaccgggtg aagtgaaact gaccctggcc | 1140 |
| ggctgcgaag aacgtaacgc gcagggcatg tgtagcctgg ccggctttac ccagattgtg | 1200 |
| aacgaagcgc gtattccggc gtgtagcctg taa | 1233 |

<210> SEQ ID NO 66
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 66

| | |
|---|---:|
| cagagcgaac cggaactgaa actggaaagc gtggtgattg tgagccgtca tggcgttcgt | 60 |
| gcgccgacca aagcgaccca gctgatgcag gatgtgaccc cggatgcgtg gccgacctgg | 120 |

```
ccggtgaaac tgggcgaact gaccccgcgt ggcggcgaac tgattgcgta tctgggccat      180
tattggcgtc agcgtctggt ggcggatggc ctgctgccga aatgcggttg cccgcagagc      240
ggtcaggtgg cgattattgc ggatgtggat gaacgtaccc gtaaaaccgg cgaagcgttt      300
gcggccggtc tggcccccgga ttgcgcgatt accgtgcata cccaggcgga taccagcagc      360
ccggacccgc tgtttaatcc gctgaaaacc ggcgtgtgcc agctggataa cgcgaacgtg      420
accgatgcga ttctggaacg tgcgggcggt agcattgcgg attttaccgg ccattatcag      480
accgcgtttc gtgaactgga acgtgtgctg aactttccgc agagcaacct gtgcctgaaa      540
cgtgaaaaac aggatgaaag ctgctctctg acgcaggccc tgccgagcga actgaaagtg      600
agcgcggatt gcgtgagcct gaccggtgcg gttagcctgg ccagcatgct gaccgaaatt      660
tttctgctgc aacaagcgca gggtatgccg gaacccgggct ggggccgtat taccgatagc      720
catcagtgga cacccctgct gtctctgcat aacgcgcagt ttgatctgct gcaacgtacc      780
ccggaagttg cgcgtagccg tgcgaccccg ctgctggatc tgattaaaac cgcgctgacc      840
ccgcatccgc cgcagaaaca ggcgtatggc gtgaccctgc cgaccagcgt gctgtttatt      900
gcgggccatg ataccaacct ggccaatctg ggcggtgcgc tggaactgaa cccgattgaa      960
ttctttcgtc tggataatac tccgccgggt ggtgaactgg tgtttgaacg ttggcgtcgt     1020
ctgagcgata cagccagtg gattcaggtg agcctggtgt ttcagacccct gcagcagatg     1080 cgtgataaaa ccccgctgtc tctgaacacc ccaccgggtg aagtgaaact gacccctggcc     1140 ggctgcgaag aacgtaacgc gcagggcatg tgtagcctgg ccggctttac ccagattgtg     1200
aacgaagcgc gtattccggc gtgtagcctg taa                                  1233

<210> SEQ ID NO 67
<211> LENGTH: 1233
<212> TYPE: DNA
<213> ORGANISM: artificial sequence
<220> FEATURE:
<223> OTHER INFORMATION: bacterial codon optimized DNA sequence

<400> SEQUENCE: 67
cagagcgaac cggaactgaa actggaaagc gtggtgattg tgagccgtca tggcgttcgt       60
gcgccgacca aagcgaccca gctgatgcag gatgtgaccc cggatgcgtg gccgacctgg      120
ccggtgaaac tgggcgaact gaccccgcgt ggcggcgaac tgattgcgta tctgggccat      180
tattggcgtc agcgtctggt ggcggatggc ctgctgccga aatgcggttg cccgcagagc      240
ggtcaggtgg cgattattgc ggatgtggat gaacgtaccc gtaaaaccgg cgaagcgttt      300
gcggccggtc tggcccccgga ttgcgcgatt accgtgcata cccaggcgga taccagcagc      360
ccggacccgc tgtttaatcc gctgaaaacc ggcgtgtgcc agctggataa cgcgaacgtg      420
accgatgcga ttctggaacg tgcgggcggt agcattgcgg attttaccgg ccattatcag      480
accgcgtttc gtgaactgga acgtgtgctg aactttccgc agagcaacct gtgcctgaaa      540
cgtgaaaaac aggatgaaag ctgctctctg acgcaggccc tgccgagcga actgaaagtg      600
agcgcggatt gcgtgagcct gaccggtgcg gttagcctgg ccagcatgct gaccgaaatt      660
tttctgctgc aacaagcgca gggtatgccg gaacccgggct ggggccgtat taccgatagc      720
catcagtgga cacccctgct gtctctgcat aacgcgcagt ttgatctgct gcaacgtacc      780
ccggaagttg cgcgtagccg tgcgaccccg ctgctggatc tgattaaaac cgcgctgacc      840
ccgcatccgc cgcagaaaca ggcgtatggc gtgaccctgc cgaccagcgt gctgtttatt      900
gcgggccatg ataccaacct ggccaatctg ggcggtgcgc tggaactgaa ctggaccctg      960
```

```
ccgggccagc cggataatac tccgccgggt ggtgaactgg tgtttgaacg ttggcgtcgt    1020
ctgagcgata acagccagtg gattcaggtg agcctggtgt ttcagaccct gcagcagatg    1080
cgtgataaac cgccggaatt ctttcgtctg ccaccgggtg aagtgaaact gaccctggcc    1140
ggctgcgaag aacgtaacgc gcagggcatg tgtagcctgg ccggctttac ccagattgtg    1200
aacgaagcgc gtattccggc gtgtagcctg taa                                 1233
```

<210> SEQ ID NO 68
<211> LENGTH: 21
<212> TYPE: DNA
<213> ORGANISM: artificial sequence
<220> FEATURE:
<223> OTHER INFORMATION: oligonucleotide sequence, primer

<400> SEQUENCE: 68

```
tcggtgatgt cggcgatata g                                                21
```

<210> SEQ ID NO 69
<211> LENGTH: 21
<212> TYPE: DNA
<213> ORGANISM: artificial sequence
<220> FEATURE:
<223> OTHER INFORMATION: oligonucleotide sequence, primer

<400> SEQUENCE: 69

```
ggatatagtt cctcctttca g                                                21
```

<210> SEQ ID NO 70
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 70

```
cagagcgagc cggagctgaa gctggagagc gtggtgatcg tgagcaggca cggcgtgagg      60
gccccgacca aggccaccca gctgatgcag gacgtgaccc cggacgcctg gccgacctgg     120
ccggtgaagc tgggcgagct gaccccgagg ggcggcgagc tgatcgccta cctgggccac     180
tactggaggc agaggctggt ggccgacggc ctgctgccga agtgcggctg cccgcagagc     240
ggccaggtgg ccatcatcgc cgacgtggac gagaggacca ggaagaccgg cgaggccttc     300
gccgccggcc tggccccgga ctgcgccatc accgtgcaca cccaggccga caccagcagc     360
ccggacccgc tgttcaaccc gctgaagacc ggcgtgtgcc agctggacaa cgcccaggtg     420
accgacgcca tcctggagag ggccggcggc agcatcgccg acttcaccgg ccactaccag     480
accgccttca gggagctgga gagggtgctg aacttcccgc agagcaacct gtgcctgaag     540
agggagaagc aggacgagag ctgcagcctg acccaggccc tgccgagcga gctgaaggtg     600
agcgccgact gcgtgagcct gaccggcgcc gtgagcctgg ccagcatgct gaccgagatc     660
ttcctgctgc agcaggccca gggcatgccg gagccgggct ggggcaggat caccgacagc     720
caccagtgga cacccctgct gagcctgcac aacgcccagt cgacctgct gcagaggacc     780 ccggaggtgg ccaggagcag ggccacccgc tgctggacc tgatcaagac cgccctgacc     840
ccgcacccgc cgcagaagca ggcctacggc gtgaccctgc gaccagcgt gctgttcatc     900 gccggccacg acaccaacct ggccaacctg gccggcgccc tggagctgca gtggacccctg     960 ccgggccagc cggacaacac cccgccgggc ggcgagctgg tgttcgagag gtggaggagg    1020
ctgagcgaca acagccagtg gatccaggtg agcctggtgt tccagaccct gcagcagatg    1080
```

```
agggacaaga ccccgctgag cctgaacacc ccgccgggcg aggtgaagct gaccctggcc   1140
ggctgcgagg agaggaacgc ccagggcatg tgcagcctgg ccggcttcac ccagatcgtg   1200
aacgaggcca ggatcccggc ctgcagcctg tga                                1233

<210> SEQ ID NO 71
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 71
cagagcgagc cggagctgaa gctggagagc gtggtgatcg tgagcaggca cggcgtgagg     60
gccccgacca aggccaccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga agtgcggctg cccgcagagc    240
ggccaggtgg ccatcatcgc cgacgtggac gagaggacca ggaagaccgg cgaggccttc    300
gccgccggcc tggcccccga ctgcgccatc accgtgcaca cccaggccga caccagcagc    360
ccggacccgc tgttcaaccc gctgaagacc ggcgtgtgcc agctggacaa cgccaacgtg    420
agggacgcca tcctggagag ggccggcggc agcatcgccg acttcaccgg ccactaccag    480
accgccttca gggagctgga gagggtgctg aacttcccgc agagcaacct gtgcctgaag    540
agggagaagc aggacgagag ctgcagcctg acccaggccc tgccgagcga gctgaaggtg    600
agcgccgact gcgtgagcct gaccggcgcc gtgagcctgg ccagcatgct gaccgagatc    660
ttcctgctgc agcaggccca gggcatgccg gagccgggct ggggcaggat caccgacagc    720
caccagtgga acaccctgct gagcctgcac aacgcccagt cgacctgct gcagaggacc    780 ccggaggtgg ccaggagcag ggccacccg ctgctggacc tgatcaagac cgccctgacc    840
ccgcacccgc gcagaagca ggcctacggc gtgaccctgc gaccagcgt gctgttcatc    900 gccggccacg acaccaacct ggccaacctg gcggcgccc tggagctgca gtggaccctg    960
ccgggccagc cggacaacac cccgccgggc ggcgagctgg tgttcgagag gtggaggagg   1020
ctgagcgaca cagccagtg gatccaggtg agcctggtgt ccagaccct gcagcagatg   1080 agggacaaga ccccgctgag cctgaacacc ccgccgggcg aggtgaagct gaccctggcc   1140
ggctgcgagg agaggaacgc ccagggcatg tgcagcctgg ccggcttcac ccagatcgtg   1200
aacgaggcca ggatcccggc ctgcagcctg tga                                1233

<210> SEQ ID NO 72
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 72
cagagcgagc cggagctgaa gctggagagc gtggtgatcg tgagcaggca cggcgtgagg     60
gccccgacca aggccaccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga agtgcggctg cccgcagagc    240
ggccaggtgg ccatcatcgc cgacgtggac gagaggacca ggaagaccgg cgaggccttc    300
gccgccggcc tggcccccga ctgcgccatc accgtgcaca cccaggccga caccagcagc    360
```

```
ccggacccgc tgttcaaccc gctgaagacc ggcgtgtgcc agctggacaa cgccaacgtg    420
agggacgcca tcctggagag ggccggcggc agcatcgccg acttcaccgg ccactaccag    480
accgccttca gggagctgga gagggtgctg aacttcccgc agagcaacct gtgcctgaag    540
agggagaagc aggacgagag ctgcagcctg acccaggccc tgccgagcga gctgaaggtg    600
agcgccgact gcgtgagcct gaccggcgcc gtgagcctgg ccagcatgct gaccgagatc    660
ttcctgctgc agcaggccca gggcatgccg agccgggct ggggcaggat caccgacagc    720
caccagtgga cacccctgct gagcctgcac aacgcccagt cgacctgct gcagaggacc    780 ccggaggtgg ccaggagcag ggccacccccg ctgctggacc tgatcaagac cgccctgacc    840
ccgcacccgc cgcagaagca ggcctacggc gtgaccctgc cgaccagcgt gctgttcatc    900 gccgccacg acaccaacct ggccaacctg ggcggcgccc tggagctgaa ctgggtgctg    960
ccgggccagc cggacaacac cccgccgggc ggcgagctgg tgttcgagag gtggaggagg   1020
ctgagcgaca cagccagtg gatccaggtg agcctggtgt ccagacccct gcagcagatg   1080
agggacaaga ccccgctgag cctgaacacc ccgccgggcg aggtgaagct gaccctggcc   1140
ggctgcgagg agaggaacgc ccagggcatg tgcagcctgg ccggcttcac ccagatcgtg   1200
aacgaggcca ggatcccggc ctgcagcctg tga                                1233
```

<210> SEQ ID NO 73
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 73

```
cagagcgagc cggagctgaa gctggagagc gtggtgatcg tgagcaggca cggcgtgagg     60
gccccgacca aggccacccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga agaagggctg cccgcagagc    240
ggccaggtgg ccatcatcgc cgacgtggac gagaggacca ggaagaccgg cgaggccttc    300
gccgccggcc tggccccgga ctgcgccatc accgtgcaca cccaggccga caccagcagc    360
ccggacccgc tgttcaaccc gctgaagacc ggcgtgtgcc agctggacaa cgccaacgtg    420
accgacgcca tcctggagag ggccggcggc agcatcgccg acttcaccgg ccactaccag    480
accgccttca gggagctgga gagggtgctg aacttcccgc agagcaacct gtgcctgaag    540
agggagaagc aggacgagag ctgcagcctg acccaggccc tgccgagcga gctgaaggtg    600
agcgccgaca cgtgagcct gaccggcgcc gtgagcctgg ccagcatgct gaccgagatc    660
ttcctgctgc agcaggccca gggcatgccg agccgggct ggggcaggat caccgacagc    720
caccagtgga cacccctgct gagcctgcac aacgcccagt cgacctgct gcagaggacc    780 ccggaggtgg ccaggagcag ggccacccccg ctgctggacc tgatcaagac cgccctgacc    840
ccgcacccgc cgcagaagca ggcctacggc gtgaccctgc cgaccagcgt gctgttcatc    900
gccggccacg acaccaacct ggccaacctg ggcggcgccc tggagctgaa ctggaccctg    960
ccgggccagc cggacaacac cccgccgggc ggcgagctgg tgttcgagag gtggaggagg   1020
ctgagcgaca cagccagtg gatccaggtg agcctggtgt ccagacccct gcagcagatg   1080
agggacaaga ccccgctgag cctgaacacc ccgccgggcg aggtgaagct gaccctggcc   1140
ggctgcgagg agaggaacgc ccagggcatg tgcagcctgg ccggcttcac ccagatcgtg   1200
```

```
aacgaggcca ggatcccggc ctgcagcctg tga                           1233
```

<210> SEQ ID NO 74
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 74

```
cagagcgagc cggagctgaa gctggagagc gtggtgatcg tgagcaggca cggcgtgagg     60
gccccgacca aggccaccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga agaagggctg cccgcagagc    240
ggccaggtgg ccatcatcgc cgacgtggac gagaggacca ggaagaccgg cgaggccttc    300
gccgccggcc tggccccgga ctgcgccatc accgtgcaca cccaggccga caccagcagc    360
ccggacccgc tgttcaaccc gctgaagacc ggcgtgtgcc agctggacaa cgccaacgtg    420
accgacgcca tcctggagag ggccggcggc agcatcgccg acttcaccgg ccactaccag    480
accgccttca gggagctgga gagggtgctg aacttcccgc agagcaacct ggccctgaag    540
agggagaagc aggacgagag cgccagcctg acccaggccc tgccgagcga gctgaaggtg    600
agcgccgaca acgtgagcct gaccggcgcc gtgagcctgg ccagcatgct gaccgagatc    660
ttcctgctgc agcaggccca gggcatgccg gagccgggct ggggcaggat caccgacagc    720
caccagtgga acaccctgct gagcctgcac aacgcccagt cgacctgct gcagaggacc    780
```
(text reads: aacgcccagt cgacctgct — likely aacgcccagt cgacctgct gcagaggacc)
```
ccggaggtgg ccaggagcag ggccacccg ctgctggacc tgatcaagac cgccctgacc    840
ccgcaccgc gcagaagca ggcctacggc gtgaccctgc cgaccagcgt gctgttcatc    900
gccggccacg acaccaacct ggccaacctg gcggcgccc tggagctgaa ctggaccctg    960
ccgggccagc cggacaacac cccgccgggc ggcgagctg tgttcgagag gtggaggagg    1020
ctgagcgaca cagccagtg gatccaggtg agcctggtgt ccagaccct gcagcagatg    1080
agggacaaga ccccgctgag cctgaacacc ccgccgggcg aggtgaagct gaccctggcc    1140
ggctgcgagg agaggaacgc ccagggcatg tgcagcctgg ccggcttcac ccagatcgtg    1200
aacgaggcca ggatcccggc ctgcagcctg tga                               1233
```

<210> SEQ ID NO 75
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 75

```
cagagcgagc cggagctgaa gctggagagc gtggtgatcg tgagcaggca cggcgtgagg     60
gccccgacca aggccaccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga agaagggctg cccgcagagc    240
ggccaggtgg ccatcatcgc cgacgtggac gagaggacca ggaagaccgg cgaggccttc    300
gccgccggcc tggccccgga ctgcgccatc accgtgcaca cccaggccga caccagcagc    360
ccggacccgc tgttcaaccc gctgaagacc ggcgtgtgcc agctggacaa cgccaacgtg    420
accgacgcca tcctggagag ggccggcggc agcatcgccg acttcaccgg ccactaccag    480
```

| | |
|---|---|
| accgccttca gggagctgga gagggtgctg aacttcccgc agagcaacct gtgcctgaag | 540 |
| agggagaagc aggacgagag ctgcagcctg acccaggccc tgccgagcga gctgaaggtg | 600 |
| agcgccgaca acgtgagcct gaccggcgcc gtgagcctgg ccagcatgct gaccgagatc | 660 |
| ttcctgctgc agcaggccca gggcatgccg gagccgggct ggggcaggat caccgacagc | 720 |
| caccagtgga acaccctgct gagcctgcac aacgcccagt tcgacctgct gcagaggacc | 780 |
| ccggaggtgg ccaggagcag ggccaccccg ctgctggacc tgatcaagac cgccctgacc | 840 |
| ccgcacccgc cgcagaagca ggcctacggc gtgaccctgc cgaccagcgt gctgttcatc | 900 |
| gccggccacg acaccaacct ggccaacctg ggcggcgccc tggagctgaa ctggaccctg | 960 |
| ccgggccagc cggacaacac cccgccgggc ggcgagctgg tgttcgagag gtggaggagg | 1020 |
| ctgagcgaca acagccagtg gatccaggtg agcctggtgt ccagacccct gcagcagatg | 1080 |
| agggacaaga ccccgctgag cctgaacacc ccgccgggcg aggtgaagct gaccctggcc | 1140 |
| ggcgccgagg agaggaacgc ccagggcatg gccagcctgg ccggcttcac ccagatcgtg | 1200 |
| aacgaggcca ggatcccggc ctgcagcctg tga | 1233 |

<210> SEQ ID NO 76
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 76

| | |
|---|---|
| cagagcgagc cggagctgaa gctggagagc gtggtgatcg tgagcaggca cggcgtgagg | 60 |
| gccccgacca aggccaccca gctgatgcag gacgtgaccc cggacgcctg gccgacctgg | 120 |
| ccggtgaagc tgggcgagct gaccccgagg ggcggcgagc tgatcgccta cctgggccac | 180 |
| tactggaggc agaggctggt ggccgacggc ctgctgccga agaagggctg cccgcagagc | 240 |
| ggccaggtgg ccatcatcgc cgacgtggac gagaggacca ggaagaccgg cgaggccttc | 300 |
| gccgccggcc tggccccgga ctgcgccatc accgtgcaca cccaggccga caccagcagc | 360 |
| ccggacccgc tgttcaaccc gctgaagacc ggcgtgtgcc agctggacaa cgccaacgtg | 420 |
| accgacgcca tcctggagag ggccggcggc agcatcgccg acttcaccgg ccactaccag | 480 |
| accgccttca gggagctgga gagggtgctg aacttcccgc agagcaacct ggccctgaag | 540 |
| agggagaagc aggacgagag cgccagcctg acccaggccc tgccgagcga gctgaaggtg | 600 |
| agcgccgaca acgtgagcct gaccggcgcc gtgagcctgg ccagcatgct gaccgagatc | 660 |
| ttcctgctgc agcaggccca gggcatgccg gagccgggct ggggcaggat caccgacagc | 720 |
| caccagtgga acaccctgct gagcctgcac aacgcccagt tcgacctgct gcagaggacc | 780 |
| ccggaggtgg ccaggagcag ggccaccccg ctgctggacc tgatcaagac cgccctgacc | 840 |
| ccgcacccgc cgcagaagca ggcctacggc gtgaccctgc cgaccagcgt gctgttcatc | 900 |
| gccggccacg acaccaacct ggccaacctg ggcggcgccc tggagctgaa ctggaccctg | 960 |
| ccgggccagc cggacaacac cccgccgggc ggcgagctgg tgttcgagag gtggaggagg | 1020 |
| ctgagcgaca acagccagtg gatccaggtg agcctggtgt ccagacccct gcagcagatg | 1080 |
| agggacaaga ccccgctgag cctgaacacc ccgccgggcg aggtgaagct gaccctggcc | 1140 |
| ggcgccgagg agaggaacgc ccagggcatg gccagcctgg ccggcttcac ccagatcgtg | 1200 |
| aacgaggcca ggatcccggc ctgcagcctg tga | 1233 |

<210> SEQ ID NO 77

```
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 77
cagagcgagc cggagctgaa gctggagagc gtggtgatcg tgagcaggca cggcgtgagg     60
gccccgacca aggccaccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga agaagggcgc cccgcagagc    240
ggccaggtgg ccatcatcgc cgacgtggac gagaggacca ggaagaccgg cgaggccttc    300
gccgccggcc tgggccccgga cgccgccatc accgtgcaca cccaggccga caccagcagc    360
ccggacccgc tgttcaaccc gctgaagacc ggcgtgtgcc agctggacaa cgccaacgtg    420
accgacgcca tcctggagag gccggcggc agcatcgccg acttcaccgg ccactaccag    480
accgccttca gggagctgga gagggtgctg aacttcccgc agagcaacct gtgcctgaag    540
agggagaagc aggacgagag ctgcagcctg acccaggccc tgccgagcga gctgaaggtg    600
agcgccgaca acgtgagcct gaccggcgcc gtgagcctgg ccagcatgct gaccgagatc    660
ttcctgctgc agcaggccca gggcatgccg agccgggct ggggcaggat caccgacagc    720
caccagtgga cacccctgct gagcctgcac aacgcccagt cgacctgct gcagaggacc    780 ccggaggtgg ccaggagcag ggccacccg ctgctggacc tgatcaagac cgccctgacc    840
ccgcacccgc cgcagaagca ggcctacggc gtgaccctgc cgaccagcgt gctgttcatc    900
gccggccacg acaccaacct ggccaacctg gcggcgccc tggagctgaa ctggaccctg    960
ccgggccagc cggacaacac cccgccgggc ggcgagctgg tgttcgagag gtggaggagg   1020
ctgagcgaca cagccagtg gatccaggtg agcctggtgt ccagaccct gcagcagatg   1080 agggacaaga cccgctgag cctgaacacc ccgccgggcg aggtgaagct gaccctggcc   1140
ggctgcgagg agaggaacgc ccagggcatg tgcagcctgg ccggcttcac ccagatcgtg   1200
aacgaggcca ggatcccggc ctgcagcctg tga                                1233

<210> SEQ ID NO 78
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 78
cagagcgagc cggagctgaa gctggagagc gtggtgatcg tgagcaggca cggcgtgagg     60
gccccgacca aggccaccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga agaagggctg cccgcagagc    240
ggccaggtgg ccatcatcgc cgacgtggac gagaggacca ggaagaccgg cgaggccttc    300
gccgccggcc tgccccgga ctgcgccatc accgtgcaca cccaggccga caccagcagc    360
ccggacccgc tgttcaaccc gctgaagacc ggcgtggccc agctggacaa cgccaacgtg    420
accgacgcca tcctggagag gccggcggc agcatcgccg acttcaccgg ccactaccag    480
accgccttca gggagctgga gagggtgctg aacttcccgc agagcaacct gtgcctgaag    540
agggagaagc aggacgagag ctgcagcctg acccaggccc tgccgagcga gctgaaggtg    600
```

```
agcgccgaca acgtgagcct gaccggcgcc gtgagcctgg ccagcatgct gaccgagatc    660
ttcctgctgc agcaggccca gggcatgccg gagccgggct ggggcaggat caccgacagc    720
caccagtgga acaccctgct gagcctgcac aacgcccagt cgacctgct gcagaggacc     780 ccggaggtgg ccaggagcag ggccaccccg ctgctggacc tgatcaagac cgccctgacc    840
ccgcacccgc cgcagaagca ggcctacggc gtgaccctgc cgaccagcgt gctgttcatc    900
gccggccacg acaccaacct ggccaacctg ggcggcgccc tggagctgaa ctggaccctg    960
ccgggccagc cggacaacac cccgccgggc ggcgagctgg tgttcgagag gtggaggagg    1020
ctgagcgaca cagccagtg gatccaggtg agcctggtgt ccagaccct gcagcagatg      1080 agggacaaga ccccgctgag cctgaacacc ccgccgggcg aggtgaagct gaccctggcc    1140
ggctgcgagg agaggaacgc ccagggcatg tgcagcctgg ccggcttcac ccagatcgtg    1200
aacgaggcca ggatcccggc cgccagcctg tga                                 1233
```

```
<210> SEQ ID NO 79
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 79
```

```
cagagcgagc cggagctgaa gctggagagc gtggtgatcg tgagcaggca cggcgtgagg     60
gccccgacca aggccaccca gctgatgcag gacgtgaccc cggacgcctt ctacacctgg    120
ccggtgaagc tgggcgagct gaccccgagg ggcggcgagc tgatcgccta cctgggccac    180
tactggaggc agaggctggt ggccgacggc ctgctgccga agtgcggctg cccgcagagc    240
ggccaggtgg ccatcatcgc cgacgtggac gagaggacca ggaagaccgg cgaggccttc    300
gccgccggcc tggccccgga ctgcgccatc accgtgcaca cccaggccga caccagcagc    360
ccggacccgc tgttcaaccc gctgaagacc ggcgtgtgcc agctggacaa cgccaacgtg    420
accgacgcca tcctggagag ggccggcggc agcatcgccg acttcaccgg ccactaccag    480
accgccttca gggagctgga gagggtgctg aacttcccgc agagcaacct gtgcctgaag    540
agggagaagc aggacgagag ctgcagcctg acccaggccc tgccgagcga gctgaaggtg    600
agcgccgact gcgtgagcct gaccggcgcc gtgagcctgg ccagcatgct gaccgagatc    660
ttcctgctgc agcaggccca gggcatgccg gagccgggct ggggcaggat caccgacagc    720
caccagtgga acaccctgct gagcctgcac aacgcccagt cgacctgct gcagaggacc     780 ccggaggtgg ccaggagcag ggccaccccg ctgctggacc tgatcaagac cgccctgacc    840
ccgcacccgc cgcagaagca ggcctacggc gtgaccctgc cgaccagcgt gctgttcatc    900
gccggccacg acaccaacct ggccaacctg ggcggcgccc tggagctgaa ctggaccctg    960
ccgggccagc cggacaacac cccgccgggc ggcgagctgg tgttcgagag gtggaggagg    1020
ctgagcgaca cagccagtg gatccaggtg agcctggtgt ccagaccct gcagcagatg      1080 agggacaaga ccccgctgag cctgaacacc ccgccgggcg aggtgaagct gaccctggcc    1140
ggctgcgagg agaggaacgc ccagggcatg tgcagcctgg ccggcttcac ccagatcgtg    1200
aacgaggcca ggatcccggc ctgcagcctg tga                                 1233
```

```
<210> SEQ ID NO 80
<211> LENGTH: 1233
<212> TYPE: DNA
<213> ORGANISM: artificial sequence
<220> FEATURE:
```

<223> OTHER INFORMATION: maize codon optimized DNA sequence

<400> SEQUENCE: 80

| | |
|---|---|
| cagagcgagc cggagctgaa gctggagagc gtggtgatcg tgagcaggca cggcgtgagg | 60 |
| gccccgacca aggccaccca gctgatgcag gacgtgaccc cggacgcctg gccgacctgg | 120 |
| ccggtgaagc tgggcgagct gaccccgagg ggcggcgagc tgatcgccta cctgggccac | 180 |
| tactggaggc agaggctggt ggccgacggc ctgctgccga agtgcggctg cccgcagagc | 240 |
| ggccaggtgg ccatcatcgc cgacgtggac gagaggacca ggaagaccgg cgaggccttc | 300 |
| gccgccggcc tgccccgga ctgcgccatc accgtgcaca cccaggccga caccagcagc | 360 |
| ccggacgagc tgttcaacct gctgaagacc ggcgtgtgcc agctggacaa cgccaacgtg | 420 |
| accgacgcca tcctggagag ggccggcggc agcatcgccg acttcaccgg ccactaccag | 480 |
| accgccttca gggagctgga gagggtgctg aacttcccgc agagcaacct gtgcctgaag | 540 |
| agggagaagc aggacgagag ctgcagcctg acccaggccc tgccgagcga gctgaaggtg | 600 |
| agcgccgact gcgtgagcct gaccggcgcc gtgagcctgg ccagcatgct gaccgagatc | 660 |
| ttcctgctgc agcaggccca gggcatgccg gagccgggct ggggcaggat caccgacagc | 720 |
| caccagtgga cacccctgct gagcctgcac aacgcccagt cgacctgct gcagaggacc | 780 |
| ccggaggtgg ccaggagcag ggccaccccg ctgctggacc tgatcaagac cgccctgacc | 840 |
| ccgcacccgc gcagaagca ggcctacggc gtgaccctgc gaccagcgt gctgttcatc | 900 |
| gccggccacg acaccaacct ggccaacctg gcggcgccc tggagctgaa ctggaccctg | 960 |
| ccgggccagc cggacaacac cccgccgggc ggcgagctgg tgttcgagag gtggaggagg | 1020 |
| ctgagcgaca cagccagtg gatccaggtg agcctggtgt ccagaccct gcagcagatg | 1080 |
| agggacaaga ccccgctgag cctgaacacc ccgccgggcg aggtgaagct gaccctggcc | 1140 |
| ggctgcgagg agaggaacgc ccagggcatg tgcagcctgg ccggcttcac ccagatcgtg | 1200 |
| aacgaggcca ggatcccggc ctgcagcctg tga | 1233 |

<210> SEQ ID NO 81
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 81

| | |
|---|---|
| cagagcgagc cggagctgaa gctggagagc gtggtgatcg tgagcaggca cggcgtgagg | 60 |
| gccccgacca aggccaccca gctgatgcag gacgtgaccc cggacgcctg gccgacctgg | 120 |
| ccggtgaagc tgggcgagct gaccccgagg ggcggcgagc tgatcgccta cctgggccac | 180 |
| tactggaggc agaggctggt ggccgacggc ctgctgccga agtgcggctg cccgcagagc | 240 |
| ggccaggtgg ccatcatcgc cgacgtggac gagaggacca ggaagaccgg cgaggccttc | 300 |
| gccgccggcc tgccccgga ctgcgccatc accgtgcaca cccaggccga caccagcagc | 360 |
| ccggacccgc tgttctacgt gctgaagacc ggcgtgtgcc agctggacaa cgccaacgtg | 420 |
| accgacgcca tcctggagag ggccggcggc agcatcgccg acttcaccgg ccactaccag | 480 |
| accgccttca gggagctgga gagggtgctg aacttcccgc agagcaacct gtgcctgaag | 540 |
| agggagaagc aggacgagag ctgcagcctg acccaggccc tgccgagcga gctgaaggtg | 600 |
| agcgccgact gcgtgagcct gaccggcgcc gtgagcctgg ccagcatgct gaccgagatc | 660 |
| ttcctgctgc agcaggccca gggcatgccg gagccgggct ggggcaggat caccgacagc | 720 |

```
caccagtgga acaccctgct gagcctgcac aacgcccagt cgacctgctg cagaggacc       780 ccggaggtgg ccaggagcag ggccaccccg ctgctggacc tgatcaagac cgccctgacc      840
ccgcacccgc cgcagaagca ggcctacggc gtgaccctgc cgaccagcgt gctgttcatc      900
gccggccacg acaccaacct ggccaacctg ggcggcgccc tggagctgaa ctggaccctg      960
ccgggccagc cggacaacac cccgccgggc ggcgagctgg tgttcgagag gtggaggagg     1020
ctgagcgaca acagccagtg gatccaggtg agcctggtgt ccagaccct gcagcagatg     1080 agggacaaga ccccgctgag cctgaacacc ccgccgggcg aggtgaagct gaccctggcc    1140
ggctgcgagg agaggaacgc ccagggcatg tgcagcctgg ccggcttcac ccagatcgtg    1200
aacgaggcca ggatcccggc ctgcagcctg tga                                  1233
```

<210> SEQ ID NO 82
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 82

```
cagagcgagc cggagctgaa gctggagagc gtggtgatcg tgagcaggca cggcgtgagg       60
gccccgacca aggccaccca gctgatgcag gacgtgaccc cggacgcctg gccgacctgg     120
ccggtgaagc tgggcgagct gaccccgagg ggcggcgagc tgatcgccta cctgggccac     180
tactggaggc agaggctggt ggccgacggc ctgctgccga gtgcggctg cccgcagagc     240 ggccaggtgg ccatcatcgc cgacgtggac gagaggacca ggaagaccgg cgaggccttc     300
gccgccggcc tggccccgga ctgcgccatc accgtgcaca cccaggccga caccagcagc     360
ccggacccgc tgttcaaccc gctgaagacc ggcgtgtgcc agctggacaa cgccaacgtg     420
accgacgcca tcctggagag gccggcggc agcatcgccg acttcaccgg ccactaccag     480
accgccttca gggagctgga gagggtgctg aacttctacc agagcaacct gtgcctgaag     540
agggagaagc aggacgagag ctgcagcctg acccaggccc tgccgagcga gctgaaggtg     600
agcgccgact gcgtgagcct gaccggcgcc gtgagcctgg ccagcatgct gaccgagatc     660
ttcctgctgc agcaggccca gggcatgccg gagccgggct ggggcaggat caccgacagc     720
caccagtgga acaccctgct gagcctgcac aacgcccagt cgacctgctg cagaggacc    780 ccggaggtgg ccaggagcag ggccaccccg ctgctggacc tgatcaagac cgccctgacc    840
ccgcacccgc cgcagaagca ggcctacggc gtgaccctgc cgaccagcgt gctgttcatc    900
gccggccacg acaccaacct ggccaacctg ggcggcgccc tggagctgaa ctggaccctg    960
ccgggccagc cggacaacac cccgccgggc ggcgagctgg tgttcgagag gtggaggagg   1020
ctgagcgaca acagccagtg gatccaggtg agcctggtgt ccagaccct gcagcagatg   1080 agggacaaga ccccgctgag cctgaacacc ccgccgggcg aggtgaagct gaccctggcc  1140
ggctgcgagg agaggaacgc ccagggcatg tgcagcctgg ccggcttcac ccagatcgtg  1200
aacgaggcca ggatcccggc ctgcagcctg tga                                1233
```

<210> SEQ ID NO 83
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 83

-continued

```
cagagcgagc cggagctgaa gctggagagc gtggtgatcg tgagcaggca cggcgtgagg      60
gccccgacca aggccaccca gctgatgcag gacgtgaccc cggacgcctg gccgacctgg     120
ccggtgaagc tgggcgagct gaccccgagg ggcggcgagc tgatcgccta cctgggccac     180
tactggaggc agaggctggt ggccgacggc ctgctgccga agtgcggctg cccgcagagc     240
ggccaggtgg ccatcatcgc cgacgtggac gagaggacca ggaagaccgg cgaggccttc     300
gccgccggcc tgccccgga ctgcgccatc accgtgcaca cccaggccga caccagcagc     360
ccggacccgc tgttcaaccc gctgaagacc ggcgtgtgcc agctggacaa cgccaacgtg     420
accgacgcca tcctggagag ggccggcggc agcatcgccg acttcaccgg ccactaccag     480
accgccttca gggagctgga gagggtgctg aacttcccgc agagcaacct gtgcctgaag     540
agggagaagc aggacgagag ctgcagcctg acccaggccc tgccgagcga gctgaaggtg     600
agcgccgact gcgtgagcct gaccggcgcc gtgagcctgg ccagcatgct gaccgagatc     660
ttcctgctgc agcaggccca gggcatgccg gagccggagt ggtacaggat caccgacagc     720
caccagtgga acaccctgct gagcctgcac aacgcccagt cgacctgct gcagaggacc      780 ccggaggtgg ccaggagcag ggccaccccg ctgctggacc tgatcaagac cgccctgacc     840
ccgcacccgc cgcagaagca ggcctacggc gtgaccctgc cgaccagcgt gctgttcatc     900
gccggccacg acaccaacct ggccaacctg ggcggcgccc tggagctgaa ctggaccctg     960
ccgggccagc cggacaacac cccgccgggc ggcgagctgg tgttcgagag gtggaggagg    1020
ctgagcgaca cagccagtg gatccaggtg agcctggtgt tccagaccct gcagcagatg     1080
agggacaaga ccccgctgag cctgaacacc ccgccgggcg aggtgaagct gaccctggcc    1140
ggctgcgagg agaggaacgc ccagggcatg tgcagcctgg ccggcttcac ccagatcgtg    1200
aacgaggcca ggatcccggc ctgcagcctg tga                                  1233
```

<210> SEQ ID NO 84
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 84

```
cagagcgagc cggagctgaa gctggagagc gtggtgatcg tgagcaggca cggcgtgagg      60
gccccgacca aggccaccca gctgatgcag gacgtgaccc cggacgcctg gccgacctgg     120
ccggtgaagc tgggcgagct gaccccgagg ggcggcgagc tgatcgccta cctgggccac     180
tactggaggc agaggctggt ggccgacggc ctgctgccga agtgcggctg cccgcagagc     240
ggccaggtgg ccatcatcgc cgacgtggac gagaggacca ggaagaccgg cgaggccttc     300
gccgccggcc tgccccgga ctgcgccatc accgtgcaca cccaggccga caccagcagc     360
ccggacccgc tgttcaaccc gctgaagacc ggcgtgtgcc agctggacaa cgccaacgtg     420
accgacgcca tcctggagag ggccggcggc agcatcgccg acttcaccgg ccactaccag     480
accgccttca gggagctgga gagggtgctg aacttcccgc agagcaacct gtgcctgaag     540
agggagaagc aggacgagag ctgcagcctg acccaggccc tgccgagcga gctgaaggtg     600
agcgccgact gcgtgagcct gaccggcgcc gtgagcctgg ccagcatgct gaccgagatc     660
ttcctgctgc agcaggccca gggcatgccg gagccgggct ggggcaggat caccgacagc     720
caccagtgga acaccctgct gagcctgcac aacgcccagt cgacctgct gcagaggacc      780 ccggaggtgg ccaggagcag ggccaccccg ctgctggacc tgatcaagac cgccctgacc     840
```

```
ccgcacccgc cgcagttcta cgcctacggc gtgaccctgc cgaccagcgt gctgttcatc      900
gccggccacg acaccaacct ggccaacctg ggcggcgccc tggagctgaa ctggaccctg      960
ccgggccagc cggacaacac cccgccgggc ggcgagctgg tgttcgagag gtggaggagg     1020
ctgagcgaca cagccagtg gatccaggtg agcctggtgt tccagaccct gcagcagatg     1080
agggacaaga ccccgctgag cctgaacacc ccgccgggcg aggtgaagct gaccctggcc     1140
ggctgcgagg agaggaacgc ccagggcatg tgcagcctgg ccggcttcac ccagatcgtg     1200
aacgaggcca ggatcccggc ctgcagcctg tga                                  1233
```

<210> SEQ ID NO 85
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 85

```
cagagcgagc cggagctgaa gctggagagc gtggtgatcg tgagcaggca cggcgtgagg       60
gccccgacca aggccaccca gctgatgcag gacgtgaccc cggacgcctg gccgacctgg      120
ccggtgaagc tgggcgagct gaccccgagg ggcggcgagc tgatcgccta cctgggccac      180
tactggaggc agaggctggt ggccgacggc ctgctgccga agtgcggctg cccgcagagc      240
ggccaggtgg ccatcatcgc cgacgtggac gagaggacca ggaagaccgg cgaggccttc      300
gccgccggcc tggccccgga ctgcgccatc accgtgcaca cccaggccga caccagcagc      360
ccggacccgc tgttcaaccc gctgaagacc ggcgtgtgcc agctggacaa cgccaacgtg      420
accgacgcca tcctggagag ggccggcggc agcatcgccg acttcaccgg ccactaccag      480
accgccttca gggagctgga gagggtgctg aacttcccgc agagcaacct gtgcctgaag      540
agggagaagc aggacgagag ctgcagcctg acccaggccc tgccgagcga gctgaaggtg      600
agcgccgact gcgtgagcct gaccggcgcc gtgagcctgg ccagcatgct gaccgagatc      660
ttcctgctgc agcaggccca gggcatgccg gagccgggct ggggcaggat caccgacagc      720
caccagtgga cacccctgct gagcctgcac aacgcccagt cgacctgct gcagaggacc      780 ccggaggtgg ccaggagcag ggccaccccg ctgctggacc tgatcaagac cgccctgacc      840
ccgcacccgc cgcagaagca ggcctacggc gtgaccctgc cgaccagcgt gctgttcatc      900
gccggccacg acaccaacct ggccaacctg ggcggcgccc tggagctgct gtacaccctg      960
ccgggccagc cggacaacac cccgccgggc ggcgagctgg tgttcgagag gtggaggagg     1020
ctgagcgaca cagccagtg gatccaggtg agcctggtgt tccagaccct gcagcagatg     1080
agggacaaga ccccgctgag cctgaacacc ccgccgggcg aggtgaagct gaccctggcc     1140
ggctgcgagg agaggaacgc ccagggcatg tgcagcctgg ccggcttcac ccagatcgtg     1200
aacgaggcca ggatcccggc ctgcagcctg tga                                  1233
```

<210> SEQ ID NO 86
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 86

```
cagagcgagc cggagctgaa gctggagagc gtggtgatcg tgagcaggca cggcgtgagg       60
gccccgacca aggccaccca gctgatgcag gacgtgaccc cggacgcctg gccgacctgg      120
```

```
ccggtgaagc tgggcgagct gaccccgagg ggcggcgagc tgatcgccta cctgggccac    180
tactggaggc agaggctggt ggccgacggc ctgctgccga agtgcggctg cccgcagagc    240
ggccaggtgg ccatcatcgc cgacgtggac gagaggacca ggaagaccgg cgaggccttc    300
gccgccggcc tggcccccgga ctgcgccatc accgtgcaca cccaggccga caccagcagc    360
ccggacccgc tgttcaaccc gctgaagacc ggcgtgtgcc agctggacaa cgccaacgtg    420
accgacgcca tcctggagag ggccggcggc agcatcgccg acttcaccgg ccactaccag    480
accgccttca gggagctgga gagggtgctg aacttcccgc agagcaacct gtgcctgaag    540
agggagaagc aggacgagag ctgcagcctg acccaggccc tgccgagcga gctgaaggtg    600
agcgccgact gcgtgagcct gaccggcgcc gtgagcctgg ccagcatgct gaccgagatc    660
ttcctgctgc agcaggccca gggcatgccg gagccgggct ggggcaggat caccgacagc    720
caccagtgga cacccctgct gagcctgcac aacgcccagt cgacctgct gcagaggacc    780 ccggaggtgg ccaggagcag ggccaccccg ctgctggacc tgatcaagac cgccctgacc    840
ccgcacccgc cgcagaagca ggcctacggc gtgaccctgc cgaccagcgt gctgttcatc    900
gccggccacg acaccaacct ggccaacctg ggcggcgccc tggagctgaa ctggaccctg    960
ccgggccagc cggacaacac cccgccgggc ggcgagctgg tgttcgagag gtggaggagg   1020
ctgagcgaca cagccagtg gatccaggtg agcctggtgt ccagacccct gcagcagatg   1080
agggacaaga ccccgctgtt cctgaacacc ccgccgggcg aggtgaagct gaccctggcc   1140
ggctgcgagg agaggaacgc ccagggcatg tgcagcctgg ccggcttcac ccagatcgtg   1200
aacgaggcca ggatcccggc ctgcagcctg tga                                1233
```

<210> SEQ ID NO 87
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 87

```
cagagcgagc cggagctgaa gctggagagc gtggtgatcg tgagcaggca cggcgtgagg     60
gccccgacca aggccaccca gctgatgcag gacgtgaccc cggacgcctt ctacacctgg    120
ccggtgaagc tgggcgagct gaccccgagg ggcggcgagc tgatcgccta cctgggccac    180
tactggaggc agaggctggt ggccgacggc ctgctgccga agtgcggctg cccgcagagc    240
ggccaggtgg ccatcatcgc cgacgtggac gagaggacca ggaagaccgg cgaggccttc    300
gccgccggcc tggcccccga ctgcgccatc accgtgcaca cccaggccga caccagcagc    360
ccggacgagc tgttcaacct gctgaagacc ggcgtgtgcc agctggacaa cgccaacgtg    420
accgacgcca tcctggagag ggccggcggc agcatcgccg acttcaccgg ccactaccag    480
accgccttca gggagctgga gagggtgctg aacttcccgc agagcaacct gtgcctgaag    540
agggagaagc aggacgagag ctgcagcctg acccaggccc tgccgagcga gctgaaggtg    600
agcgccgact gcgtgagcct gaccggcgcc gtgagcctgg ccagcatgct gaccgagatc    660
ttcctgctgc agcaggccca gggcatgccg gagccgggct ggggcaggat caccgacagc    720
caccagtgga cacccctgct gagcctgcac aacgcccagt cgacctgct gcagaggacc    780 ccggaggtgg ccaggagcag ggccaccccg ctgctggacc tgatcaagac cgccctgacc    840
ccgcacccgc cgcagaagca ggcctacggc gtgaccctgc cgaccagcgt gctgttcatc    900
gccggccacg acaccaacct ggccaacctg ggcggcgccc tggagctgaa ctggaccctg    960
```

```
ccgggccagc cggacaacac cccgccgggc ggcgagctgg tgttcgagag gtggaggagg    1020
ctgagcgaca acagccagtg gatccaggtg agcctggtgt tccagaccct gcagcagatg    1080
agggacaaga ccccgctgag cctgaacacc ccgccgggcg aggtgaagct gaccctggcc    1140
ggctgcgagg agaggaacgc ccagggcatg tgcagcctgg ccggcttcac ccagatcgtg    1200
aacgaggcca ggatcccggc ctgcagcctg tga                                 1233
```

<210> SEQ ID NO 88
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 88

```
cagagcgagc cggagctgaa gctggagagc gtggtgatcg tgagcaggca cggcgtgagg     60
gccccgacca aggccaccca gctgatgcag gacgtgaccc cggacgcctt ctacacctgg    120
ccggtgaagc tgggcgagct gaccccgagg ggcggcgagc tgatcgccta cctgggccac    180
tactggaggc agaggctggt ggccgacggc ctgctgccga agtgcggctg cccgcagagc    240
ggccaggtgg ccatcatcgc cgacgtggac gagaggacca ggaagaccgg cgaggccttc    300
gccgccggcc tggccccgga ctgcgccatc accgtgcaca cccaggccga caccagcagc    360
ccggacccgc tgttctacgt gctgaagacc ggcgtgtgcc agctggacaa cgccaacgtg    420
accgacgcca tcctggagag ggccggcggc agcatcgccg acttcaccgg ccactaccag    480
accgccttca gggagctgga gagggtgctg aacttcccgc agagcaacct gtgcctgaag    540
agggagaagc aggacgagag gctgcagcct gacccaggccc tgccgagcga gctgaaggtg    600
agcgccgact gcgtgagcct gaccggcgcc gtgagcctgg ccagcatgct gaccgagatc    660
ttcctgctgc agcaggccca gggcatgccg gagccgggct ggggcaggat caccgacagc    720
caccagtgga cacccctgct gagcctgcac aacgcccagt cgacctgct gcagaggacc    780 ccggaggtgg ccaggagcag ggccaccccg ctgctggacc tgatcaagac cgccctgacc    840
ccgcacccgc cgcagaagca ggcctacggc gtgaccctgc cgaccagcgt gctgttcatc    900
gccggccacg acaccaacct ggccaacctg ggcggcgccc tggagctgaa ctggaccctg    960
ccgggccagc cggacaacac cccgccgggc ggcgagctgg tgttcgagag gtggaggagg    1020
ctgagcgaca acagccagtg gatccaggtg agcctggtgt tccagaccct gcagcagatg    1080
agggacaaga ccccgctgag cctgaacacc ccgccgggcg aggtgaagct gaccctggcc    1140
ggctgcgagg agaggaacgc ccagggcatg tgcagcctgg ccggcttcac ccagatcgtg    1200
aacgaggcca ggatcccggc ctgcagcctg tga                                 1233
```

<210> SEQ ID NO 89
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 89

```
cagagcgagc cggagctgaa gctggagagc gtggtgatcg tgagcaggca cggcgtgagg     60
gccccgacca aggccaccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga agtgcggctg cccgcagagc    240
```

```
ggccaggtgg ccatcatcgc cgacgtggac gagaggacca ggaagaccgg cgaggccttc      300
gccgccggcc tggcccccgga ctgcgccatc accgtgcaca cccaggccga caccagcagc     360
ccggacccgc tgttcaaccc gctgaagacc ggcgtgtgcc agctggacaa cgccaacgtg     420
accgacgcca tcctggagag ggccggcggc agcatcgccg acttcaccgg ccactaccag     480
accgccttca gggagctgga gagggtgctg aacttctacc agagcaacct gtgcctgaag     540
agggagaagc aggacgagag ctgcagcctg acccaggccc tgccgagcga gctgaaggtg     600
agcgccgact gcgtgagcct gaccggcgcc gtgagcctgg ccagcatgct gaccgagatc     660
ttcctgctgc agcaggccca gggcatgccg agccgggct ggggcaggat caccgacagc     720
caccagtgga caccctgct gagcctgcac aacgcccagt tcgacctgct gcagaggacc     780
ccggaggtgg ccaggagcag ggccaccccg ctgctggacc tgatcaagac cgccctgacc     840
ccgcacccgc cgcagaagca ggcctacggc gtgaccctgc cgaccagcgt gctgttcatc     900
gccggccacg acaccaacct ggccaacctg ggcggcgccc tggagctgct gtacaccctg     960
ccgggccagc cggacaacac cccgccgggc ggcgagctgg tgttcgagag gtggaggagg    1020
ctgagcgaca cagccagtg gatccaggtg agcctggtgt ccagacccct gcagcagatg    1080
agggacaaga ccccgctgag cctgaacacc ccgccgggcg aggtgaagct gaccctggcc    1140
ggctgcgagg agaggaacgc ccagggcatg tgcagcctgg ccggcttcac ccagatcgtg    1200
aacgaggcca ggatcccggc ctgcagcctg tga                                 1233

<210> SEQ ID NO 90
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 90
cagagcgagc cggagctgaa gctggagagc gtggtgatcg tgagcaggca cggcgtgagg      60
gccccgacca agttcaccca gctgatgcag gacgtgaccc cggacgcctg gccgacctgg     120
ccggtgaagc tgggcgagct gacccccgag ggcggcgagc tgatcgccta cctgggccac     180
tactggaggc agaggctggt ggccgacggc ctgctgccga aggtgggctg cccgcagagc     240
ggccaggtgg ccatcatcgc cgacgtggac gagaggacca ggaagaccgg cgaggccttc     300
gccgccggcc tggcccccgga ctgcgccatc accgtgcacc accaggccga caccagcagc     360
ccggacccgc tgttcaaccc gctgaagacc ggcgtgtgcc agctggacga ggccaacgtg     420
agggacgcca tcctgaggag ggccggcggc agcatcgccg acttcaccag cactaccag     480 accgccttca gggagctgga gagggtgctg aacttcccgc agagcaacct ggccctgaag     540
agggagaagc aggacgagag cgccagcctg acccaggccc tgccgagcga gctgaaggtg     600
agcgccgacg acgtgagcct gaccggcgcc tggagcctgg ccagcatgct gaccgagatc     660
ttcctgctgc agcaggccca gggcatgccg agccgggct ggggcaggat caccgacagc     720
caccagtgga caccctgct gagcctgcac aacgccgtgt tcgacctgct gcagaggacc     780
ccggaggtgg ccaggagcgc cgccaccccg ctgctggacc tgatcaagac cgccctgacc     840
ccgcacccgc cgcagaagca ggcctacggc gtgaccctgc cgaccagcgt gctgttcatc     900
gccggccacg acaccaacct ggccaacctg ggcggcgccc tggagctgaa ctggaccctg     960
ccgggccagc cggacaacta cccgccgggc ggcgagctgg tgttcgagag gtggaggagg    1020
ctgagcgaca cagccagtg gatccaggtg agcctggtgt ccagacccct gcagcagatg    1080
```

-continued

| | |
|---|---|
| agggacaaga ccccgctgag cctgaacacc ccgccgggcg aggtgaagct gaccctggcc | 1140 |
| ggctgcgagg agaggaacgc ccagggcatg tgcagcctgg ccggcttcac ccagatcgtg | 1200 |
| aacgaggcca ggatcccggc ctgcagcctg tga | 1233 |

<210> SEQ ID NO 91
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 91

| | |
|---|---|
| cagagcgagc cggagctgaa gctggagagc gtggtgatcg tgagcaggca cggcgtgagg | 60 |
| gccccgacca agttcaccca gctgatgcag gacgtgaccc cggacgcctg gccgacctgg | 120 |
| ccggtgaagc tgggcgagct gaccccgagg ggcggcgagc tgatcgccta cctgggccac | 180 |
| tactggaggc agaggctggt ggccgacggc ctgctgccga aggtgggctg cccgcagagc | 240 |
| ggccaggtgg ccatcatcgc cgacgtggac gagaggacca ggaagaccgg cgaggccttc | 300 |
| gccgccggcc tggccccgga ctgcgccatc accgtgcacc accaggccga caccagcagc | 360 |
| ccggacccgc tgttcaaccc gctgaagacc ggcgtgtgcc agctggacga ggccaacgtg | 420 |
| agggacgcca tcctgaggag ggccggcggc agcatcgccg acttcaccag cactaccag | 480 |
| accgccttca gggagctgga gagggtgctg aacttcccgc agagcaacct gtgcctgaag | 540 |
| agggagaagc aggacgagag ctgcagcctg acccaggccc tgccgagcga gctgaaggtg | 600 |
| agcgccgacg acgtgagcct gaccggcgcc tggagcctgg ccagcatgct gaccgagatc | 660 |
| ttcctgctgc agcaggccca gggcatgccg agcccgggct ggggcaggat caccgacagc | 720 |
| caccagtgga acaccctgct gagcctgcac aacgccgtgt cgacctgct gcagaggacc | 780 |
| ccggaggtgg ccaggagcgc cgccacccg ctgctggacc tgatcaagac cgccctgacc | 840 |
| ccgcacccgc cgcagaagca ggcctacggc gtgaccctgc cgaccagcgt gctgttcatc | 900 |
| gccggccacg acaccaacct ggccaacctg gcggcgccc tggagctgaa ctggaccctg | 960 |
| ccgggccagc cggacaacta cccgccgggc ggcgagctgg tgttcgagag gtggaggagg | 1020 |
| ctgagcgaca cagccagtg gatccaggtg agcctggtgt ccagaccct gcagcagatg | 1080 |
| agggacaaga ccccgctgag cctgaacacc ccgccgggcg aggtgaagct gaccctggcc | 1140 |
| ggcgccgagg agaggaacgc ccagggcatg gccagcctgg ccggcttcac ccagatcgtg | 1200 |
| aacgaggcca ggatcccggc ctgcagcctg tga | 1233 |

<210> SEQ ID NO 92
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 92

| | |
|---|---|
| cagagcgagc cggagctgaa gctggagagc gtggtgatcg tgagcaggca cggcgtgagg | 60 |
| gccccgacca agttcaccca gctgatgcag gacgtgaccc cggacgcctg gccgacctgg | 120 |
| ccggtgaagc tgggcgagct gaccccgagg ggcggcgagc tgatcgccta cctgggccac | 180 |
| tactggaggc agaggctggt ggccgacggc ctgctgccga aggtgggctg cccgcagagc | 240 |
| ggccaggtgg ccatcatcgc cgacgtggac gagaggacca ggaagaccgg cgaggccttc | 300 |
| gccgccggcc tggccccgga ctgcgccatc accgtgcacc accaggccga caccagcagc | 360 |

```
ccggacccgc tgttcaaccc gctgaagacc ggcgtgtgcc agctggacga ggccaacgtg      420
agggacgcca tcctgaggag ggccggcggc agcatcgccg acttcaccag gcactaccag      480
accgccttca gggagctgga gagggtgctg aacttcccgc agagcaacct ggccctgaag      540
agggagaagc aggacgagag cgccagcctg acccaggccc tgccgagcga gctgaaggtg      600
agcgccgacg acgtgagcct gaccggcgcc tggagcctgg ccagcatgct gaccgagatc      660
ttcctgctgc agcaggccca gggcatgccg agcccgggct ggggcaggat caccgacagc      720
caccagtgga acaccctgct gagcctgcac aacgccgtgt cgacctgctg cagaggacc      780 ccggaggtgg ccaggagcgc cgccacccg ctgctggacc tgatcaagac cgccctgacc      840
ccgcacccgc cgcagaagca ggcctacggc gtgaccctgc cgaccagcgt gctgttcatc      900
gccggccacg acaccaacct ggccaacctg ggcggcgccc tggagctgaa ctggaccctg      960
ccgggccagc cggacaacta cccgccgggc ggcgagctgg tgttcgagag gtggaggagg     1020
ctgagcgaca cagccagtg gatccaggtg agcctggtgt ccagacccct gcagcagatg     1080
agggacaaga ccccgctgag cctgaacacc ccgccgggcg aggtgaagct gaccctggcc     1140
ggcgccgagg agaggaacgc ccagggcatg gccagcctgg ccggcttcac ccagatcgtg     1200
aacgaggcca ggatcccggc ctgcagcctg tga                                   1233
```

<210> SEQ ID NO 93
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 93

```
cagagcgagc cggagctgaa gctggagagc gtggtgatcg tgagcaggca cggcgtgagg       60
gccccgacca agttcaccca gctgatgcag gacgtgaccc cggacgcctg gccgacctgg      120
ccggtgaagc tgggcgagct gaccccgagg ggcggcgagc tgatcgccta cctgggccac      180
tactggaggc agaggctggt ggccgacggc ctgctgccga aggtgggcgc cccgcagagc      240
ggccaggtgg ccatcatcgc cgacgtggac gagaggacca ggaagaccgg cgaggccttc      300
gccgccggcc tggccccgga cgccgccatc accgtgcacc accaggccga caccagcagc      360
ccggacccgc tgttcaaccc gctgaagacc ggcgtgtgcc agctggacga ggccaacgtg      420
agggacgcca tcctgaggag ggccggcggc agcatcgccg acttcaccag gcactaccag      480
accgccttca gggagctgga gagggtgctg aacttcccgc agagcaacct gtgcctgaag      540
agggagaagc aggacgagag ctgcagcctg acccaggccc tgccgagcga gctgaaggtg      600
agcgccgacg acgtgagcct gaccggcgcc tggagcctgg ccagcatgct gaccgagatc      660
ttcctgctgc agcaggccca gggcatgccg agcccgggct ggggcaggat caccgacagc      720
caccagtgga acaccctgct gagcctgcac aacgccgtgt cgacctgctg cagaggacc      780 ccggaggtgg ccaggagcgc cgccacccg ctgctggacc tgatcaagac cgccctgacc      840
ccgcacccgc cgcagaagca ggcctacggc gtgaccctgc cgaccagcgt gctgttcatc      900
gccggccacg acaccaacct ggccaacctg ggcggcgccc tggagctgaa ctggaccctg      960
ccgggccagc cggacaacta cccgccgggc ggcgagctgg tgttcgagag gtggaggagg     1020
ctgagcgaca cagccagtg gatccaggtg agcctggtgt ccagacccct gcagcagatg     1080
agggacaaga ccccgctgag cctgaacacc ccgccgggcg aggtgaagct gaccctggcc     1140
ggctgcgagg agaggaacgc ccagggcatg tgcagcctgg ccggcttcac ccagatcgtg     1200
```
aacgaggcca ggatcccggc ctgcagcctg tga                          1233

<210> SEQ ID NO 94
<211> LENGTH: 1233
<212> TYPE: DNA
<213> ORGANISM: artificial sequence
<220> FEATURE:
<223> OTHER INFORMATION: maize codon optimized DNA sequence

<400> SEQUENCE: 94
cagagcgagc cggagctgaa gctggagagc gtggtgatcg tgagcaggca cggcgtgagg     60
gccccgacca agttcaccca gctgatgcag gacgtgaccc cggacgcctg gccgacctgg    120
ccggtgaagc tgggcgagct gaccccgagg ggcggcgagc tgatcgccta cctgggccac    180
tactggaggc agaggctggt ggccgacggc ctgctgccga aggtgggctg cccgcagagc    240
ggccaggtgg ccatcatcgc cgacgtggac gagaggacca ggaagaccgg cgaggccttc    300
gccgccggcc tggcccccga ctgcgccatc accgtgcacc accaggccga caccagcagc    360
ccggacccgc tgttcaaccc gctgaagacc ggcgtggccc agctggacga ggccaacgtg    420
agggacgcca tcctgaggag ggccggcggc agcatcgccg acttcaccag cactaccag     480
accgccttca gggagctgga gagggtgctg aacttcccgc agagcaacct gtgcctgaag    540
agggagaagc aggacgagag ctgcagcctg acccaggccc tgccgagcga gctgaaggtg    600
agcgccgacg acgtgagcct gaccggcgcc tggagcctgg ccagcatgct gaccgagatc    660
ttcctgctgc agcaggccca gggcatgccg gagccgggct ggggcaggat caccgacagc    720
caccagtgga acaccctgct gagcctgcac aacgccgtgt cgacctgct gcagaggacc     780
ccggaggtgg ccaggagcgc cgccaccccg ctgctggacc tgatcaagac cgccctgacc    840
ccgcacccgc gcagaagca ggcctacggc gtgaccctgc cgaccagcgt gctgttcatc     900
gccggccacg acaccaacct ggccaacctg gcggcgccc tggagctgaa ctggaccctg     960
ccgggccagc cggacaacta cccgccgggc ggcgagctgg tgttcgagag gtggaggagg   1020
ctgagcgaca cagccagtg gatccaggtg agcctggtgt ccagaccct gcagcagatg    1080
agggacaaga ccccgctgag cctgaacacc ccgccgggcg aggtgaagct gacccctggcc  1140
ggctgcgagg agaggaacgc ccagggcatg tgcagcctgg ccggcttcac ccagatcgtg  1200
aacgaggcca ggatcccggc cgccagcctg tga                                1233

<210> SEQ ID NO 95
<211> LENGTH: 1275
<212> TYPE: DNA
<213> ORGANISM: artificial sequence
<220> FEATURE:
<223> OTHER INFORMATION: maize codon optimized DNA sequence

<400> SEQUENCE: 95
caccaccacc accaccacgg cgccgacatc gagggcagga tgcagagcga gccggagctg     60
aagctggaga gcgtggtgat cgtgagcagg cacggcgtga gggcccccgac caaggccacc   120
cagctgatgc aggacgtgac cccgatcgag ttcttcaggc tgccggtgaa gctgggcgag    180
ctgaccccga ggggcggcga gctgatcgcc tacctgggcc actactggag gcagaggctg    240
gtggccgacg gcctgctgcc gaagtgcggc tgcccgcaga gcggccaggt ggccatcatc    300
gccgacgtgg acgagaggac caggaagacc ggcgaggcct tcgccgccgg cctggccccg    360
gactgcgcca tcaccgtgca cacccaggcc gacaccagca gccgggaccc gctgttcaac    420
ccgctgaaga ccggcgtgtg ccagctggac aacgccaacg tgaccgacgc catcctggag    480

```
agggccggcg gcagcatcgc cgacttcacc ggccactacc agaccgcctt cagggagctg      540
gagagggtgc tgaacttccc gcagagcaac ctgtgcctga gagggagaa gcaggacgag       600 agctgcagcc tgacccaggc cctgccgagc gagctgaagg tgagcgccga ctgcgtgagc      660
ctgaccggcg ccgtgagcct ggccagcatg ctgaccgaga tcttcctgct gcagcaggcc      720
cagggcatgc cggagccggg ctggggcagg atcaccgaca gccaccagtg aacaccctg       780 ctgagcctgc acaacgccca gttcgacctg ctgcagagga ccccgaggt ggccaggagc      840 agggccaccc cgctgctgga cctgatcaag accgccctga ccccgcaccc gccgcagaag     900
caggcctacg gcgtgaccct gccgaccagc gtgctgttca tcgccggcca cgacaccaac     960
ctggccaacc tgggcggcgc cctggagctg aactggaccc tgccgggcca gccggacaac    1020
accccgccgg gcgcgagct ggtgttcgag aggtggagga ggctgagcga caacagccag     1080
tggatccagg tgagcctggt gttccagacc ctgcagcaga tgagggacaa gaccccgctg    1140
agcctgaaca ccccgccggg cgaggtgaag ctgaccctgg ccggctgcga ggagaggaac    1200
gcccagggca tgtgcagcct ggccggcttc acccagatcg tgaacgaggc caggatcccg    1260
gcctgcagcc tgtga                                                     1275
```

<210> SEQ ID NO 96
<211> LENGTH: 1275
<212> TYPE: DNA
<213> ORGANISM: artificial sequence
<220> FEATURE:
<223> OTHER INFORMATION: maize codon optimized DNA sequence

<400> SEQUENCE: 96

```
caccaccacc accaccacgg cgccgacatc gagggcagga tgcagagcga gccggagctg       60
aagctggaga gcgtggtgat cgtgagcagg cacgcgtga gggccccgac caaggccacc      120
cagctgatgc aggacgtgac cccggacgcc tggccgacct ggccggtgaa gctgggcgag     180
ctgaccccga ggggcggcga gctgatcgcc tacctgggcc actactggag gcagaggctg     240
gtggccgacg gcctgctgcc gaagtgcggc tgcccgcaga gcggccaggt ggccatcatc     300
gccgacgtgg acgagaggac caggaagacc ggcgaggcct cgccgccgg cctggccccg     360 gactgcgcca tcaccgtgca caccccgacc gagttcttca ggctggaccc gctgttcaac     420
ccgctgaaga ccggcgtgtg ccagctggac aacgccaacg tgaccgacgc catcctggag     480
agggccggcg gcagcatcgc cgacttcacc ggccactacc agaccgcctt cagggagctg     540
gagagggtgc tgaacttccc gcagagcaac ctgtgcctga gagggagaa gcaggacgag      600 agctgcagcc tgacccaggc cctgccgagc gagctgaagg tgagcgccga ctgcgtgagc     660
ctgaccggcg ccgtgagcct ggccagcatg ctgaccgaga tcttcctgct gcagcaggcc     720
cagggcatgc cggagccggg ctggggcagg atcaccgaca gccaccagtg aacaccctg      780 ctgagcctgc acaacgccca gttcgacctg ctgcagagga ccccgaggt ggccaggagc     840 agggccaccc cgctgctgga cctgatcaag accgccctga ccccgcaccc gccgcagaag    900
caggcctacg gcgtgaccct gccgaccagc gtgctgttca tcgccggcca cgacaccaac    960
ctggccaacc tgggcggcgc cctggagctg aactggaccc tgccgggcca gccggacaac   1020
accccgccgg gcgcgagct ggtgttcgag aggtggagga ggctgagcga caacagccag    1080
tggatccagg tgagcctggt gttccagacc ctgcagcaga tgagggacaa gaccccgctg   1140
agcctgaaca ccccgccggg cgaggtgaag ctgaccctgg ccggctgcga ggagaggaac   1200
gcccagggca tgtgcagcct ggccggcttc acccagatcg tgaacgaggc caggatcccg   1260
```
gcctgcagcc tgtga                                                  1275

<210> SEQ ID NO 97
<211> LENGTH: 1275
<212> TYPE: DNA
<213> ORGANISM: artificial sequence
<220> FEATURE:
<223> OTHER INFORMATION: maize codon optimized DNA sequence

<400> SEQUENCE: 97
caccaccacc accaccacgg cgccgacatc gagggcagga tgcagagcga gccggagctg      60
aagctggaga gcgtggtgat cgtgagcagg cacggcgtga gggccccgac caaggccacc     120
cagctgatgc aggacgtgac cccggacgcc tggccgacct ggccggtgaa gctgggcgag     180
ctgaccccga gggcggcga gctgatcgcc tacctgggcc actactggag gcagaggctg     240
gtggccgacg gcctgctgcc gaagtgcggc tgcccgcaga gcggccaggt ggccatcatc     300
gccgacgtgg acgagaggac caggaagacc ggcgaggcct cgccgccgg cctggccccg     360
gactgcgcca tcaccgtgca cacccaggcc gacaccagca gcccgatcga gttcttcagg     420
ctgctgaaga ccggcgtgtg ccagctggac aacgccaacg tgaccgacgc catcctggag     480
agggccggcg gcagcatcgc cgacttcacc ggccactacc agaccgcctt cagggagctg     540
gagagggtgc tgaacttccc gcagagcaac ctgtgcctga gagggagaa gcaggacgag     600
agctgcagcc tgacccaggc cctgccgagc gagctgaagg tgagcgccga ctgcgtgagc     660
ctgaccggcg ccgtgagcct ggccagcatg ctgaccgaga tcttcctgct gcagcaggcc     720
cagggcatgc cggagccggg ctggggcagg atcaccgaca gccaccagtg gaacaccctg     780
ctgagcctgc acaacgccca gttcgacctg ctgcagagga ccccggaggt ggccaggagc     840
agggccaccc cgctgctgga cctgatcaag accgccctga cccgcaccc gccgcagaag     900
caggcctacg gcgtgaccct gccgaccagc gtgctgttca cgccggcca cgacaccaac     960
ctggccaacc tgggcggcgc cctggagctg aactggaccc tgccgggcca gccggacaac    1020
acccccgccgg gcggcgagct ggtgttcgag aggtggagga ggctgagcga caacagccag    1080
tggatccagg tgagcctggt gttccagacc ctgcagcaga tgaggacaa gaccccgctg    1140
agcctgaaca ccccgccggg cgaggtgaag ctgaccctgg ccggctgcga ggagaggaac    1200
gcccagggca tgtgcagcct ggccggcttc acccagatcg tgaacgaggc caggatcccg    1260
gcctgcagcc tgtga                                                    1275

<210> SEQ ID NO 98
<211> LENGTH: 1293
<212> TYPE: DNA
<213> ORGANISM: artificial sequence
<220> FEATURE:
<223> OTHER INFORMATION: maize codon optimized DNA sequence

<400> SEQUENCE: 98
caccaccacc accaccacgg cgccgacatc gagggcagga tgcagagcga gccggagctg      60
aagctggaga gcgtggtgat cgtgagcagg cacggcgtga gggccccgac caaggccacc     120
cagctgatgc aggacgtgac cccggacgcc tggccgacct ggccggtgaa gctgggcgag     180
ctgaccccga gggcggcga gctgatcgcc tacctgggcc actactggag gcagaggctg     240
gtggccgacg gcctgctgcc gaagtgcggc tgcccgcaga gcggccaggt ggccatcatc     300
gccgacgtgg acgagaggac caggaagacc ggcgaggcct cgccgccgg cctggccccg     360
gactgcgcca tcaccgtgca cacccaggcc gacaccagca gcccggaccc gctgttcaac     420

```
ccgctgaaga ccggcgtgtg ccagctggac aacgccaacg tgaccgacgc catcctggag    480
agggccggcg gcagcatcgc cgacttcacc ggccactacc agaccgcctt cagggagctg    540
gagagggtgc tgaacttccc gatcgagttc ttcaggctgc agagcaacct gtgcctgaag    600
agggagaagc aggacgagag ctgcagcctg acccaggccc tgccgagcga gctgaaggtg    660
agcgccgact gcgtgagcct gaccggcgcc gtgagcctgg ccagcatgct gaccgagatc    720
ttcctgctgc agcaggccca gggcatgccg agcccgggct ggggcaggat caccgacagc    780
caccagtgga cacccctgct gagcctgcac aacgcccagt cgacctgct gcagaggacc     840 ccggaggtgg ccaggagcag ggccaccccg ctgctggacc tgatcaagac cgccctgacc    900
ccgcacccgc cgcagaagca ggcctacggc gtgaccctgc cgaccagcgt gctgttcatc    960
gccggccacg acaccaacct ggccaacctg ggcggcgccc tggagctgaa ctggaccctg    1020
ccgggccagc cggacaacac cccgccgggc ggcgagctgg tgttcgagag gtggaggagg    1080
ctgagcgaca cagccagtg gatccaggtg agcctggtgt ccagaccct gcagcagatg      1140 agggacaaga ccccgctgag cctgaacacc ccgccgggcg aggtgaagct gaccctggcc    1200
ggctgcgagg agaggaacgc ccagggcatg tgcagcctgg ccggcttcac ccagatcgtg    1260
aacgaggcca ggatcccggc ctgcagcctg tga                                 1293

<210> SEQ ID NO 99
<211> LENGTH: 1275
<212> TYPE: DNA
<213> ORGANISM: artificial sequence
<220> FEATURE:
<223> OTHER INFORMATION: maize codon optimized DNA sequence

<400> SEQUENCE: 99
caccaccacc accaccacgg cgccgacatc gagggcagga tgcagagcga gccggagctg     60
aagctggaga gcgtggtgat cgtgagcagg cacggcgtga gggccccgac caaggccacc    120
cagctgatgc aggacgtgac cccggacgcc tggccgacct ggccggtgaa gctgggcgag    180
ctgaccccga ggggcggcga gctgatcgcc tacctggccc actactgag gcagaggctg     240 gtggccgacg gcctgctgcc gaagtgcggc tgcccgcaga gcggccaggt ggccatcatc    300
gccgacgtgg acgagaggac caggaagacc ggcgaggcct cgccgccgg cctggccccg      360 gactgcgcca tcaccgtgca cacccaggcc gacaccagca gcccggaccc gctgttcaac    420
ccgctgaaga ccggcgtgtg ccagctggac aacgccaacg tgaccgacgc catcctggag    480
agggccggcg gcagcatcgc cgacttcacc ggccactacc agaccgcctt cagggagctg    540
gagagggtgc tgaacttccc gcagagcaac ctgtgcctga gagggagaa gcaggacgag    600 agctgcagcc tgacccaggc cctgccgagc gagctgaagg tgagcgccga ctgcgtgagc    660
ctgaccggcg ccgtgagcct ggccagcatg ctgaccgaga tcttcctgct gcagcaggcc    720
cagggcatgc cgccgatcga gttcttcagg ctgaccgaca gccaccagtg gaacaccctg    780
ctgagcctgc acaacgccca gttcgacctg ctgcagagga cccggaggt ggccaggagc     840 agggccaccc cgctgctgga cctgatcaag accgccctga cccgcaccc gccgcagaag    900 caggcctacg gcgtgaccct gccgaccagc gtgctgttca tcgccggcca cgacaccaac    960
ctggccaacc tggcggcgc cctggagctg aactggaccc tgccgggcca gccggacaac    1020
accccgccgg gcggcgagct ggtgttcgag aggtggagga ggctgagcga caacagccag    1080
tggatccagg tgagcctggt gttccagacc ctgcagcaga tgagggacaa gaccccgctg    1140
agcctgaaca cccccgccggg cgaggtgaag ctgaccctgg ccggctgcga ggagaggaac    1200
```

| gcccagggca tgtgcagcct ggccggcttc acccagatcg tgaacgaggc caggatcccg | 1260 |
| gcctgcagcc tgtga | 1275 |

<210> SEQ ID NO 100
<211> LENGTH: 1275
<212> TYPE: DNA
<213> ORGANISM: artificial sequence
<220> FEATURE:
<223> OTHER INFORMATION: maize codon optimized DNA sequence

<400> SEQUENCE: 100

| caccaccacc accaccacgg cgccgacatc gagggcagga tgcagagcga gccggagctg | 60 |
| aagctggaga gcgtggtgat cgtgagcagg cacggcgtga gggccccgac caaggccacc | 120 |
| cagctgatgc aggacgtgac cccggacgcc tggccgacct ggccggtgaa gctgggcgag | 180 |
| ctgaccccga ggggcggcga gctgatcgcc tacctgggcc actactggag gcagaggctg | 240 |
| gtggccgacg gcctgctgcc gaagtgcggc tgcccgcaga gggccaggt ggccatcatc | 300 |
| gccgacgtgg acgagaggac caggaagacc ggcgaggcct cgccgccgg cctggccccg | 360 |
| gactgcgcca tcaccgtgca cacccaggcc gacaccagca gcccggaccc gctgttcaac | 420 |
| ccgctgaaga ccggcgtgtg ccagctggac aacgccaacg tgaccgacgc catcctggag | 480 |
| agggccggcg gcagcatcgc cgacttcacc ggccactacc agaccgcctt cagggagctg | 540 |
| gagagggtgc tgaacttccc gcagagcaac ctgtgcctga gagggagaa caggacgag | 600 |
| agctgcagcc tgacccaggc cctgccgagc gagctgaagg tgagcgccga ctgcgtgagc | 660 |
| ctgaccggcg ccgtgagcct ggccagcatg ctgaccgaga tcttcctgct gcagcaggcc | 720 |
| cagggcatgc cggagccggg ctggggcagg atcaccgaca gccaccagtg gaacaccctg | 780 |
| ctgagcctgc acaacgccca gttcgacctg ctgcagagga cccggaggt ggccaggagc | 840 |
| agggccaccc cgctgctgga cctgatcaag accgccctga cccgcaccc gccggagttc | 900 |
| ttcaggctgg gcgtgaccct gccgaccagc gtgctgttca cgccggcca cgacaccaac | 960 |
| ctggccaacc tgggcggcgc cctggagctg aactggaccc tgccgggcca gccggacaac | 1020 |
| accccgccgg gcggcgagct ggtgttcgag aggtggagga ggctgagcga caacagccag | 1080 |
| tggatccagg tgagcctggt gttccagacc ctgcagcaga tgaggacaa gaccccgctg | 1140 |
| agcctgaaca ccccgccggg cgaggtgaag ctgaccctgg ccggctgcga ggagaggaac | 1200 |
| gcccagggca tgtgcagcct ggccggcttc acccagatcg tgaacgaggc caggatcccg | 1260 |
| gcctgcagcc tgtga | 1275 |

<210> SEQ ID NO 101
<211> LENGTH: 1275
<212> TYPE: DNA
<213> ORGANISM: artificial sequence
<220> FEATURE:
<223> OTHER INFORMATION: maize codon optimized DNA sequence

<400> SEQUENCE: 101

| caccaccacc accaccacgg cgccgacatc gagggcagga tgcagagcga gccggagctg | 60 |
| aagctggaga gcgtggtgat cgtgagcagg cacggcgtga gggccccgac caaggccacc | 120 |
| cagctgatgc aggacgtgac cccggacgcc tggccgacct ggccggtgaa gctgggcgag | 180 |
| ctgaccccga ggggcggcga gctgatcgcc tacctgggcc actactggag gcagaggctg | 240 |
| gtggccgacg gcctgctgcc gaagtgcggc tgcccgcaga gggccaggt ggccatcatc | 300 |
| gccgacgtgg acgagaggac caggaagacc ggcgaggcct cgccgccgg cctggccccg | 360 |

```
gactgcgcca tcaccgtgca cacccaggcc gacaccagca gcccggaccc gctgttcaac        420
ccgctgaaga ccggcgtgtg ccagctggac aacgccaacg tgaccgacgc catcctggag        480
agggccggcg gcagcatcgc cgacttcacc ggccactacc agaccgcctt cagggagctg        540
gagagggtgc tgaacttccc gcagagcaac ctgtgcctga gagggagaa gcaggacgag         600 agctgcagcc tgacccaggc cctgccgagc gagctgaagg tgagcgccga ctgcgtgagc        660
ctgaccggcg ccgtgagcct ggccagcatg ctgaccgaga tcttcctgct gcagcaggcc        720
cagggcatgc cggagccggg ctggggcagg atcaccgaca gccaccagtg gaacaccctg        780
ctgagcctgc acaacgccca gttcgacctg ctgcagagga ccccggaggt ggccaggagc        840
agggccaccc cgctgctgga cctgatcaag accgccctga ccccgcaccc gccgcagaag        900
caggcctacg gcgtgaccct gccgaccagc gtgctgttca tcgccggcca cgacaccaac        960
ctggccaacc tgggcggcgc cctggagctg aacccgatcg agttcttcag gctggacaac       1020
accccgccgg gcggcgagct ggtgttcgag aggtggagga ggctgagcga caacagccag       1080
tggatccagg tgagcctggt gttccagacc ctgcagcaga tgagggacaa gaccccgctg       1140
agcctgaaca ccccgccggg cgaggtgaag ctgaccctgg ccggctgcga ggagaggaac       1200
gcccagggca tgtgcagcct ggccggcttc acccagatcg tgaacgaggc caggatcccg       1260
gcctgcagcc tgtga                                                        1275

<210> SEQ ID NO 102
<211> LENGTH: 1275
<212> TYPE: DNA
<213> ORGANISM: artificial sequence
<220> FEATURE:
<223> OTHER INFORMATION: maize codon optimized DNA sequence

<400> SEQUENCE: 102
caccaccacc accaccacgg cgccgacatc gagggcagga tgcagagcga gccggagctg         60
aagctggaga gcgtggtgat cgtgagcagg cacgcgtga gggccccgac caaggccacc        120
cagctgatgc aggacgtgac cccggacgcc tggccgacct ggccggtgaa gctgggcgag        180
ctgaccccga ggggcggcga gctgatcgcc tacctgggcc actactggag gcagaggctg        240
gtggccgacg gcctgctgcc gaagtgcggc tgcccgcaga gcggccaggt ggccatcatc        300
gccgacgtgg acgagaggac caggaagacc ggcgaggcct tcgccgccgg cctggccccg        360
gactgcgcca tcaccgtgca cacccaggcc gacaccagca gcccggaccc gctgttcaac        420
ccgctgaaga ccggcgtgtg ccagctggac aacgccaacg tgaccgacgc catcctggag        480
agggccggcg gcagcatcgc cgacttcacc ggccactacc agaccgcctt cagggagctg        540
gagagggtgc tgaacttccc gcagagcaac ctgtgcctga gagggagaa gcaggacgag         600 agctgcagcc tgacccaggc cctgccgagc gagctgaagg tgagcgccga ctgcgtgagc        660
ctgaccggcg ccgtgagcct ggccagcatg ctgaccgaga tcttcctgct gcagcaggcc        720
cagggcatgc cggagccggg ctggggcagg atcaccgaca gccaccagtg gaacaccctg        780
ctgagcctgc acaacgccca gttcgacctg ctgcagagga ccccggaggt ggccaggagc        840
agggccaccc cgctgctgga cctgatcaag accgccctga ccccgcaccc gccgcagaag        900
caggcctacg gcgtgaccct gccgaccagc gtgctgttca tcgccggcca cgacaccaac        960
ctggccaacc tgggcggcgc cctggagctg aactggaccc tgccgggcca gccggacaac       1020
accccgccgg gcggcgagct ggtgttcgag aggtggagga ggctgagcga caacagccag       1080
tggatccagg tgagcctggt gttccagacc ctgcagcaga tgagggacaa gccgccggag       1140
```

```
ttcttcaggc tgccgccggg cgaggtgaag ctgaccctgg ccggctgcga ggagaggaac   1200
gcccagggca tgtgcagcct ggccggcttc acccagatcg tgaacgaggc caggatcccg   1260
gcctgcagcc tgtga                                                    1275
```

<210> SEQ ID NO 103
<211> LENGTH: 411
<212> TYPE: PRT
<213> ORGANISM: Artificial Sequence
<220> FEATURE:
<223> OTHER INFORMATION: Engineered Protein

<400> SEQUENCE: 103

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Gly Gly Glu Leu Val Phe
                325                 330                 335

Glu Arg Trp Arg Arg Leu Ser Asp Asn Ser Gln Trp Ile Gln Val Ser
```

```
              340                 345                 350
Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 104
<211> LENGTH: 411
<212> TYPE: PRT
<213> ORGANISM: Artificial Sequence
<220> FEATURE:
<223> OTHER INFORMATION: engineered protein

<400> SEQUENCE: 104

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300
```

```
Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
            370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
            405                 410

<210> SEQ ID NO 105
<211> LENGTH: 411
<212> TYPE: PRT
<213> ORGANISM: Artificial Sequence
<220> FEATURE:
<223> OTHER INFORMATION: engineered protein

<400> SEQUENCE: 105

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Phe Tyr Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255
```

```
Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Leu Tyr Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 106
<211> LENGTH: 411
<212> TYPE: PRT
<213> ORGANISM: Artificial Sequence
<220> FEATURE:
<223> OTHER INFORMATION: engineered protein

<400> SEQUENCE: 106

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
```

```
                210                 215                 220
Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
                260                 265                 270

Leu Asp Leu Ile Lys Thr Ala Leu Thr Pro His Pro Pro Gln Lys Gln
                275                 280                 285

Ala Tyr Gly Val Thr Leu Pro Thr Ser Val Leu Phe Ile Ala Gly His
                290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Phe
                355                 360                 365

Leu Asn Thr Pro Pro Gly Glu Val Lys Leu Thr Leu Ala Gly Cys Glu
                370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 107
<211> LENGTH: 411
<212> TYPE: PRT
<213> ORGANISM: Artificial Sequence
<220> FEATURE:
<223> OTHER INFORMATION: Engineered protein

<400> SEQUENCE: 107

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
50                  55                  60

Gln Arg Leu Val Ala Asp Gly Leu Leu Pro Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
                100                 105                 110

Val His Thr Gln Ala Asp Thr Ser Ser Pro Asp Pro Leu Phe Asn Pro
            115                 120                 125

Leu Lys Thr Gly Val Cys Gln Leu Asp Asn Ala Gln Val Thr Asp Ala
            130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175
```

```
Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
            195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
            245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
            275                 280                 285

Ala Tyr Gly Val Thr Leu Pro Thr Ser Val Leu Phe Ile Ala Gly His
            290                 295                 300

Asp Thr Asn Leu Ala Asn Leu Gly Gly Ala Leu Glu Leu Leu Tyr Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
            370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
            405                 410

<210> SEQ ID NO 108
<211> LENGTH: 411
<212> TYPE: PRT
<213> ORGANISM: Artificial Sequence
<220> FEATURE:
<223> OTHER INFORMATION: Engineered protein

<400> SEQUENCE: 108

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125
```

```
Leu Lys Thr Gly Val Cys Gln Leu Asp Asn Ala Gln Val Thr Asp Ala
            130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
                195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
            275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Phe
                355                 360                 365

Leu Asn Thr Pro Pro Gly Glu Val Lys Leu Thr Leu Ala Gly Cys Glu
            370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 109
<211> LENGTH: 411
<212> TYPE: PRT
<213> ORGANISM: Artificial Sequence
<220> FEATURE:
<223> OTHER INFORMATION: Engineered protein

<400> SEQUENCE: 109

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
```

```
                   85                  90                  95
Thr Gly Glu Ala Phe Ala Gly Leu Ala Pro Asp Cys Ala Ile Thr
            100                 105                 110
Val His Thr Gln Ala Asp Thr Ser Ser Pro Asp Glu Leu Phe Asn Leu
        115                 120                 125
Leu Lys Thr Gly Val Cys Gln Leu Asp Asn Ala Gln Val Thr Asp Ala
    130                 135                 140
Ile Leu Glu Arg Ala Gly Gly Ser Ile Ala Asp Phe Thr Gly His Tyr
145                 150                 155                 160
Gln Thr Ala Phe Arg Glu Leu Glu Arg Val Leu Asn Phe Pro Gln Ser
                165                 170                 175
Asn Leu Cys Leu Lys Arg Glu Lys Gln Asp Glu Ser Cys Ser Leu Thr
            180                 185                 190
Gln Ala Leu Pro Ser Glu Leu Lys Val Ser Ala Asp Asn Val Ser Leu
        195                 200                 205
Thr Gly Ala Val Ser Leu Ala Ser Met Leu Thr Glu Ile Phe Leu Leu
    210                 215                 220
Gln Gln Ala Gln Gly Met Pro Glu Pro Gly Trp Gly Arg Ile Thr Asp
225                 230                 235                 240
Ser His Gln Trp Asn Thr Leu Leu Ser Leu His Asn Ala Gln Phe Asp
                245                 250                 255
Leu Leu Gln Arg Thr Pro Glu Val Ala Arg Ser Arg Ala Thr Pro Leu
            260                 265                 270
Leu Asp Leu Ile Lys Thr Ala Leu Thr Pro His Pro Gln Lys Gln
        275                 280                 285
Ala Tyr Gly Val Thr Leu Pro Thr Ser Val Leu Phe Ile Ala Gly His
    290                 295                 300
Asp Thr Asn Leu Ala Asn Leu Gly Gly Ala Leu Glu Leu Leu Tyr Thr
305                 310                 315                 320
Leu Pro Gly Gln Pro Asp Asn Thr Pro Gly Gly Glu Leu Val Phe
                325                 330                 335
Glu Arg Trp Arg Arg Leu Ser Asp Asn Ser Gln Trp Ile Gln Val Ser
            340                 345                 350
Leu Val Phe Gln Thr Leu Gln Gln Met Arg Asp Lys Thr Pro Leu Ser
        355                 360                 365
Leu Asn Thr Pro Pro Gly Glu Val Lys Leu Thr Leu Ala Gly Cys Glu
    370                 375                 380
Glu Arg Asn Ala Gln Gly Met Cys Ser Leu Ala Gly Phe Thr Gln Ile
385                 390                 395                 400
Val Asn Glu Ala Arg Ile Pro Ala Cys Ser Leu
                405                 410

<210> SEQ ID NO 110
<211> LENGTH: 411
<212> TYPE: PRT
<213> ORGANISM: Artificial Sequence
<220> FEATURE:
<223> OTHER INFORMATION: Engineered protein

<400> SEQUENCE: 110

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45
```

Thr Pro Arg Gly Gly Glu Leu Ile Ala Tyr Leu Gly His Tyr Trp Arg
          50                  55                  60

Gln Arg Leu Val Ala Asp Gly Leu Leu Pro Lys Lys Gly Cys Pro Gln
 65                  70                  75                  80

Ser Gly Gln Val Ala Ile Ile Ala Asp Val Asp Glu Arg Thr Arg Lys
                     85                  90                  95

Thr Gly Glu Ala Phe Ala Ala Gly Leu Ala Pro Asp Cys Ala Ile Thr
                100                 105                 110

Val His Thr Gln Ala Asp Thr Ser Ser Pro Asp Pro Leu Phe Tyr Val
            115                 120                 125

Leu Lys Thr Gly Val Cys Gln Leu Asp Asn Ala Gln Val Thr Asp Ala
        130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Phe
        355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 111
<211> LENGTH: 411
<212> TYPE: PRT
<213> ORGANISM: Artificial Sequence
<220> FEATURE:
<223> OTHER INFORMATION: Engineered protein

<400> SEQUENCE: 111

```
Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
            165                 170                 175

Asn Leu Cys Leu Lys Arg Glu Lys Gln Asp Glu Ser Cys Ser Leu Thr
        180                 185                 190

Gln Ala Leu Pro Ser Glu Leu Lys Val Ser Ala Asp Asn Val Ser Leu
    195                 200                 205

Thr Gly Ala Trp Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
            245                 250                 255

Leu Leu Gln Arg Thr Pro Glu Val Ala Arg Ser Arg Ala Thr Pro Leu
        260                 265                 270

Leu Asp Leu Ile Lys Thr Ala Leu Thr Pro His Pro Gln Lys Gln
    275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
        340                 345                 350

Leu Val Phe Gln Thr Leu Gln Gln Met Arg Asp Lys Thr Pro Leu Ser
    355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 112
```

-continued

```
<211> LENGTH: 411
<212> TYPE: PRT
<213> ORGANISM: Artificial Sequence
<220> FEATURE:
<223> OTHER INFORMATION: Engineered protein

<400> SEQUENCE: 112
```

| | | | | | | | | | | | | | | | |
|---|---|---|---|---|---|---|---|---|---|---|---|---|---|---|---|
| Met | Gln | Ser | Glu | Pro | Glu | Leu | Lys | Leu | Glu | Ser | Val | Val | Ile | Val | Ser |
| 1 | | | | 5 | | | | | 10 | | | | | 15 | |
| Arg | His | Gly | Val | Arg | Ala | Pro | Thr | Lys | Phe | Thr | Gln | Leu | Met | Gln | Asp |
| | | | 20 | | | | | 25 | | | | | 30 | | |
| Val | Thr | Pro | Asp | Ala | Phe | Tyr | Thr | Trp | Pro | Val | Lys | Leu | Gly | Glu | Leu |
| | | 35 | | | | | 40 | | | | | 45 | | | |
| Thr | Pro | Arg | Gly | Gly | Glu | Leu | Ile | Ala | Tyr | Leu | Gly | His | Tyr | Trp | Arg |
| | 50 | | | | | 55 | | | | | 60 | | | | |
| Gln | Arg | Leu | Val | Ala | Asp | Gly | Leu | Leu | Pro | Lys | Lys | Gly | Cys | Pro | Gln |
| 65 | | | | | 70 | | | | | 75 | | | | | 80 |
| Ser | Gly | Gln | Val | Ala | Ile | Ile | Ala | Asp | Val | Asp | Glu | Arg | Thr | Arg | Lys |
| | | | | 85 | | | | | 90 | | | | | 95 | |
| Thr | Gly | Glu | Ala | Phe | Ala | Ala | Gly | Leu | Ala | Pro | Asp | Cys | Ala | Ile | Thr |
| | | | 100 | | | | | 105 | | | | | 110 | | |
| Val | His | Thr | Gln | Ala | Asp | Thr | Ser | Ser | Pro | Asp | Pro | Leu | Phe | Asn | Pro |
| | | 115 | | | | | 120 | | | | | 125 | | | |
| Leu | Lys | Thr | Gly | Val | Cys | Gln | Leu | Asp | Val | Ala | Gln | Val | Thr | Asp | Ala |
| | 130 | | | | | 135 | | | | | 140 | | | | |
| Ile | Leu | Glu | Arg | Ala | Gly | Gly | Ser | Ile | Ala | Asp | Phe | Thr | Gly | His | Tyr |
| 145 | | | | | 150 | | | | | 155 | | | | | 160 |
| Gln | Thr | Ala | Phe | Arg | Glu | Leu | Glu | Arg | Val | Leu | Asn | Phe | Pro | Gln | Ser |
| | | | | 165 | | | | | 170 | | | | | 175 | |
| Asn | Leu | Cys | Leu | Lys | Arg | Glu | Lys | Gln | Asp | Glu | Ser | Cys | Ser | Leu | Thr |
| | | | 180 | | | | | 185 | | | | | 190 | | |
| Gln | Ala | Leu | Pro | Ser | Glu | Leu | Lys | Val | Ser | Ala | Asp | Asn | Val | Ser | Leu |
| | | 195 | | | | | 200 | | | | | 205 | | | |
| Thr | Gly | Ala | Trp | Ser | Leu | Ala | Ser | Met | Leu | Thr | Glu | Ile | Phe | Leu | Leu |
| | 210 | | | | | 215 | | | | | 220 | | | | |
| Gln | Gln | Ala | Gln | Gly | Met | Pro | Glu | Pro | Gly | Trp | Gly | Arg | Ile | Thr | Asp |
| 225 | | | | | 230 | | | | | 235 | | | | | 240 |
| Ser | His | Gln | Trp | Asn | Thr | Leu | Leu | Ser | Leu | His | Asn | Ala | Gln | Phe | Asp |
| | | | | 245 | | | | | 250 | | | | | 255 | |
| Leu | Leu | Gln | Arg | Thr | Pro | Glu | Val | Ala | Arg | Ser | Arg | Ala | Thr | Pro | Leu |
| | | | 260 | | | | | 265 | | | | | 270 | | |
| Leu | Asp | Leu | Ile | Lys | Thr | Ala | Leu | Thr | Pro | His | Pro | Gln | Lys | Gln |
| | | 275 | | | | | 280 | | | | | 285 | | | |
| Ala | Tyr | Gly | Val | Thr | Leu | Pro | Thr | Ser | Val | Leu | Phe | Ile | Ala | Gly | His |
| | | 290 | | | | | 295 | | | | | 300 | | | |
| Asp | Thr | Asn | Leu | Ala | Asn | Leu | Gly | Gly | Ala | Leu | Glu | Leu | Gln | Trp | Thr |
| 305 | | | | | 310 | | | | | 315 | | | | | 320 |
| Leu | Pro | Gly | Gln | Pro | Asp | Asn | Thr | Pro | Pro | Gly | Gly | Glu | Leu | Val | Phe |
| | | | | 325 | | | | | 330 | | | | | 335 | |
| Glu | Arg | Trp | Arg | Arg | Leu | Ser | Asp | Asn | Ser | Gln | Trp | Ile | Gln | Val | Ser |
| | | | 340 | | | | | 345 | | | | | 350 | | |
| Leu | Val | Phe | Gln | Thr | Leu | Gln | Gln | Met | Arg | Asp | Lys | Thr | Pro | Leu | Ser |
| | | 355 | | | | | 360 | | | | | 365 | | | |
| Leu | Asn | Thr | Pro | Pro | Gly | Glu | Val | Lys | Leu | Thr | Leu | Ala | Gly | Cys | Glu |
| | 370 | | | | | 375 | | | | | 380 | | | | |

```
Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 113
<211> LENGTH: 411
<212> TYPE: PRT
<213> ORGANISM: Artificial Sequence
<220> FEATURE:
<223> OTHER INFORMATION: Engineered protein

<400> SEQUENCE: 113

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Glu Leu Phe Asn Leu
        115                 120                 125

Leu Lys Thr Gly Val Cys Gln Leu Asp Val Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Trp Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
```

```
                         340                 345                 350
Leu Val Phe Gln Thr Leu Gln Gln Met Arg Asp Lys Thr Pro Leu Ser
                355                 360                 365
Leu Asn Thr Pro Pro Gly Glu Val Lys Leu Thr Leu Ala Gly Cys Glu
            370                 375                 380
Glu Arg Asn Ala Gln Gly Met Cys Ser Leu Ala Gly Phe Thr Gln Ile
385                 390                 395                 400
Val Asn Glu Ala Arg Ile Pro Ala Cys Ser Leu
                405                 410

<210> SEQ ID NO 114
<211> LENGTH: 411
<212> TYPE: PRT
<213> ORGANISM: Artificial Sequence
<220> FEATURE:
<223> OTHER INFORMATION: Engineered protein

<400> SEQUENCE: 114

Met Gln Ser Glu Pro Glu Leu Lys Leu Glu Ser Val Val Ile Val Ser
1               5                   10                  15
Arg His Gly Val Arg Ala Pro Thr Lys Phe Thr Gln Leu Met Gln Asp
                20                  25                  30
Val Thr Pro Asp Ala Trp Pro Thr Trp Pro Val Lys Leu Gly Glu Leu
            35                  40                  45
Thr Pro Arg Gly Gly Glu Leu Ile Ala Tyr Leu Gly His Tyr Trp Arg
        50                  55                  60
Gln Arg Leu Val Ala Asp Gly Leu Leu Pro Lys Lys Gly Cys Pro Gln
65                  70                  75                  80
Ser Gly Gln Val Ala Ile Ile Ala Asp Val Asp Glu Arg Thr Arg Lys
                85                  90                  95
Thr Gly Glu Ala Phe Ala Ala Gly Leu Ala Pro Asp Cys Ala Ile Thr
            100                 105                 110
Val His Thr Gln Ala Asp Thr Ser Ser Pro Asp Pro Leu Phe Tyr Val
        115                 120                 125
Leu Lys Thr Gly Val Cys Gln Leu Asp Val Ala Gln Val Thr Asp Ala
    130                 135                 140
Ile Leu Glu Arg Ala Gly Gly Ser Ile Ala Asp Phe Thr Gly His Tyr
145                 150                 155                 160
Gln Thr Ala Phe Arg Glu Leu Glu Arg Val Leu Asn Phe Pro Gln Ser
                165                 170                 175
Asn Leu Cys Leu Lys Arg Glu Lys Gln Asp Glu Ser Cys Ser Leu Thr
            180                 185                 190
Gln Ala Leu Pro Ser Glu Leu Lys Val Ser Ala Asp Asn Val Ser Leu
        195                 200                 205
Thr Gly Ala Trp Ser Leu Ala Ser Met Leu Thr Glu Ile Phe Leu Leu
    210                 215                 220
Gln Gln Ala Gln Gly Met Pro Glu Pro Gly Trp Gly Arg Ile Thr Asp
225                 230                 235                 240
Ser His Gln Trp Asn Thr Leu Leu Ser Leu His Asn Ala Gln Phe Asp
                245                 250                 255
Leu Leu Gln Arg Thr Pro Glu Val Ala Arg Ser Arg Ala Thr Pro Leu
            260                 265                 270
Leu Asp Leu Ile Lys Thr Ala Leu Thr Pro His Pro Pro Gln Lys Gln
        275                 280                 285
Ala Tyr Gly Val Thr Leu Pro Ser Val Leu Phe Ile Ala Gly His
    290                 295                 300
```

```
Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
        340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
            405                 410

<210> SEQ ID NO 115
<211> LENGTH: 411
<212> TYPE: PRT
<213> ORGANISM: Artificial Sequence
<220> FEATURE:
<223> OTHER INFORMATION: Engineered protein

<400> SEQUENCE: 115

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Trp Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Ser Leu His Asn Ala Gln Phe Asp
                245                 250                 255
```

```
Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Leu Tyr Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 116
<211> LENGTH: 411
<212> TYPE: PRT
<213> ORGANISM: Artificial Sequence
<220> FEATURE:
<223> OTHER INFORMATION: Engineered protein

<400> SEQUENCE: 116

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Trp Ser Leu Ala Ser Met Leu Thr Glu Ile Phe Leu Leu
```

-continued

```
                210                 215                 220
Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
                260                 265                 270

Leu Asp Leu Ile Lys Thr Ala Leu Thr Pro His Pro Pro Gln Lys Gln
                275                 280                 285

Ala Tyr Gly Val Thr Leu Pro Thr Ser Val Leu Phe Ile Ala Gly His
                290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Phe
                355                 360                 365

Leu Asn Thr Pro Pro Gly Glu Val Lys Leu Thr Leu Ala Gly Cys Glu
                370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410
```

<210> SEQ ID NO 117
<211> LENGTH: 411
<212> TYPE: PRT
<213> ORGANISM: Artificial Sequence
<220> FEATURE:
<223> OTHER INFORMATION: Engineered protein

<400> SEQUENCE: 117

```
Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
                100                 105                 110

Val His Thr Gln Ala Asp Thr Ser Ser Pro Asp Glu Leu Phe Asn Leu
            115                 120                 125

Leu Lys Thr Gly Val Cys Gln Leu Asp Val Ala Gln Val Thr Asp Ala
        130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175
```

```
Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
            195                 200                 205

Thr Gly Ala Trp Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
            245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
            275                 280                 285

Ala Tyr Gly Val Thr Leu Pro Thr Ser Val Leu Phe Ile Ala Gly His
            290                 295                 300

Asp Thr Asn Leu Ala Asn Leu Gly Gly Ala Leu Glu Leu Leu Tyr Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
            370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 118
<211> LENGTH: 411
<212> TYPE: PRT
<213> ORGANISM: Artificial Sequence
<220> FEATURE:
<223> OTHER INFORMATION: Engineered protein

<400> SEQUENCE: 118

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Tyr Val
        115                 120                 125
```

```
Leu Lys Thr Gly Val Cys Gln Leu Asp Val Ala Gln Val Thr Asp Ala
            130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
                195                 200                 205

Thr Gly Ala Trp Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
            245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
            275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Phe
            355                 360                 365

Leu Asn Thr Pro Pro Gly Glu Val Lys Leu Thr Leu Ala Gly Cys Glu
            370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 119
<211> LENGTH: 411
<212> TYPE: PRT
<213> ORGANISM: Artificial Sequence
<220> FEATURE:
<223> OTHER INFORMATION: Engineered protein

<400> SEQUENCE: 119

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
```

```
            85                  90                  95
Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
            115                 120                 125

Leu Lys Thr Gly Val Cys Gln Leu Asp Val Ala Gln Val Thr Asp Ala
            130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Ala Leu Lys Arg Glu Lys Gln Asp Glu Ser Ala Ser Leu Thr
            180                 185                 190

Gln Ala Leu Pro Ser Glu Leu Lys Val Ser Ala Asp Asn Val Ser Leu
            195                 200                 205

Thr Gly Ala Trp Ser Leu Ala Ser Met Leu Thr Glu Ile Phe Leu Leu
            210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
            275                 280                 285

Ala Tyr Gly Val Thr Leu Pro Thr Ser Val Leu Phe Ile Ala Gly His
            290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
            370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 120
<211> LENGTH: 411
<212> TYPE: PRT
<213> ORGANISM: Artificial Sequence
<220> FEATURE:
<223> OTHER INFORMATION: Engineered protein

<400> SEQUENCE: 120

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Phe Tyr Thr Trp Pro Val Lys Leu Gly Glu Leu
        35                  40                  45
```

Thr Pro Arg Gly Gly Glu Leu Ile Ala Tyr Leu Gly His Tyr Trp Arg
 50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Gln Val Thr Asp Ala
130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Ala Leu Lys Arg Glu Lys Gln Asp Glu Ser Ala Ser Leu Thr
            180                 185                 190

Gln Ala Leu Pro Ser Glu Leu Lys Val Ser Ala Asp Asn Val Ser Leu
        195                 200                 205

Thr Gly Ala Trp Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Leu Tyr Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 121
<211> LENGTH: 411
<212> TYPE: PRT
<213> ORGANISM: Artificial Sequence
<220> FEATURE:
<223> OTHER INFORMATION: Engineered protein

<400> SEQUENCE: 121

-continued

```
Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Ala Leu Lys Arg Glu Lys Gln Asp Glu Ser Ala Ser Leu Thr
            180                 185                 190

Gln Ala Leu Pro Ser Glu Leu Lys Val Ser Ala Asp Asn Val Ser Leu
        195                 200                 205

Thr Gly Ala Trp Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Phe
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410
```

<210> SEQ ID NO 122

<211> LENGTH: 411
<212> TYPE: PRT
<213> ORGANISM: Artificial Sequence
<220> FEATURE:
<223> OTHER INFORMATION: Engineered protein

<400> SEQUENCE: 122

```
Met Gln Ser Glu Pro Glu Leu Lys Leu Glu Ser Val Val Ile Val Ser
1               5                   10                  15
Arg His Gly Val Arg Ala Pro Thr Lys Phe Thr Gln Leu Met Gln Asp
            20                  25                  30
Val Thr Pro Asp Ala Trp Pro Thr Trp Pro Val Lys Leu Gly Glu Leu
        35                  40                  45
Thr Pro Arg Gly Gly Glu Leu Ile Ala Tyr Leu Gly His Tyr Trp Arg
    50                  55                  60
Gln Arg Leu Val Ala Asp Gly Leu Leu Pro Lys Lys Gly Cys Pro Gln
65                  70                  75                  80
Ser Gly Gln Val Ala Ile Ile Ala Asp Val Asp Glu Arg Thr Arg Lys
                85                  90                  95
Thr Gly Glu Ala Phe Ala Ala Gly Leu Ala Pro Asp Cys Ala Ile Thr
            100                 105                 110
Val His Thr Gln Ala Asp Thr Ser Ser Pro Asp Pro Leu Phe Asn Pro
        115                 120                 125
Leu Lys Thr Gly Val Ala Gln Leu Asp Val Ala Gln Val Thr Asp Ala
    130                 135                 140
Ile Leu Glu Arg Ala Gly Gly Ser Ile Ala Asp Phe Thr Gly His Tyr
145                 150                 155                 160
Gln Thr Ala Phe Arg Glu Leu Glu Arg Val Leu Asn Phe Pro Gln Ser
                165                 170                 175
Asn Leu Cys Leu Lys Arg Glu Lys Gln Asp Glu Ser Cys Ser Leu Thr
            180                 185                 190
Gln Ala Leu Pro Ser Glu Leu Lys Val Ser Ala Asp Asn Val Ser Leu
        195                 200                 205
Thr Gly Ala Trp Ser Leu Ala Ser Met Leu Thr Glu Ile Phe Leu Leu
    210                 215                 220
Gln Gln Ala Gln Gly Met Pro Glu Pro Gly Trp Gly Arg Ile Thr Asp
225                 230                 235                 240
Ser His Gln Trp Asn Thr Leu Leu Ser Leu His Asn Ala Gln Phe Asp
                245                 250                 255
Leu Leu Gln Arg Thr Pro Glu Val Ala Arg Ser Arg Ala Thr Pro Leu
            260                 265                 270
Leu Asp Leu Ile Lys Thr Ala Leu Thr Pro His Pro Pro Gln Lys Gln
    275                 280                 285
Ala Tyr Gly Val Thr Leu Pro Thr Ser Val Leu Phe Ile Ala Gly His
    290                 295                 300
Asp Thr Asn Leu Ala Asn Leu Gly Gly Ala Leu Glu Leu Gln Trp Thr
305                 310                 315                 320
Leu Pro Gly Gln Pro Asp Asn Thr Pro Pro Gly Gly Glu Leu Val Phe
                325                 330                 335
Glu Arg Trp Arg Arg Leu Ser Asp Asn Ser Gln Trp Ile Gln Val Ser
            340                 345                 350
Leu Val Phe Gln Thr Leu Gln Gln Met Arg Asp Lys Thr Pro Leu Ser
        355                 360                 365
Leu Asn Thr Pro Pro Gly Glu Val Lys Leu Thr Leu Ala Gly Cys Glu
    370                 375                 380
```

```
Glu Arg Asn Ala Gln Gly Met Cys Ser Leu Ala Gly Phe Thr Gln Ile
385                 390                 395                 400

Val Asn Glu Ala Arg Ile Pro Ala Ala Ser Leu
            405                 410

<210> SEQ ID NO 123
<211> LENGTH: 411
<212> TYPE: PRT
<213> ORGANISM: Artificial Sequence
<220> FEATURE:
<223> OTHER INFORMATION: Engineered protein

<400> SEQUENCE: 123

Met Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Ala Gln Leu Asp Val Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asn Val Ser Leu
        195                 200                 205

Thr Gly Ala Trp Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
```

```
            340                 345                 350
Leu Val Phe Gln Thr Leu Gln Gln Met Arg Asp Lys Thr Pro Leu Phe
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Ala Ser Leu
                405                 410

<210> SEQ ID NO 124
<211> LENGTH: 1236
<212> TYPE: DNA
<213> ORGANISM: Artificial Sequence
<220> FEATURE:
<223> OTHER INFORMATION: Engineered DNA

<400> SEQUENCE: 124
atgcagagcg aaccggaact gaaactggaa agcgtggtga ttgtgagccg tcatggcgtt      60
cgtgcgccga ccaaagcgac ccagctgatg caggatgtga ccccggatgc gtggccgacc     120
tggccggtga actgggcga actgaccccg cgtggcggcg aactgattgc gtatctgggc      180
cattattggc gtcagcgtct ggtggcggat ggcctgctgc cgaaaaaagg ttgcccgcag     240
agcggtcagg tggcgattat tgcggatgtg atgaacgta cccgtaaaac cggcgaagcg     300
tttgcggccg tctggccccc ggattgcgcg attaccgtgc ataccaggc ggataccagc      360 agcccggacc cgctgtttaa tccgctgaaa accggcgtgt gccagctgga taacgcgcag     420
gtgaccgatg cgattctgga acgtgcgggc ggtagcattg cggatttac cggccattat      480 cagaccgcgt tcgtgaact ggaacgtgtg ctgaactttc gcagagcaa cctgtgcctg       540 aaacgtgaaa acaggatga agctgctct ctgacgcagg ccctgccgag cgaactgaaa       600
gtgagcgcgg ataacgtgag cctgaccggt gcggttagcc tggccagcat gctgaccgaa     660
atttttctgc tgcaacaagc gcagggtatg ccggaaccgg ctggggccg tattaccgat      720 agccatcagt ggaacaccct gctgtctctg cataacgcgc agtttgatct gctgcaacgt     780
accccggaag ttgcgcgtag ccgtgcgacc ccgctgctgg atctgattaa accgcgctg     840 accccgcatc cgccgcagaa acaggcgtat ggcgtgaccc tgccgaccag cgtgctgttt     900
attgcgggcc atgataccaa cctggccaat ctgggcggtg cgctggaact gcagtggacc     960
ctgccgggcc agccggataa tactccgccg ggtggtgaac tggtgtttga cgttggcgt    1020 cgtctgagcg ataacagcca gtggattcag gtgagcctgg tgtttcagac cctgcagcag    1080
atgcgtgata aaccccgct gtctctgaac accccaccgg gtgaagtgaa actgaccctg    1140
gccggctgcg aagaacgtaa cgcgcagggc atgtgtagcc tggccggctt tacccagatt    1200
gtgaacgaag cgcgtattcc ggcgtgtagc ctgtaa                              1236

<210> SEQ ID NO 125
<211> LENGTH: 1236
<212> TYPE: DNA
<213> ORGANISM: Artificial Sequence
<220> FEATURE:
<223> OTHER INFORMATION: Engineered DNA

<400> SEQUENCE: 125
atgcagagcg aaccggaact gaaactggaa agcgtggtga ttgtgagccg tcatggcgtt      60
cgtgcgccga ccaaagcgac ccagctgatg caggatgtga ccccggatgc gttttatacc    120
```

```
tggccggtga aactgggcga actgaccccg cgtggcggcg aactgattgc gtatctgggc      180
cattattggc gtcagcgtct ggtggcggat ggcctgctgc cgaaaaaagg ttcccgcag      240 agcggtcagg tggcgattat tgcggatgtg gatgaacgta cccgtaaaac cggcgaagcg      300
tttgcggccg gtctggcccc ggattgcgcg attaccgtgc atacccaggc ggataccagc      360
agcccggacc cgctgtttaa tccgctgaaa accggcgtgt gccagctgga taacgcgcag      420
gtgaccgatg cgattctgga acgtgcgggc ggtagcattg cggattttac cggccattat      480
cagaccgcgt tcgtgaact ggaacgtgtg ctgaactttc gcagagcaa cctgtgcctg      540 aaacgtgaaa acaggatga agctgctct ctgacgcagg ccctgccgag cgaactgaaa      600
gtgagcgcgg ataacgtgag cctgaccggt gcggttagcc tggccagcat gctgaccgaa      660
atttttctgc tgcaacaagc gcagggtatg ccggaaccgg gctggggccg tattaccgat      720
agccatcagt ggaacaccct gctgtctctg cataacgcgc agtttgatct gctgcaacgt      780
accccggaag ttgcgcgtag ccgtgcgacc ccgctgctgg atctgattaa aaccgcgctg      840
accccgcatc cgccgcagaa acaggcgtat ggcgtgaccc tgccgaccag cgtgctgttt      900
attgcgggcc atgataccaa cctggccaat ctgggcggtg cgctggaact gcagtggacc      960
ctgccgggcc agccggataa tactccgccg ggtggtgaac tggtgtttga acgttggcgt     1020
cgtctgagcg ataacagcca gtggattcag gtgagcctgg tgtttcagac cctgcagcag     1080
atgcgtgata aacccccgct gtctctgaac accccaccgg gtgaagtgaa actgaccctg     1140
gccggctgcg aagaacgtaa cgcgcagggc atgtgtagcc tggccggctt tacccagatt     1200
gtgaacgaag cgcgtattcc ggcgtgtagc ctgtaa                              1236
```

<210> SEQ ID NO 126
<211> LENGTH: 1236
<212> TYPE: DNA
<213> ORGANISM: Artificial Sequence
<220> FEATURE:
<223> OTHER INFORMATION: Engineered DNA

<400> SEQUENCE: 126

```
atgcagagcg aaccggaact gaaactggaa agcgtggtga ttgtgagccg tcatggcgtt       60
cgtgcgccga ccaaagcgac ccagctgatg caggatgtga ccccggatgc gtttataccc      120
tggccggtga aactgggcga actgaccccg cgtggcggcg aactgattgc gtatctgggc      180
cattattggc gtcagcgtct ggtggcggat ggcctgctgc cgaaaaaagg ttcccgcag      240 agcggtcagg tggcgattat tgcggatgtg gatgaacgta cccgtaaaac cggcgaagcg      300
tttgcggccg gtctggcccc ggattgcgcg attaccgtgc atacccaggc ggataccagc      360
agcccggacc cgctgtttaa tccgctgaaa accggcgtgt gccagctgga taacgcgcag      420
gtgaccgatg cgattctgga acgtgcgggc ggtagcattg cggattttac cggccattat      480
cagaccgcgt tcgtgaact ggaacgtgtg ctgaactttc gcagagcaa cctgtgcctg      540 aaacgtgaaa acaggatga agctgctct ctgacgcagg ccctgccgag cgaactgaaa      600
gtgagcgcgg ataacgtgag cctgaccggt gcggttagcc tggccagcat gctgaccgaa      660
atttttctgc tgcaacaagc gcagggtatg ccggaaccgg gctggggccg tattaccgat      720
agccatcagt ggaacaccct gctgtctctg cataacgcgc agtttgatct gctgcaacgt      780
accccggaag ttgcgcgtag ccgtgcgacc ccgctgctgg atctgattaa aaccgcgctg      840
accccgcatc cgccgcagaa acaggcgtat ggcgtgaccc tgccgaccag cgtgctgttt      900
attgcgggcc atgataccaa cctggccaat ctgggcggtg cgctggaact gctgtatacc      960
```

```
ctgccgggcc agccggataa tactccgccg ggtggtgaac tggtgtttga acgttggcgt    1020
cgtctgagcg ataacagcca gtggattcag gtgagcctgg tgtttcagac cctgcagcag    1080
atgcgtgata aaccccgct gtctctgaac accccaccgg gtgaagtgaa actgaccctg     1140
gccggctgcg aagaacgtaa cgcgcagggc atgtgtagcc tggccggctt tacccagatt    1200
gtgaacgaag cgcgtattcc ggcgtgtagc ctgtaa                              1236
```

<210> SEQ ID NO 127
<211> LENGTH: 1236
<212> TYPE: DNA
<213> ORGANISM: Artificial Sequence
<220> FEATURE:
<223> OTHER INFORMATION: Engineered DNA

<400> SEQUENCE: 127

```
atgcagagcg aaccggaact gaaactggaa agcgtggtga ttgtgagccg tcatggcgtt    60
cgtgcgccga ccaaagcgac ccagctgatg caggatgtga ccccggatgc gttttatacc    120
tggccggtga actgggcga actgaccccg cgtggcggcg aactgattgc gtatctgggc     180
cattattggc gtcagcgtct ggtggcggat ggcctgctgc cgaaaaaagg ttgcccgcag    240
agcggtcagg tggcgattat tgcggatgtg atgaacgta cccgtaaaac cggcgaagcg     300
tttgcggccg gtctggcccc ggattgcgcg attaccgtgc ataccaggc ggataccagc     360 agcccggacc cgctgtttaa tccgctgaaa accggcgtgt gccagctgga taacgcgcag    420
gtgaccgatg cgattctgga acgtgcgggc ggtagcattg cggattttac cggccattat    480
cagaccgcgt ttcgtgaact ggaacgtgtg ctgaactttc gcagagcaa cctgtgcctg    540 aaacgtgaaa acaggatga agctgctct ctgacgcagg ccctgccgag cgaactgaaa     600
gtgagcgcgg ataacgtgag cctgaccggt gcggttagcc tggccagcat gctgaccgaa    660
atttttctgc tgcaacaagc gcagggtatg ccggaaccgg gctggggccg tattaccgat    720
agccatcagt ggaacaccct gctgtctctg cataacgcg agtttgatct gctgcaacgt    780
accccggaag ttgcgcgtag ccgtgcgacc ccgctgctgg atctgattaa aaccgcgctg    840
accccgcatc cgccgcagaa acaggcgtat ggcgtgaccc tgccgaccag cgtgctgttt    900
attgcgggcc atgataccaa cctggccaat ctgggcggtg cgctggaact gcagtggacc    960
ctgccgggcc agccggataa tactccgccg ggtggtgaac tggtgtttga acgttggcgt    1020
cgtctgagcg ataacagcca gtggattcag gtgagcctgg tgtttcagac cctgcagcag    1080
atgcgtgata aaccccgct gtttctgaac accccaccgg gtgaagtgaa actgaccctg     1140
gccggctgcg aagaacgtaa cgcgcagggc atgtgtagcc tggccggctt tacccagatt    1200
gtgaacgaag cgcgtattcc ggcgtgtagc ctgtaa                              1236
```

<210> SEQ ID NO 128
<211> LENGTH: 1236
<212> TYPE: DNA
<213> ORGANISM: Artificial Sequence
<220> FEATURE:
<223> OTHER INFORMATION: Engineered DNA

<400> SEQUENCE: 128

```
atgcagagcg aaccggaact gaaactggaa agcgtggtga ttgtgagccg tcatggcgtt    60
cgtgcgccga ccaaagcgac ccagctgatg caggatgtga ccccggatgc gtggccgacc    120
tggccggtga actgggcga actgaccccg cgtggcggcg aactgattgc gtatctgggc     180
cattattggc gtcagcgtct ggtggcggat ggcctgctgc cgaaaaaagg ttgcccgcag    240
```

```
agcggtcagg tggcgattat tgcggatgtg gatgaacgta cccgtaaaac cggcgaagcg    300
tttgcggccg gtctggcccc ggattgcgcg attaccgtgc atacccaggc ggataccagc    360
agcccggacc cgctgtttaa tccgctgaaa accggcgtgt gccagctgga taacgcgcag    420
gtgaccgatg cgattctgga acgtgcgggc ggtagcattg cggattttac cggccattat    480
cagaccgcgt tcgtgaact  ggaacgtgtg ctgaactttc gcagagcaa  cctgtgcctg    540
aaacgtgaaa acaggatga  aagctgctct ctgacgcagg ccctgccgag cgaactgaaa    600
gtgagcgcgg ataacgtgag cctgaccggt gcggttagcc tggccagcat gctgaccgaa    660
atttttctgc tgcaacaagc gcagggtatg ccggaaccgg gctggggccg tattaccgat    720
agccatcagt ggaacaccct gctgtctctg cataacgcgc agtttgatct gctgcaacgt    780
accccggaag ttgcgcgtag ccgtgcgacc ccgctgctgg atctgattaa aaccgcgctg    840
accccgcatc cgccgcagaa acaggcgtat ggcgtgaccc tgccgaccag cgtgctgttt    900
attgcgggcc atgataccaa cctggccaat ctgggcggtg cgctggaact gctgtatacc    960
ctgccgggcc agccggataa tactccgccg ggtggtgaac tggtgtttga acgttggcgt   1020
cgtctgagcg ataacagcca gtggattcag gtgagcctgg tgtttcagac cctgcagcag   1080
atgcgtgata aaccccgct  gtctctgaac accccaccgg gtgaagtgaa actgaccctg   1140
gccggctgcg aagaacgtaa cgcgcagggc atgtgtagcc tggccggctt tacccagatt   1200
gtgaacgaag cgcgtattcc ggcgtgtagc ctgtaa                            1236
```

<210> SEQ ID NO 129
<211> LENGTH: 1236
<212> TYPE: DNA
<213> ORGANISM: Artificial Sequence
<220> FEATURE:
<223> OTHER INFORMATION: Engineered DNA

<400> SEQUENCE: 129

```
atgcagagcg aaccggaact gaaactggaa agcgtggtga ttgtgagccg tcatggcgtt     60
cgtgcgccga ccaaagcgac ccagctgatg caggatgtga ccccggatgc gtggccgacc    120
tggccggtga aactgggcga actgaccccg cgtggcggcg aactgattgc gtatctgggc    180
cattattggc gtcagcgtct ggtggcggat ggcctgctgc cgaaaaaagg ttgcccgcag    240
agcggtcagg tggcgattat tgcggatgtg gatgaacgta cccgtaaaac cggcgaagcg    300
tttgcggccg gtctggcccc ggattgcgcg attaccgtgc atacccaggc ggataccagc    360
agcccggacc cgctgtttaa tccgctgaaa accggcgtgt gccagctgga taacgcgcag    420
gtgaccgatg cgattctgga acgtgcgggc ggtagcattg cggattttac cggccattat    480
cagaccgcgt tcgtgaact  ggaacgtgtg ctgaactttc gcagagcaa  cctgtgcctg    540
aaacgtgaaa acaggatga  aagctgctct ctgacgcagg ccctgccgag cgaactgaaa    600
gtgagcgcgg ataacgtgag cctgaccggt gcggttagcc tggccagcat gctgaccgaa    660
atttttctgc tgcaacaagc gcagggtatg ccggaaccgg gctggggccg tattaccgat    720
agccatcagt ggaacaccct gctgtctctg cataacgcgc agtttgatct gctgcaacgt    780
accccggaag ttgcgcgtag ccgtgcgacc ccgctgctgg atctgattaa aaccgcgctg    840
accccgcatc cgccgcagaa acaggcgtat ggcgtgaccc tgccgaccag cgtgctgttt    900
attgcgggcc atgataccaa cctggccaat ctgggcggtg cgctggaact gcagtggacc    960
ctgccgggcc agccggataa tactccgccg ggtggtgaac tggtgtttga acgttggcgt   1020
cgtctgagcg ataacagcca gtggattcag gtgagcctgg tgtttcagac cctgcagcag   1080
```

| | |
|---|---|
| atgcgtgata aaacccegct gtttctgaac accccaccgg gtgaagtgaa actgaccctg | 1140 |
| gccggctgcg aagaacgtaa cgcgcagggc atgtgtagcc tggccggctt tacccagatt | 1200 |
| gtgaacgaag cgcgtattcc ggcgtgtagc ctgtaa | 1236 |

<210> SEQ ID NO 130
<211> LENGTH: 1236
<212> TYPE: DNA
<213> ORGANISM: Artificial Sequence
<220> FEATURE:
<223> OTHER INFORMATION: Engineered DNA

<400> SEQUENCE: 130

| | |
|---|---|
| atgcagagcg aaccggaact gaaactggaa agcgtggtga ttgtgagccg tcatggcgtt | 60 |
| cgtgcgccga ccaaagcgac ccagctgatg caggatgtga ccccggatgc gtggccgacc | 120 |
| tggccggtga aactgggcga actgaccccg cgtggcggcg aactgattgc gtatctgggc | 180 |
| cattattggc gtcagcgtct ggtggcggat ggcctgctgc gaaaaaagg ttgcccgcag | 240 |
| agcggtcagg tggcgattat tgcggatgtg atgaacgta cccgtaaaac cggcgaagcg | 300 |
| tttgcggccg gtctggcccc ggattgcgcg attaccgtgc ataccaggc ggataccagc | 360 |
| agcccggacg aactgtttaa tctgctgaaa accggcgtgt gccagctgga taacgcgcag | 420 |
| gtgaccgatg cgattctgga acgtgcgggc ggtagcattg cggattttac cggccattat | 480 |
| cagaccgcgt ttcgtgaact ggaacgtgtg ctgaactttc gcagagcaa cctgtgcctg | 540 |
| aaacgtgaaa acaggatga aagctgctct ctgacgcagg ccctgccgag cgaactgaaa | 600 |
| gtgagcgcgg ataacgtgag cctgaccggt gcggttagcc tggccagcat gctgaccgaa | 660 |
| attttctgc tgcaacaagc gcagggtatg ccggaaccgg gctggggccg tattaccgat | 720 |
| agccatcagt ggaacaccct gctgtctctg cataacgcgc agtttgatct gctgcaacgt | 780 |
| accccggaag ttgcgcgtag ccgtgcgacc ccgctgctgg atctgattaa aaccgcgctg | 840 |
| accccgcatc cgccgcagaa acaggcgtat ggcgtgaccc tgccgaccag cgtgctgttt | 900 |
| attgcgggcc atgataccaa cctggccaat ctgggcggtg cgctggaact gttatatacc | 960 |
| ctgccgggcc agccggataa tactccgccg ggtggtgaac tggtgtttga acgttggcgt | 1020 |
| cgtctgagcg ataacagcca gtggattcag gtgagcctgg tgtttcagac cctgcagcag | 1080 |
| atgcgtgata aaccccgct gtctctgaac accccaccgg gtgaagtgaa actgaccctg | 1140 |
| gccggctgcg aagaacgtaa cgcgcagggc atgtgtagcc tggccggctt tacccagatt | 1200 |
| gtgaacgaag cgcgtattcc ggcgtgtagc ctgtaa | 1236 |

<210> SEQ ID NO 131
<211> LENGTH: 1236
<212> TYPE: DNA
<213> ORGANISM: Artificial Sequence
<220> FEATURE:
<223> OTHER INFORMATION: Engineered DNA

<400> SEQUENCE: 131

| | |
|---|---|
| atgcagagcg aaccggaact gaaactggaa agcgtggtga ttgtgagccg tcatggcgtt | 60 |
| cgtgcgccga ccaaagcgac ccagctgatg caggatgtga ccccggatgc gtggccgacc | 120 |
| tggccggtga aactgggcga actgaccccg cgtggcggcg aactgattgc gtatctgggc | 180 |
| cattattggc gtcagcgtct ggtggcggat ggcctgctgc gaaaaaagg ttgcccgcag | 240 |
| agcggtcagg tggcgattat tgcggatgtg atgaacgta cccgtaaaac cggcgaagcg | 300 |
| tttgcggccg gtctggcccc ggattgcgcg attaccgtgc ataccaggc ggataccagc | 360 |

```
agcccggacc cgctgtttta tgtgctgaaa accggcgtgt gccagctgga taacgcgcag    420
gtgaccgatg cgattctgga acgtgcgggc ggtagcattg cggattttac cggccattat    480
cagaccgcgt ttcgtgaact ggaacgtgtg ctgaactttc gcagagcaa cctgtgcctg     540
aaacgtgaaa acaggatga aagctgctct ctgacgcagg ccctgccgag cgaactgaaa    600
gtgagcgcgg ataacgtgag cctgaccggt gcggttagcc tggccagcat gctgaccgaa   660
atttttctgc tgcaacaagc gcagggtatg ccggaaccgg ctggggccg tattaccgat     720
agccatcagt ggaacaccct gctgtctctg cataacgcgc agtttgatct gctgcaacgt   780
accccggaag ttgcgcgtag ccgtgcgacc ccgctgctgg atctgattaa aaccgcgctg   840
accccgcatc cgccgcagaa acaggcgtat ggcgtgaccc tgccgaccag cgtgctgttt    900
attgcgggcc atgataccaa cctggccaat ctgggcggtg cgctggaact gcagtggacc   960
ctgccgggcc agccggataa tactccgccg gtggtgaac tggtgtttga acgttggcgt    1020
cgtctgagcg ataacagcca gtggattcag gtgagcctgg tgtttcagac cctgcagcag   1080
atgcgtgata aaccccgct gtttctgaac accccaccgg gtgaagtgaa actgaccctg    1140
gccggctgcg aagaacgtaa cgcgcagggc atgtgtagcc tggccggctt tacccagatt   1200
gtgaacgaag cgcgtattcc ggcgtgtagc ctgtaa                             1236

<210> SEQ ID NO 132
<211> LENGTH: 1236
<212> TYPE: DNA
<213> ORGANISM: Artificial Sequence
<220> FEATURE:
<223> OTHER INFORMATION: Engineered DNA

<400> SEQUENCE: 132
atgcagagcg aaccggaact gaaactggaa agcgtggtga ttgtgagccg tcatggcgtt     60
cgtgcgccga ccaaattcac ccagctgatg caggatgtga ccccggatgc gtggccgacc   120
tggccggtga aactgggcga actgaccccg cgtggcggcg aactgattgc gtatctgggc   180
cattattggc gtcagcgtct ggtggcggat ggcctgctgc cgaaaaaagg ttgcccgcag   240
agcggtcagg tggcgattat tgcggatgtg gatgaacgta cccgtaaaac cggcgaagcg   300
tttgcggccg gtctggcccc ggattgcgcg attaccgtgc ataccaggc ggataccagc    360
agcccggacc cgctgtttaa tccgctgaaa accggcgtgt gccagctgga tgtggcgcag   420
gtgaccgatg cgattctgga acgtgcgggc ggtagcattg cggattttac cggccattat    480
cagaccgcgt ttcgtgaact ggaacgtgtg ctgaactttc gcagagcaa cctgtgcctg     540
aaacgtgaaa acaggatga aagctgctct ctgacgcagg ccctgccgag cgaactgaaa    600
gtgagcgcgg ataacgtgag cctgaccggt gcgtggagcc tggccagcat gctgaccgaa   660
atttttctgc tgcaacaagc gcagggtatg ccggaaccgg ctggggccg tattaccgat     720
agccatcagt ggaacaccct gctgtctctg cataacgcgc agtttgatct gctgcaacgt   780
accccggaag ttgcgcgtag ccgtgcgacc ccgctgctgg atctgattaa aaccgcgctg   840
accccgcatc cgccgcagaa acaggcgtat ggcgtgaccc tgccgaccag cgtgctgttt    900
attgcgggcc atgataccaa cctggccaat ctgggcggtg cgctggaact gcagtggacc   960
ctgccgggcc agccggataa tactccgccg gtggtgaac tggtgtttga acgttggcgt    1020
cgtctgagcg ataacagcca gtggattcag gtgagcctgg tgtttcagac cctgcagcag   1080
atgcgtgata aaccccgct gtctctgaac accccaccgg gtgaagtgaa actgaccctg    1140
gccggctgcg aagaacgtaa cgcgcagggc atgtgtagcc tggccggctt tacccagatt   1200
```

-continued

| gtgaacgaag cgcgtattcc ggcgtgtagc ctgtaa | 1236 |

<210> SEQ ID NO 133
<211> LENGTH: 1236
<212> TYPE: DNA
<213> ORGANISM: Artificial Sequence
<220> FEATURE:
<223> OTHER INFORMATION: Engineered DNA

<400> SEQUENCE: 133

| atgcagagcg aaccggaact gaaactggaa agcgtggtga ttgtgagccg tcatggcgtt | 60 |
| cgtgcgccga ccaaattcac ccagctgatg caggatgtga ccccggatgc gttttatacc | 120 |
| tggccggtga actgggcga actgaccccg cgtggcggcg aactgattgc gtatctgggc | 180 |
| cattattggc gtcagcgtct ggtggcggat ggcctgctgc gaaaaaagg ttgcccgcag | 240 |
| agcggtcagg tggcgattat tgcggatgtg atgaacgta cccgtaaaac cggcgaagcg | 300 |
| tttgcggccg gtctggcccc ggattgcgcg attaccgtgc atacccaggc ggataccagc | 360 |
| agcccggacc cgctgtttaa tccgctgaaa accggcgtgt gccagctgga tgtggcgcag | 420 |
| gtgaccgatg cgattctgga acgtgcgggc ggtagcattg cggattttac cggccattat | 480 |
| cagaccgcgt ttcgtgaact ggaacgtgtg ctgaactttc gcagagcaa cctgtgcctg | 540 |
| aaacgtgaaa acaggatga agctgctct ctgacgcagg ccctgccgag cgaactgaaa | 600 |
| gtgagcgcgg ataacgtgag cctgaccggt gcgtggagcc tggccagcat gctgaccgaa | 660 |
| attttctgc tgcaacaagc gcagggtatg ccggaaccgg ctggggccg tattaccgat | 720 |
| agccatcagt ggaacaccct gctgtctctg cataacgcgc agtttgatct gctgcaacgt | 780 |
| accccggaag ttgcgcgtag ccgtgcgacc ccgctgctgg atctgattaa accgcgctg | 840 |
| accccgcatc cgccgcagaa acaggcgtat ggcgtgaccc tgccgaccag cgtgctgttt | 900 |
| attgcgggcc atgataccaa cctggccaat ctgggcggtg cgctggaact gcagtggacc | 960 |
| ctgccgggcc agccggataa tactccgccg ggtggtgaac tggtgtttga acgttggcgt | 1020 |
| cgtctgagcg ataacagcca gtggattcag gtgagcctgg tgtttcagac cctgcagcag | 1080 |
| atgcgtgata aaccccgct gtctctgaac accccaccgg tgaagtgaa actgaccctg | 1140 |
| gccggctgcg aagaacgtaa cgcgcagggc atgtgtagcc tggccggctt tacccagatt | 1200 |
| gtgaacgaag cgcgtattcc ggcgtgtagc ctgtaa | 1236 |

<210> SEQ ID NO 134
<211> LENGTH: 1236
<212> TYPE: DNA
<213> ORGANISM: Artificial Sequence
<220> FEATURE:
<223> OTHER INFORMATION: Engineered DNA

<400> SEQUENCE: 134

| atgcagagcg aaccggaact gaaactggaa agcgtggtga ttgtgagccg tcatggcgtt | 60 |
| cgtgcgccga ccaaattcac ccagctgatg caggatgtga ccccggatgc gtggccgacc | 120 |
| tggccggtga actgggcga actgaccccg cgtggcggcg aactgattgc gtatctgggc | 180 |
| cattattggc gtcagcgtct ggtggcggat ggcctgctgc gaaaaaagg ttgcccgcag | 240 |
| agcggtcagg tggcgattat tgcggatgtg atgaacgta cccgtaaaac cggcgaagcg | 300 |
| tttgcggccg gtctggcccc ggattgcgcg attaccgtgc atacccaggc ggataccagc | 360 |
| agcccggacg aactgtttaa tctgctgaaa accggcgtgt gccagctgga tgtggcgcag | 420 |
| gtgaccgatg cgattctgga acgtgcgggc ggtagcattg cggattttac cggccattat | 480 |

| | |
|---|---|
| cagaccgcgt ttcgtgaact ggaacgtgtg ctgaactttc cgcagagcaa cctgtgcctg | 540 |
| aaacgtgaaa aacaggatga aagctgctct ctgacgcagg ccctgccgag cgaactgaaa | 600 |
| gtgagcgcgg ataacgtgag cctgaccggt gcgtggagcc tggccagcat gctgaccgaa | 660 |
| attttctgc tgcaacaagc gcagggtatg ccggaaccgg gctggggccg tattaccgat | 720 |
| agccatcagt ggaacaccct gctgtctctg cataacgcgc agtttgatct gctgcaacgt | 780 |
| accccggaag ttgcgcgtag ccgtgcgacc ccgctgctgg atctgattaa aaccgcgctg | 840 |
| accccgcatc cgccgcagaa acaggcgtat ggcgtgaccc tgccgaccag cgtgctgttt | 900 |
| attgcgggcc atgataccaa cctggccaat ctgggcggtg cgctggaact gcagtggacc | 960 |
| ctgccgggcc agccggataa tactccgccg gtggtgaac tggtgtttga cgttggcgt | 1020 |
| cgtctgagcg ataacagcca gtggattcag gtgagcctgg tgtttcagac cctgcagcag | 1080 |
| atgcgtgata aaccccgct gtctctgaac accccaccgg gtgaagtgaa actgaccctg | 1140 |
| gccggctgcg aagaacgtaa cgcgcagggc atgtgtagcc tggccggctt tacccagatt | 1200 |
| gtgaacgaag cgcgtattcc ggcgtgtagc ctgtaa | 1236 |

<210> SEQ ID NO 135
<211> LENGTH: 1236
<212> TYPE: DNA
<213> ORGANISM: Artificial Sequence
<220> FEATURE:
<223> OTHER INFORMATION: Engineered DNA

<400> SEQUENCE: 135

| | |
|---|---|
| atgcagagcg aaccggaact gaaactggaa agcgtggtga ttgtgagccg tcatggcgtt | 60 |
| cgtgcgccga ccaaattcac ccagctgatg caggatgtga ccccggatgc gtggccgacc | 120 |
| tggccggtga aactgggcga actgaccccg cgtggcggcg aactgattgc gtatctgggc | 180 |
| cattattggc gtcagcgtct ggtggcggat ggcctgctgc cgaaaaaagg ttgcccgcag | 240 |
| agcggtcagg tggcgattat tgcggatgtg atgaacgta cccgtaaaac cggcgaagcg | 300 |
| tttgcggccg gtctggcccc ggattgcgcg attaccgtgc ataccaggc ggataccagc | 360 |
| agcccggacc cgctgttta tgtgctgaaa accggcgtgt gccagctgga tgtggcgcag | 420 |
| gtgaccgatg cgattctgga acgtgcgggc ggtagcattg cggattttac cggccattat | 480 |
| cagaccgcgt ttcgtgaact ggaacgtgtg ctgaactttc cgcagagcaa cctgtgcctg | 540 |
| aaacgtgaaa aacaggatga aagctgctct ctgacgcagg ccctgccgag cgaactgaaa | 600 |
| gtgagcgcgg ataacgtgag cctgaccggt gcgtggagcc tggccagcat gctgaccgaa | 660 |
| attttctgc tgcaacaagc gcagggtatg ccggaaccgg gctggggccg tattaccgat | 720 |
| agccatcagt ggaacaccct gctgtctctg cataacgcgc agtttgatct gctgcaacgt | 780 |
| accccggaag ttgcgcgtag ccgtgcgacc ccgctgctgg atctgattaa aaccgcgctg | 840 |
| accccgcatc cgccgcagaa acaggcgtat ggcgtgaccc tgccgaccag cgtgctgttt | 900 |
| attgcgggcc atgataccaa cctggccaat ctgggcggtg cgctggaact gcagtggacc | 960 |
| ctgccgggcc agccggataa tactccgccg gtggtgaac tggtgtttga cgttggcgt | 1020 |
| cgtctgagcg ataacagcca gtggattcag gtgagcctgg tgtttcagac cctgcagcag | 1080 |
| atgcgtgata aaccccgct gtctctgaac accccaccgg gtgaagtgaa actgaccctg | 1140 |
| gccggctgcg aagaacgtaa cgcgcagggc atgtgtagcc tggccggctt tacccagatt | 1200 |
| gtgaacgaag cgcgtattcc ggcgtgtagc ctgtaa | 1236 |

<210> SEQ ID NO 136

<211> LENGTH: 1236
<212> TYPE: DNA
<213> ORGANISM: Artificial Sequence
<220> FEATURE:
<223> OTHER INFORMATION: Engineered DNA

<400> SEQUENCE: 136

| | |
|---|---|
| atgcagagcg aaccggaact gaaactggaa agcgtggtga ttgtgagccg tcatggcgtt | 60 |
| cgtgcgccga ccaaattcac ccagctgatg caggatgtga ccccggatgc gttttatacc | 120 |
| tggccggtga aactgggcga actgaccccg cgtggcggcg aactgattgc gtatctgggc | 180 |
| cattattggc gtcagcgtct ggtggcggat ggcctgctgc gaaaaaagg ttgcccgcag | 240 |
| agcggtcagg tggcgattat tgcggatgtg gatgaacgta cccgtaaaac cggcgaagcg | 300 |
| tttgcggccg gtctggcccc ggattgcgcg attaccgtgc atacccaggc ggataccagc | 360 |
| agcccggacc cgctgtttaa tccgctgaaa accggcgtgt gccagctgga tgtggcgcag | 420 |
| gtgaccgatg cgattctgga acgtgcgggc ggtagcattg cggattttac cggccattat | 480 |
| cagaccgcgt ttcgtgaact ggaacgtgtg ctgaactttc gcagagcaa cctgtgcctg | 540 |
| aaacgtgaaa acaggatga agctgctct ctgacgcagg ccctgccgag cgaactgaaa | 600 |
| gtgagcgcgg ataacgtgag cctgaccggt gcgtggagcc tggccagcat gctgaccgaa | 660 |
| attttctgc tgcaacaagc gcagggtatg ccggaaccgg ctggggccg tattaccgat | 720 |
| agccatcagt ggaacaccct gctgtctctg cataacgcgc agtttgatct gctgcaacgt | 780 |
| accccggaag ttgcgcgtag ccgtgcgacc ccgctgctgg atctgattaa accgcgctg | 840 |
| accccgcatc cgccgcagaa acaggcgtat ggcgtgaccc tgccgaccag cgtgctgttt | 900 |
| attgcgggcc atgataccaa cctggccaat ctgggcggtg cgctggaact gctgtatacc | 960 |
| ctgccgggcc agccggataa tactccgccg ggtggtgaac tggtgtttga acgttggcgt | 1020 |
| cgtctgagcg ataacagcca gtggattcag gtgagcctgg tgtttcagac cctgcagcag | 1080 |
| atgcgtgata aaccccgct gtctctgaac accccaccgg gtgaagtgaa actgaccctg | 1140 |
| gccggctgcg aagaacgtaa cgcgcagggc atgtgtagcc tggccggctt tacccagatt | 1200 |
| gtgaacgaag cgcgtattcc ggcgtgtagc ctgtaa | 1236 |

<210> SEQ ID NO 137
<211> LENGTH: 1236
<212> TYPE: DNA
<213> ORGANISM: Artificial Sequence
<220> FEATURE:
<223> OTHER INFORMATION: Engineered DNA

<400> SEQUENCE: 137

| | |
|---|---|
| atgcagagcg aaccggaact gaaactggaa agcgtggtga ttgtgagccg tcatggcgtt | 60 |
| cgtgcgccga ccaaattcac ccagctgatg caggatgtga ccccggatgc gttttatacc | 120 |
| tggccggtga aactgggcga actgaccccg cgtggcggcg aactgattgc gtatctgggc | 180 |
| cattattggc gtcagcgtct ggtggcggat ggcctgctgc gaaaaaagg ttgcccgcag | 240 |
| agcggtcagg tggcgattat tgcggatgtg gatgaacgta cccgtaaaac cggcgaagcg | 300 |
| tttgcggccg gtctggcccc ggattgcgcg attaccgtgc atacccaggc ggataccagc | 360 |
| agcccggacc cgctgtttaa tccgctgaaa accggcgtgt gccagctgga tgtggcgcag | 420 |
| gtgaccgatg cgattctgga acgtgcgggc ggtagcattg cggattttac cggccattat | 480 |
| cagaccgcgt ttcgtgaact ggaacgtgtg ctgaactttc gcagagcaa cctgtgcctg | 540 |
| aaacgtgaaa acaggatga agctgctct ctgacgcagg ccctgccgag cgaactgaaa | 600 |

```
gtgagcgcgg ataacgtgag cctgaccggt gcgtggagcc tggccagcat gctgaccgaa      660 attttctgc tgcaacaagc gcagggtatg ccggaaccgg gctggggccg tattaccgat       720
agccatcagt ggaacaccct gctgtctctg cataacgcgc agtttgatct gctgcaacgt     780
accccggaag ttgcgcgtag ccgtgcgacc ccgctgctgg atctgattaa aaccgcgctg     840
accccgcatc cgccgcagaa acaggcgtat ggcgtgaccc tgccgaccag cgtgctgttt     900
attgcgggcc atgataccaa cctggccaat ctgggcggtg cgctggaact gcagtggacc     960
ctgccgggcc agccggataa tactccgccg gtggtgaac tggtgtttga acgttggcgt     1020
cgtctgagcg ataacagcca gtggattcag gtgagcctgg tgtttcagac cctgcagcag     1080
atgcgtgata aaccccgct gtttctgaac accccaccgg gtgaagtgaa actgaccctg      1140
gccggctgcg aagaacgtaa cgcgcagggc atgtgtagcc tggccggctt tacccagatt     1200
gtgaacgaag cgcgtattcc ggcgtgtagc ctgtaa                                1236

<210> SEQ ID NO 138
<211> LENGTH: 1236
<212> TYPE: DNA
<213> ORGANISM: Artificial Sequence
<220> FEATURE:
<223> OTHER INFORMATION: Engineered DNA

<400> SEQUENCE: 138
atgcagagcg aaccggaact gaaactggaa agcgtggtga ttgtgagccg tcatggcgtt       60
cgtgcgccga ccaaattcac ccagctgatg caggatgtga ccccggatgc gtggccgacc     120
tggccggtga aactgggcga actgaccccg cgtggcggcg aactgattgc gtatctgggc     180
cattattggc gtcagcgtct ggtggcggat ggcctgctgc cgaaaaaagg ttgcccgcag      240
agcggtcagg tggcgattat tgcggatgtg atgaacgta cccgtaaaac cggcgaagcg       300
tttgcggccg gtctggcccc ggattgcgcg attaccgtgc ataccaggc ggataccagc       360 agcccggacg aactgtttaa tctgctgaaa accggcgtgt gccagctgga tgtggcgcag     420
gtgaccgatg cgattctgga acgtgcgggc ggtagcattg cggattttac cggccattat     480
cagaccgcgt ttcgtgaact ggaacgtgtg ctgaactttc gcagagcaa cctgtgcctg      540 aaacgtgaaa acaggatga agctgctct ctgacgcagg ccctgccgag cgaactgaaa      600
gtgagcgcgg ataacgtgag cctgaccggt gcgtggagcc tggccagcat gctgaccgaa     660 attttctgc tgcaacaagc gcagggtatg ccggaaccgg gctggggccg tattaccgat       720
agccatcagt ggaacaccct gctgtctctg cataacgcgc agtttgatct gctgcaacgt     780
accccggaag ttgcgcgtag ccgtgcgacc ccgctgctgg atctgattaa aaccgcgctg     840
accccgcatc cgccgcagaa acaggcgtat ggcgtgaccc tgccgaccag cgtgctgttt     900
attgcgggcc atgataccaa cctggccaat ctgggcggtg cgctggaact gctgtatacc     960
ctgccgggcc agccggataa tactccgccg gtggtgaac tggtgtttga acgttggcgt     1020
cgtctgagcg ataacagcca gtggattcag gtgagcctgg tgtttcagac cctgcagcag     1080
atgcgtgata aaccccgct gtctctgaac accccaccgg gtgaagtgaa actgaccctg      1140
gccggctgcg aagaacgtaa cgcgcagggc atgtgtagcc tggccggctt tacccagatt     1200
gtgaacgaag cgcgtattcc ggcgtgtagc ctgtaa                                1236

<210> SEQ ID NO 139
<211> LENGTH: 1236
<212> TYPE: DNA
<213> ORGANISM: Artificial Sequence
<220> FEATURE:
```

<223> OTHER INFORMATION: Engineered DNA

<400> SEQUENCE: 139

```
atgcagagcg aaccggaact gaaactggaa agcgtggtga ttgtgagccg tcatggcgtt      60
cgtgcgccga ccaaattcac ccagctgatg caggatgtga ccccggatgc gtggccgacc     120
tggccggtga aactgggcga actgaccccg cgtggcggcg aactgattgc gtatctgggc     180
cattattggc gtcagcgtct ggtggcggat ggcctgctgc gaaaaaagg ttgcccgcag      240
agcggtcagg tggcgattat tgcggatgtg gatgaacgta cccgtaaaac cggcgaagcg     300
tttgcggccg gtctggcccc ggattgcgcg attaccgtgc atacccaggc ggataccagc     360
agcccggacc cgctgtttta tgtgctgaaa accggcgtgt gccagctgga tgtggcgcag     420
gtgaccgatg cgattctgga acgtgcgggc ggtagcattg cggattttac cggccattat     480
cagaccgcgt ttcgtgaact ggaacgtgtg ctgaactttc gcagagcaa cctgtgcctg      540
aaacgtgaaa acaggatga agctgctct ctgacgcagg ccctgccgag cgaactgaaa       600
gtgagcgcgg ataacgtgag cctgaccggt gcgtggagcc tggccagcat gctgaccgaa     660
attttttctgc tgcaacaagc gcagggtatg ccggaaccgg gctggggccg tattaccgat    720
agccatcagt ggaacacccc tgctgtctctg cataacgcgc agtttgatct gctgcaacgt    780
accccgaag ttgcgcgtag ccgtgcgacc ccgctgctgg atctgattaa accgcgctg       840
accccgcatc cgccgcagaa acaggcgtat ggcgtgaccc tgccgaccag cgtgctgttt    900
attgcgggcc atgataccaa cctggccaat ctgggcggtg cgctggaact gcagtggacc    960
ctgccgggcc agccggataa tactccgccg ggtggtgaac tggtgttttga acgttggcgt   1020
cgtctgagcg ataacagcca gtggattcag gtgagcctgg tgtttcagac cctgcagcag   1080
atgcgtgata aaccccgct gtttctgaac accccaccgg gtgaagtgaa actgaccctg    1140
gccggctgcg aagaacgtaa cgcgcagggc atgtgtagcc tggccggctt tacccagatt   1200
gtgaacgaag cgcgtattcc ggcgtgtagc ctgtaa                             1236
```

<210> SEQ ID NO 140
<211> LENGTH: 1236
<212> TYPE: DNA
<213> ORGANISM: Artificial Sequence
<220> FEATURE:
<223> OTHER INFORMATION: Engineered DNA

<400> SEQUENCE: 140

```
atgcagagcg aaccggaact gaaactggaa agcgtggtga ttgtgagccg tcatggcgtt      60
cgtgcgccga ccaaattcac ccagctgatg caggatgtga ccccggatgc gtggccgacc     120
tggccggtga aactgggcga actgaccccg cgtggcggcg aactgattgc gtatctgggc     180
cattattggc gtcagcgtct ggtggcggat ggcctgctgc gaaaaaagg ttgcccgcag      240
agcggtcagg tggcgattat tgcggatgtg gatgaacgta cccgtaaaac cggcgaagcg     300
tttgcggccg gtctggcccc ggattgcgcg attaccgtgc atacccaggc ggataccagc     360
agcccggacc cgctgtttaa tccgctgaaa accggcgtgt gccagctgga tgtggcgcag     420
gtgaccgatg cgattctgga acgtgcgggc ggtagcattg cggattttac cggccattat     480
cagaccgcgt ttcgtgaact ggaacgtgtg ctgaactttc gcagagcaa cctgcgctg       540
aaacgtgaaa acaggatga agcgcgtct ctgacgcagg ccctgccgag cgaactgaaa      600
gtgagcgcgg ataacgtgag cctgaccggt gcgtggagcc tggccagcat gctgaccgaa     660
attttttctgc tgcaacaagc gcagggtatg ccggaaccgg gctggggccg tattaccgat    720
```

```
agccatcagt ggaacaccct gctgtctctg cataacgcgc agtttgatct gctgcaacgt    780
accccggaag ttgcgcgtag ccgtgcgacc ccgctgctgg atctgattaa aaccgcgctg    840
accccgcatc cgccgcagaa acaggcgtat ggcgtgaccc tgccgaccag cgtgctgttt    900
attgcgggcc atgataccaa cctggccaat ctgggcggtg cgctggaact gcagtggacc    960
ctgccgggcc agccggataa tactccgccg ggtggtgaac tggtgtttga acgttggcgt   1020
cgtctgagcg ataacagcca gtggattcag gtgagcctgg tgtttcagac cctgcagcag   1080
atgcgtgata aaccccgct gtctctgaac accccaccgg gtgaagtgaa actgaccctg    1140
gccggctgcg aagaacgtaa cgcgcagggc atgtgtagcc tggccggctt tacccagatt   1200
gtgaacgaag cgcgtattcc ggcgtgtagc ctgtaa                             1236
```

<210> SEQ ID NO 141
<211> LENGTH: 1236
<212> TYPE: DNA
<213> ORGANISM: Artificial Sequence
<220> FEATURE:
<223> OTHER INFORMATION: Engineered DNA

<400> SEQUENCE: 141

```
atgcagagcg aaccggaact gaaactggaa agcgtggtga ttgtgagccg tcatggcgtt     60
cgtgcgccga ccaaattcac ccagctgatg caggatgtga ccccggatgc gttttatacc    120
tggccggtga aactgggcga actgaccccg cgtggcggcg aactgattgc gtatctgggc    180
cattattggc gtcagcgtct ggtggcggat ggcctgctgc cgaaaaaagg ttgcccgcag    240
agcggtcagg tggcgattat tgcggatgtg atgaacgta cccgtaaaac cggcgaagcg    300
tttgcggccg gtctggcccc ggattgcgcg attaccgtgc ataccaggc ggataccagc    360 agcccggacc cgctgtttaa tccgctgaaa accggcgtgt gccagctgga tgtggcgcag    420
gtgaccgatg cgattctgga acgtgcgggc ggtagcattg cggattttac cggccattat    480
cagaccgcgt ttcgtgaact ggaacgtgtg ctgaactttc gcagagcaa cctggcgctg    540 aaacgtgaaa acaggatga aagcgcgtct ctgacgcagg ccctgccgag cgaactgaaa    600
gtgagcgcgg ataacgtgag cctgaccggt gcgtggagcc tggccagcat gctgaccgaa    660
atttttctgc tgcaacaagc gcagggtatg ccggaaccgg gctggggccg tattaccgat    720
agccatcagt ggaacaccct gctgtctctg cataacgcgc agtttgatct gctgcaacgt    780
accccggaag ttgcgcgtag ccgtgcgacc ccgctgctgg atctgattaa aaccgcgctg    840
accccgcatc cgccgcagaa acaggcgtat ggcgtgaccc tgccgaccag cgtgctgttt    900
attgcgggcc atgataccaa cctggccaat ctgggcggtg cgctggaact gctgtatacc    960
ctgccgggcc agccggataa tactccgccg ggtggtgaac tggtgtttga acgttggcgt   1020
cgtctgagcg ataacagcca gtggattcag gtgagcctgg tgtttcagac cctgcagcag   1080
atgcgtgata aaccccgct gtctctgaac accccaccgg gtgaagtgaa actgaccctg    1140
gccggctgcg aagaacgtaa cgcgcagggc atgtgtagcc tggccggctt tacccagatt   1200
gtgaacgaag cgcgtattcc ggcgtgtagc ctgtaa                             1236
```

<210> SEQ ID NO 142
<211> LENGTH: 1236
<212> TYPE: DNA
<213> ORGANISM: Artificial Sequence
<220> FEATURE:
<223> OTHER INFORMATION: Engineered DNA

<400> SEQUENCE: 142

```
atgcagagcg aaccggaact gaaactggaa agcgtggtga ttgtgagccg tcatggcgtt    60
cgtgcgccga ccaaattcac ccagctgatg caggatgtga ccccggatgc gttttatacc   120
tggccggtga aactgggcga actgaccccg cgtggcggcg aactgattgc gtatctgggc   180
cattattggc gtcagcgtct ggtggcggat ggcctgctgc cgaaaaaagg ttgcccgcag   240
agcggtcagg tggcgattat tgcggatgtg gatgaacgta cccgtaaaac cggcgaagcg   300
tttgcggccg gtctggcccc ggattgcgcg attaccgtgc ataccaggc ggataccagc    360 agcccggacc cgctgtttaa tccgctgaaa accggcgtgt gccagctgga tgtggcgcag   420
gtgaccgatg cgattctgga acgtgcgggc ggtagcattg cggattttac cggccattat   480
cagaccgcgt ttcgtgaact ggaacgtgtg ctgaactttc gcagagcaa cctggcgctg    540 aaacgtgaaa acaggatga aagcgcgtct ctgacgcagg ccctgccgag cgaactgaaa    600
gtgagcgcgg ataacgtgag cctgaccggt gcgtggagcc tggccagcat gctgaccgaa   660 attttctgc tgcaacaagc gcagggtatg ccggaaccgg gctggggccg tattaccgat    720
agccatcagt ggaacaccct gctgtctctg cataacgcgc agtttgatct gctgcaacgt   780
accccggaag ttgcgcgtag ccgtgcgacc ccgctgctgg atctgattaa aaccgcgctg   840
accccgcatc cgccgcagaa acaggcgtat ggcgtgaccc tgccgaccag cgtgctgttt   900
attgcgggcc atgataccaa cctggccaat ctgggcggtg cgctggaact gcagtggacc   960
ctgccgggcc agccggataa tactccgccg ggtggtgaac tggtgtttga acgttggcgt  1020
cgtctgagcg ataacagcca gtggattcag gtgagcctgg tgtttcagac cctgcagcag  1080
atgcgtgata aacccccgct gtttctgaac accccaccgg gtgaagtgaa actgaccctg  1140
gccggctgcg aagaacgtaa cgcgcagggc atgtgtagcc tggccggctt tacccagatt  1200
gtgaacgaag cgcgtattcc ggcgtgtagc ctgtaa                            1236
```

<210> SEQ ID NO 143  
<211> LENGTH: 1236  
<212> TYPE: DNA  
<213> ORGANISM: Artificial Sequence  
<220> FEATURE:  
<223> OTHER INFORMATION: Engineered DNA

<400> SEQUENCE: 143

```
atgcagagcg aaccggaact gaaactggaa agcgtggtga ttgtgagccg tcatggcgtt    60
cgtgcgccga ccaaattcac ccagctgatg caggatgtga ccccggatgc gtggccgacc   120
tggccggtga aactgggcga actgaccccg cgtggcggcg aactgattgc gtatctgggc   180
cattattggc gtcagcgtct ggtggcggat ggcctgctgc cgaaaaaagg ttgcccgcag   240
agcggtcagg tggcgattat tgcggatgtg gatgaacgta cccgtaaaac cggcgaagcg   300
tttgcggccg gtctggcccc ggattgcgcg attaccgtgc ataccaggc ggataccagc    360 agcccggacc cgctgtttaa tccgctgaaa accggcgtgg cgcagctgga tgtggcgcag   420
gtgaccgatg cgattctgga acgtgcgggc ggtagcattg cggattttac cggccattat   480
cagaccgcgt ttcgtgaact ggaacgtgtg ctgaactttc gcagagcaa cctgtgcctg    540 aaacgtgaaa acaggatga aagctgctct ctgacgcagg ccctgccgag cgaactgaaa    600
gtgagcgcgg ataacgtgag cctgaccggt gcgtggagcc tggccagcat gctgaccgaa   660 attttctgc tgcaacaagc gcagggtatg ccggaaccgg gctggggccg tattaccgat    720
agccatcagt ggaacaccct gctgtctctg cataacgcgc agtttgatct gctgcaacgt   780
accccggaag ttgcgcgtag ccgtgcgacc ccgctgctgg atctgattaa aaccgcgctg   840
```

```
acccccgcatc cgccgcagaa acaggcgtat ggcgtgaccc tgccgaccag cgtgctgttt    900
attgcgggcc atgataccaa cctggccaat ctgggcggtg cgctggaact gcagtggacc    960
ctgccgggcc agccggataa tactccgccg ggtggtgaac tggtgtttga acgttggcgt   1020
cgtctgagcg ataacagcca gtggattcag gtgagcctgg tgtttcagac cctgcagcag   1080
atgcgtgata aaccccgct gtctctgaac accccaccgg gtgaagtgaa actgaccctg    1140
gccggctgcg aagaacgtaa cgcgcagggc atgtgtagcc tggccggctt acccagatt    1200 gtgaacgaag cgcgtattcc ggcggcgagc ctgtaa                             1236
```

<210> SEQ ID NO 144
<211> LENGTH: 1236
<212> TYPE: DNA
<213> ORGANISM: Artificial Sequence
<220> FEATURE:
<223> OTHER INFORMATION: Engineered DNA

<400> SEQUENCE: 144

```
atgcagagcg aaccggaact gaaactggaa agcgtggtga ttgtgagccg tcatggcgtt     60
cgtgcgccga ccaaattcac ccagctgatg caggatgtga ccccggatgc gttttatacc    120
tggccggtga aactgggcga actgaccccg cgtggcggcg aactgattgc gtatctgggc    180
cattattggc gtcagcgtct ggtggcggat ggcctgctgc cgaaaaaagg ttgcccgcag    240
agcggtcagg tggcgattat tgcggatgtg gatgaacgta cccgtaaaac cggcgaagcg    300
tttgcggccg tctggccccc ggattgcgcg attaccgtgc ataccaggc ggataccagc     360 agcccggacc cgctgtttaa tccgctgaaa accggcgtgg cgcagctgga tgtggcgcag    420
gtgaccgatg cgattctgga acgtgcgggc ggtagcattg cggatttac cggccattat    480 cagaccgcgt ttcgtgaact ggaacgtgtg ctgaactttc gcagagcaa cctgtgcctg    540 aaacgtgaaa acaggatga agctgctct ctgacgcagg ccctgccgag cgaactgaaa     600
gtgagcgcgg ataacgtgag cctgaccggt gcgtggagcc tggccagcat gctgaccgaa    660
atttttctgc tgcaacaagc gcagggtatg ccggaaccgg ctggggccg tattaccgat    720 agccatcagt ggaacaccct gctgtctctg cataacgcgc agtttgatct gctgcaacgt    780
accccggaag ttgcgcgtag ccgtgcgacc ccgctgctgg atctgattaa accgcgctg     840 accccgcatc cgccgcagaa acaggcgtat ggcgtgaccc tgccgaccag cgtgctgttt    900
attgcgggcc atgataccaa cctggccaat ctgggcggtg cgctggaact gcagtggacc    960
ctgccgggcc agccggataa tactccgccg ggtggtgaac tggtgtttga acgttggcgt   1020
cgtctgagcg ataacagcca gtggattcag gtgagcctgg tgtttcagac cctgcagcag   1080
atgcgtgata aaccccgct gtttctgaac accccaccgg gtgaagtgaa actgaccctg    1140
gccggctgcg aagaacgtaa cgcgcagggc atgtgtagcc tggccggctt acccagatt    1200 gtgaacgaag cgcgtattcc ggcggcgagc ctgtaa                             1236
```

<210> SEQ ID NO 145
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 145

```
atgcagagcg agccggagct gaagctggag agcgtggtga tcgtgagcag gcacggcgtg     60 agggcccga ccaaggccac ccagctgatg caggacgtga ccccggacgc ctggccgacc    120
```

| | | |
|---|---|---|
| tggccggtga agctgggcga gctgaccccg aggggcggcg agctgatcgc ctacctgggc | 180 | |
| cactactgga ggcagaggct ggtggccgac ggcctgctgc cgaagaaggg ctgcccgcag | 240 | |
| agcggccagg tggccatcat cgccgacgtg gacgagagga ccaggaagac cggcgaggcc | 300 | |
| ttcgccgccg gcctggcccc ggactgcgcc atcaccgtgc acacccaggc cgacaccagc | 360 | |
| agcccggacc cgctgttcaa cccgctgaag accggcgtgt gccagctgga caacgcccag | 420 | |
| gtgaccgacg ccatcctgga gagggccggc ggcagcatcg ccgacttcac cggccactac | 480 | |
| cagaccgcct tcagggagct ggagagggtg ctgaacttcc gcagagcaa cctgtgcctg | 540 | |
| aagagggaga agcaggacga gagctgcagc ctgacccagg ccctgccgag cgagctgaag | 600 | |
| gtgagcgccg acaacgtgag cctgaccggc gccgtgagcc tggccagcat gctgaccgag | 660 | |
| atcttcctgc tgcagcaggc ccagggcatg ccggagccgg gctggggcag gatcaccgac | 720 | |
| agccaccagt ggaacaccct gctgagcctg cacaacgccc agttcgacct gctgcagagg | 780 | |
| accccggagg tggccaggag cagggccacc ccgctgctgg acctgatcaa gaccgccctg | 840 | |
| accccgcacc cgccgcagaa gcaggcctac ggcgtgaccc tgccgaccag cgtgctgttc | 900 | |
| atcgccggcc acgacaccaa cctggccaac ctgggcggcg ccctggagct gcagtggacc | 960 | |
| ctgccgggcc agccggacaa caccccgccg ggcggcgagc tggtgttcga gaggtggagg | 1020 | |
| aggctgagcg acaacagcca gtggatccag gtgagcctgg tgttccagac cctgcagcag | 1080 | |
| atgagggaca agacccgct gagcctgaac accccgccgg gcgaggtgaa gctgaccctg | 1140 | |
| gccggctgcg aggagaggaa cgcccagggc atgtgcagcc tggccggctt cacccagatc | 1200 | |
| gtgaacgagg ccaggatccc ggcctgcagc ctgtga | 1236 | |

<210> SEQ ID NO 146
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 146

| | | |
|---|---|---|
| atgcagagcg agccggagct gaagctggag agcgtggtga tcgtgagcag gcacggcgtg | 60 | |
| agggccccga ccaaggccac ccagctgatg caggacgtga ccccggacgc cttctacacc | 120 | |
| tggccggtga agctgggcga gctgaccccg aggggcggcg agctgatcgc ctacctgggc | 180 | |
| cactactgga ggcagaggct ggtggccgac ggcctgctgc cgaagaaggg ctgcccgcag | 240 | |
| agcggccagg tggccatcat cgccgacgtg gacgagagga ccaggaagac cggcgaggcc | 300 | |
| ttcgccgccg gcctggcccc ggactgcgcc atcaccgtgc acacccaggc cgacaccagc | 360 | |
| agcccggacc cgctgttcaa cccgctgaag accggcgtgt gccagctgga caacgcccag | 420 | |
| gtgaccgacg ccatcctgga gagggccggc ggcagcatcg ccgacttcac cggccactac | 480 | |
| cagaccgcct tcagggagct ggagagggtg ctgaacttcc gcagagcaa cctgtgcctg | 540 | |
| aagagggaga agcaggacga gagctgcagc ctgacccagg ccctgccgag cgagctgaag | 600 | |
| gtgagcgccg acaacgtgag cctgaccggc gccgtgagcc tggccagcat gctgaccgag | 660 | |
| atcttcctgc tgcagcaggc ccagggcatg ccggagccgg gctggggcag gatcaccgac | 720 | |
| agccaccagt ggaacaccct gctgagcctg cacaacgccc agttcgacct gctgcagagg | 780 | |
| accccggagg tggccaggag cagggccacc ccgctgctgg acctgatcaa gaccgccctg | 840 | |
| accccgcacc cgccgcagaa gcaggcctac ggcgtgaccc tgccgaccag cgtgctgttc | 900 | |
| atcgccggcc acgacaccaa cctggccaac ctgggcggcg ccctggagct gcagtggacc | 960 | |

```
ctgccgggcc agccggacaa caccccgccg ggcggcgagc tggtgttcga gaggtggagg    1020
aggctgagcg acaacagcca gtggatccag gtgagcctgg tgttccagac cctgcagcag    1080
atgagggaca agaccccgct gagcctgaac accccgccgg gcgaggtgaa gctgaccctg    1140
gccggctgcg aggagaggaa cgcccagggc atgtgcagcc tggccggctt cacccagatc    1200
gtgaacgagg ccaggatccc ggcctgcagc ctgtga                              1236
```

<210> SEQ ID NO 147
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 147

```
atgcagagcg agccggagct gaagctggag agcgtggtga tcgtgagcag gcacggcgtg     60
agggccccga ccaaggccac ccagctgatg caggacgtga ccccggacgc cttctacacc    120
tggccggtga agctgggcga gctgaccccg aggggcggcg agctgatcgc ctacctgggc    180
cactactgga ggcagaggct ggtggccgac ggcctgctgc cgaagaaggg ctgcccgcag    240
agcggccagg tggccatcat cgccgacgtg gacgagagga ccaggaagac cggcgaggcc    300
ttcgccgccg gcctggcccc ggactgcgcc atcaccgtgc acacccaggc cgacaccagc    360
agcccggacc cgctgttcaa cccgctgaag accggcgtgt gccagctgga caacgcccag    420
gtgaccgacg ccatcctgga gggccggc ggcagcatcg ccgacttcac cggccactac    480
cagaccgcct tcagggagct ggagagggtg ctgaacttcc cgcagagcaa cctgtgcctg    540
aagagggaga gcaggacga gagctgcagc ctgacccagg ccctgccgag cgagctgaag    600
gtgagcgccg acaacgtgag cctgaccggc gccgtgagcc tggccagcat gctgaccgag    660
atcttcctgc tgcagcaggc ccagggcatg ccggagccgg gctggggcag gatcaccgac    720
agccaccagt ggaacaccct gctgagcctg cacaacgccc agttcgacct gctgcagagg    780
accccggagg tggccaggag cagggccacc ccgctgctgg acctgatcaa gaccgccctg    840
accccgcacc cgccgcagaa gcaggcctac ggcgtgaccc tgccgaccag cgtgctgttc    900
atcgccggcc acgacaccaa cctggccaac ctgggcggcg ccctggagct gctgtacacc    960
ctgccgggcc agccggacaa caccccgccg ggcggcgagc tggtgttcga gaggtggagg    1020
aggctgagcg acaacagcca gtggatccag gtgagcctgg tgttccagac cctgcagcag    1080
atgagggaca agaccccgct gagcctgaac accccgccgg gcgaggtgaa gctgaccctg    1140
gccggctgcg aggagaggaa cgcccagggc atgtgcagcc tggccggctt cacccagatc    1200
gtgaacgagg ccaggatccc ggcctgcagc ctgtga                              1236
```

<210> SEQ ID NO 148
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 148

```
atgcagagcg agccggagct gaagctggag agcgtggtga tcgtgagcag gcacggcgtg     60
agggccccga ccaaggccac ccagctgatg caggacgtga ccccggacgc cttctacacc    120
tggccggtga agctgggcga gctgaccccg aggggcggcg agctgatcgc ctacctgggc    180
cactactgga ggcagaggct ggtggccgac ggcctgctgc cgaagaaggg ctgcccgcag    240
```

```
agcggccagg tggccatcat cgccgacgtg gacgagagga ccaggaagac cggcgaggcc      300
ttcgccgccg gcctggcccc ggactgcgcc atcaccgtgc acacccaggc cgacaccagc      360
agcccggacc cgctgttcaa cccgctgaag accggcgtgt gccagctgga caacgcccag      420
gtgaccgacg ccatcctgga gggccggc ggcagcatcg ccgacttcac cggccactac        480
cagaccgcct tcagggagct ggagagggtg ctgaacttcc gcagagcaa cctgtgcctg       540 aagagggaga agcaggacga gagctgcagc ctgacccagg ccctgccgag cgagctgaag      600
gtgagcgccg acaacgtgag cctgaccggc gccgtgagcc tggccagcat gctgaccgag      660
atcttcctgc tgcagcaggc ccagggcatg ccggagccgg gctggggcag gatcaccgac      720
agccaccagt ggaacacccct gctgagcctg cacaacgccc agttcgacct gctgcagagg     780
accccggagg tggccaggag cagggccacc ccgctgctgg acctgatcaa gaccgccctg      840
accccgcacc cgccgcagaa gcaggcctac ggcgtgaccc tgccgaccag cgtgctgttc      900
atcgccggcc acgacaccaa cctggccaac ctgggcggcg ccctggagct gcagtggacc      960
ctgccgggcc agccggacaa caccccgccg ggcggcgagc tggtgttcga gaggtggagg     1020
aggctgagcg acaacagcca gtggatccag gtgagcctgg tgttccagac cctgcagcag    1080
atgagggaca agaccccgct gttcctgaac ccccgccgg gcgaggtgaa gctgaccctg      1140
gccggctgcg aggagaggaa cgcccagggc atgtgcagcc tggccggctt cacccagatc     1200
gtgaacgagg ccaggatccc ggcctgcagc ctgtga                              1236
```

<210> SEQ ID NO 149
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 149

```
atgcagagcg agccggagct gaagctggag agcgtggtga tcgtgagcag gcacggcgtg       60
agggccccga ccaaggccac ccagctgatg caggacgtga ccccggacgc ctggccgacc      120
tggccggtga agctgggcga gctgaccccg aggggcggcg agctgatcgc ctacctgggc      180
cactactgga ggcagaggct ggtggccgac ggcctgctgc cgaagaaggg ctgcccgcag      240
agcggccagg tggccatcat cgccgacgtg gacgagagga ccaggaagac cggcgaggcc      300
ttcgccgccg gcctggcccc ggactgcgcc atcaccgtgc acacccaggc cgacaccagc      360
agcccggacc cgctgttcaa cccgctgaag accggcgtgt gccagctgga caacgcccag      420
gtgaccgacg ccatcctgga gggccggc ggcagcatcg ccgacttcac cggccactac        480
cagaccgcct tcagggagct ggagagggtg ctgaacttcc gcagagcaa cctgtgcctg       540 aagagggaga agcaggacga gagctgcagc ctgacccagg ccctgccgag cgagctgaag      600
gtgagcgccg acaacgtgag cctgaccggc gccgtgagcc tggccagcat gctgaccgag      660
atcttcctgc tgcagcaggc ccagggcatg ccggagccgg gctggggcag gatcaccgac      720
agccaccagt ggaacacccct gctgagcctg cacaacgccc agttcgacct gctgcagagg     780
accccggagg tggccaggag cagggccacc ccgctgctgg acctgatcaa gaccgccctg      840
accccgcacc cgccgcagaa gcaggcctac ggcgtgaccc tgccgaccag cgtgctgttc      900
atcgccggcc acgacaccaa cctggccaac ctgggcggcg ccctggagct gctgtacacc      960
ctgccgggcc agccggacaa caccccgccg ggcggcgagc tggtgttcga gaggtggagg     1020
aggctgagcg acaacagcca gtggatccag gtgagcctgg tgttccagac cctgcagcag    1080
```

-continued

| | |
|---|---|
| atgagggaca agaccccgct gagcctgaac accccgccgg gcgaggtgaa gctgaccctg | 1140 |
| gccggctgcg aggagaggaa cgcccagggc atgtgcagcc tggccggctt cacccagatc | 1200 |
| gtgaacgagg ccaggatccc ggcctgcagc ctgtga | 1236 |

<210> SEQ ID NO 150
<211> LENGTH: 1236
<212> TYPE: DNA
<213> ORGANISM: Artificial Sequence
<220> FEATURE:
<223> OTHER INFORMATION: Maize Optimized DNA

<400> SEQUENCE: 150

| | |
|---|---|
| atgcagagcg agccggagct gaagctggag agcgtggtga tcgtgagcag gcacggcgtg | 60 |
| agggccccga ccaaggccac ccagctgatg caggacgtga ccccggacgc ctggccgacc | 120 |
| tggccggtga agctgggcga gctgaccccg aggggcggcg agctgatcgc ctacctgggc | 180 |
| cactactgga ggcagaggct ggtggccgac ggcctgctgc gaagaagggg ctgcccgcag | 240 |
| agcggccagg tggccatcat cgccgacgtg gacgagagga ccaggaagac cggcgaggcc | 300 |
| ttcgccgccg gcctggcccc ggactgcgcc atcaccgtgc acacccaggc cgacaccagc | 360 |
| agcccggacc cgctgttcaa cccgctgaag accggcgtgt gccagctgga caacgcccag | 420 |
| gtgaccgacg ccatcctgga gagggccggc ggcagcatcg ccgacttcac cggccactac | 480 |
| cagaccgcct tcagggagct ggagagggtg ctgaacttcc cgcagagcaa cctgtgcctg | 540 |
| aagagggaga agcaggacga gagctgcagc ctgacccagg ccctgccgag cgagctgaag | 600 |
| gtgagcgccg acaacgtgag cctgaccggc gccgtgagcc tggccagcat gctgaccgag | 660 |
| atcttcctgc tgcagcaggc ccagggcatg ccggagccgg gctggggcag gatcaccgac | 720 |
| agccaccagt ggaacaccct gctgagcctg cacaacgccc agttcgacct gctgcagagg | 780 |
| accccggagg tggccaggag cagggccacc ccgctgctgg acctgatcaa gaccgccctg | 840 |
| accccgcacc cgccgcagaa gcaggcctac ggcgtgaccc tgccgaccag cgtgctgttc | 900 |
| atcgccggcc acgacaccaa cctggccaac ctgggcggcg ccctggagct gcagtggacc | 960 |
| ctgccgggcc agccggacaa caccccgccg ggcggcgagc tggtgttcga gaggtggagg | 1020 |
| aggctgagcg acaacagcca gtggatccag gtgagcctgg tgttccagac cctgcagcag | 1080 |
| atgagggaca agacccccgct gttcctgaac accccgccgg gcgaggtgaa gctgaccctg | 1140 |
| gccggctgcg aggagaggaa cgcccagggc atgtgcagcc tggccggctt cacccagatc | 1200 |
| gtgaacgagg ccaggatccc ggcctgcagc ctgtga | 1236 |

<210> SEQ ID NO 151
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 151

| | |
|---|---|
| atgcagagcg agccggagct gaagctggag agcgtggtga tcgtgagcag gcacggcgtg | 60 |
| agggccccga ccaaggccac ccagctgatg caggacgtga ccccggacgc ctggccgacc | 120 |
| tggccggtga agctgggcga gctgaccccg aggggcggcg agctgatcgc ctacctgggc | 180 |
| cactactgga ggcagaggct ggtggccgac ggcctgctgc gaagaagggg ctgcccgcag | 240 |
| agcggccagg tggccatcat cgccgacgtg gacgagagga ccaggaagac cggcgaggcc | 300 |
| ttcgccgccg gcctggcccc ggactgcgcc atcaccgtgc acacccaggc cgacaccagc | 360 |

-continued

```
agcccggacg agctgttcaa cctgctgaag accggcgtgt gccagctgga caacgcccag    420
gtgaccgacg ccatcctgga gagggccggc ggcagcatcg ccgacttcac cggccactac    480
cagaccgcct tcagggagct ggagagggtg ctgaacttcc gcagagcaa cctgtgcctg     540
aagagggaga agcaggacga gagctgcagc ctgacccagg ccctgccgag cgagctgaag    600
gtgagcgccg acaacgtgag cctgaccggc gccgtgagcc tggccagcat gctgaccgag    660
atcttcctgc tgcagcaggc ccagggcatg ccggagccgg ctggggcag gatcaccgac     720
agccaccagt ggaacaccct gctgagcctg cacaacgccc agttcgacct gctgcagagg    780
accccggagg tggccaggag cagggccacc ccgctgctgg acctgatcaa gaccgccctg    840
accccgcacc cgccgcagaa gcaggcctac ggcgtgaccc tgccgaccag cgtgctgttc    900
atcgccggcc acgacaccaa cctggccaac ctgggcggcg ccctggagct gctgtacacc    960
ctgccgggcc agccggacaa caccccgccg ggcggcgagc tggtgttcga gaggtggagg   1020
aggctgagcg acaacagcca gtggatccag gtgagcctgg tgttccagac cctgcagcag   1080
atgagggaca agaccccgct gagcctgaac accccgccgg gcgaggtgaa gctgaccctg   1140
gccggctgcg aggagaggaa cgcccagggc atgtgcagcc tggccggctt cacccagatc   1200
gtgaacgagg ccaggatccc cggcctgcag cctgtga                             1236
```

<210> SEQ ID NO 152
<211> LENGTH: 1236
<212> TYPE: DNA
<213> ORGANISM: Artificial Sequence
<220> FEATURE:
<223> OTHER INFORMATION: maize optimized DNA

<400> SEQUENCE: 152

```
atgcagagcg agccggagct gaagctggag agcgtggtga tcgtgagcag gcacggcgtg     60
agggccccga ccaaggccac ccagctgatg caggacgtga ccccggacgc ctggccgacc    120
tggccggtga agctgggcga gctgaccccg aggggcggcg agctgatcgc ctacctgggc    180
cactactgga ggcagaggct ggtggccgac ggcctgctgc cgaagaaggg ctgcccgcag    240
agcggccagg tggccatcat cgccgacgtg acgagagga ccaggaagac cggcgaggcc     300
ttcgccgccg cgctggcccc ggactgcgcc atcaccgtgc acacccaggc cgacaccagc    360
agcccggacc cgctgttcta cgtgctgaag accggcgtgt gccagctgga caacgcccag    420
gtgaccgacg ccatcctgga gagggccggc ggcagcatcg ccgacttcac cggccactac    480
cagaccgcct tcagggagct ggagagggtg ctgaacttcc gcagagcaa cctgtgcctg     540
aagagggaga agcaggacga gagctgcagc ctgacccagg ccctgccgag cgagctgaag    600
gtgagcgccg acaacgtgag cctgaccggc gccgtgagcc tggccagcat gctgaccgag    660
atcttcctgc tgcagcaggc ccagggcatg ccggagccgg ctggggcag gatcaccgac     720
agccaccagt ggaacaccct gctgagcctg cacaacgccc agttcgacct gctgcagagg    780
accccggagg tggccaggag cagggccacc ccgctgctgg acctgatcaa gaccgccctg    840
accccgcacc cgccgcagaa gcaggcctac ggcgtgaccc tgccgaccag cgtgctgttc    900
atcgccggcc acgacaccaa cctggccaac ctgggcggcg ccctggagct gcagtggacc    960
ctgccgggcc agccggacaa caccccgccg ggcggcgagc tggtgttcga gaggtggagg   1020
aggctgagcg acaacagcca gtggatccag gtgagcctgg tgttccagac cctgcagcag   1080
atgagggaca agaccccgct gagcctgaac accccgccgg gcgaggtgaa gctgaccctg   1140
gccggctgcg aggagaggaa cgcccagggc atgtgcagcc tggccggctt cacccagatc   1200
```

```
gtgaacgagg ccaggatccc ggcctgcagc ctgtga                              1236
```

<210> SEQ ID NO 153
<211> LENGTH: 1236
<212> TYPE: DNA
<213> ORGANISM: Artificial Sequence
<220> FEATURE:
<223> OTHER INFORMATION: maize optimized DNA

<400> SEQUENCE: 153

```
atgcagagcg agccggagct gaagctggag agcgtggtga tcgtgagcag gcacggcgtg     60
agggccccga ccaagttcac ccagctgatg caggacgtga ccccggacgc ctggccgacc    120
tggccggtga agctgggcga gctgaccccg aggggcggcg agctgatcgc ctacctgggc    180
cactactgga ggcagaggct ggtggccgac ggcctgctgc gaagaagggg ctgcccgcag    240
agcggccagg tggccatcat cgccgacgtg gacgagagga ccaggaagac cggcgaggcc    300
ttcgccgccg gcctggcccc ggactgcgcc atcaccgtgc acacccaggc cgacaccagc    360
agcccggacc cgctgttcaa cccgctgaag accggcgtgt gccagctgga cgtggcccag    420
gtgaccgacg ccatcctgga gagggccggc ggcagcatcg ccgacttcac cggccactac    480
cagaccgcct tcagggagct ggagagggtg ctgaacttcc cgcagagcaa cctgtgcctg    540
aagagggaga agcaggacga gagctgcagc ctgacccagg ccctgccgag cgagctgaag    600
gtgagcgccg acaacgtgag cctgaccggc gcctggagcc tggccagcat gctgaccgag    660
atcttcctgc tgcagcaggc ccagggcatg ccggagccgg gctggggcag gatcaccgac    720
agccaccagt ggaacaccct gctgagcctg cacaacgccc agttcgacct gctgcagagg    780
accccggagg tggccaggag cagggccacc ccgctgctgg acctgatcaa gaccgccctg    840
accccgcacc cgccgcagaa gcaggcctac ggcgtgaccc tgccgaccag cgtgctgttc    900
atcgccggcc acgacaccaa cctggccaac ctgggcggcg ccctggagct gcagtggacc    960
ctgccgggcc agccggacaa caccccgccg ggcggcgagc tggtgttcga gaggtggagg   1020
aggctgagcg acaacagcca gtggatccag gtgagcctgg tgttccagac cctgcagcag   1080
atgagggaca agacccgct gagcctgaac accccgccgg cgaggtgaa gctgaccctg   1140
gccggctgcg aggagaggaa cgcccagggc atgtgcagcc tggccggctt cacccagatc   1200
gtgaacgagg ccaggatccc ggcctgcagc ctgtga                              1236
```

<210> SEQ ID NO 154
<211> LENGTH: 1236
<212> TYPE: DNA
<213> ORGANISM: Artificial Sequence
<220> FEATURE:
<223> OTHER INFORMATION: maize optimized DNA

<400> SEQUENCE: 154

```
atgcagagcg agccggagct gaagctggag agcgtggtga tcgtgagcag gcacggcgtg     60
agggccccga ccaagttcac ccagctgatg caggacgtga ccccggacgc cttctacacc    120
tggccggtga agctgggcga gctgaccccg aggggcggcg agctgatcgc ctacctgggc    180
cactactgga ggcagaggct ggtggccgac ggcctgctgc gaagaagggg ctgcccgcag    240
agcggccagg tggccatcat cgccgacgtg gacgagagga ccaggaagac cggcgaggcc    300
ttcgccgccg gcctggcccc ggactgcgcc atcaccgtgc acacccaggc cgacaccagc    360
agcccggacc cgctgttcaa cccgctgaag accggcgtgt gccagctgga cgtggcccag    420
gtgaccgacg ccatcctgga gagggccggc ggcagcatcg ccgacttcac cggccactac    480
```

| | |
|---|---|
| cagaccgcct tcagggagct ggagagggtg ctgaacttcc cgcagagcaa cctgtgcctg | 540 |
| aagagggaga agcaggacga gagctgcagc ctgacccagg ccctgccgag cgagctgaag | 600 |
| gtgagcgccg acaacgtgag cctgaccggc gcctggagcc tggccagcat gctgaccgag | 660 |
| atcttcctgc tgcagcaggc ccagggcatg ccggagccgg gctggggcag gatcaccgac | 720 |
| agccaccagt ggaacaccct gctgagcctg cacaacgccc agttcgacct gctgcagagg | 780 |
| accccggagg tggccaggag cagggccacc ccgctgctgg acctgatcaa gaccgccctg | 840 |
| accccgcacc cgccgcagaa gcaggcctac ggcgtgaccc tgccgaccag cgtgctgttc | 900 |
| atcgccggcc acgacaccaa cctggccaac ctgggcggcg ccctggagct gcagtggacc | 960 |
| ctgccgggcc agccggacaa caccccgccg ggcggcgagc tggtgttcga gaggtggagg | 1020 |
| aggctgagcg acaacagcca gtggatccag gtgagcctgg tgttccagac cctgcagcag | 1080 |
| atgagggaca agaccccgct gagcctgaac accccgccgg gcgaggtgaa gctgaccctg | 1140 |
| gccggctgcg aggagaggaa cgcccagggc atgtgcagcc tggccggctt cacccagatc | 1200 |
| gtgaacgagg ccaggatccc ggcctgcagc ctgtga | 1236 |

<210> SEQ ID NO 155
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 155

| | |
|---|---|
| atgcagagcg agccggagct gaagctggag agcgtggtga tcgtgagcag gcacggcgtg | 60 |
| agggccccga ccaagttcac ccagctgatg caggacgtga ccccggacgc ctggccgacc | 120 |
| tggccggtga agctgggcga gctgacccg aggggcggcg agctgatcgc ctacctgggc | 180 |
| cactactgga ggcagaggct ggtggccgac ggcctgctgc cgaagaaggg ctgcccgcag | 240 |
| agcggccagg tggccatcat cgccgacgtg gacgagagga ccaggaagac cggcgaggcc | 300 |
| ttcgccgccg gcctggcccc ggactgcgcc atcaccgtgc acacccaggc cgacaccagc | 360 |
| agcccggacg agctgttcaa cctgctgaag accggcgtgt gccagctgga cgtggcccag | 420 |
| gtgaccgacg ccatcctgga gagggccggc ggcagcatcg ccgacttcac cggccactac | 480 |
| cagaccgcct tcagggagct ggagagggtg ctgaacttcc cgcagagcaa cctgtgcctg | 540 |
| aagagggaga agcaggacga gagctgcagc ctgacccagg ccctgccgag cgagctgaag | 600 |
| gtgagcgccg acaacgtgag cctgaccggc gcctggagcc tggccagcat gctgaccgag | 660 |
| atcttcctgc tgcagcaggc ccagggcatg ccggagccgg gctggggcag gatcaccgac | 720 |
| agccaccagt ggaacaccct gctgagcctg cacaacgccc agttcgacct gctgcagagg | 780 |
| accccggagg tggccaggag cagggccacc ccgctgctgg acctgatcaa gaccgccctg | 840 |
| accccgcacc cgccgcagaa gcaggcctac ggcgtgaccc tgccgaccag cgtgctgttc | 900 |
| atcgccggcc acgacaccaa cctggccaac ctgggcggcg ccctggagct gcagtggacc | 960 |
| ctgccgggcc agccggacaa caccccgccg ggcggcgagc tggtgttcga gaggtggagg | 1020 |
| aggctgagcg acaacagcca gtggatccag gtgagcctgg tgttccagac cctgcagcag | 1080 |
| atgagggaca agaccccgct gagcctgaac accccgccgg gcgaggtgaa gctgaccctg | 1140 |
| gccggctgcg aggagaggaa cgcccagggc atgtgcagcc tggccggctt cacccagatc | 1200 |
| gtgaacgagg ccaggatccc ggcctgcagc ctgtga | 1236 |

<210> SEQ ID NO 156

```
<211> LENGTH: 1236
<212> TYPE: DNA
<213> ORGANISM: Artificial Sequence
<220> FEATURE:
<223> OTHER INFORMATION: maize optimized DNA

<400> SEQUENCE: 156
atgcagagcg agccggagct gaagctggag agcgtggtga tcgtgagcag gcacggcgtg      60
agggccccga ccaagttcac ccagctgatg caggacgtga ccccggacgc ctggccgacc     120
tggccggtga agctgggcga gctgaccccg aggggcggcg agctgatcgc ctacctgggc     180
cactactgga ggcagaggct ggtggccgac ggcctgctgc gaagaaggg ctgcccgcag      240
agcggccagg tggccatcat cgccgacgtg gacgagagga ccaggaagac cggcgaggcc     300
ttcgccgccg gcctggcccc ggactgcgcc atcaccgtgc acacccaggc cgacaccagc     360
agcccggacc cgctgttcta cgtgctgaag accggcgtgt gccagctgga cgtggcccag     420
gtgaccgacg ccatcctgga gagggccggc ggcagcatcg ccgacttcac cggccactac     480
cagaccgcct tcagggagct ggagagggtg ctgaacttcc cgcagagcaa cctgtgcctg     540
aagagggaga agcaggacga gagctgcagc ctgacccagg ccctgccgag cgagctgaag     600
gtgagcgccg acaacgtgag cctgaccggc gcctggagcc tggccagcat gctgaccgag     660
atcttcctgc tgcagcaggc ccagggcatg ccggagccgg gctggggcag gatcaccgac     720
agccaccagt ggaacacccc tgctgagcctg cacaacgccc agttcgacct gctgcagagg    780
accccggagg tggccaggag cagggccacc ccgctgctgg acctgatcaa gaccgccctg     840
accccgcacc cgccgcagaa gcaggcctac ggcgtgaccc tgccgaccag cgtgctgttc     900
atcgccggcc acgacaccaa cctggccaac ctgggcggcg ccctggagct gcagtggacc     960
ctgccgggcc agccggacaa caccccgccg ggcggcgagc tggtgttcga gaggtggagg    1020
aggctgagcg acaacagcca gtggatccag gtgagcctgg tgttccagac cctgcagcag    1080
atgagggaca gacccccgct gagcctgaac accccgccgg cgaggtgaa gctgaccctg     1140
gccggctgcg aggagaggaa cgcccagggc atgtgcagcc tggccggctt cacccagatc    1200
gtgaacgagg ccaggatccc ggcctgcagc ctgtga                              1236

<210> SEQ ID NO 157
<211> LENGTH: 1236
<212> TYPE: DNA
<213> ORGANISM: Artificial Sequence
<220> FEATURE:
<223> OTHER INFORMATION: maize optimized DNA

<400> SEQUENCE: 157
atgcagagcg agccggagct gaagctggag agcgtggtga tcgtgagcag gcacggcgtg      60
agggccccga ccaagttcac ccagctgatg caggacgtga ccccggacgc cttctacacc     120
tggccggtga agctgggcga gctgaccccg aggggcggcg agctgatcgc ctacctgggc     180
cactactgga ggcagaggct ggtggccgac ggcctgctgc gaagaaggg ctgcccgcag      240
agcggccagg tggccatcat cgccgacgtg gacgagagga ccaggaagac cggcgaggcc     300
ttcgccgccg gcctggcccc ggactgcgcc atcaccgtgc acacccaggc cgacaccagc     360
agcccggacc cgctgttcaa cccgctgaag accggcgtgt gccagctgga cgtggcccag     420
gtgaccgacg ccatcctgga gagggccggc ggcagcatcg ccgacttcac cggccactac     480
cagaccgcct tcagggagct ggagagggtg ctgaacttcc cgcagagcaa cctgtgcctg     540
aagagggaga agcaggacga gagctgcagc ctgacccagg ccctgccgag cgagctgaag     600
```

```
gtgagcgccg acaacgtgag cctgaccggc gcctggagcc tggccagcat gctgaccgag      660
atcttcctgc tgcagcaggc ccagggcatg ccggagccgg gctggggcag gatcaccgac      720
agccaccagt ggaacaccct gctgagcctg cacaacgccc agttcgacct gctgcagagg      780
accccggagg tggccaggag cagggccacc ccgctgctgg acctgatcaa gaccgccctg      840
accccgcacc cgccgcagaa gcaggcctac ggcgtgaccc tgccgaccag cgtgctgttc      900
atcgccggcc acgacaccaa cctggccaac ctgggcggcg ccctggagct gctgtacacc      960
ctgccgggcc agccggacaa caccccgccg ggcggcgagc tggtgttcga gaggtggagg     1020
aggctgagcg acaacagcca gtggatccag gtgagcctgg tgttccagac cctgcagcag     1080
atgagggaca agaccccgct gagcctgaac accccgccgg gcgaggtgaa gctgaccctg     1140
gccggctgcg aggagaggaa cgcccagggc atgtgcagcc tggccggctt cacccagatc     1200
gtgaacgagg ccaggatccc ggcctgcagc ctgtga                               1236
```

<210> SEQ ID NO 158
<211> LENGTH: 1236
<212> TYPE: DNA
<213> ORGANISM: Artificial Sequence
<220> FEATURE:
<223> OTHER INFORMATION: maize optimized DNA

<400> SEQUENCE: 158

```
atgcagagcg agccggagct gaagctggag agcgtggtga tcgtgagcag gcacggcgtg       60
agggccccga ccaagttcac ccagctgatg caggacgtga ccccggacgc cttctacacc      120
tggccggtga agctgggcga gctgaccccg aggggcggcg agctgatcgc ctacctgggc      180
cactactgga ggcagaggct ggtggccgac ggcctgctgc cgaagaaggg gctgcccgcag     240 agcggccagg tggccatcat cgccgacgtg gacgagagga ccaggaagac cggcgaggcc      300
ttcgccgccg gcctggcccc ggactgcgcc atcaccgtgc acacccaggc cgacaccagc      360
agcccggacc cgctgttcaa cccgctgaag accggcgtgt gccagctgga cgtggcccag      420
gtgaccgacg ccatcctgga gggccggc ggcagcatcg ccgacttcac cggccactac        480
cagaccgcct tcagggagct ggagagggtg ctgaacttcc gcagagcaa cctgtgcctg       540 aagagggaga gcaggacga gagctgcagc ctgacccagg ccctgccgag cgagctgaag       600
gtgagcgccg acaacgtgag cctgaccggc gcctggagcc tggccagcat gctgaccgag      660
atcttcctgc tgcagcaggc ccagggcatg ccggagccgg gctggggcag gatcaccgac      720
agccaccagt ggaacaccct gctgagcctg cacaacgccc agttcgacct gctgcagagg      780
accccggagg tggccaggag cagggccacc ccgctgctgg acctgatcaa gaccgccctg      840
accccgcacc cgccgcagaa gcaggcctac ggcgtgaccc tgccgaccag cgtgctgttc      900
atcgccggcc acgacaccaa cctggccaac ctgggcggcg ccctggagct gcagtggacc      960
ctgccgggcc agccggacaa caccccgccg ggcggcgagc tggtgttcga gaggtggagg     1020
aggctgagcg acaacagcca gtggatccag gtgagcctgg tgttccagac cctgcagcag     1080
atgagggaca agaccccgct gttcctgaac accccgccgg gcgaggtgaa gctgaccctg     1140
gccggctgcg aggagaggaa cgcccagggc atgtgcagcc tggccggctt cacccagatc     1200
gtgaacgagg ccaggatccc ggcctgcagc ctgtga                               1236
```

<210> SEQ ID NO 159
<211> LENGTH: 1236
<212> TYPE: DNA
<213> ORGANISM: Artificial Sequence
<220> FEATURE:

<223> OTHER INFORMATION: Maize optimized DNA

<400> SEQUENCE: 159

```
atgcagagcg agccggagct gaagctggag agcgtggtga tcgtgagcag gcacggcgtg      60
agggccccga ccaagttcac ccagctgatg caggacgtga ccccggacgc ctggccgacc     120
tggccggtga agctgggcga gctgaccccg aggggcggcg agctgatcgc ctacctgggc     180
cactactgga ggcagaggct ggtggccgac ggcctgctgc gaagaaggg ctgcccgcag      240
agcggccagg tggccatcat cgccgacgtg gacgagagga ccaggaagac cggcgaggcc     300
ttcgccgccg gcctggcccc ggactgcgcc atcaccgtgc acacccaggc cgacaccagc     360
agcccggacg agctgttcaa cctgctgaag accggcgtgt gccagctgga cgtggcccag     420
gtgaccgacg ccatcctgga gagggccggc ggcagcatcg ccgacttcac cggccactac     480
cagaccgcct tcagggagct ggagagggtg ctgaacttcc cgcagagcaa cctgtgcctg     540
aagagggaga gcaggacga gagctgcagc ctgacccagg ccctgccgag cgagctgaag      600
gtgagcgccg acaacgtgag cctgaccggc gcctggagcc tggccagcat gctgaccgag     660
atcttcctgc tgcagcaggc ccagggcatg ccggagccgg gctggggcag gatcaccgac     720
agccaccagt ggaacacccct gctgagcctg cacaacgccc agttcgacct gctgcagagg    780
accccggagg tggccaggag cagggccacc ccgctgctgg acctgatcaa gaccgccctg     840
accccgcacc cgccgcagaa gcaggcctac ggcgtgaccc tgccgaccag cgtgctgttc     900
atcgccggcc acgacaccaa cctggccaac ctgggcggcg ccctggagct gctgtacacc     960
ctgccgggcc agccggacaa caccccgccg ggcggcgagc tggtgttcga gaggtggagg    1020
aggctgagcg acaacagcca gtggatccag gtgagcctgg tgttccagac cctgcagcag    1080
atgagggaca gacccgct gagcctgaac accccgccgg gcgaggtgaa gctgaccctg       1140
gccggctgcg aggagaggaa cgcccagggc atgtgcagcc tggccggctt cacccagatc    1200
gtgaacgagg ccaggatccc cggcctgcag cctgtga                              1236
```

<210> SEQ ID NO 160
<211> LENGTH: 1236
<212> TYPE: DNA
<213> ORGANISM: Artificial Sequence
<220> FEATURE:
<223> OTHER INFORMATION: maize optimized DNA

<400> SEQUENCE: 160

```
atgcagagcg agccggagct gaagctggag agcgtggtga tcgtgagcag gcacggcgtg      60
agggccccga ccaagttcac ccagctgatg caggacgtga ccccggacgc ctggccgacc     120
tggccggtga agctgggcga gctgaccccg aggggcggcg agctgatcgc ctacctgggc     180
cactactgga ggcagaggct ggtggccgac ggcctgctgc gaagaaggg ctgcccgcag      240
agcggccagg tggccatcat cgccgacgtg gacgagagga ccaggaagac cggcgaggcc     300
ttcgccgccg gcctggcccc ggactgcgcc atcaccgtgc acacccaggc cgacaccagc     360
agcccggacc gctgttcta cgtgctgaag accggcgtgt gccagctgga cgtggcccag     420
gtgaccgacg ccatcctgga gagggccggc ggcagcatcg ccgacttcac cggccactac     480
cagaccgcct tcagggagct ggagagggtg ctgaacttcc cgcagagcaa cctgtgcctg     540
aagagggaga gcaggacga gagctgcagc ctgacccagg ccctgccgag cgagctgaag      600
gtgagcgccg acaacgtgag cctgaccggc gcctggagcc tggccagcat gctgaccgag     660
atcttcctgc tgcagcaggc ccagggcatg ccggagccgg gctggggcag gatcaccgac     720
```

| | |
|---|---|
| agccaccagt ggaacaccct gctgagcctg cacaacgccc agttcgacct gctgcagagg | 780 |
| accccggagg tggccaggag cagggccacc ccgctgctgg acctgatcaa gaccgccctg | 840 |
| accccgcacc cgccgcagaa gcaggcctac ggcgtgaccc tgccgaccag cgtgctgttc | 900 |
| atcgccggcc acgacaccaa cctggccaac ctgggcggcg ccctggagct gcagtggacc | 960 |
| ctgccgggcc agccggacaa caccccgccg ggcggcgagc tggtgttcga gaggtggagg | 1020 |
| aggctgagcg acaacagcca gtggatccag gtgagcctgg tgttccagac cctgcagcag | 1080 |
| atgagggaca agaccccgct gttcctgaac accccgccgg gcgaggtgaa gctgaccctg | 1140 |
| gccggctgcg aggagaggaa cgcccagggc atgtgcagcc tggccggctt cacccagatc | 1200 |
| gtgaacgagg ccaggatccc ggcctgcagc ctgtga | 1236 |

<210> SEQ ID NO 161
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 161

| | |
|---|---|
| atgcagagcg agccggagct gaagctggag agcgtggtga tcgtgagcag gcacggcgtg | 60 |
| agggccccga ccaagttcac ccagctgatg caggacgtga ccccgacgc ctggccgacc | 120 |
| tggccggtga agctgggcga gctgaccccg aggggcggcg agctgatcgc ctacctgggc | 180 |
| cactactgga ggcagaggct ggtggccgac ggcctgctgc gaagaaggg ctgcccgcag | 240 |
| agcggccagg tggccatcat cgccgacgtg gacgagagga ccaggaagac cggcgaggcc | 300 |
| ttcgccgccg gcctggcccc ggactgcgcc atcaccgtgc acaccaggc cgacaccagc | 360 |
| agcccggacc cgctgttcaa cccgctgaag accggcgtgt gccagctgga cgtggcccag | 420 |
| gtgaccgacg ccatcctgga gagggccggc ggcagcatcg ccgacttcac cggccactac | 480 |
| cagaccgcct tcagggagct ggagagggtg ctgaacttcc cgcagagcaa cctggccctg | 540 |
| aagagggaga agcaggacga gagcgccagc ctgacccagg ccctgccgag cgagctgaag | 600 |
| gtgagcgccg acaacgtgag cctgaccggc gcctggagcc tggccagcat gctgaccgag | 660 |
| atcttcctgc tgcagcaggc ccagggcatg ccggagccgg gctggggcag gatcaccgac | 720 |
| agccaccagt ggaacaccct gctgagcctg cacaacgccc agttcgacct gctgcagagg | 780 |
| accccggagg tggccaggag cagggccacc ccgctgctgg acctgatcaa gaccgccctg | 840 |
| accccgcacc cgccgcagaa gcaggcctac ggcgtgaccc tgccgaccag cgtgctgttc | 900 |
| atcgccggcc acgacaccaa cctggccaac ctgggcggcg ccctggagct gcagtggacc | 960 |
| ctgccgggcc agccggacaa caccccgccg ggcggcgagc tggtgttcga gaggtggagg | 1020 |
| aggctgagcg acaacagcca gtggatccag gtgagcctgg tgttccagac cctgcagcag | 1080 |
| atgagggaca agaccccgct gagcctgaac accccgccgg gcgaggtgaa gctgaccctg | 1140 |
| gccggctgcg aggagaggaa cgcccagggc atgtgcagcc tggccggctt cacccagatc | 1200 |
| gtgaacgagg ccaggatccc ggcctgcagc ctgtga | 1236 |

<210> SEQ ID NO 162
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 162

```
atgcagagcg agccggagct gaagctggag agcgtggtga tcgtgagcag gcacggcgtg      60 agggcccga ccaagttcac ccagctgatg caggacgtga ccccggacgc cttctacacc      120
tggccggtga agctgggcga gctgaccccg aggggcggcg agctgatcgc ctacctgggc      180
cactactgga ggcagaggct ggtggccgac ggcctgctgc gaagaaggg ctgcccgcag      240 agcggccagg tggccatcat cgccgacgtg gacgagagga ccaggaagac cggcgaggcc      300
ttcgccgccg gcctggcccc ggactgcgcc atcaccgtgc acacccaggc cgacaccagc      360
agcccggacc cgctgttcaa cccgctgaag accggcgtgt gccagctgga cgtggcccag      420
gtgaccgacg ccatcctgga ggggccggc ggcagcatcg ccgacttcac cggccactac      480
cagaccgcct tcagggagct ggagagggtg ctgaacttcc gcagagcaa cctggccctg      540 aagagggaga agcaggacga gagcgccagc ctgacccagg ccctgccgag cgagctgaag      600
gtgagcgccg acaacgtgag cctgaccggc gcctggagcc tggccagcat gctgaccgag      660
atcttcctgc tgcagcaggc ccagggcatg ccggagccgg gctggggcag gatcaccgac      720
agccaccagt ggaacaccct gctgagcctg cacaacgccc agttcgacct gctgcagagg      780
accccggagg tggccaggag cagggccacc ccgctgctgg acctgatcaa gaccgccctg      840
accccgcacc cgccgcagaa gcaggcctac ggcgtgaccc tgccgaccag cgtgctgttc      900
atcgccggcc acgacaccaa cctggccaac ctgggcggcg ccctggagct gctgtacacc      960
ctgccgggcc agccggacaa caccccgccg ggcggcgagc tggtgttcga gaggtggagg     1020
aggctgagcg acaacagcca gtggatccag gtgagcctgg tgttccagac cctgcagcag     1080
atgagggaca agaccccgct gagcctgaac accccgccgg cgaggtgaa gctgacccctg     1140 gccggctgcg aggagaggaa cgcccagggc atgtgcagcc tggccggctt cacccagatc     1200
gtgaacgagg ccaggatccc ggcctgcagc ctgtga                             1236
```

<210> SEQ ID NO 163
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 163

```
atgcagagcg agccggagct gaagctggag agcgtggtga tcgtgagcag gcacggcgtg      60 agggcccga ccaagttcac ccagctgatg caggacgtga ccccggacgc cttctacacc      120
tggccggtga agctgggcga gctgaccccg aggggcggcg agctgatcgc ctacctgggc      180
cactactgga ggcagaggct ggtggccgac ggcctgctgc gaagaaggg ctgcccgcag      240 agcggccagg tggccatcat cgccgacgtg gacgagagga ccaggaagac cggcgaggcc      300
ttcgccgccg gcctggcccc ggactgcgcc atcaccgtgc acacccaggc cgacaccagc      360
agcccggacc cgctgttcaa cccgctgaag accggcgtgt gccagctgga cgtggcccag      420
gtgaccgacg ccatcctgga ggggccggc ggcagcatcg ccgacttcac cggccactac      480
cagaccgcct tcagggagct ggagagggtg ctgaacttcc gcagagcaa cctggccctg      540 aagagggaga agcaggacga gagcgccagc ctgacccagg ccctgccgag cgagctgaag      600
gtgagcgccg acaacgtgag cctgaccggc gcctggagcc tggccagcat gctgaccgag      660
atcttcctgc tgcagcaggc ccagggcatg ccggagccgg gctggggcag gatcaccgac      720
agccaccagt ggaacaccct gctgagcctg cacaacgccc agttcgacct gctgcagagg      780
accccggagg tggccaggag cagggccacc ccgctgctgg acctgatcaa gaccgccctg      840
```

| | |
|---|---|
| accccgcacc cgccgcagaa gcaggcctac ggcgtgaccc tgccgaccag cgtgctgttc | 900 |
| atcgccggcc acgacaccaa cctggccaac ctgggcggcg ccctggagct gcagtggacc | 960 |
| ctgccgggcc agccggacaa caccccgccg ggcggcgagc tggtgttcga gaggtggagg | 1020 |
| aggctgagcg acaacagcca gtggatccag gtgagcctgg tgttccagac cctgcagcag | 1080 |
| atgagggaca agaccccgct gttcctgaac accccgccgg gcgaggtgaa gctgaccctg | 1140 |
| gccggctgcg aggagaggaa cgcccagggc atgtgcagcc tggccggctt cacccagatc | 1200 |
| gtgaacgagg ccaggatccc ggcctgcagc ctgtga | 1236 |

<210> SEQ ID NO 164
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 164

| | |
|---|---|
| atgcagagcg agccggagct gaagctggag agcgtggtga tcgtgagcag gcacggcgtg | 60 |
| agggccccga ccaagttcac ccagctgatg caggacgtga ccccggacgc ctggccgacc | 120 |
| tggccggtga agctgggcga gctgacccCg aggggcggcg agctgatcgc ctacctgggc | 180 |
| cactactgga ggcagaggct ggtggccgac ggcctgctgc cgaagaaggg ctgcccgcag | 240 |
| agcggccagg tggccatcat cgccgacgtg gacgagagga ccaggaagac cggcgaggcc | 300 |
| ttcgccgccg gcctggcccc ggactgcgcc atcaccgtgc acacccaggc cgacaccagc | 360 |
| agcccggacc cgctgttcaa cccgctgaag accggcgtgg cccagctgga cgtggcccag | 420 |
| gtgaccgacg ccatcctgga gggccggc ggcagcatcg ccgacttcac cggccactac | 480 |
| cagaccgcct tcagggagct ggagagggtg ctgaacttcc cgcagagcaa cctgtgcctg | 540 |
| aagagggaga gcaggacga gctgcagcc ctgacccagg ccctgccgag cgagctgaag | 600 |
| gtgagcgccg acaacgtgag cctgaccggc gcctggagcc tggccagcat gctgaccgag | 660 |
| atcttcctgc tgcagcaggc ccagggcatg ccggagccgg gctggggcag gatcaccgac | 720 |
| agccaccagt ggaacaccct gctgagcctg cacaacgccc agttcgacct gctgcagagg | 780 |
| accccggagg tggccaggag cagggccacc ccgctgctgg acctgatcaa gaccgccctg | 840 |
| accccgcacc cgccgcagaa gcaggcctac ggcgtgaccc tgccgaccag cgtgctgttc | 900 |
| atcgccggcc acgacaccaa cctggccaac ctgggcggcg ccctggagct gcagtggacc | 960 |
| ctgccgggcc agccggacaa caccccgccg ggcggcgagc tggtgttcga gaggtggagg | 1020 |
| aggctgagcg acaacagcca gtggatccag gtgagcctgg tgttccagac cctgcagcag | 1080 |
| atgagggaca agaccccgct gagcctgaac accccgccgg gcgaggtgaa gctgaccctg | 1140 |
| gccggctgcg aggagaggaa cgcccagggc atgtgcagcc tggccggctt cacccagatc | 1200 |
| gtgaacgagg ccaggatccc ggccgccagc ctgtga | 1236 |

<210> SEQ ID NO 165
<211> LENGTH: 1236
<212> TYPE: DNA
<213> ORGANISM: Artificial Sequence
<220> FEATURE:
<223> OTHER INFORMATION: Maize optimized DNA

<400> SEQUENCE: 165

| | |
|---|---|
| atgcagagcg agccggagct gaagctggag agcgtggtga tcgtgagcag gcacggcgtg | 60 |
| agggccccga ccaagttcac ccagctgatg caggacgtga ccccggacgc cttctacacc | 120 |

-continued

```
tggccggtga agctgggcga gctgaccccg aggggcggcg agctgatcgc ctacctgggc      180
cactactgga ggcagaggct ggtggccgac ggcctgctgc cgaagaaggg ctgcccgcag      240
agcggccagg tggccatcat cgccgacgtg gacgagagga ccaggaagac cggcgaggcc      300
ttcgccgccg gcctggcccc ggactgcgcc atcaccgtgc acacccaggc cgacaccagc      360
agcccggacc cgctgttcaa cccgctgaag accggcgtgg cccagctgga cgtggcccag      420
gtgaccgacg ccatcctgga gagggccggc ggcagcatcg ccgacttcac cggccactac      480
cagaccgcct tcagggagct ggagagggtg ctgaacttcc cgcagagcaa cctgtgcctg      540
aagagggaga agcaggacga gagctgcagc ctgacccagg ccctgccgag cgagctgaag      600
gtgagcgccg acaacgtgag cctgaccggc gcctggagcc tggccagcat gctgaccgag      660
atcttcctgc tgcagcaggc ccagggcatg ccggagccgg gctggggcag gatcaccgac      720
agccaccagt ggaacaccct gctgagcctg cacaacgccc agttcgacct gctgcagagg      780
accccggagg tggccaggag cagggccacc ccgctgctgg acctgatcaa gaccgccctg      840
accccgcacc cgccgcagaa gcaggcctac ggcgtgaccc tgccgaccag cgtgctgttc      900
atcgccggcc acgacaccaa cctggccaac ctgggcggcg ccctggagct gcagtggacc      960
ctgccgggcc agccggacaa caccccgccg ggcggcgagc tggtgttcga gaggtggagg     1020
aggctgagcg acaacagcca gtggatccag gtgagcctgg tgttccagac cctgcagcag     1080
atgagggaca agacccccgct gttcctgaac accccgccgg gcgaggtgaa gctgaccctg     1140
gccggctgcg aggagaggaa cgcccagggc atgtgcagcc tggccggctt cacccagatc     1200
gtgaacgagg ccaggatccc ggccgccagc ctgtga                              1236
```

ENGINEERING ENZYMATICALLY SUSCEPTIBLE PHYTASES

FIELD OF INVENTION

The present invention generally relates to the field of molecular biology, computational biology, and more specifically, to methods of protein engineering by rational design to generate proteins with increased enzymatic susceptibility.

BACKGROUND OF THE INVENTION

Industrial processes frequently require the addition of proteins to perform a specific function within a process. The demand for proteins with new or different characteristics grows as industrial processes evolve and become more efficient. One method for developing proteins with new characteristics is to engineer currently used proteins to contain new features, and thus creating new variants of the protein. Protein engineering has focused on the development of thermotolerance in many enzymes. The instant application describes using protein engineering techniques to engineer enzymatically susceptible variants of a protein. The methods described can be used on a variety of proteins. In addition, the methods described can be used to engineer enzymatic susceptibility to a wide range of proteases.

SUMMARY OF THE INVENTION

A method of engineering proteins with increased susceptibility to a protease is described. Protein engineering by rational design is based upon the three-dimensional structural model of a protein and subsequent identification of protein domains that can be altered without deleterious effects on binding sites, active sites and overall three-dimensional structure. Any protein can be engineered for increased susceptibility to any protease.

DETAILED DESCRIPTION OF THE INVENTION

Industrial processes use proteins as a component of manufacturing. Proteins that are enzymes are particularly useful as components in industrial processes as they catalyze reactions that convert a substrate from one form into another. The characteristics of a protein and, in particular, the activity profile (i.e. optimum temperature, pH, salt concentration, ions, etc.) of an enzyme contribute to the usefulness of a protein for a particular process. As new industrial processes develop, there is an increasing demand for proteins with altered characteristics. The new characteristics sought can be in addition to the proteins current set of characteristics or could involve altering a characteristic. Protein characteristics can include, but are not limited to, features of the activity profile, ability to absorb water, ability to prevent water absorption, gelling capacity, etc. For example, it may be desired to engineer a protein that displays thermotolerance and acid stability with the additional characteristic of enhanced susceptibility to protease digestion. In this example, the original characteristics of the protein (thermotolerance and acid stability) need to be maintained while the new characteristic (enhanced sensitivity to a protease) is added. One may also take into account the specific activity of an enzyme where "specific activity" of an enzyme being defined as the amount of substrate an enzyme is able to convert or catalyze over a given unit of time.

There are several techniques available for evolving proteins to create variants with altered characteristics. For example, techniques based upon random amino acid changes or random mutagenesis include chemical mutagenesis (Smith, Ann. Rev. Genet. 19:423-462 (1985)), DirectEvolution; (U.S. Pat. No. 5,830,696); Gene Site Saturation Mutagenesis (GSSM) (U.S. Pat. Nos. 6,171,820 and 6,579,258), Exonuclease-Mediated Gene Assembly in Directed Evolution (U.S. Pat. Nos. 6,361,974 and 6,352,842), End Selection in Directed Evolution (U.S. Pat. Nos. 6,358,709 and 6,238,884), Recombination-Based Synthesis Shuffling (U.S. Pat. Nos. 5,965,408 and 6,440,668, and Australian Patent No. AU724521), and Directed Evolution of Thermophilic Enzymes (U.S. Pat. Nos. 5,830,696 and 6,335,179). These techniques give rise to a pool of variants with random mutations and this pool of variants is then screened to identify those individual variants with the desired set of characteristics.

An alternative to random mutagenesis is rational design in which specific regions of the protein are identified for alteration based upon what is known about the protein itself. Rational design incorporates knowledge of the three-dimensional structure, the location of the active site(s) and the location of important binding site(s) to predict regions of the protein that can be altered. With this information, proteins with specific alterations can be generated and tested for activity. Specific alterations can be made singly or in combinations with other alterations to observe the combined effects of several changes to the protein structure (Fersht, et al. Angewandte Chemie Int. Ed. 23:467-538 (1984)).

Rational design takes into consideration that the relationship between the protein's characteristics, the three-dimensional model and the degree to which the protein can be altered is complex. The mutations to be generated in the protein are mapped onto the three-dimensional model and there is consideration of binding sites, active sites and protein structure; this analysis is intended to increase the probability of generating variants that maintain activity in addition to displaying the new characteristics. In addition, the number of variants screened is relatively low compared to the number of variants screened using random mutagenesis.

Rational design is facilitated by an understanding of the three-dimensional model of the protein. The three-dimensional model can be elucidated by methods which physically determine the three-dimensional structure of the protein such as X-ray crystallography and NMR (nuclear magnetic resonance) or can be modeled computationally. Methods for solving the protein crystal structure physically are well known in the art (Schuetz, et al. EMBO J. 25:4245-4252 (2006); Peterson et al. Mol. Cell 13:665-676 (2004); Allingham et al. Cell 128; 1161-1172 (2007)).

In computational biology, there are three different methods for prediction/modeling a protein's three-dimensional structure; ab initio, homology modeling and protein threading. Ab initio- or de novo-protein modeling methods seek to build three-dimensional protein models "from scratch", i.e., based on physical principles rather than directly on previously solved physical structures. There are many possible procedures that either attempt to mimic protein folding or apply some stochastic method to search possible solutions. These procedures tend to require large computational resources, and have been carried out for small proteins.

Homology modeling is based on the reasonable assumption that two homologous proteins will share very similar structures. Because a protein's fold is more evolutionarily conserved than its amino acid sequence, a target sequence can be modeled with reasonable accuracy on a very distantly related template, provided that the relationship between target and template can be discerned through sequence alignment. It has been suggested that the primary bottleneck in comparative modeling arises from difficulties in alignment rather than from errors in structure prediction given a known good alignment. Unsurprisingly, homology modeling is most accurate when the target and template have similar sequences. The homology modeling method, as provided by computer program Modeler (Accelrys Inc.), can be used to model the three-dimensional structure of homologous protein without the need to solve the actual structure by X-ray or NMR (Webster "Protein Structure Prediction, Methods and Protocols"; Methods in Molecular Biology; Humana Press vol 143 (2000) and Bourne and Weissig, "Structural Bioinformatics", Wiley-Liss Publisher (2003)).

The protein threading method threads the amino acid sequence of a target sequence with unknown structure through a library of classified protein structure folds. In each case, a scoring function is used to assess the compatibility of the sequence to the structure, thus selecting the best possible three-dimensional template for modeling the target protein. This type of method is also known as 3D-1D fold recognition due to its compatibility analysis between three-dimensional structures and linear protein sequences. This method has also given rise to methods performing an inverse folding search by evaluating the compatibility of a given structure with a large database of sequences, thus predicting which sequences have the potential to produce a given fold.

Once the three-dimensional model of the protein is created, this serves as the foundation for adding additional information known about the protein. It is important to identify regions of the protein known to be required for basic activity, such as binding domains and active sites. Conserved regions of a protein can provide insight into areas of the protein that should be avoided when making modifications. Understanding the physical structures of the protein that are required for activity helps to identify areas that may be modified. Generally, areas that may be modified are those that do not contribute to the formation of binding domains or active sites. In addition, areas of the protein selected for modification should not interfere with binding domains or actives sites once alterations have been made. Hence, all alterations to the protein are mapped onto the three-dimensional model using computational techniques, such as the Accelyrs MODELER program, in order to determine if the basic structure of the protein is maintained.

The activity of variant proteins generated by either random mutagenesis or rational design is evaluated to select variants that meet specific criteria. These specific criteria coincide with the new characteristics desired in the protein. These new characteristics can include, but is not limited to, altered catalytic activity of an enzyme, activity at a higher or lower temperature, activity in a wide or narrow range of temperature, activity at a higher or lower pH, activity in a wide or narrow range of pH, sensitivity to degradation at a higher or lower pH, increased susceptibility to digestion by a protease, or increased resistance to digestion by a protease. A person of ordinary skill in the art would be able to take the information disclosed herein and design and generate a range of variants of a protein with altered protein characteristics or activity.

Rational design techniques have been employed to develop protein variants with specific characteristics such as thermotolerance (Perry and Wetzel, Science 226:555-557 (1984); Sauer et al. Biochemistry 25:5992-5998 (1986); Volkin et al J. of Biol. Chem. 262:2945-2950 (1987); Roesler et al Protein Science 9:1642-1650 (2000)), stability in the presence of proteases (Wyss et al. Applied and Enviro. Micro. 65:359-366 (1999)) and stability at low pH (Kim et al. Applied and Enviro. Micro. 72:4397-4403 (2006)). Rational design techniques have also been employed to develop insecticidal protoxins that when exposed to an insect gut, are cleaved by an insect gut protease to release an insecticidal toxin (U.S. patent application Ser. No. 10/229,346). Described herein are methods for using rational design techniques for the purpose of developing proteins with enhanced susceptibility to proteases wherein susceptibility leads to an inactivation of the protein.

The following factors relating to protein structure may contribute to increasing protein sensitivity to proteases; degree and location of glycosylation, degree of disulfide bridge formation, location and sequence of potential protease cleavage sites and protein loops which can be altered to contain highly favorable protease cleavage sites.

Glycosylation may have a number of effects on the properties of an enzyme. First, it may have an impact on the stability of a protein, or it may influence the catalytic properties. Second, in case of acidic carbohydrate modification, it may influence the pI of a protein and thereby change the behavior of the protein during purification. And third, by diverting metabolic energy, it may lower the level of expression of an enzyme. (Wyss et al. Applied and Enviro. Micro. 65:359-366 (1999)). Glycosylation of a protein involves adding glycan chains to the protein which may physically interfere with the ability of a protease to contact a binding site (Bagger et al. Biochemistry 42:10295-10300 (2003)). Decreasing glycosylation of a protein may increase sensitivity to a protease by opening up the structure of the protein to allow interaction of the protease with potential binding sites.

Highly stable protein structures (or protein folding) can prevent the protein from unfolding enough to allow a protease to access potential cleavage sites that are within the three-dimensional protein structure. Disulfide bridges contribute to the stability of a three-dimensional structure by forming bridges between cysteine resides that come into physical proximity to each other when the protein is folding. These cysteine residues are not necessarily near each other when examining the linear amino acid sequence of the protein. See Stryer, Biochemistry $4^{th}$ Ed., W.H. Freeman and Co, New York (1995). Replacing specific cysteine residues can decrease the extent of intramolecular disulfide bonds which may destabilize a protein enough to allow a protease to access a cleavage site that is internal to the folded protein.

Incorporating protease cleavage sites can increase sensitivity to a protease. Native protein sequences that are similar to a high affinity protease cleavage site can be altered to reflect a highly favorable site. This type of modification to the protein sequence represents a minor modification to the protein. Alternatively, highly favorable protease cleavage sites can be introduced into the protein de novo which represents a major modification to the protein. In either case, the minor or major change to the protein, the three-dimensional model is used to identify regions of the folded protein that are candidates for such modification. In particular, protein loops that are exposed to the surrounding medium are candidates for alteration. In addition, these loops should not interfere with binding sites or active sites in the protein.

It is generally believed that structural stability of a protein is linked to the ability of the protein to withstand extreme conditions such as temperature and pH. Structural features such as glycosylation and disulfide bridge formation contribute to the stability of a protein and may also contribute to increasing a proteins ability to withstand extreme conditions of temperature and pH. These same structural features, i.e. glycosylation and disulfide bridge formation, are targeted to engineer enzymatic susceptibility. The uncoupling of activity at extreme conditions from features that enhanced stability of the folded protein is a challenge for engineering enzymatically susceptible proteins.

The above described considerations for engineering proteins with enhanced susceptibility to proteases lead to the designing of a variety of mutations that affect glycosylation, formation of disulfide bridges, and creating highly favorable protease cleavage sites. The predicted alterations in the protein sequence can be generated as single alterations or in various combinations (Roesler et al. Protein Science 9:1642-1650 (2000)). For instance, it may be that multiple glycosylation sites are found to exist on a particular protein. These sites can be altered one at a time or they can all be altered in a single variant. As another example, a glycosylation site and altering a disulfide bond can be combined into a single variant. In essence, the variations identified through analysis of the three-dimensional model can be considered modules that can be combined at will to generate variants for testing.

The terms domain and site when referring to a protein are used interchangeably and can refer to linear amino acid sequences identified within a protein or may refer to structural areas that exist when the protein is in a folded state.

One embodiment of the invention is a method of increasing enzymatic susceptibility by rational design techniques wherein the three-dimensional structure of a protein is modeled and subsequent feature identification of the protein selected from the group consisting of binding sites, active sites, glycosylation sites, disulfide bonds, and protein loops exposed to the surrounding medium.

Another embodiment of the invention is a method of increasing enzymatic susceptibility by rational design techniques wherein the target protein is first engineered to have a more stable three-dimensional structure. Stability can be increased through rational design or random mutagenesis techniques. Stability can be measured by the ability of the protein to function under conditions of higher temperature (thermodynamic stability) or extreme pH conditions. Stability can take many forms such as disulfide-bridges which stabilize intramolecular interactions, in addition to alterations to folding structures that make for a more compact three-dimensional structure (conformational stability). Techniques for engineering thermostability into a protein are known in the art such as Nosoh et al. TIBTECH Vol 8:16-20 (1990) and Imanaka et al. Nature vol 324:695-697 (1986).

Thermodynamic stability is defined in terms of temperature and activity and is determined by comparing the activity of the variant with the starting protein. The temperature maximum of the protein is determined by holding the protein at a specified temperature and then measuring the activity of the protein. The temperature maximum is defined as the temperature at which the protein retains about 50% activity after being held for 5 minutes at a specified temperature. A thermostable variant is one in which the variant displays at least 50% activity when held for 5 minutes at a temperature that is 5 degrees C. higher than the maximum temperature of the protein. For example, if the starting protein retains 50% activity when held for 5 minutes at 45 degrees C., then thermostable variants would be all variants that retain at least 50% activity when held at 50 degrees C. for 5 minutes.

Any protein can be engineered to be more enzymatically susceptible based upon the above disclosure. Proteins that have a function in an industrial process serve as good candidates for targeted engineering because structural and functional characteristics of the protein may already be known. The structural and functional information serves as a foundation for further modifying the protein to be enzymatically susceptible. A variety of proteins with importance to industrial processes exist including: enzymes or proteins that contribute to a value-added trait, proteins that confer resistance to diseases or pests in transgenic plants, proteins or enzymes that confer herbicide tolerance to a transgenic plant.

Examples of genes that confer or contribute to a value-added trait include but are not limited to, a phytase enzyme which breaks down phytate, a non-nutritive element in cereal based animal feeds. For example, see Van Hartingsveldt et al., Gene 127: 87 (1993), for a disclosure of the nucleotide sequence of an *Aspergillus niger* phytase gene. A gene could be introduced that reduces phytate content. In maize, this, for example, could be accomplished, by cloning and then reintroducing DNA associated with the single allele which is responsible for maize mutants characterized by low levels of phytic acid. See Raboy et al., Maydica 35: 383 (1990). Modified carbohydrate composition effected, for example, by transforming plants with a gene coding for an enzyme that alters the branching pattern of starch. See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus licheniformis* $\alpha$-amylase), Elliot et al., Plant Molec. Biol. 21: 515 (1993) (nucleotide sequences of tomato invertase genes), S.o-gaard et al., J. Biol. Chem. 268: 22480 (1993) (site-directed mutagenesis of barley ($\alpha$-amylase gene), and Fisher et al., Plant Physiol. 102: 1045 (1993) (maize endosperm starch branching enzyme II). Proteins that alter the flavor of food such as the protein brrazein.

Genes that confer resistance to pests or disease can also be engineered to be enzymatically susceptible. Plant defenses are often activated by specific interaction between the product of a disease resistance gene in the plant and the product of a corresponding avirulence gene in the pathogen. A plant can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al. Cell 78:1089 (1994) (Arabidopsis RSP2 gene for resistance to *Pseudomonas syringae*). A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Many examples of *Bacillus thuringiensis* proteins exist including but not limited to Cry1A, Cry1B, Cry3A, Cry4A, and Cry9C. A lectin as described by Van Damme et al., Plant Molec. Biol. 24: 25 (1994), who disclose the nucleotide sequences of several *Clivia miniata* mannose-binding lectin genes. A vitamin-binding protein such as avidin, as described in PCT application US93/06487, teaches the use of avidin and avidin homologues as larvicides against insect pests. An enzyme inhibitor, for example, a protease inhibitor or an amylase inhibitor, for example, Abe et al., J. Biol. Chem. 262: 16793 (1987) (nucleotide sequence of rice cysteine proteinase inhibitor), Huub et al., Plant Molec. Biol. 21: 985 (1993) (nucleotide sequence of cDNA encoding tobacco proteinase inhibitor I), and Sumitani et al., Biosci. Biotech. Biochem. 57: 1243 (1993) (nucleotide sequence of *Streptomyces nitrosporeus* (x-amylase inhibitor). An insect-specific peptide or neuropeptide which, upon expression, disrupts the physiology of the affected pest. For example, see the disclosures of Regan, J. Biol. Chem. 269: 9 (1994) (expression cloning yields DNA coding for insect diuretic hormone receptor), and Pratt et al., Biochem. Biophys. Res. Comm. 163: 1243 (1989) (an allostatin is identified in *Diploptera puntata*). See also U.S. Pat. No. 5,266,317 which discloses genes encoding insect-specific, paralytic neurotoxins. An insect-specific venom produced in nature by a snake, a wasp, etc. For example, see Pang et al., Gene 116: 165 (1992), for disclosure of heterologous expression in plants of a gene coding for a scorpion insectotoxic peptide. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene. A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a maize calmodulin cDNA clone. A membrane permease, a channel former or a channel blocker, for example, see the disclosure by Jaynes et al., Plant Sci. 89: 43 (1993), of heterologous expression of a cecropin-beta-lytic peptide analog to render transgenic tobacco plants resistant to *Pseudomonas solanacearum*. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium On Molecular Plant-Microbe Interactions (Edinburgh, Scotland, 1994) (enzymatic inactivation in transgenic tobacco via production of single-chain antibody fragments). A virus-specific antibody. See, for example, Tavladoraki et al., Nature 366:469 (1993), who show that transgenic plants expressing recombinant antibody genes are protected from virus attack. A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10: 1436 (1992). The cloning and characterization of a gene which encodes a bean endopolygalacturonase-inhibiting protein is described by Toubart et al., Plant J. 2: 367 (1992). A developmental-arrestive protein produced in nature by a plant. For example, Logemann et al., Bio/Technology 10:

305 (1992), have shown that transgenic plants expressing the barley ribosome-inactivating gene have an increased resistance to fungal disease.

Genes that confer resistance to an herbicide, for example, can also be engineered to be enzymatically susceptible. For example, proteins that mediate tolerance to an herbicide that inhibits the growing point or meristem, such as an imidazalinone or a sulfonylurea. Exemplary genes in this category code for mutant ALS and AHAS enzyme as described, for example, by Lee et al., EMBO J. 7: 1241 (1988), and Miki et al., Theor. Appl. Genet. 80: 449 (1990), respectively. Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricin-acetyl-transferase gene is provided in European application No. 0 242 246. De Greef et al., Bio/Technology 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acct-S1, Accl-S2 and Accl-S3 genes described by Marshall et al., Theor. Appl. Genet. 83: 435 (1992). A herbicide that inhibits photosynthesis, such as a triazine (psbA and gs+ genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648, and DNA molecules containing these genes are available under ATCC Accession Nos. 53435, 67441 and 67442. Cloning and expression of DNA coding for a glutathione S-transferase is described by Hayes et al., Biochem J. 285: 173 (1992).

Enzymatic susceptibility can be engineered to make a protein susceptible to any protease. Proteases are enzymes that hydrolyze peptide bonds (Barrett, et al. Handbook of Proteolytic Enzymes, Academic Press. San Diego, San Francisco, New York, Boston, London, Sydney, Tokyo (1998)). Proteases can be referred to as peptidases and generally fall into one of the classes of serine peptidases, cysteine peptidases, aspartic peptidases, and metallopeptidases. Specific proteases include but are not limited to pepsin, trypsin, chymotrypsin, pancreatic endopeptidase, cathepsin G, chymase, tryptase, papain, elastase, carboxypeptidase, chymopapain, caspase-1, and dipeptidase E. An extensive list of proteases can be found in the Handbook of Proteolytic Enzymes referenced above.

Another embodiment of the invention is an expression cassette wherein an enzymatically susceptible protein is operably linked to at least one regulatory element, such as a promoter, an enhancer, an intron, a termination sequence, or any combination thereof, and, optionally, to a signal sequence, which directs the enzymatically susceptible protein to a particular cellular location e.g., vacuole, aleurone, embryo or endoplasmic reticulum. The expression cassettes may also comprise any further elements required or selected for the expression of the enzymatically susceptible protein. Such elements include, but are not restricted to, transcription terminators, extraneous sequences to enhance expression such as introns, viral sequences, and sequences intended for the targeting of the gene product to specific organelles and cell compartments. Operably linked refers to joined as part of the same nucleic acid molecule, suitably positioned and oriented. In the case of regulatory elements, orientation of the regulatory elements (i.e. sense or anti-sense) may not affect the ability of the regulatory elements to affect transcription.

Representative examples of promoters include, but are not limited to, promoters known to control expression of genes in prokaryotic or eukaryotic cells or their viruses. Prokaryotic cells are defined as cells that do not have a nucleus and are intended to include the recently identified class of archaebacteria. In one embodiment, the expression cassette comprises a bacterial promoter. Examples of bacterial promoters include but are not limited to *E. coli* lac or trp, the phage lambda $P_L$ promoter, lacI, lacZ, T3, T7, gpt, and lambda $P_R$. Eukaryotic promoters include but are not limited to CMV immediate early, HSV thymidine kinase, early and late SV40, LTRs from retrovirus, and mouse metallothionein-1. Prokaryotic and eukaryotic promoters are generally described in Sambrook et al. Molecular Cloning: A Laboratory Manual, Second edition, Cold Spring Harbor Laboratory Press, (1989); Ausubel et al., Current Protocols in Molecular Biology, John Wiley & Sons, New York, (1987); Kriegler, Gene Transfer and Expression: A Laboratory Manual (1990).

Another embodiment of the invention is an expression cassette wherein an enzymatically susceptible protein is operably linked to a promoter capable of expression in a yeast cell. Any promoter capable of expressing in yeast hosts can be used as the promoter. Examples include promoters for genes of hexokinase and the like in the glycolytic pathway, and promoters such as gal 1 promoter, gal 10 promoter, heat shock protein promoter, MFα-1 promoter and CUP 1 promoter. Examples of yeast promoters can be found in MacPherson et al Micro. and Molec. Bio. Revs. 70:583-604 (2006).

Another embodiment of the invention is an expression cassette wherein an enzymatically susceptible protein is operably linked to a promoter capable of expression in filamentous fungi. Any promoter capable of expressing in filamentous fungi may be used. Examples are a promoter for glucoamylase or alpha-amylase from the genus *Aspergillus* (DeVries et al. Micro, and Molec. Bio. Revs. 65:497-522 (2001)) or cellulase (cellobiohydrase) from the genus *Thichoderma*, a promoter for enzymes in the glycolytic pathway, such as phosphoglycerate kinase (pgk) and glycerylaldehyde 3-phosphate dehydrogenase (gpd), etc. Examples of promoters characterized in filamentous fungi can be found in Lorang et al. Appl. and Enviro. Micro. 67:1987-1994 (2001).

Another embodiment of the invention is an expression cassette wherein an enzymatically susceptible protein is operably liked to a promoter capable of expression in plants. Selection of the promoter to be used in expression cassettes will determine the spatial and temporal expression pattern of the enzymatically susceptible protein in the transgenic plant. Selected promoters will express transgenes in preferred cell types (such as leaf epidermal cells, mesophyll cells, root cortex cells) or in preferred tissues or organs (roots, leaves or flowers, for example) or in preferred stages of plant development (flower development, leaf development or growth stage of plant, for example) and selection should reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. Promoters which are useful for plant transgene expression include those that are inducible, viral, synthetic, constitutive, temporally regulated, spatially regulated, tissue-specific, and spatio-temporally regulated.

One embodiment of the invention is an expression cassette wherein the enzymatically susceptible protein is operably linked to a constitutive promoter capable of expression in plants. Examples of some constitutive promoters which have been described include the rice actin 1 (Wang et al., Mol. Cell. Biol., 12:3399 (1992); U.S. Pat. No. 5,641,876; McElroy et al. Plant Cell 2: 163-171 (1990)). CaMV 35S (Odell et al., Nature 313:810 (1985)), CaMV 19S (Lawton et al., Mol. Cell. Biol. 7:335 (1987)), sucrose synthase, and the ubiquitin promoters (Binet et al. Plant Science 79: 87-94 (1991); Christensen et al. Plant Molec. Biol. 12: 619-632 (1989); Norris et al., Plant Mol. Biol. 21:895-906 (1993)).

One embodiment of the invention is an expression cassette wherein the enzymatically susceptible protein is operably linked to an inducible plant promoter. Inducible promoters that have been described include the ABA- and turgor-inducible promoters, the promoter of the auxin-binding protein gene (Schwob et al., Plant J. 4:423 (1993)), the UDP glucose flavonoid glycosyl-transferase gene promoter (Ralston et al., Genetics, 119:185 (1988)), the MPI proteinase inhibitor promoter (Cordero et al., Plant J. 6:141 (1994)), and the glyceraldehyde-3-phosphate dehydrogenase gene promoter (Kohler et al., Plant Mo. Biol. 29:1293 (1995); Quigley et al., J. Mol. Evol. 29:412 (1989); Martinez et al., J. Mol. Biol, 208:551 (1989)); the PR-1a promoter which is chemically inducible is described in U.S. Pat. No. 5,614,395; the PR-1a promoter is also wound inducible (Lebel et al., *Plant J.* 16:223-233 (1998)). Various chemical regulators may be employed to induce expression of the selected polynucleotide sequence in transgenic plants, including the benzothiadiazole, isonicotinic acid, and salicylic acid compounds disclosed in U.S. Pat. Nos. 5,523,311 and 5,614,395. Such a promoter is, for example, the alcA gene promoter from *Aspergillus nidulans* (Caddick et al. Nat. Biotechnol 16:177-180 (1998)). In *A. nidulans*, the alcA gene encodes alcohol dehydrogenase I, the expression of which is regulated by the AlcR transcription factors in the presence of the chemical induce. The glucocorticoid-mediated induction system can also be used (Aoyama and Chua (1997) The Plant Journal 11: 605-612) Wound-inducible promoters may also be suitable for gene expression. Numerous such promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22:129-142 (1993), Warner et al. Plant J. 3: 191-201 (1993)). Several inducible promoters are known in the art. Many are described in a review by Gatz, Current Opinion in Biotechnology 7:168 (1996) (see also Gatz, Annual Rev. Plant Physiol. Plant Mol. Biol 48:89 1997). Examples include tetracycline repressor system, Lac repressor system, copper-inducible systems, salicylate-inducible systems (such as the PR1a system), glucocorticoid-inducible (Aoyama T. et al., N-H Plant Journal, 11:605 (1997)) and ecdysone-inducible systems (patent application WO 01/52620). Also included are the benzene sulphonamide-inducible (U.S. Pat. No. 5,364,780) and alcohol-inducible (WO 97/06269, WO 97/06268 and WO 02/061102) systems and glutathione S-transferase promoters and the chimeric insect hormone and receptor system described in WO 02/061102.

One embodiment of the invention is an expression cassette wherein the enzymatically susceptible protein is operably linked to a tissue-preferred promoter capable of expression in plants. Examples of tissue preferred promoters which have been described include but are not limited to the lectin (Vodkin, Prog. Glin. Bio. Res., 138:87 (1983); Lindstrom et al., Der. Genet., (1990)), corn alcohol dehydrogenase 1 (Vogel et al., EMBO J., 11:157 (1989); Dennis et al., Nucleic Acids Res., 12:3983 (1984)), corn light harvesting complex (Simpson, Plant Mo. Bio., 19:699 (1986); Bansal et al., Proc. Natl. Acad. Sci. USA, 89:3654 (1992)), corn heat shock protein (Odell et al., Nature, 313: 810 (1985)), pea small subunit RuBP carboxylase (Poulsen et al., Mol. Gen. Genet. 205:193 (1986)), Ti plasmid mannopine synthase (Langridge et al., Cell 34:1015 (1989)), Ti plasmid nopaline synthase (Langridge et al., Cell 34:1015 (1989)), petunia chalcone isomerase (vanTunen et al., EMBO J. 7:1257 (1988)), bean glycine rich protein 1 (Keller et al., EMBO J. 8:1309 (1989)), truncated CaMV 35s (Odell et al., Nature 313:810 (1985)), potato patatin (Wender et al., Plant Mol. Biol. 13:347 (1989)), root cell (Yamamoto et al., Nucleic Acids Res. 18:7449 (1990)), maize zein (Reina et al., Nucleic Acids Res. 18:7449 (1990); Kriz et al., Mol. Gen. Genet. 207:90 (1987)); Wandelt et al., Nucleic Acids Res. 17:2354 (1989); Langridge et al., Cell 34:1015 (1983); Reina et al., Nucleic Acids Res, 18:7449 (1990)), globulin-1 (Belanger et al., Genetics 129:863 (1991)), alpha-tubulin, cab (Sullivan et al., Mol. Gen. Genet. 215:431 (1989)), PEPCase (Hudspeth et al., Plant Mo. Bio., 12:579 (1989)), R gene complex-associated promoters (Chandler et al., Plant Cell 1:1175 (1989)), and chalcone synthase promoters (Franken et al., EMBO J. 10:2605 (1991)). These include, for example, the rbcS promoter, preferred for green tissue; the ocs, nos and mas promoters which have higher activity in roots or wounded leaf tissue; a truncated (−90 to +8) 35S promoter which directs enhanced expression in roots, an alpha-tubulin gene that directs expression in roots and promoters derived from zein storage protein genes which direct expression in endosperm.

In one embodiment, the promoter is an endosperm preferred promoter such as a maize gamma-zein glutelin-2 promoter, or the maize 27-KD gamma-zein glutelin-2 promoter, (Woo et al. The Plant Cell 13:2297-2317 (2001)) or a maize ADP-glucose pyrophosphorylase promoter (Brangeon, et al. Plant Physiol. Biochem. 35:847-858 (1997)). The promoter may be an embryo-specific promoter such as a maize globulin 1 or maize oleosin 18 KD promoter (Qu et al. J. of Biol. Chem. 265:2238-2243 (1990).

In the case of a multicellular organism, the promoter can also be specific to a particular tissue, organ or stage of development. Examples of such promoters include, but are not limited to, the *Zea mays* ADP-gpp (Greene et al. Proc. Natl. Acad. Sci. USA 95:13342-13347 (1998)) and the *Zea mays* gamma-zein promoter (Woo et al. The Plant Cell 13:2297-2317 (2001)).

Several tissue-specific regulated genes and/or promoters have been reported in plants. These include but are not limited to genes encoding the seed storage proteins (such as napin, cruciferin, beta-conglycinin, and phaseolin) zein or oil body proteins (such as oleosin), or genes involved in fatty acid biosynthesis (including acyl carrier protein, stearoyl-ACP desaturase. And fatty acid desaturases (fad 2-1)), and other genes expressed during embryo development (such as Bce4, see, for example, EP 255378 and Kridl et al., Seed Science Research 1:209 (1991). Also useful for seed-specific expression is the pea vicilin promoter (Czako et al., Mol. Gen. Genet., 235:33 (1992); See also U.S. Pat. No. 5,625,136)). Other useful promoters for expression in mature leaves are those that are switched on at the onset of senescence, such as the SAG promoter from *Arabidopsis* (Gan et al., Science 270:1986 (1995)). Root preferred promoters include the promoter of the maize metallothionein-like (MTL) gene described by de Framond (FEBS 290: 103-106 (1991)) and also in U.S. Pat. No. 5,466,785. Patent Application WO 93/07278 describes the isolation of the maize trpA gene, which is preferentially expressed in pith cells. A maize gene encoding phosphoenol carboxylase (PEPC) has been described by Hudspeth et al. (Plant Molec Biol 12: 579-589 (1989)). Using standard molecular biological techniques the promoter for this gene can be used to drive the expression of any gene in a leaf-specific manner in transgenic plants. WO 93/07278 describes the isolation of the maize calcium-dependent protein kinase (CDPK) gene which is expressed in pollen cells.

A class of fruit-specific promoters expressed at or during anthesis through fruit development, at least until the beginning of ripening, is discussed in U.S. Pat. No. 4,943,674. CDNA clones that are preferentially expressed in cotton fiber have been isolated (John et al., Proc. Natl. Acad. Sci. USA 89:5769 (1992)). CDNA clones from tomato displaying differential expression during fruit development have been isolated and characterized (Mansson et al., Gen. Genet., 200:356 (1985), Slater et al., Plant Mol. Biol. 5:137 (1985)). The promoter for polygalacturonase gene is active in fruit ripening. The polygalacturonase gene is described in U.S. Pat. No. 4,535,060, U.S. Pat. No. 4,769,061, U.S. Pat. No. 4,801,590, and U.S. Pat. No. 5,107,065 and the ripening-enhanced tomato polygalacturonase promoter is described in Bird et al., Plant Molecular Biology 11:651 (1988).

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., Proc. Natl. Acad. Sci. USA 89:5769 (1992)). The E6 gene is most active in fiber, although low levels of transcripts are found in leaf, ovule and flower.

The tissue-specificity of some "tissue-specific" or "tissue-preferred" promoters may not be absolute and may be tested by one skilled in the art using the diphtheria toxin sequence. One can also achieve tissue-preferred expression with "leaky" expression by a combination of different tissue-specific promoters (Beals et al., Plant Cell 9:1527 (1997)). Other tissue-preferred promoters can be isolated by one skilled in the art (see U.S. Pat. No. 5,589,379). Tissue-specific or tissue-preferred promoters are not intended to be construed as promoters that only express in a specific tissue. Tissue-specific or tissue-preferred refers to promoters that favor a particular tissue for expression but this favoring of a tissue type is not always absolute.

Another embodiment of the invention is an expression cassette comprising an enzymatically susceptible protein operatively linked to a targeting sequence. A targeting sequence is any sequence which directs the transcript of a specific gene product within the cells of a transgenic plant or directs a protein to a particular intracellular or extracellular environment. The terms targeting sequence, sorting sequence and signal sequence are interchangeable. Targeting sequences comprise transit peptides or signal peptides or retention sequences which may be separate peptide sequences or may be used in combinations either joined together directly or joined to the enzymatically susceptible protein singly or in multiples.

Targeting will generally be achieved by joining a DNA sequence encoding a transit sequence to the polynucleotide sequence of a particular gene. The transit sequence can be joined at either the amino terminus (N-terminus) of the enzymatically susceptible phytase or at the carboxy terminus (C-terminus) of the enzymatically susceptible phytase. The resultant transit peptide will transport the protein to a particular intracellular, or extracellular destination, respectively, and can then be post-translationally removed. Transit peptides act by facilitating the transport of proteins through intracellular membranes, e.g., vacuole, vesicle, plastid and mitochondrial membranes, or direct proteins through the extracellular membrane.

In plants, the signal sequence can target the polypeptide encoded by the polynucleotide to a specific compartment within a plant. Examples of such targets include, but are not limited to, a vacuole, amyloplast, endoplasmic reticulum, chloroplast, apoplast or starch granule. An example of a signal sequence includes the maize gamma-zein N-terminal signal sequence for targeting to the endoplasmic reticulum and secretion into the apoplast (Torrent et al., Plant Mol. Biol. 34:139 (1997)). Another signal sequence is the amino acid sequence SEKDEL for retaining polypeptides in the endoplasmic reticulum (Munro et al. Cell 48:899 (1987)). A polypeptide may also be targeted to the amyloplast by fusion to the waxy amyloplast targeting peptide (Klosgren et al., Mol. Gen. Genet. 203:237 (1986)) or to a starch granule.

Another embodiment of the invention is a transformed plant cell, plant part or a plant comprising a nucleic acid molecule which encodes a polypeptide comprising an enzymatically susceptible protein operatively linked to signal sequence. In one embodiment, the plant comprises a polypeptide comprising a gamma-zein N-terminal signal sequence operably linked to the enzymatically susceptible protein. In another embodiment, the plant comprises a polypeptide comprising SEKDEL operably linked to the C-terminus of an enzymatically susceptible protein. In another embodiment, the plant comprises a polypeptide comprising an N-terminal waxy amyloplast targeting peptide operably linked to an enzymatically susceptible protein. In another embodiment, the plant comprises a polypeptide comprising a waxy starch encapsulating domain operably linked to the C-terminus of an enzymatically susceptible protein.

Another embodiment of the invention is an expression cassette comprising an enzymatically susceptible protein and further comprising an enhancer to gene expression. Numerous sequences have been found to enhance gene expression from within the transcriptional unit and these sequences can be used in conjunction with the polynucleotide encoding an enzymatically susceptible protein to increase its expression in transgenic plants.

Introns have demonstrated the potential for enhancing transgene expression. For example, Callis et al. Genes and Develop. 1:1183 (1987) describe an intron from the corn alcohol dehydrogenase gene, which is capable of enhancing the expression of transgenes in transgenic plant cells. Similarly, Vasil et al. Mol. Microbiol. 3:371 (1989) describe an intron from the corn sucrose synthase gene having similar enhancing activity. The rice actin 1 intron, has been widely used in the enhancement of transgene expression in a number of different transgenic crops. (McElroy et al., Mol. Gen. Genet. 231:150 (1991)).

An enhancer is a DNA sequence which can stimulate promoter activity and may be an innate element of the promoter or a heterologous element inserted to enhance the level or tissue preferredity of a particular promoter. An enhancer is capable of operating in both orientations (5' to 3' and 3' to 5' relative to the gene of interest polynucleotide sequence), and is capable of functioning even when moved either upstream or downstream from the promoter. An example of an enhancer element is the ocs enhancer element. This element was first identified as a 16 bp palindromic enhancer from the octopine synthase (ocs) gene of *Agrobacterium* (Ellis et al., EMBO J. 6:3203 (1987)), and is present in at least 10 other promoters (Boucher et al., EMBO J. 8:4197 (1989)). The use of an enhancer element, such as the ocs element and particularly multiple copies of the element, will act to increase the level of transcription from adjacent promoters.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus); MDMV leader (Maize Dwarf Mosaic Virus); human immunoglobulin heavy-chain binding protein (BiP) leader, (Macejak et al., Nature 353: 90-94 (1991); untranslated leader from the coat protein mRNA of alfalfa mosaic virus (AMV RNA 4), (Jobling et al., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel et al., Virology 81:382-385 (1991). See also, Della-Cioppa et al., Plant Physiology 84:965-968 (1987). INPACT is another method available for increasing gene expression (WO 01/72996).

Another embodiment of the invention is an expression cassette comprising an enzymatically susceptible protein operably linked to a transcriptional terminator. A variety of transcriptional terminators are available for use in the expression cassettes. Transcription terminators are responsible for the termination of transcription beyond the transgene and correct mRNA polyadenylation. Suitable transcriptional terminators are those that are known to function in plants and include, but are not limited to, the CaMV 35S terminator, the tml terminator, the nopaline synthase terminator derived from *Agrobacterium tumefaciens* (Bevan et al. Nucl. Acids Res., 11:369 (1983)) and the pea rbcS E9 terminator, the terminator for the T7 transcript from the octopine synthase gene of *Agrobacterium tumefaciens*, and the 3' end of the protease inhibitor I or II genes from potato or tomato. Regulatory elements such as Adh intron 1 (Callis et al., Genes and Develop., 1:1183 (1987)), sucrose synthase intron (Vasil et al., Plant Physiol. 91:1575 (1989)) or TMV omega element (Gallie, et al., Plant Cell 1:301 (1989)), may further be included where desired. Convenient plant termination regions are available from the Ti-plasmid of *A. tumefaciens*, such as the octopine synthase and nopaline synthase termination regions. See also, Guerineau et al., Mol. Gen. Genet., 262:141 (0.1991); Mogen et al., Plant Cell, 2:1261 (1990); Munroe et al., Gene, 91:151 (1990); Ballas et al., Nucleic Acids Res., 17:7891 (1989); Joshi et al., Nucleic Acid Res., 15:9627 (1987). These can be used in both monocotyledons and dicotyledons. In addition, a gene's native transcription terminator may be used.

Other regulatory elements include those that can be regulated by endogenous or exogenous agents, e.g., by zinc finger proteins, including naturally occurring zinc finger proteins or chimeric zinc finger proteins. See, e.g., U.S. Pat. No. 5,789, 538, WO 99/48909; WO 99/45132; WO 98/53060; WO 98/53057; WO 98/53058; WO 00/23464; WO 95/19431; and WO 98/54311.

Another embodiment of the invention is a transformation vector comprising an enzymatically susceptible protein that is suitable for transformation of bacteria. Typically a bacterial expression vector contains (1) prokaryotic DNA elements coding for a bacterial origin of replication and an antibiotic resistance gene to provide for the amplification and selection of the expression vector in a bacterial host; (2) DNA elements that control initiation of transcription such as a promoter; (3) DNA elements that control the processing of transcripts; (4) enhancer elements; and (5) a gene of interest that is operatively linked to the DNA elements that control transcription initiation. The expression vector used may be one capable of autonomously replicating in the above host (such as in a plasmid) or capable of integrating into the chromosome, originally containing a promoter at a site enabling transcription of the linked gene encoding an enzymatically susceptible protein.

Suitable vectors include by way of example: for bacteria, pQE70, pQE60, pQE-9 (Qiagen), pBluescript II (Stratagene), pTRC99a, pKK223-3, pDR540, pRIT2T (Pharmacia). Such commercial vectors include, for example, pKK223-3 (Pharmacia Fine Chemicals, Uppsala, Sweden) and GEM1 (Promega Biotec, Madison, Wis., USA). However, any other plasmid or vector may be used as long as they are replicable and viable in the host.

As representative examples of appropriate bacterial hosts, there may be mentioned: bacterial cells, such as *E. coli, Streptomyces, Bacillus subtilis*; and various species within the genera *Escherichia, Pseudomonas, Serratia, Streptomyces, Corynebacterium, Brevibacterium, Bacillus, Microbacterium*, and *Staphylococcus*, although others may also be employed as a matter of choice.

Another embodiment of the invention is a transformation vector comprising an enzymatically susceptible protein capable of transforming fungus. Transformation of fungus may be accomplished according to Gonni et al. Agric. Biol. Chem., 51:2549 (1987). As representative examples of appropriate fungal hosts, there may be mentioned: fungal cells, such as fungal cells belonging to the genera *Aspergillus, Rhizopus, Trichoderma, Neurospora, Mucor, Penicillium*, etc., such as yeast belonging to the genera *Kluyveromyces, Saccharomyces, Schizosaccharomyces, Trichosporon, Schwanniomyces*, etc.

Another embodiment of the invention is a transformation vector comprising an enzymatically susceptible protein capable of transforming a eukaryotic cell. A number of eukaryotic cell lines (including animal and insect cells) are available as hosts that can be transformed to express an enzymatically susceptible protein. Insect cells such as *Drosophila* S2 and *Spodoptera* Sf9; animal cells such as CHO, COS or Bowes melanoma, C127, 3T3, CHO, HeLa and BHK cell lines. Any host can be used insofar as it can express the gene of interest. The American Type Culture Collection (http://www.atcc.org/) maintains cell lines from a wide variety of sources and many of these cultures can be used to generate a transgenic cell line capable of expressing an enzymatically susceptible protein. Transformation vectors appropriate for eukaryotic cells are available commercially such as pXT1, pSG5 (Stratagene) pSVK3, pBPV, pMSG, and pSVLSV40 (Pharmacia). Techniques for transformation and selection of transgenic eukaryotic cells are well known in the art.

Another embodiment of the invention is a transformation vector comprising an enzymatically susceptible protein capable of transforming a plant. A general description of plant transformation vectors, expression cassettes and reporter genes can be found in Gruber, et al., Methods in Plant Molecular Biology & Biotechnology, Glich et al., Eds. pp. 89-119, CRC Press (1993).

In certain embodiments, it is contemplated that one may wish to employ replication-competent viral vectors in monocot transformation. Such vectors include, for example, wheat dwarf virus (WDV) "shuttle" vectors, such as pW1-11 and pW1-GUS (Ugaki et al. Nucl. Acids Res., 19:371 (1991)). These vectors are capable of autonomous replication in maize cells as well as *E. coli*, and as such may provide increased sensitivity for detecting DNA delivered to transgenic cells. A replicating vector may also be useful for delivery of genes flanked by DNA sequences from transposable elements such as Ac, Ds, or Mu. It is also contemplated that transposable elements would be useful for introducing DNA fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells.

The construction of vectors which may be employed in conjunction with the present invention will be known to those of skill of the art in light of the present disclosure (see, e.g., Sambrook et al., Molecular Cloning: A Laboratory Manual (2d ed., Cold Spring Harbor Laboratory Press, Plainview, N.Y.) (1989); Gelvin et al., Plant Molecular Biology Manual (1990)).

Methods of preparing and using a nucleic acid molecule (polynucleotide) which encodes an enzymatically susceptible protein are described. It is known in the art that protein expression may be enhanced by optimizing the coding regions of genes to the codon preference of the host. For expression in a microbial host cell such as yeast, bacteria, fungal and the like it may be necessary to codon optimize the ORF for microbial expression. The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems associated with efficient gene expression in plants can be overcome. Briefly, a codon usage table indicating the optimal codons used by the target organism is obtained and optimal codons are selected to replace those in the target polynucleotide and the optimized sequence is then chemically synthesized. Preferred codons for maize are described in U.S. Pat. No. 5,625,136.

A variety of techniques are available and known to those skilled in the art for introduction of constructs into a cellular host. One embodiment of the invention is a transgenic host wherein a polynucleotide sequence encoding an enzymatically susceptible protein is maintained by the host. The host may be selected from the group consisting of bacteria, eukaryotic cells, animal cells, insect cells, fungal cells, yeast cells and plants.

Transformation of bacteria and many eukaryotic cells may be accomplished through use of polyethylene glycol, calcium chloride, viral infection, DEAE dextran, phage infection, electroporation and other methods known in the art. Introduction of the recombinant vector into yeasts can be accomplished by methods including electroporation, use of spheroplasts, lithium acetate, and the like. Any method capable of introducing DNA into animal cells can be used: for example, electroporation, calcium phosphate, lipofection and the like.

The expression cassette may be inserted into an insect cell using a baculovirus (See e.g. Baculovirus Expression Vectors, A Laboratory Manual (1992)). For example, the vector into which the recombinant gene has been introduced may be introduced together with baculovirus into an insect cell such that a recombinant virus is obtained in the supernatant of the cultured insect cell. Insect cells are then infected with the recombinant virus whereby the protein can be expressed. The gene-introducing vector used in this method may include e.g. pLV1392, pVL1393, and pBlueBacIII (which all are products of Invitrogen). The baculovirus, may be, e.g., *Autographa californica* nuclear polyhedrosis virus, which is a virus infecting certain moth insects. The insect cells may be ovary cells Sf9 and Sf21 from *Spodoptera frugiperda* and High 5 (Invitrogen), which is an ovary cell from *Trichoplusia ni*, etc. For co-introduction of both the vector having the recombinant gene and the baculovirus into an insect cell to prepare a recombinant virus, the calcium phosphate or lipofection methods may be used.

Host plants used for transformation may be from any plant species, including, but not limited to, corn (*Zea mays*), *Brassica* sp. (e.g., *B. napus, B. rapa, B. juncea*): particularly those *Brassica* species useful as sources of seed oil, such as canola; alfalfa (*Medicago sativa*), rice (*Oryza sativa*), rye (*Secale cereale*), sorghum (*Sorghum bicolor, Sorghum vulgare*), millet (e.g., pearl millet (*Penniselum glaucum*), proso millet (*Panicurn miliaceum*), foxtail millet (*Setaria italica*), finger millet (*Eleusine coracana*)), sunflower (*Helianthus annuus*), safflower (*Carthamus tinctorius*), wheat (*Tritium aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea aniericana*), fig (*Ficus casica*), guava (*Psidium guajava*), mango (*Mangijera indica*), olive (*Olea europaca*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsugu canadensis*); Sitka spruce (*Picea glauca*); redwood (*Sequoia sempervirens*); true firs such as silver fir (*Abies amahilis*) and balsam fir (*Abies balsamea*); and cedars such as Western red cedar (*Thuja plicata*) and Alaska yellow-cedar (*Chamaecyparis nootkwensis*). Leguminous plants include beans and peas. Beans include guar, locust bean, fenugreek, soybean, garden beans, cowpea, mungbean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, *Lotus*, e.g., trefoil, lens, e.g., lentil, and false indigo. Forage and turf grass for use as host plants include but is not limited to alfalfa, orchard grass, tall fescue, perennial ryegrass, creeping bent grass, switchgrass (*Panicum virgatum*), *Miscanthus* and redtop.

Host plants include but are not limited to crop plants or plants used to produce food or feed, for example, maize, alfalfa, sunflower, *Brassica*, soybean, cotton, sunflower, safflower, peanut, sorghum, wheat, oat, rye, millet, tobacco, barley, rice, tomato, potato, squash, melons, sugarcane, legume crops, e.g., pea, bean and soybean, and starchy tuber/roots, e.g. potato, sweet potato, cassaya, taro, *canna*, and sugar beet and the like.

Transformation techniques for plants are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3:2717-2722 (1984), Potrykus et al., Mol. Gen. Genet. 199:169-177 (1985), Reich et al., Biotechnology 4:1001-1004 (1986), and Klein et al., Nature 327:70-73 (1987). Transformation of monocotyledons using *Agrobacterium* has also been described. See, WO 94/00977 and U.S. Pat. No. 5,591,616. In each case the transformed cells are regenerated to whole plants using standard techniques known in the art.

Many vectors are available for transformation using *Agrobacterium tumefaciens*. These typically carry at least one T-DNA border sequence and include vectors such as pBIN19 (Bevan, Nucl. Acies Res. 11:369 (1984)). The binary vector pCIB10 contains a gene encoding kanamycin resistance for selection in plants and T-DNA right and left border sequences and incorporate sequences from the wide host-range plasmid pRK252 allowing it to replicate in both *E. coli* and *Agrobacterium* (Rothstein et al. Gene 53:153-161 (1987)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming a plant cell with a gene involves propelling inert or biologically active particles at plant tissues and cells. This technique is disclosed in U.S. Pat. Nos. 4,945,050, 5,036,006, and 5,100,792. Generally, this procedure involves propelling inert or biologically active particles at the cells under conditions effective to penetrate the outer surface of the cell.

Patent Applications EP 0 292 435, EP 0 392 225 and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. Plant Cell 2:603-618 (1990) and Fromm et al. Biotechnology 8:833-839 (1990) have published techniques for transformation of A188-derived maize line using particle bombardment. Furthermore, WO 93/07278 and Koziel et al. Biotechnology 11:194-200 (1993) describe techniques for the transformation of elite inbred lines of maize by particle bombardment.

Transformation of plastids using particle bombardment has been described (Svab et al. PNAS 90:913-917 (1993); Svab et al PNAS 87:8526-8530 (1990); McBride et al. PNAS 91:7301-7305 (1994)). Plastid transformation can be used to produce plants expressing the enzymatically susceptible protein without the need for nuclear genome transformation. Methods for plastid transformation are well known in the art.

Selection of transformed cells is facilitated by the use of antibiotic or herbicide selection markers which are operably linked to polynucleotide sequence encoding an enzymatically susceptible protein. For certain target species, different antibiotic or herbicide selection markers may be preferred. Selection markers used routinely in transformation include the nptII gene, which confers resistance to kanamycin and related antibiotics (Messing et al. Gene 19:259-268 (1982); Bevan et al., Nature 304:184-187 (1983)), the bar gene, which confers resistance to the herbicide phosphinothricin (White et al., Nucl. Acids Res 18:1062 (1990), Spencer et al. Theor. Appl. Genet. 79:625-631 (1990)), the hph gene, which confers resistance to the antibiotic hygromycin (Blochinger et al. Mol Cell Biol 4:2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,835 and 5,188,642), and the mannose-6-phosphate isomerase gene (also referred to herein as the phosphomannose isomerase gene), which provides the ability to metabolize mannose (U.S. Pat. Nos. 5,767,378 and 5,994,629).

Another embodiment of the invention is a transgenic host wherein the polynucleotide sequence encoding an enzymatically susceptible protein is chromosornally integrated. Chromosomal integration refers to the integration of a foreign gene or DNA construct into the host DNA by covalent bonds. Chromosomally integrated DNA is genetically stable and heritable by progeny through successive generations. Another embodiment of the invention is a transgenic host cell wherein the polynucleotide encoding an enzymatically susceptible phytase is transiently expressed. Transient expression of a gene refers to the expression of a gene that is not integrated into the host chromosome but functions independently, either as part of an autonomously replicating plasmid or expression cassette.

Host plants transformed with an enzymatically susceptible protein may propagate the polynucleotide sequence encoding an enzymatically susceptible protein into other varieties of the same species, particularly including commercial varieties, using traditional breeding techniques (Plant Breeding Reviews Vol. 14, Edited by Jules Janick, John Wiley & Sons Publisher (1997)). Another embodiment of the invention is transgenic plants comprising an enzymatically susceptible protein in addition to other transgenic sequences. Transgenic plants comprising an enzymatically susceptible protein may be bred with other transgenic plants using traditional breeding techniques to stack one or more transgenic traits into a single plant or hybrid.

In one embodiment of the method of the invention, the enzymatically susceptible protein accumulates in the seed of the plant. Another embodiment of the invention is the seed of a transgenic plant comprising the enzymatically susceptible protein. Host plants comprising an enzymatically susceptible protein may take a variety of forms. The host plants may be chimeras of transformed cells and non-transformed cells; the host plants may be clonal transformants (e.g., all cells transformed to contain the expression cassette); the host plants may comprise grafts of transformed and untransformed tissues (e.g., a transformed root stock grafted to an untransformed scion i.e. citrus species). The host plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Rational design techniques for protein engineering as outlined above were demonstrated using the phytase enzyme, Nov9X, to generate enzymatically susceptible phytase enzymes with sensitivity to the protease pepsin. Nov9X is a phytase derived from *Escherichia coli* appA gene modified for high thermostability as well as maize optimized plant expression. The term "phytase" describes a broad-range class of enzymes that catalyze phytate (myo-inositol-hexaphosphate) into inositol and inorganic phosphate. Phytase enzymes have been identified in multiple sources of prokaryotic and eukaryotic organisms (i.e. *Aspergillus ficuum, Sacchoromyces cerevisiae, Escherichia coli*, etc). One embodiment of the invention is an enzymatically susceptible phytase encoded by one of the polypeptide sequences of SEQ ID NO:1-33 or a polypeptide with 98% identity to one of the polypeptide sequences of SEQ ID NO:1-33 or a conservative variant of one of the polypeptide sequences of SEQ ID NO:1-33.

For sequence comparison, typically one sequence acts as a reference sequence to which test sequences are compared. When using a sequence comparison algorithm, test and reference sequences are input into a computer, subsequent coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol. 215:403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

A preparation containing the enzymatically susceptible phytase may take many forms including but not limited to a dry preparation, a liquid preparation, a preparation containing transgenic plant material and the like.

In one embodiment of the invention, the method comprises isolating the enzymatically susceptible phytase. The enzymatically susceptible phytase is isolated from any host expressing the phytase enzyme. The host may be transgenic or may express the enzymatically susceptible phytase transiently. The host cell is selected from the group consisting of bacteria, yeast, fungi, insect and plants. The plant host cell may be monocotyledonous, such as a maize or wheat cell or dicotyledonous, such as a soybean cell.

Another embodiment of the invention is an extract from a host containing an enzymatically susceptible phytase enzyme. For preparation of recombinant phytase, following transformation of a suitable host and growth of the host, a selected promoter may be induced by appropriate means (e.g., temperature shill or chemical induction) and cells cultured for an additional period to yield recombinant enzyme. Cells are then typically harvested by centrifugation, disrupted by physical or chemical means, and the resulting crude extract retained for further purification.

Cells employed in expression of proteins can be disrupted by any convenient method, including freeze-thaw cycling, sonication, mechanical disruption, or use of cell lysing agents, such methods are well known to those skilled in the art.

The enzyme can be recovered from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps. Recovery of the enzyme refers to any method used to collect the enzyme from the host. Recovered enzyme preparations may contain contaminants such as protein, lipid, carbohydrate and DNA from the host. Recovered enzyme preparations may also be highly purified enzyme preparations which are greater than 95% pure protein.

The extract containing an enzymatically susceptible phytase may be a product of chemical synthetic procedures, or produced by recombinant techniques from a host. The host may be a prokaryotic host such as bacteria or a eukaryotic host such as a higher plant.

The extract containing an enzymatically susceptible phytase enzyme may be employed for any purpose in which such enzyme activity is necessary or desired. One embodiment of the invention is a method of producing animal feed wherein an enzymatically susceptible phytase is employed for catalyzing the hydrolysis of phytate in animal feed. In another embodiment, the enzyme is employed for catalyzing the hydrolysis of phytate in food.

Another embodiment of the invention is a liquid composition containing an enzymatically susceptible phytase enzyme. Liquid compositions need not contain anything more than the phytase enzyme. However, a stabilizer such as glycerol, sorbitol or mono propylene glycol may be added. The liquid composition may also comprise other additives, such as salts, sugars, preservatives, pH-adjusting agents, proteins, and phytate (a phytase substrate). Typical liquid compositions are aqueous or oil-based slurries. The liquid compositions may be added to a food or feed before or after an optional pelleting of the feed composition.

Another embodiment of the invention is a dry composition containing an enzymatically susceptible phytase. Dry compositions may be freeze-dried or spray dried compositions, in which case the composition need not contain anything more than the phytase in a dry form. Dry compositions may be granulates which may readily be mixed with, e.g., food or feed components, or form a component of a pre-mix. The particle size of the enzyme granulates is compatible with that of the other components of the mixture. This provides a safe and convenient means of incorporating phytases into, e.g., processed food or animal feed.

For example, a stable phytase enzyme formulation can be prepared by freezing a mixture of liquid enzyme solution with a bulking agent such as ground soybean meal, and then lyophilizing the mixture. The reduction in moisture and the binding interactions of the phytase with the bulking agent protect the enzyme from external environmental factors such as the temperature extremes experienced during compound feed manufacture. Dry formulations can further enhance stability by minimizing the activity of potential proteolytic enzymes that may be present as by-products in the liquid fermentation mixture used to manufacture the target enzyme. The resulting dry enzyme-soy flour mixture can withstand high extremes of temperature. The formulated enzyme mixture can be used as a feed supplement for use in poultry and swine production.

Another embodiment of the invention is a plant or plant part containing an enzymatically susceptible phytase enzyme. Plants or plant parts can be used as a delivery mechanism for the enzyme. Plants may be selected from the group consisting of maize, wheat, soy and a grain of any of these plants. The intact grain protects the target enzyme from external environmental factors. The grain-containing enzyme may be added to animal feed in the form of cracked seed, ground seed, or in a more refined form. Alternatively, a protein extract may be made from seed, and that extract can be further processed into either a stabilized liquid or into a dry state by lyophilization or spray drying.

Another embodiment of the invention is a composition comprising an enzymatically susceptible phytase enzyme. An example of a composition is agglomeration granulates. Agglomeration granulates are prepared using agglomeration techniques in a high shear mixer during which a filler material and the enzyme are co-agglomerated to form granules. Absorption granulates are prepared by having cores of a carrier material to absorb/be coated by the enzyme.

Compositions or agglomeration granules may also contain filler materials. Typical filler materials are salts such as disodium sulphate. Other fillers include kaolin, talc, magnesium aluminum silicate and cellulose fibers. Optionally, binders such as dextrins are also included in agglomeration granulates.

Compositions or agglomeration granules may also contain carrier materials. Typical carrier materials include starch, e.g., in the form of cassaya, corn, potato, rice and wheat. Salts may also be used.

Optionally, the granulates are coated with a coating mixture. Such a mixture comprises coating agents, preferably hydrophobic coating agents, such as hydrogenated palm oil and beef tallow, and if desired, other additives such as calcium carbonate or kaolin.

Additionally, compositions may contain other substituents such as coloring agents, aroma compounds, stabilizers, vitamins, minerals, other feed or food enhancing enzymes etc. This is so in particular for the so-called pre-mixes. One embodiment of the invention is a pre-mix comprising an enzymatically susceptible phytase enzyme.

Another embodiment of the invention is a food or feed additive comprising an enzymatically susceptible thermotolerant phytase. A food or feed additive is an essentially pure compound or a multi component composition intended for or suitable for being added to food or feed. It is a substance that by its intended use is becoming a component of a food or feed product or affects any characteristics of a food or feed product. Thus, an enzymatically susceptible phytase additive is understood to mean a phytase which is not a natural constituent of the main feed or food substances or is not present at its natural concentration therein, e.g., the enzymatically susceptible phytase is added to the feed separately from the feed substances, alone or in combination with other feed additives, or the enzymatically susceptible phytase is an integral part of one of the feed substances but has been produced therein by recombinant DNA technology. A typical additive usually comprises one or more compounds such as vitamins, minerals or feed enhancing enzymes and suitable carriers and/or excipients.

A ready for use enzymatically susceptible phytase additive is herein defined as an additive that is not produced in slim in animal feed or in processed food. A ready for use enzymatically susceptible phytase additive may be fed to humans or animals directly or, preferably, directly after mixing with other feed or food constituents. For example, a feed additive can be combined with other feed components to produce feed. Such other feed components include one or more other enzyme supplements, vitamin feed additives, mineral feed additives and amino acid feed additives. The resulting (combined) feed additive including possibly several different types of compounds can then be mixed in an appropriate amount with the other feed components such as cereal and protein supplements to form an animal feed. Processing of these components into an animal feed can be performed using means of any of the currently used processing apparatuses such as a double-pelleting machine, a steam pelleter, an expander or an extruder. Another embodiment of the invention is an animal feed comprising an enzymatically susceptible phytase enzyme.

Another embodiment of the invention is a food additive comprising an enzymatically susceptible phytase further comprising other food components to produce processed food products. Such other food components include one or more other enzyme supplements, vitamin food additives and mineral food additives. The resulting (combined) food additive, including possibly several different types, of compounds can then be mixed in an appropriate amount with the other food components such as cereal and plant proteins to form a processed food product. Processing of these components into a processed food product can be performed by using any of the currently used processing apparatuses. An animal feed additive is supplemented to the animal before or simultaneously with the diet. The enzymatically susceptible phytase may be active during the manufacture only and may not be active in the final food or feed product. This aspect is particularly relevant, for instance, in dough making and baking and the production of other ready-to-eat cereal based products.

Another embodiment of invention is an enzymatically susceptible phytase composition additionally comprising an effective amount of one or more feed, food or fuel enhancing enzymes. Enhancing enzymes selected from the group consisting of alpha-galactosidases, beta-galactosidases, lactases, other phytases, beta-glucanases, in particular endo-beta-1,4-glucanases and endo-beta-1,3(4)-glucanases, cellulases, xylosidases, galactanases, in particular arabinogalactan endo-1,4-beta-galactosidases and arabinogalactan endo-1,3-beta-galactosidases, endoglucanases, in particular endo-1,2-beta-glucanase, endo-1,3-alpha-glucanase, and endo-1,3-beta-glucanase, pectin degrading enzymes, pectinases, pectinesterases, pectin lyases, polygalacturonases, arabinanases, rhamnogalacturonases, rhamnogalacturonan acetyl esterases, rhamnogalacturonan-alpha-rhamnosidase, pectate lyases, and alpha-galacturonisidases, mannanases, beta-mannosidases, mannan acetyl esterases, xylan acetyl esterases, proteases, xylanases, arabinoxylanases and lipolytic enzymes such as lipases, phospholipases, cutinases, alpha-amylase, glucoamylase, glucose isomerase, glucanase, beta-amylase, alpha-glucosidase, isoamylase, pullulanase, neo-pullulanase, iso-pullulanase, amylopullulanase, cellulase, exo-1,4-beta-cellobiohydrolase, exo-1,3-beta-D-glucanase, beta-glucosidase, endoglucanase, L-arabinase, alpha-arabinosidase, galactanase, galactosidase, mannanase, mannosidase, xylanase, xylosidase, protease, glucanase, xylanase, esterase, ferrulic acid esterase, phytase, and lipase.

Another embodiment of invention is an enzymatically susceptible phytase composition additionally comprising an effective amount of one or more enhancing enzymes.

In another embodiment it may be desirable to create a protein with decreased gastric stability. A protein's gastric stability can be determined by carrying out a simulated gastric fluid (SGF) digestibility assay as described in Thomas et al., Regulatory Toxicology and Pharmacology 39:87-98 (2004)) and example 9 of the current application. Proteins that exhibit gastric stability are typically stable in SGF for at least 10, 15, 20, 30, 60 minutes or more. A stable protein is a protein that does not decrease in molecular weight as indicated visually on a protein gel in a SGF analysis wherein the SGF analysis was carried out for at least 10, 15, 20, 30, 60 minutes or more.

Another embodiment of the invention is a method of producing human or animal feeds comprising an enzymatically susceptible phytase enzyme. Grains and flours destined for human foods can be enzymatically treated with an enzymatically susceptible phytase to reduce the phytin content of the material. The reduced levels of phytin enhance the quality of the food by increasing the nutrient availability of essential minerals such as iron, calcium, and zinc. In addition to increasing the nutritional quality of food, enzymatically susceptible phytase used during food processing can improve the overall efficiency of the food production method. For example, addition of an enzymatically susceptible phytase to white soybean flakes during soy protein isolate manufacturing can significantly increase the yield and quality of extractable protein. During food manufacture the enzymatically susceptible phytase is active during manufacture and processing only, and is not active in the final food product. This aspect is relevant for instance in dough making and baking. Similarly, animal feed grain, such as toasted soybean meal or canola meal, may be pre-processed with an enzymatically susceptible phytase prior to compound feed manufacture. Removal of the anti-nutritive factors in animal feed components prior to compound feed manufacture produces a nutritionally higher quality and more valuable animal feed ingredient. In this processing method the enzymatically susceptible phytase is active during feed manufacturing, and may or may not be active in the digestive tract of the animal upon ingestion of the treated feed.

Another possibility for the addition of enzymatically susceptible phytase to animal feed and processed food is to add enzymatically susceptible phytase-containing transgenic plant material or seed to the feed. The parts of the plants which express the enzymatically susceptible phytase, e.g., the seed of the transgenic plants or other plant materials such as roots, stems, leaves, wood, flowers, bark, and/or fruit may be included in animal feed, either as such or after further processing. In a cereal-based feed or food, the cereal is preferably wheat, barley, maize, sorghum, rye, oats, triticale or rice. The enzymatically susceptible phytase may also be used advantageously in monogastrics as well as in polygastrics, especially young calves. Diets for fish and crustaceans may also be supplemented with enzymatically susceptible phytase to further improve feed conversion ratio and reduce the level of excreted phosphorus for intensive production systems. The feed may also be provided to animals such as poultry, e.g., turkeys, geese, ducks, as well as swine, equine, bovine, ovine, caprine, canine and feline, as well as fish and crustaceans. The feed may also be provided to pigs or to poultry, including, but not limited to, broiler chickens, hens, laying hens, turkeys and ducks. The animal feed can be used on monogastric or polygastric animals. The animal feed can be feed for poultry, or swine, or calves, or companion animals such as dogs or cats or horses.

Another embodiment of the invention is an animal feed comprising an enzymatically susceptible phytase. An enzymatically susceptible thermotolerant phytase is capable of surviving the heat conditioning step encountered in a commercial pellet mill during feed formulation, thus a method of preparing animal feed, e.g., hard granular feed pellets comprising an enzymatically susceptible phytase is described. To make feed, the formulated enzymatically susceptible phytase may be mixed with feed components, the mixture steam conditioned in a pellet mill such that at least 50% of the pre-heat treated enzymatic activity is retained, and the feed extruded through a pellet dye. The enzymatically susceptible phytase may thus be used as a supplement in animal feed by itself, in addition with vitamins, minerals, other feed enzymes, agricultural co-products (e.g., wheat middlings or corn gluten meal), or in a combination therewith. The enzyme may also be added to mash diets, i.e., diets that have not been through a pelletizer.

Another embodiment of the invention is a method for preparing animal feed wherein a preparation comprising the enzymatically susceptible phytase is treated with heat, at a temperature greater than 50° C., so as to yield a heat-treated animal feed mixture. The enzymatically susceptible phytase preparation may be transgenic plant material. The transgenic plant material may be corn grain, cracked corn, corn flour, or an enzyme extract prepared from corn.

Intensive animal production operations aim to limit the phosphate pollution that is contained in the feces of the animals that are produced. The amount of phosphate present in the diet and the availability of the phosphate in the diet to the animal are the primary factors influencing the excreted phosphate present in the feces of the animal. Currently, the availability of the plant, or grain-derived phosphate, present in soybean meal, corn grain (and other feedstuffs) is low as the phosphate is primarily in the form of phytic acid. In order to maximize the growth efficiencies of the animals, inorganic phosphate is added to feed resulting in a feed composition that contains adequate levels of available phosphate. However, these feed formulations contain too much total phosphate and result in phosphate pollution.

Another embodiment of the invention is an animal feed composition comprising an enzymatically susceptible phytase and further comprises substantially lowered inorganic phosphorus levels. The feed compositions comprise typical feed ingredients, micronutrients, vitamins, etc. and an effective amount of enzymatically susceptible phytase and inorganic phosphate where the amounts of the enzymatically susceptible phytase and phosphorus are from about between the levels of 50-20,000 units of enzymatically susceptible phytase per kg of feed and less than 0.45% inorganic phosphorus; between the levels of 100-10,000 units of enzymatically susceptible phytase per kg of feed and less than 0.225% inorganic phosphorus; between the levels of 150-10,000 units of phytase per kg of feed and less than 0.15% inorganic phosphorus, or between the levels of 250-20,000 units of phytase per kg of feed and no exogenously added inorganic phosphorus.

Another embodiment of the invention is a method of using an enzymatically susceptible phytase to improve weight gains, and feed conversion ratios (FCR) associated with production of farm animals. An enzymatically susceptible phytase of the present invention allows improved weight gain and FCR. Methods for improved weight gain and FCR may also include a diet that is low in inorganic phosphate. The method to improve the FCR, or weight gain through a low inorganic phosphate diet by feeding a diet to an animal comprising an enzymatically susceptible phytase and a level of inorganic phosphate at or below the level of 0.45%. The method may comprise feeding a diet containing an enzymatically susceptible phytase and less than 0.225% inorganic phosphate, or the method comprises feeding a diet containing the enzymatically susceptible phytase and no added inorganic phosphorus.

A method of improving the nutritive value of a processed grain product or a method of processing grain comprising adding an enzymatically susceptible phytase to the grain product during grain processing in an amount effective to improve the nutritive value of the feed is described. In one embodiment, the grain is corn and the grain processing method is wet milling and the products of the processing are corn gluten feed, corn gluten, and corn starch. In other embodiments, the grain is corn, wheat, soybean, canola, or sugarcane. In other embodiments, the grain is an oilseed, such as soybean or canola or oilseed rape, and the processed grain product is the oilseed meal.

One embodiment of the invention is the product of a transformed plant cell comprising a polynucleotide encoding an enzymatically susceptible phytase. The product may be a seed, grain or fruit. The product may be a plant, and in particular a hybrid plant or an inbred plant. The product may also be a grain processing product comprising the thermotolerant phytase of the invention, such as the corn grain processing product and the oilseed grain processing product previously described herein or an oilseed processing product.

Animals within the scope of the invention include polygastric animals, e.g., calves, as well as monogastric animals such as swine, poultry (e.g., chickens, turkeys, geese, ducks, pheasant, grouse, quail and ostrich), equine, ovine, caprine, canine and feline, as well as fish and crustaceans. Another embodiment of the invention include feed or animal feed prepared as poultry or swine feed.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

EXAMPLES

The invention will be further described by the following examples, which are not intended to limit the scope of the invention in any manner.

Example 1

Protein Modeling of Nov9X

Nov9X was selected as the phytase molecule for protein modeling. Six *E. coli* phytase crystal structures have been solved and deposited into the Research Collaboratory for Structural Bioinformation Protein Data Base (PDB) (http://www.rcsb.org/pdb/home/home.do), with PDB ID: 1DKL, 1DKM, 1DKN, 1DKO, 1DKP, 1DKQ. To choose a proper template for protein modeling Nov9X, all of the phytase crystal structures were extracted from PDB. The structure 1DKM (Resolution: 2.25 Angstrom) was chosen as the template for modeling Nov9X. Five optimized models were created by the software program Modeler within Insight II package from Accelrys, Inc., and the models with the lowest objective function value were chosen. The chosen Nov9X model was very similar to 1DKM with only 0.23 Angstrom difference with respect to backbone C-alpha RMS.

Mutations for deglycosolation, removing potential intramolecular disulfide bonds and introducing pepsin cleavage sites were modeled with the help of software SwissPdb Viewer (Guex, N. and Peitsch, M. C. SWISS-MODEL and the Swiss-PdbViewer: An environment for comparative protein modeling. Electrophoresis, 18, 2714-2723 (1997)) structure inspection, surface analysis and graph creation.

The amino acid changes to Nov9X to create the variants are recorded in Tables 1, 2, 3, 4, and 9. The amino acid positions changed are with respect to the position in the Nov9X protein described in SEQ ID NO:34. The Nov9X protein begins with the amino acid "A". The variant phytase molecules were created without the "A" and in addition, the phytase variants can begin with any or no amino acid in the first position. This variability in the first amino acid for the variant phytase enzymes is outlined in the sequence listing and denoted by an "X" at the start of the amino acid sequence.

Example 2

Rational Design of Nov9X Variants: Glycosylation Sites

Two N-glycosylation sites in Nov9X were identified computationally as well as by mass-spectrometric analysis of protein variants of Nov9X expressed in *Pichia* and corn endosperm. These two sites of the protein that were glycosylated during expression in eukaryotic expression systems were selected for modification. These glycosylation sites correspond to amino acid residues 139-161 and amino acid residues 318-320 of Nov9X (SEQ ID NO:34). Table 1 outlines the amino acid changes made in the glycosylation domains identified to give rise to the polypeptides described in SEQ ID NO:1-3.

TABLE 1

Modifications to Nov9X based on glycosylation

| Site | Previous amino acid - base position - new amino acid | SEQ ID NO: (mutant name) |
|---|---|---|
| Glycosylation | N140Q; N318Q | 1 (Mut1) |
| Glycosylation | T142R; N318Q | 2 (Mut2) |
| Glycosylation | T142R; T320V | 3 (Mut3) |

Example 3

Rational Design of Nov9X Variants: Disulfide Bridges

Specific cysteine residues in the Nov9X phytase were identified from the amino acid sequence of Nov9X and the structural information (Lim et al. Nature, 7(2) 108-113 (2000)). Cysteine residues participating in intramolecular disulfide bridges were targeted for alteration. In addition, cysteine residues potentially participating in intermolecular disulfide bridges were targeted for alteration. Alterations in disulfide bridge formation were mapped onto the three-dimensional model of the protein to avoid making alterations to the overall structure and ability of the protein to fold into the correct conformation. Cysteine amino acids in Nov9X were altered to generate the sequences described in SEQ ID NO:4-14. The specific amino acid changes are outlined in Table 2.

TABLE 2

Modification to Nov9X based on disulfide bridges

| Domain | Previous amino acid - base position - new amino acid | SEQ ID NO: (mutant name) |
|---|---|---|
| Cysteine | C76K; C205N | 4 (Mut4) |
| Cysteine | C76K; C205N; C179A; C189A | 5 (Mut5) |
| Cysteine | C76K; C205N; C383A; C392A | 6 (Mut6) |
| Cysteine | C76K; C205N; C179A; C189A; C383A, C392A | 7 (Mut7) |
| Cysteine | C76K; C205N; C78A; C109A | 8 (Mut8) |
| Cysteine | C76K; C205N; C134A; C409A | 9 (Mut9) |
| Cysteine | A26F, C76V, T115H, N138E, T142R, E147R, G158R, C205D, V212W, Q254V, R268A, T328Y, C179A, C189A | 10 (Mut10) |
| Cysteine | A26F, C76V, T115H, N138E, T142R, E147R, G158R, C205D, V212W, Q254V, R268A, T328Y, C383A, C392A | 11 (Mut11) |

TABLE 2-continued

Modification to Nov9X based on disulfide bridges

| Domain | Previous amino acid - base position - new amino acid | SEQ ID NO: (mutant name) |
|---|---|---|
| Cysteine | A26F, C76V, T115H, N138E, T142R, E147R, G158R, C205D, V212W, Q254V, R268A, T328Y, C179A, C189A, C383A, C392A | 12 (Mut12) |
| Cysteine | A26F, C76V, T115H, N138E, T142R, E147R, G158R, C205D, V212W, Q254V, R268A, T328Y, C78A, C109A | 13 (Mut13) |
| Cysteine | A26F, C76V, T115H, N138E, T142R, E147R, G158R, C205D, V212W, Q254V, R268A, T328Y, C134A, C409A | 14 (Mut14) |

Example 4

Rational Design of Nov9X Variants: Potential Pepsin Cleavage Sites

The three-dimensional structure model of Nov9X was analyzed to identify loops in the protein structure that were candidates for engineering with potential pepsin cleavage site(s). The particular loops identified for modification had to meet several criteria including: 1) the loop was not buried within the three-dimensional structure of the protein, 2) the loop was on the surface of the protein and thus exposed to the surrounding medium and accessible to proteases when the protein was correctly folded, 3) the loop was not involved in forming the active site or substrate or product binding site of the enzyme, and 4) the loop contained an amino acid sequence similar to a favorable pepsin cleave site so as to facilitate making a minor change in the amino acid sequence (one or two residues changed) in order to introduce favorable pepsin cleavage sites into the loop.

This approach does not change the length of the loops and keeps the mutations at a minimal level in order to avoid disturbance to the local and overall structure of the folded protein. Several protein loops were identified that met the above criteria and these loops correspond to the following amino acid residues in Nov9X (SEQ ID NO:34), 33-46, 105-137, 172-177, 229-240, 281-293, 316-330, and 364-373. Potential pepsin cleavage sites within one or more of these loops were engineered to contain an amino acid sequence that is known to be more readily attacked by the pepsin enzyme. The enzymatically susceptible phytase enzymes are outlined in Table 3 and correspond to the amino acid sequences described in SEQ ID NO:15-25.

TABLE 3

Modifications to Nov9X based upon potential protease cleave sites

| Site | Previous amino acid - base position - new amino acid | SEQ ID NO: (mutant name) |
|---|---|---|
| Pepsin cleavage site | W37F; P38Y | 15 (Pep1) |
| Pepsin cleavage site | P124E; P127L | 16 (Pep2) |
| Pepsin cleavage site | N126Y; P127V | 17 (Pep3) |
| Pepsin cleavage site | P174Y | 18 (Pep4) |
| Pepsin cleavage site | G233E; G235Y | 19 (Pep5) |
| Pepsin cleavage site | K286F; Q287Y | 20 (Pep6) |
| Pepsin cleavage site | N317L; W318Y | 21 (Pep7) |
| Pepsin cleavage site | S367F | 22 (Pep8) |
| Pepsin cleavage site | W37F; P38Y; P124E; P127L | 23 (Pep9) |
| Pepsin cleavage site | W37F; P38Y; N126Y; P127V | 24 (Pep10) |
| Pepsin cleavage site | P174Y; N317L; W318Y | 25 (Pep11) |

Example 5

Rational Design of Nov9X Mutants: Insertion of Highly Favorable Pepsin Cleavage Sites The protein loops identified in Example 4 were modified by inserting into or replacing the loop sequence entirely. The loop sequence was replaced with the sequence of a highly favorable pepsin cleavage site sequence (Keil B., *Specificity of Proteolysis*. Springer-Verlag Berlin-Heidelber-New York p. 335 (1992)). The modifications to the Nov9X protein were moderate due to the insertion of an entirely new sequence that was several amino acids long. Table 4 outlines the amino acid modifications made to Nov9X and correspond to the amino acid sequences described in SEQ ID NO:26-33.

TABLE 4

Modifications to Nov9X based upon high affinity pepsin binding sites

| Site | Previous amino acids - base positions - new amino acids | SEQ ID NO: (mutant name) |
|---|---|---|
| Site Insertion | DAWPTW 36-41 IEFFRL | 26 (Pep41) |
| Site Insertion | QADTSSP 116-122 PTEFFRL | 27 (Pep42) |
| Site Insertion | PDPLFNP 122-128 PIEFFRL | 28 (Pep43) |
| Site Insertion | PQ 174-175 PIEFFRLQ | 29 (Pep44) |
| Site Insertion | EPGWGRI 232-238 PIEFFRL | 30 (Pep45) |
| Site Insertion | PPQKQAY 284-290 PPEFFRL | 31 (Pep46) |
| Site Insertion | WTLPGQP 319-325 PIEFFRL | 32 (Pep47) |
| Site Insertion | TPLSLNT 365-371 PPEFFRL | 33 (Pep48) |

Example 6

Codon Optimization of Variants for Bacterial Expression

The protein sequence of the enzymatically susceptible phytase enzyme was converted into a polynucleotide sequence. The polynucleotide sequence was modified so that the codon used for translation into amino acids reflected the optimum codon used in *E. coli*.

The *E. coli* optimized polynucleotide sequences as described in SEQ ID NO:35-67 were synthesized and sub-cloned into pFLEX HX *E. coli* expression vector by GeneArt, Regensburg, Germany. The final vector contained an expression cassette that included the codon optimized polynucleotide sequence for the enzymatically susceptible phytase linked to a sequence that added an N-terminal His-tag. For ease of reference, Table 5 outlines the relationship between polypeptide and polynucleotide sequences contained in the Sequence Listing.

TABLE 5

Codon optimized polynucleotide sequences and polypeptide sequences

| Polypeptide sequence SEQ ID NO: (mutant name) | Corresponding *E. coli* codon optimized polynucleotide sequence (SEQ ID NO:) | Corresponding plant optimized polynucleotide sequence (SEQ ID NO:) |
|---|---|---|
| 1 (Mut1) | 35 | 70 |
| 2 (Mut2) | 36 | 71 |
| 3 (Mut3) | 37 | 72 |
| 4 (Mut4) | 38 | 73 |
| 5 (Mut5) | 39 | 74 |
| 6 (Mut6) | 40 | 75 |

TABLE 5-continued

Codon optimized polynucleotide sequences and polypeptide sequences

| Polypeptide sequence SEQ ID NO: (mutant name) | Corresponding E. coli codon optimized polynucleotide sequence (SEQ ID NO:) | Corresponding plant optimized polynucleotide sequence (SEQ ID NO:) |
|---|---|---|
| 7 (Mut7) | 41 | 76 |
| 8 (Mut8) | 42 | 77 |
| 9 (Mut9) | 43 | 78 |
| 10 (Mut10) | 55 | 90 |
| 11 (Mut11) | 56 | 91 |
| 12 (Mut12) | 57 | 92 |
| 13 (Mut13) | 58 | 93 |
| 14 (Mut14) | 59 | 94 |
| 15 (Pep1) | 44 | 79 |
| 16 (Pep2) | 45 | 80 |
| 17 (Pep3) | 46 | 81 |
| 18 (Pep4) | 47 | 82 |
| 19 (Pep5) | 48 | 83 |
| 20 (Pep6) | 49 | 84 |
| 21 (Pep7) | 50 | 85 |
| 22 (Pep8) | 51 | 86 |
| 23 (Pep9) | 52 | 87 |
| 24 (Pep10) | 53 | 88 |
| 25 (Pep11) | 54 | 89 |
| 26 (Pep41) | 60 | 95 |
| 27 (Pep42) | 61 | 96 |
| 28 (Pep43) | 62 | 97 |
| 29 (Pep44) | 63 | 98 |
| 30 (Pep45) | 64 | 99 |
| 31 (Pep46) | 65 | 100 |
| 32 (Pep47) | 66 | 101 |
| 33 (Pep48) | 67 | 102 |
| 103 (Mut 15) | 124 | 145 |
| 104 (Mut 17) | 125 | 146 |
| 105 (Mut 18) | 126 | 147 |
| 106 (Mut 19) | 127 | 148 |
| 107 (Mut 20) | 128 | 149 |
| 108 (Mut 21) | 129 | 150 |
| 109 (Mut 22) | 130 | 151 |
| 110 (Mut 23) | 131 | 152 |
| 111 (Mut 24) | 132 | 153 |
| 112 (Mut 25) | 133 | 154 |
| 113 (Mut 26) | 134 | 155 |
| 114 (Mut 27) | 135 | 156 |
| 115 (Mut 28) | 136 | 157 |
| 116 (Mut 29) | 137 | 158 |
| 117 (Mut 30) | 138 | 159 |
| 118 (Mut 31) | 139 | 160 |
| 119 (Mut 32) | 140 | 161 |
| 120 (Mut 33) | 141 | 162 |
| 121 (Mut 34) | 142 | 163 |
| 122 (Mut 35) | 143 | 164 |
| 123 (Mut 36) | 144 | 165 |

Example 7

Vector Construction for Bacterial Expression

The bacterial codon optimized expression cassettes described in Example 6 were cloned into expression vector pET24a (Invitrogen).

Expression cassettes containing the polynucleotide sequences described in SEQ ID NO: 35, 36, and 38 were cloned as NdeI/XhoI fragments.

Expression cassettes containing the polynucletide sequences described in SEQ ID NO: 37, 39-43, and 59 were cloned as NdeI/NotI fragments.

The restriction digests to generate the vector and insert fragments were carried out following standard protocols (Sambrook et al. Molecular Cloning: A Laboratory Manual 2$^{nd}$ ed., Cold Spring Harbor Laboratory Press, Plainview, N.Y. (1989)). The digest products were separated by gel electrophoresis on a 0.8% agarose gel, and the correct bands were cut from the gel and purified using the Gene clean spin kit from Qbiogene. The purified insert and vector fragments were then ligated together using either Clonables ligase from Novagen, or the T4 DNA ligase from Epicentre Biotechnologies, following the manufacturers' protocols. The ligated vectors were then transformed into TOP 10 E. coli cells from Invitrogen following the manufacturer prescribed protocol, and selected on Luria agar+kanamycin (50 μg/ml) plates.

Colonies which grew on plates were screened by colony-PCR with forward primer described in SEQ ID NO: 68 and reverse primer described in SEQ ID NO:69 to confirm the presence of the correct plasmid. The PCR's were set up as follows: 2.8 pmol of each primer, 2×PCR Jumpstart mix from Sigma, E. coli colony as template and water to a final reaction volume of 5 The following cycling conditions were used: an initial denaturation of 94° C. for 3 minutes followed by 25 cycles of 94° C. for 30 seconds, 55° C. for 30 seconds and 72° C. for 60 seconds, followed by a final extension step of 72° C. for 10 minutes. Colonies with the desired plasmids were then grown overnight in Luria broth+kanamycin (50 ug/ml) at 37° C., 260 rpm, and the plasmid DNA was extracted using the Qiagen miniprep kit. The inserted gene in the resultant plasmid DNA was sequenced to fully confirm the correct construct had been made.

The expression cassettes containing the enzymatically susceptible phytases whose polynucleotide sequence is described in SEQ ID NO: 44-54 were cloned as BsgI/AscI fragments into vector pFLEXHX T7. pFLEXHX T7 was generated by replacing the pFLEX HX promoter with the T7 promoter from pET24a using standard molecular biology techniques.

Example 8

Method of Isolating Proteins from Bacteria

The pET24 vectors and pFLEXHX T7 vectors containing the expression cassettes containing the polynucleotide sequences as described in Example 7, were transformed into BL21[DE3] E. coli cells (Invitrogen). 10 ml aliquots of LB medium containing Kanamycin (50 μg/ml) (Sigma) were inoculated with a colony from the transformation plates and incubated overnight with shaking at 30° C. 5-10 ml of these cultures were transferred to 500 ml aliquots of LB medium containing Kanamycin at 50 μg/ml in lL shake-flasks. The flasks were incubated at 37° C. with shaking until an OD$_{600}$ of approximately 0.6 was achieved. The shake-flasks were transferred to an incubator at 15° C. IPTG (Sigma) was added to give a final concentration of 0.1 mM, and the flasks were incubated overnight with shaking. The cell biomass was harvested by centrifugation at 24,000×g for 15 minutes. The cell-density at harvest was in the range of 2.5 to 3.5 OD$_{600}$. The cell biomass was frozen at −20° C.

The cell biomass samples were thawed and re-suspended in 50 ml extraction buffer (20 mM Tris, 25 mM Imidazole, 500 mM NaCl, pH7.5). The cells were lysed by passing the suspension through a Constant Systems cell disrupter at 25,000 psi, and the sample was flushed through with 25 ml extraction buffer. Insoluble material was removed by centrifugation at 24,000×g for 30 minutes, followed by filtration through 0.22 μm vacuum filter devices (Millipore Steritop). The clarified lysates were kept on ice.

A HisTrap FF 5 ml column (GE Healthcare, Ni-Sepharose FF resin, 1.6 cm bed diameter) was equilibrated with extraction buffer. 43 ml of the clarified lysate samples were loaded at 4 ml/min. Unbound material was washed through the column with extraction buffer at 4 ml/min. Affinity purified proteins were eluted with elution buffer (20 mM Tris, 500 mM Imidazole, 500 mM NaCl, pH7.5) at 4 ml/min and the $A_{280}$ nm elution peak collected. The collected elutions were buffer exchanged into 20 mM Tris pH7.5 using 10 kDa MWCO centrifugal concentrators (Millpore Amicon Ultra-15) and concentrated to approximately 3 ml in the same devices. Samples were centrifuged at 3700×g for 10 minutes to remove any precipitate. Protein concentrations were estimated by $A_{280}$ nm using the specific extinction coefficients. Concentrations were in the range of 4-15 mg/ml and yields were typically 15-30 mg from 500 ml of culture. Samples were stored at −80° C.

Example 9

Stability in Simulated Gastric Fluid (SGF)

Simulated gastric fluid digestibility of protein samples was performed basically as described in Thomas et al., Regulatory Toxicology and Pharmacology 39:87-98 (2004)). Each test protein was purified as described in Example 8. The protein concentration of each sample was determined using Pierces' BCA Kit.

The G-Con solution was prepared according to the following protocol: 200 mg of sodium chloride were dissolved in 90 ml of milli-Q water with mixing. This solution was titrated to pH 1.2 using 6 N NCl and milli-Q water was added to a final volume of 100 ml.

Simulated Gastric Fluid with pepsin (1×SGF) was prepared for each test protein to give 10 unit of pepsin per 1 g of test protein in the reaction solutions. Thus, a ratio of 10 U of pepsin activity/1 g of test protein was used throughout the study. Pepsin was purchased from Sigma Chemical (St. Louis, Mo.) in a single lot having 3460 U/mg of protein as analyzed by Sigma. The 200 mM $NaHCO_3$ was prepared with 1.68 g $NaHCO_3$ in 100 ml of milli-Q water and titrated with HCl to a pH or 11.0.

Each test protein was incubated in three different reaction mixtures for 60 minutes at 37° C. on a hot-plate. Each tube containing G-Con or SGF was incubated at 37° C. for 2 minutes prior to adding the test protein. The reaction mixtures were prepared as follows:

Reaction Mixture 1: 400 μl total, volume containing SGF (pepsin at ratio of 10 units pepsin per 1 μg test protein in G-Con) and test protein solution Reaction Mixture 2: 150 μl total volume, containing G-Con (dilute HCl, 100 mM NaCl) at pH 1.2 and test protein solution (0.135 mg/ml final concentration); this is a control sample for test protein stability in reaction buffer without pepsin Reaction Mixture 3: 150 μl of SGF and water; this is a control samples for pepsin auto-digestion (pepsin without test protein)

50 μl samples were removed from reaction mixtures 1 & 3 (controls) at 0 and 60 minutes, and from reaction mixture 2 (test) at 0.5, 2, 5, 10, 20, 30, and 60 minutes. Each of these samples were transferred into a stop solution containing 35 μl of both 200 mM NaHCO3 (pH 11.0) and 4× Bio-Rad XT loading buffer. The zero time point protein digestion samples were prepared by quenching the pepsin in the solution before adding the test protein. All samples were incubated for 5 minutes in a 70° C. water bath to stop the reaction and then analyzed using SDS-PAGE. 20 μl of each sample were analyzed on a 4-12% Bis-Tris Gel (Biorad) in XT MOPS running buffer (Biorad). The total amount of protein loaded per lane was 1.9 μg. SeeBlue Plus2 Prestained Standard (Invitrogen) was used as the molecular weight marker. Following electrophoresis, the gels were stained with SimplyBlue SafeStain (Invitrogen). Digestion samples were analyzed by visually inspecting stained protein bands following electrophoresis.

Stability in simulated gastric fluid for the enzymatically susceptible phytase variants generated is outlined in Table 6. SGF-stability of each protein is indicated as the length of time (in minute) the protein or its peptide fragment(s) is visually detectable by staining of the gel following SDS-PAGE.

TABLE 6

SGF stability of enzymatically susceptible phytase enzymes.

| Variant | SGF stability (minutes) | Presence of polymers |
|---|---|---|
| Mut1 | 60+ | Yes |
| Mut2 | 60+ | Yes |
| Mut3 | 60+ | Yes |
| Mut4 | 60+ | No |
| Mut5 | <20 | No |
| Mut6 | 60+ | No |
| Mut7 | <20 | No |
| Mut8 | 60+ | No |
| Mut9 | <5 | No |
| Pep1 | <10 | Yes |
| Pep2 | <10 | Yes |
| Pep3 | <10 | Yes |
| Pep4 | 60+ | Yes |
| Pep5 | <30 | Yes |
| Pep6 | 60+ | Yes |
| Pep7 | <30 | Yes |
| Pep8 | <30 | Yes |
| Pep9 | <20 | Yes |
| Pep10 | <2 | Yes |
| Pep11 | <30 | Yes |

There is conflicting information available regarding whether phytase enzymes function as monomeric proteins or whether they function as multimers. Phytases isolated from *Aspergillus niger, Aspergillus terreus, Aspergillus fumigatus, Emericella nidulus, Myceliophihora thermophila* and *Talamyces thermaphilus* (Wyss et al. Appl. And Envior. Micro. 65:359-366 (1999)) function as monomeric proteins. In addition, phytases from soybean seeds (Gibson et al. Arch. Biochem. Biophys. 260:503-513 (1988)), *E. coli* and *Klebsiella terrigena* (Greiner, et al. Arch. Biochem. Biophys. 303:107-113 (1993); Greiner, et al. Arch. Biochem. Biophys. 341:201-206 (1997)), and *Bacillus subtilis* (Schimizu, Biosci. Biotechnol. Biochem. 56:1266-1269 (1992)) appear to be monomeric. Evidence for multimer formation in phytases from *Aspergillus terrus, Aspergillus oryzae, Schwanniomyces castellii* has been demonstrated by Hubel, et al. Plant Physiol 112:1429-1436 (1996); Segueilha, et al. J. Ferment. Bioeng. 74:7-11 (1992); Schimizu Biosci. Biotechnol. Biochem, 57:1364-1365 (1993) and Yamamoto et al. Agric. Biol. Chem. 36:2097-2103.

Multimer formation of the enzymatically susceptible phytase was observed in in the SDS-PAGE analysis of the SGF assay. No multimers were observed in the SGF assay in the cysteine variants described in SEQ ID NO:4-9.

Example 10

Phytase Activity of the Mutant Proteins Over a pH Range

Phytase activity assays were carried out following the assay method described by Engelen et al. Journal of AOAC Int. 77(3):760-764 (1994). Enzyme (Nov9X or the enzymatically susceptible phytase variants at concentrations range of 0.5-10 mg/ml) was diluted 10000 to 50000-fold in water before assay at different pH. Buffer solutions with phytate substrate were prepared as follows:

Glycine-HCl Buffer—100 mM glycine containing 3 mM phytic acid was used for pH values 2.0, 2.5, 3.0, and 3.5.

Acetate Buffer—100 mM acetate containing 3 mM phytic acid was used for pH values 4.0, 4.5, 5.0, and 5.5.

Mes Buffer—100 mM Mes containing 3 mM phytic acid was used for pH values 6, 6.5, and 7.0.

Assay reactions at different pH were carried out in duplicate with 300 µl buffer with phytate substrate 150 µl of diluted. The incubations, for 10 and 20 minutes, were carried out at 37° C. followed by simultaneous quenching and colorimetric detection. The inorganic phosphate product generated complexes with molybdate and vanadate ions resulting in a color formation. The absorbance of the yellow color vanadomolybdophosphoric acid, whose concentration is proportional to the phosphate ion concentration in the reaction mixture, was measured at a wavelength of 415 nm. The measured absorbance was used to determine the phosphate ion concentration by comparison to a phosphate standard calibration curve.

Relative phytase activity at pH 4.5 at 37° C. in the presence of 3 mM phytate is outlined in Table 7. Relative activity is expressed as a percentage of Nov9X activity. Relative phytase activity at pH 2.5 at 27° C. in the presence of 3 mM phytate is outlined in Table 7. Relative activity is expressed as a percentage of Nov9X activity at pH 4.5.

TABLE 7

Relative activity of enzymatically susceptible phytase variants

| Variant | Relative activity at pH 4.5 | Relative activity at pH 2.5 |
|---|---|---|
| Mut1 | 142.0 | 84.7 |
| Mut2 | 33.7 | ND |
| Mut3 | 60.1 | ND |
| Mut4 | 175.7 | 105.0 |
| Mut5 | 161.7 | 97.4 |
| Mut6 | 173.3 | ND |
| Mut7 | 176.9 | 102.0 |
| Mut8 | 184.4 | ND |
| Mut9 | 176.9 | 110.7 |
| Pep1 | 64.5 | 38.9 |
| Pep2 | 60.0 | ND |
| Pep3 | 55.2 | 30.0 |
| Pep4 | 161.8 | 83.8 |
| Pep5 | 121.4 | 68.8 |
| Pep6 | 66.7 | ND |
| Pep7 | 138.3 | 110.7 |
| Pep8 | 195.3 | 120.5 |
| Pep9 | 122.5 | 52.6 |
| Pep10 | 13.5 | ND |
| Pep11 | 100.2 | 67.4 |

ND: data not generated

Example 11

Comparison of the Thermotolerance of the Mutant Proteins

Test protein was diluted in 100 mM acetate buffer (pH 4.5), containing 0.01% Tween 20, prior to the heat-treatment. 100 µl of each diluted enzyme solution was heat-treated using a Gradient PCR Cycler at 40-95° C. (5° C. increments per incubation) for 5 minutes. The heat-shocked enzymes were immediately placed, and kept in chilled condition until assay dilution was done. The residual phytase activity in heat-treated enzyme fraction was estimated using standardized phytase assay after 10000 to 50000 fold dilution in 100 mM acetate buffer (pH 4.5), containing 3 mM phytate substrate and 0.01% Tween 20. Phytase reaction mixture was incubated at 37° C. for 15-40 minutes. The assay of each heat treated fraction was done in duplicate in 96-deep well block and the amount of inorganic phosphate released was estimated by comparison of the absorbance of the colorometric reactions to the standard phosphate curve. The residual phytase activity was calculated by comparison to the activity observed in the un-treated enzyme fraction.

Relative thermotolerance of the enzymatically susceptible phytase enzymes was determined from a plot of the residual phytase activity versus pre-treatment temperature. The values shown in Table 8 represent the temperature at which 5 minutes of heat treatment will result in 50% loss of phytase activity as compared to untreated enzyme.

TABLE 8

Relative thermotolerance of enzymatically susceptible thermotolerant phytase

| Variant | Temperature |
|---|---|
| Mut1 | 68 |
| Mut2 | 68 |
| Mut3 | 63 |
| Mut4 | 70 |
| Mut5 | 68 |
| Mut6 | 68 |
| Mut7 | 66.5 |
| Mut8 | 68 |
| Mut9 | 63 |
| Pep1 | 70 |
| Pep2 | 70 |
| Pep3 | 70 |
| Pep4 | 68 |
| Pep5 | 65 |
| Pep6 | ND |
| Pep7 | 68 |
| Pep8 | 68 |
| Pep9 | 66.5 |
| Pep10 | ND |
| Pep11 | 70 |

ND: data not generated

Example 12

Combinations of Mutations

Based upon the data generated in Examples 9-11, specific combinations of variants were selected for analysis. These combinations are described in Table 9. Polynucleotide sequences codon optimized for bacterial expression were generated to encode the polypeptide variants described in Table 9 essentially as described in Example 6. The bacterial codon optimized polynucleotide sequences were then incorporated into a bacterial expression vector essentially as described in Example 7 and the enzymatically susceptible phytase proteins purified essentially as described in Example 8. Codon optimized polynucleotide sequences and corresponding combination mutant polypeptide sequences are referenced in Table 5 to outline the relationship between polypeptide and polynucleotide sequences contained in the Sequence Listing.

TABLE 9

Combinations of enzymatically susceptible phytase variants

| Mutant name (SEQ ID NO:) | Previous amino acids - base positions - new amino acids | Mutants combined |
|---|---|---|
| mut15 (103) | C76K, N140Q, C205N, N318Q | mut1, mut4 |
| mut17 (104) | W38F, P39Y, C76K, N140Q, C205N, N318Q | mut1, mut4, Pep1 |
| mut18 (105) | W38F, P39Y, C76K, N140Q, C205N, N318L, W319Y | mut1, mut4, Pep1, Pep7 |
| mut19 (106) | W38F, P39Y, C76K, N140Q, C205N, N318Q, S368F | mut1, mut4, Pep1, Pep8 |
| mut20 (107) | C76K, N140Q, C205N, N318L, W319Y | mut1, mut4, Pep7 |
| mut21 (108) | C76K, N140Q, C205N, N318Q, S368F | mut1, mut4, Pep8 |
| mut22 (109) | C76K, P124E, P128L, N140Q, C205N, N318L, W319Y | mut1, mut4, Pep2, Pep7 |
| mut23 (110) | C76K, N127Y, P128V, N140Q, C205N, N318Q, S368F | mut1, mut4, Pep3, Pep8 |
| mut24 (111) | A26F, C76K, N138V, N140Q, C205N, V212W, N318Q | mut1, mut4 |
| mut25 (112) | A26F, W38F, P39Y, C76K, N138V, N140Q, C205N, V212W, N318Q | mut1, mut4, Pep1 |
| mut26 (113) | A26F, C76K, P124E, P128L, N138V, N140Q, C205N, V212W, N318Q | mut1, mut4, Pep2 |
| mut27 (114) | A26F, C76K, N127Y, P128V, N138V, N140Q, C205N, V212W, N318Q | mut1, mut4, Pep3 |
| mut28 (115) | A26F, W38F, P39Y, C76K, N138V, N140Q, C205N, V212W, N318L, W319Y | mut1, mut4, Pep1, Pep7 |
| mut29 (116) | A26F, W38F, P39Y, C76K, N138V, N140Q, C205N, V212W, N318Q, S368F | mut1, mut4, Pep1, Pep8 |
| mut30 (117) | A26F, C76K, P124E, P128L, N138V, N140Q, C205N, V212W, N318L, W319Y | mut1, mut4, Pep2, Pep7 |
| mut31 (118) | A26F, C76K, N127Y, P128V, N138V, N140Q, C205N, V212W, N318Q, S368F | mut1, mut4, Pep3, Pep8 |
| mut32 (119) | A26F, C76K, N138W, N140Q, C205N, C179A, C189A, V212W, N318Q | mut1, mut5 |
| mut33 (120) | A26F, W38F, P39Y, C76K, N138W, N140Q, C205N, C179A, C189A, V212W, N318L, W319Y | mut1, mut5, Pep1, Pep7 |
| mut34 (121) | A26F, W38F, P39Y, C76K, N138V N140Q, C205N, C179A, C189A, V212W, N318Q, S368F | mut1, mut5, Pep1, Pep8 |
| mut35 (122) | A26F, C76K, C134A, N138V, N140Q, C205N, V212W, N318Q, C409A | mut1, mut9 |
| mut36 (123) | A26F, W38F, P39Y, C76K, C134A, N138V, N140Q, C205N, V212W, N318Q, S368F, C409A | mut1, mut9, Pep1, Pep8 |

Example 13

Stability of Combination Phytase Variants in Simulated Gastric Fluid (SGF)

Purified proteins of combination phytase variants were analyzed for sensitivity to pepsin essentially as described in Example 9. SGF stability is outlined in Table 10

TABLE 10

SGF stability of combination phytase variants

| Variant | SGF stability (minutes) | Presence of polymers |
|---|---|---|
| mut15 (103) | 60+ | No |
| mut17 (104) | <10 | No |
| mut18 (105) | <5 | No |
| mut19 (106) | <5 | No |
| mut20 (107) | <40 | No |
| mut21 (108) | <40 | No |
| mut22 (109) | <10 | No |
| mut23 (110) | <10 | No |
| mut24 (111) | 60+ | No |
| mut25 (112) | <30 | No |
| mut26 (113) | 60+ | No |
| mut27 (114) | 60+ | No |
| mut28 (115) | 60+ | No |
| mut29 (116) | <30 | No |
| mut30 (117) | 60+ | No |
| mut31 (118) | 60+ | No |
| mut32 (119) | 60+ | No |
| mut33 (120) | <10 | No |
| mut34 (121) | <10 | No |
| mut35 (122) | <40 | No |
| mut36 (123) | <10 | No |

ND: data not generated

Example 14

Relative Phytase Activity of Combination Variants at pH 4.5

Purified proteins from combination phytase variants were analyzed for activity at pH 4.5 essentially as described in example 10. Relative activity results for the combination phytase variants at pH 4.5 are outlined in Table 11.

TABLE 11

Relative phytase activity of combination variants at pH 4.5

| Variant | Relative activity at pH 4.5 |
|---|---|
| mut15 (103) | 327.9 |
| mut17 (104) | 126.8 |
| mut18 (105) | 182.3 |
| mut19 (106) | 189.2 |
| mut20 (107) | ND |
| mut21 (108) | ND |
| mut22 (109) | ND |
| mut23 (110) | 81.5 |
| mut24 (111) | 277.4 |
| mut25 (112) | ND |
| mut26 (113) | ND |
| mut27 (114) | ND |
| mut28 (115) | ND |
| mut29 (116) | 243 |
| mut30 (117) | ND |
| mut31 (118) | ND |
| mut32 (119) | 307.6 |
| mut33 (120) | 263.3 |
| mut34 (121) | 280.6 |

TABLE 11-continued

Relative phytase activity of combination variants at pH 4.5

| Variant | Relative activity at pH 4.5 |
| --- | --- |
| mut35 (122) | ND |
| mut36 (123) | ND |

ND: data not generated

Example 15

Thermotolerance of Combination Phytase Variants

Purified proteins from combination phytase variants were analyzed for thermotolerance essentially as described in example 11. Thermotolerance data for the combination phytase variants are outlined in Table 12. The values shown in Table 11 represent the temperature at which 5 minutes of heat treatment will result in 50% loss of phytase activity as compared to untreated enzyme.

TABLE 12

Relative thermotolerance of combination phytase variants

| Variant | Temperature |
| --- | --- |
| mut15 (103) | 72 |
| mut17 (104) | 68 |
| mut18 (105) | 63 |
| mut19 (106) | 63 |
| mut20 (107) | ND |
| mut21 (108) | ND |
| mut22 (109) | 59 |
| mut23 (110) | 63 |
| mut24 (111) | 70 |
| mut25 (112) | 73 |
| mut26 (113) | ND |
| mut27 (114) | 68 |
| mut28 (115) | ND |
| mut29 (116) | 69 |
| mut30 (117) | ND |
| mut31 (118) | ND |
| mut32 (119) | 72 |
| mut33 (120) | 64 |
| mut34 (121) | 64 |
| mut35 (122) | 68 |
| mut36 (123) | 58 |

ND: data not generated

Example 16

Codon Optimization of Variants for Plant Expression

The protein sequence of the enzymatically susceptible phytase enzyme is converted into a polynucleotide sequence. The polynucleotide sequence is modified so that the codon reflects the optimum codon in maize.

The maize optimized polynucleotide sequences as described in SEQ ID NO: 70-102 are synthesized and sub-cloned into pFLEX HX E. coli expression vector by GeneArt, Regensburg, Germany. The final vector contains an expression cassette that includes the codon optimized polynucleotide sequence for the enzymatically susceptible phytase linked to a sequence that adds an N-terminal His-tag. For ease of reference, Table 5 outlines the relationship between polypeptide and polynucleotide sequences that are in the Sequence Listing

Example 17

Method of Making a Plant Transformation Vector

Binary vectors for maize transformation are constructed in two steps. In the first step, three fragments are fused to generate an expression cassette. The expression cassette consists of a HindIII-BamHI rice glutelin promoter cassette fused to a BamHI-SacI cassette (containing the gene of interest) including a SEKDEL ER retention sequence. This cassette is then fused to a SacI-KpnI CMV 35s terminator cassette. The terminator cassette includes an inverted PEPC intron. The expression cassette is then transferred as a HindIII-KpnI fragment into the binary vector pNOV2117, which contains the phosphomannose isomerase (PMI) gene allowing for selection of transgenic cells with mannose.

Transformation of immature maize embryos is performed essentially as described in Negrotto et al., Plant Cell Reports 19:798-803 (2000). Various media constituents described therein can be substituted.

Agrobacterium strain LBA4404 (Invitrogen) containing the plant transformation plasmid is grown on YEP (yeast extract (5 g/L), peptone (10 g/L), NaCl (5 g/L), 15 g/l agar, pH 6.8) solid medium for 2 to 4 days at 28° C. Approximately $0.8 \times 10^9$ Agrobacteria are suspended in LS-inf media supplemented with 100 µM acetosyringone (As) (LSAs medium) (Negrotto et al., Plant Cell Rep 19:798-803*(2000)). Bacteria are pre-induced in this medium for 30-60 minutes.

Immature embryos from maize line, A188, or other suitable maize genotypes are excised from 8-12 day old ears into liquid LS-inf+100 µM As (LSAs). Embryos are vortexed for 5 seconds and rinsed once with fresh infection medium. Infection media is removed and Agrobacterium solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) (Negrotto et al., Plant Cell Rep 19:798-803 (2000)) and cultured in the dark for 28° C. for 10 days.

Immature embryos producing embryogenic callus are transferred to LSD1M0.5S medium (LSDc with 0.5 mg/l 2,4-D instead of Dicamba, 10 g/l mannose, 5 g/l sucrose and no silver nitrate). The cultures are selected on this medium for 6 weeks with a subculture step at 3 weeks. Surviving calli are transferred either to LSD1M0.5S medium to be bulked-up or to Reg1 medium (as described in Negrotto et al., Plant Cell Rep 19:798-803 (2000). Following culturing in the light (16 hour light/8 hour dark regiment), green tissues are then transferred to Reg2 medium without growth regulators (as described in Negrotto et al., Plant Cell Rep 19:798-803 (2000) and incubated for 1-2 weeks. Plantlets are transferred to Magenta GA-7 boxes (Magenta Corp, Chicago Ill.) containing Reg3 medium (as described in Negrotto et al. 2000) and grown in the light. Plants that are PCR positive for the enzymatically susceptible phytase expression cassette are transferred to soil and grown in the greenhouse.

The presence of the enzymatically susceptible phytase gene is determined by +/−PCR assay or by a Taqman® copy number assay. The presence of the PMI selective marker is determined by a Taqman® copy number assay. The presence of the spectinomycin resistance gene selective marker is determined by +/−PCR assay.

Example 18

Analysis of Transgenic Maize Plants Expressing an Enzymatically Susceptible Phytase Transgenic corn will be ground in a Perten 3100 hammer mill equipped with a 2.0 mm screen thus generating transgenic corn flour. Flour samples (1 gram) from PCR positive transgenic events are extracted in 50 mM Tris-HCl (pH 8.0), 100 mM NaCl, 2 mM for 1 hour at ambient temperature with stirring. Extraction volume is 100 ml. Extracts are clarified by centrifugation and diluted with sodium acetate buffer (pH 5.5). Phytase activity is measured at a range of pH essentially as described in Example 10. Assays are performed in microplates at a final reaction volume of 1 ml.

Example 19

Animal Feeding Studies

Microbial expressed phytase (8 variants) will be premixed onto a wheat carrier for inclusion in multiple broiler chicken feeding studies. The phytase enzyme pre-mixture will be standardized at approximately 3,500 FTU/g of premix. The premixed phytase enzyme will be included in typical corn-SBM based rations formulated to meet the all requirements of young, growing broiler chickens with the exception of phosphorus. Phytase will be added to the starter rations resulting in a final concentration of 250 to 600 FTU of phytase activity per kg of the final ration. Experimental diets will be ad libitum fed in either a mash or a pelleted form to several (4 to 10) replicate groups of 5 to 8 chickens housed in battery cages in environmentally controlled rooms. In addition to diets containing experimental enzymes, positive control (phosphorus adequate), negative control (phosphorus deficient) and stepwise additions of phosphorus (standard curve) will feed fed to similar replicate groups of chickens to allow for analysis of the enzyme response. Enzyme evaluation and characterization will be determined using performance characteristics (feed intake, body weight gain and the ratio of feed to gain over the feeding period and using the tibia ash content of chickens at the end of the feeding period. Analysis of enzyme utility will be accomplished using a combination of slope-ratio, stand curve, ANOVA and protected LSD comparisons of performance and tibia ash data.

Example 20

Pelleting Studies

Microbial expressed phytase (8 variants) will be premixed onto a wheat carrier for inclusion in multiple high temperature feed pelleting studies. The phytase enzyme pre-mixture will be standardized at approximately 3,500 FTU/g of premix. The premixed phytase enzyme will be included in typical corn-SBM based rations formulated to meet the all requirements of young, growing broiler chickens with the exception of phosphorus. Phytase will be added to the starter rations resulting in a final concentration of 250 to 750 FTU of phytase activity per kg of the final ration. Fully mixed mash diets containing experimental phytase enzymes will be pelleted using mills representative of current research feed processing mills and methods. Pelleting diet temperature will be varied to include pelleted feed samples taken between 70 and 100° C. Feed will be pelleted across multiple days and analyzed for residual phytase activity and will be expressed as a percentage activity remaining from the mash (before pelleting) samples. Analysis of remaining enzyme activity will be accomplished using ANOVA and protected LDS analysis.

Example 21

Method of Making an Enzymatically Susceptible Xylanase

Xylanase genes such as those listed as SEQ ID 14 or 16 from U.S. Pat. No. 7,291,493 can be modeled as described in Example 1 using crystal structures available in the Research Collaboratory for Structural Bioinformation Protein Data Base (PDB) (http://www.rcsb.org/pdb/home/home.do), with the PBD ID: 1XXN, 2DCY, 1BVV, 2Z79. A xylanase computational model can be created using the software program Modeler within Insight II package from Accelrys, Inc. and the models with the lowest objective function value will be chosen.

Mutations for deglycosolation, removal of potential intramolecular disulfide bonds and introducing pepsin cleavage sites can be modeled using SwissPdb Viewer (Guex, N. and Peitsch, M. C. SWISS-MODEL and the Swiss Pdb-Viewer: an environment for comparative protein modeling. Electrophoresis, 18, 2714-2723 (1997)). Xylanase variants can then be modified using rational design as described in Examples 2-5. N-glycosylation sites for xylanase can be identified computationally as well as by mass-spectrometric analysis of the protein variants expressed in *Pichia* and corn endosperm. Corresponding glycosylated amino acid residues can be modified to remove glycosylation sites in xylanase mutants. Specific cysteine residues in xylanase can be identified from the amino acid sequence of SEQ ID 14 or 16 from U.S. Pat. No. 7,291,493. Cysteine residues participating in intramolecular disulfide bridges will be targeted for alteration. Xylanase cysteine residues participating in intermolecular disulfide bridges may also be targeted for alteration.

Alterations can be mapped onto the three-dimensional mode of the xylanase protein to avoid making alterations to the overall structure of the protein and its' ability to fold into the correct conformation. Loops in the xylanase protein structure can be identified from the three-dimensional structure model of xylanase. The particular loops will need to meet the same three criteria as identified in Example 4. Identified loops can then be modified by inserting into or replacing the loop entirely with highly favorable pepsin cleavage site sequence (Keil B., *Specificity of Proteolysis*. Springer-Verlag Berlin-Heidelber-New York p. 335 (1992)).

Variants can then be optimized for bacterial expression by computationally converting the protein sequence into polynucleotide sequence. The polynucleotide sequence can then be optimized for *E. coli* expression. The *E. coli* optimized polynucleotide sequences can then be synthesized and subcloned into pFLEX HX *E. coli* expression vector by GeneArt, Regensbur, Germany. The final vector will contain an expression cassette which includes the codon optimized polynucleotide sequence for the enzymatically susceptible phytase linked to a N-terminal His-tag. Bacterial codon optimized expression cassettes containing enzymatically susceptible xylanases from pFLEX HX can then be cloned into pET24a (Invitrogen) and pFLEXHX T7 expression vectors as described in Example 7. The pET24 and pFLEXHX T7 vectors containing the expression cassettes can then be transformed into BL21[DE3] *E. coli* cells (Invitrogen) and grown up in LB medium containing Kanamycin (50 μg/ml) as described in Example 8. Xylanase can be isolated from these *E. coli* transformants as described in Example 8.

Simulated gastric fluid digestibility of xylanase protein samples will be performed basically as described in Thomas et al., Regulatory Toxicology and Pharmacology 39:87-98 (2004) and as described in Example 9. Xylanase activity can be analyzed over various pH ranges, polymerization and thermotolerance as described in Examples 10-11 using a xylanase assay method as disclosed in PCT patent publication number WO2007/146944. Based upon the data generated from the xylanase mutants expressed and isolated from bacteria, specific combinations of variants will be selected for analysis as described in Examples 12-15 using the xylanase assay method from PCT patent publication number WO2007/146944.

Selected xylanase variants will be codon optimized for plant expression, synthesized and subcloned into pFLEX HX E. coli expression vector as described in Example 16. Plant transformation vectors containing mutated xylanase genes can be constructed essentially as described in Example 17. Transgenic plants will be created expressing enzymatically susceptible xylanases using Agrobacterium transformation as described in Example 16. Transgenic maize plants expressing an enzymatically susceptible xylanase can then be analyzed using the xylanase method disclosed in PCT patent publication number WO2007/146944.

What is claimed is:

1. An isolated phytase comprising a polypeptide comprising an amino acid sequence selected from the group consisting of: SEQ ID NO: 5, SEQ ID NO: 7, SEQ ID NO: 9, SEQ ID NO: 19, SEQ ID NO: 21, SEQ ID NO: 22, SEQ ID NO: 23, SEQ ID NO: 25, SEQ ID NO: 104, SEQ ID NO: 105, SEQ ID NO: 106, SEQ ID NO: 120, AND SEQ ID NO: 121.

2. A preparation comprising the isolated phytase of claim 1.

3. An animal feed comprising the isolated phytase of claim 1.

4. The animal feed of claim 3, wherein the animal feed is prepared as a mash diet, pellet, or extruded feed.

5. The preparation of claim 2, wherein the preparation is a liquid preparation.

6. The preparation of claim 2, wherein the preparation comprises transgenic plant material.

* * * * *